(12) United States Patent
Yan et al.

(10) Patent No.: US 10,695,327 B2
(45) Date of Patent: Jun. 30, 2020

(54) MACROCYCLIC LACTONE COMPOUNDS AND METHODS FOR THEIR USE

(71) Applicant: Elixir Medical Corporation, Milpitas, CA (US)

(72) Inventors: John Yan, Los Gatos, CA (US); Xiaoxia Zheng, Fremont, CA (US); Vinayak D. Bhat, Cupertino, CA (US)

(73) Assignee: Elixir Medical Corporation, Milpitas, CA (US)

( * ) Notice: Subject to any disclaimer, the term of this patent is extended or adjusted under 35 U.S.C. 154(b) by 0 days.

(21) Appl. No.: 16/154,501

(22) Filed: Oct. 8, 2018

(65) Prior Publication Data

US 2019/0275013 A1 Sep. 12, 2019

Related U.S. Application Data

(63) Continuation of application No. 15/181,284, filed on Jun. 13, 2016, now Pat. No. 10,123,996, which is a (Continued)

(51) Int. Cl.
*A61K 45/06* (2006.01)
*A61K 9/00* (2006.01)
(Continued)

(52) U.S. Cl.
CPC .......... *A61K 31/436* (2013.01); *A61K 9/0004* (2013.01); *A61K 31/439* (2013.01); *A61K 31/4525* (2013.01); *A61K 45/06* (2013.01)

(58) Field of Classification Search
CPC ................ A61K 31/436; A61K 31/439; A61K 31/4525; A61K 45/06; A61K 9/0004; A61K 31/427; A61K 9/00; A61K 31/365
(Continued)

(56) References Cited

U.S. PATENT DOCUMENTS 3,929,992 A 12/1975 Sehgal et al.
5,595,756 A 1/1997 Bally et al.
(Continued)

FOREIGN PATENT DOCUMENTS

CN 1477980 A 2/2004
EP 1236478 A1 9/2002
(Continued)

OTHER PUBLICATIONS

Auerbach et al. Angiogenesis assays: problems and pitfalls. Cancer Metastasis Rev. 19(1-2):167-172 (2000).
(Continued)

*Primary Examiner* — Julie Ha

(74) *Attorney, Agent, or Firm* — Wilson Sonsini Goodrich & Rosati

(57) ABSTRACT

A pharmaceutical composition comprising a pharmaceutically acceptable excipient and a compound of the formula:

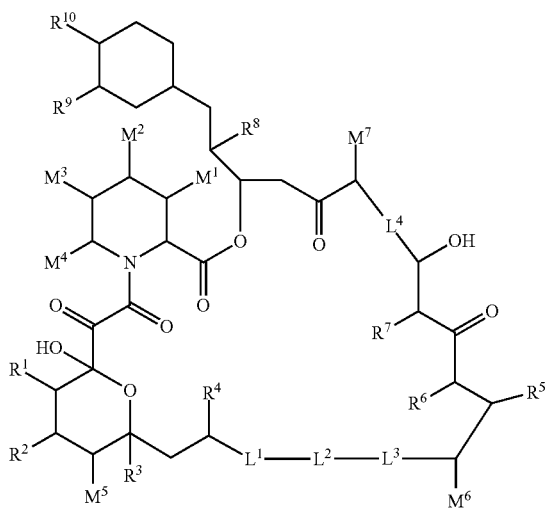

wherein $R^1$, $R^2$, $R^3$, $R^5$, $R^6$, $R^8$, $M^1$, $M^2$, $M^3$, $M^4$, $M^5$, $M^6$ and $M^7$ are each independently a member selected from the group consisting of H, $C_{1-6}$ alkyl, OH and $C_{1-6}$ hydroxyalkyl; $R^4$, $R^7$ and $R^9$ are each independently selected from the group consisting of $C_{1-6}$ alkoxy and OH; $R^{10}$ is a member selected from the group consisting of H, —OH, —OP(O)Me$_2$,

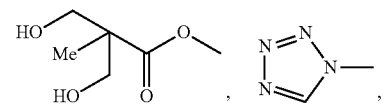

—O—(CH$_2$)$_n$—OH and —O—(CH$_2$)$_m$—O—(CH$_2$)$_o$—CH$_3$, wherein subscripts n and m are each independently from 2 to 8 and subscript o is from 1 to 6; each of $L^1$ and $L^4$ are independently selected from the group consisting of:

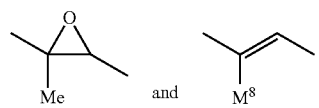

wherein each $M^8$ is independently a member selected from the group consisting of $C_{1-6}$ alkyl, OH and $C_{1-6}$ hydroxyalkyl; each of $L^2$ and $L^3$ are independently selected from the group consisting of:

(Continued)

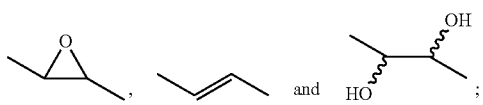

and salts, isomers, or N-oxides thereof.

6 Claims, 111 Drawing Sheets

Related U.S. Application Data continuation of application No. 14/831,747, filed on Aug. 20, 2015, now abandoned, which is a continuation of application No. 13/302,588, filed on Nov. 22, 2011, now Pat. No. 9,149,470, which is a continuation of application No. 12/046,024, filed on Mar. 11, 2008, now Pat. No. 8,088,789, which is a continuation-in-part of application No. 11/854,312, filed on Sep. 12, 2007, now Pat. No. 7,867,988.

(60) Provisional application No. 60/825,531, filed on Sep. 13, 2006.

(51) Int. Cl.
  *A61K 31/436* (2006.01)
  *A61K 31/439* (2006.01)
  *A61K 31/4525* (2006.01)

(58) Field of Classification Search
  USPC ............. 514/291, 172, 175, 211.11; 424/427
  See application file for complete search history.

(56) References Cited

U.S. PATENT DOCUMENTS

| | | | |
|---|---|---|---|
| 5,646,160 | A | 7/1997 | Morris et al. |
| 5,665,772 | A | 9/1997 | Cottens et al. |
| 5,728,710 | A | 3/1998 | Luengo |
| 5,957,975 | A | 9/1999 | Lafont et al. |
| 5,985,890 | A | 11/1999 | Cottens et al. |
| 6,001,998 | A | 12/1999 | Nishida et al. |
| 6,015,815 | A | 1/2000 | Mollison |
| 6,187,568 | B1 | 2/2001 | Nishida et al. |
| 6,273,913 | B1 | 8/2001 | Wright et al. |
| 6,585,764 | B2 | 7/2003 | Wright et al. |
| 6,641,611 | B2 | 11/2003 | Jayaraman |
| 6,805,703 | B2 | 10/2004 | McMorrow |
| 7,025,734 | B1 | 4/2006 | Ellis et al. |
| 7,056,942 | B2 | 6/2006 | Hildesheim et al. |
| 7,812,032 | B2 | 10/2010 | Viswanath et al. |
| 7,820,812 | B2 | 10/2010 | Viswanath et al. |
| 7,867,988 | B2 | 1/2011 | Yan et al. |
| 8,088,789 | B2 | 1/2012 | Yan et al. |
| 8,367,081 | B2 | 2/2013 | Yan et al. |
| 8,404,641 | B2 | 3/2013 | Yan et al. |
| 9,149,470 | B2 | 10/2015 | Yan et al. |
| 1,012,399 | A1 | 11/2018 | Yan et al. |
| 2001/0027340 | A1 | 10/2001 | Wright et al. |
| 2001/0029351 | A1 | 10/2001 | Falotico et al. |
| 2002/0005206 | A1 | 1/2002 | Falotico et al. |
| 2002/0007213 | A1 | 1/2002 | Falotico et al. |
| 2002/0082680 | A1 | 6/2002 | Shanley et al. |
| 2002/0123505 | A1 | 9/2002 | Mollison et al. |
| 2003/0099712 | A1 | 5/2003 | Jayaraman |
| 2003/0129215 | A1 | 7/2003 | Mollison et al. |
| 2004/0072857 | A1 | 4/2004 | Waugh et al. |
| 2004/0197372 | A1 | 10/2004 | Llanos et al. |
| 2005/0033417 | A1 | 2/2005 | Borges et al. |
| 2005/0101624 | A1 | 5/2005 | Betts et al. |
| 2005/0152842 | A1 | 7/2005 | Li et al. |
| 2005/0175660 | A1 | 8/2005 | Mollison et al. |
| 2005/0208095 | A1 | 9/2005 | Hunter et al. |
| 2005/0209244 | A1 | 9/2005 | Prescott et al. |
| 2005/0239178 | A1 | 10/2005 | Ruppen et al. |
| 2006/0094744 | A1 | 5/2006 | Maryanoff et al. |
| 2006/0229711 | A1 | 10/2006 | Yan et al. |
| 2007/0015697 | A1 | 1/2007 | Peyman |
| 2007/0059336 | A1 | 3/2007 | Hughes et al. |
| 2007/0207186 | A1 | 9/2007 | Scanlon et al. |
| 2008/0086198 | A1 | 4/2008 | Owens et al. |
| 2008/0234309 | A1 | 9/2008 | Yan et al. |
| 2011/0097364 | A1 | 4/2011 | Yan et al. |
| 2012/0093891 | A1 | 4/2012 | Yan et al. |
| 2015/0352089 | A1 | 12/2015 | Yan et al. |

FOREIGN PATENT DOCUMENTS

| | | |
|---|---|---|
| EP | 1588727 A1 | 10/2005 |
| JP | 2005537854 A | 12/2005 |
| WO | WO-9316189 A1 | 8/1993 |
| WO | WO-9402136 A1 | 2/1994 |
| WO | WO-9409010 A1 | 4/1994 |
| WO | WO-9412655 A1 | 6/1994 |
| WO | WO-9606847 A1 | 3/1996 |
| WO | WO-9641807 A1 | 12/1996 |
| WO | WO-9807415 A2 | 2/1998 |
| WO | WO-9807415 A3 | 5/1998 |
| WO | WO-0187263 A2 | 11/2001 |
| WO | WO-0187342 A2 | 11/2001 |
| WO | WO-0187372 A1 | 11/2001 |
| WO | WO-0187373 A1 | 11/2001 |
| WO | WO-0187374 A1 | 11/2001 |
| WO | WO-0187375 A1 | 11/2001 |
| WO | WO-0187376 A1 | 11/2001 |
| WO | WO-0187263 A3 | 4/2002 |
| WO | WO-0187342 A3 | 4/2002 |
| WO | WO-02056790 A2 | 7/2002 |
| WO | WO-02065947 A2 | 8/2002 |
| WO | WO-02056790 A3 | 1/2003 |
| WO | WO-03064383 A2 | 8/2003 |
| WO | WO-02065947 A3 | 9/2003 |
| WO | WO-03064383 A3 | 1/2004 |
| WO | WO-2004022124 A1 | 3/2004 |
| WO | WO-2006116716 A2 | 11/2006 |
| WO | WO-2006116716 A3 | 5/2007 |
| WO | WO-2008033956 A2 | 3/2008 |
| WO | WO-2008033956 A9 | 9/2008 |
| WO | WO-2008033956 A3 | 11/2008 |
| WO | WO-2009114010 A1 | 9/2009 |

OTHER PUBLICATIONS

Autoimmune disorder. MedlinePlus. p. 1-3. Accessed Jan. 18, 2012.
Buech; et al., "Formulation of sirolimus eye drops and corneal permeation studies. J Ocul Pharmacol Ther. Jun. 2007;23(3):292-303.".
Cai, et al. In Vitro Metabolic Study of Temsirolimus: Preparation, Isolation, and Identification of the Metabolites. DMD, Sep. 2007, 35(9):1554-1563.
Cell proliferation definition. Accessed Jul. 28, 2009. www.cancer.gov/Templates/db_alpha.aspx?CdrID=46479.
Chang, et al. Rapamycin for treatment of refractory dysthyroid compressive optic neuropathy. Ophthal Plast Reconstr Surg. May-Jun. 2007;23(3):225-6.
Chirality and thalidomide. Www/skingenious.com/faq.html. Accessed Jul. 29, 2009.
Definition of analog from http://cancerweb.ncl.ac.uk/omd/about.html, pp. 1-5. Accessed Jul. 7, 2005.
Definition of inhibit. Www.dictionary.com. Accessed Jul. 29, 2009.
Definition of isomer. Www.answers.com/topic/isomer. Accessed Jul. 29, 2009.
Definition of metabolite from www.answers.com/topic/metabolite, pp. 1-2. Accessed Jul. 29, 2009.
Dickman, et al. Antifungal rapamycin analogues with reduced immunosuppressive activity. Bioorg Med Chem Lett. Jul. 3, 2000;10(13):1405-8.

(56) References Cited

OTHER PUBLICATIONS

"Drugs.com. MacuSight Announces Positive Preliminary Results From Phase 1 Study of Sirolimus in Wet Age-Related Macular Degeneration, Published Feb. 25, 2008.".

Dupont, et al. The Evolving Role of Sirolimus in Renal Transplantation. QJMed, 2003, 96(6):401-409.

Edwards et al., "The Rapamycin-binding Domain of the Protein Kinase Mammalian Target of Rapamycin Is a Destabilizing Domain", J. Biol. Chem., May 4, 2007, 282(18):13395-13401.

European search report and opinion dated Feb. 20, 2012 for EP Application No. 11191788.6.

European search report and opinion dated Apr. 5, 2012 for EP Application No. 08731883.8.

European search report and opinion dated Oct. 13, 2010 for EP Application No. 07842371.2.

European search report and search opinion dated Feb. 4, 2014 for EP Application No. 13181253.9.

Fingar, et al. Target of rapamycin (TOR): an integrator of nutrient and growth factor signals and coordinator of cell growth and cell cycle progression. Oncogene, Apr. 19, 2004, 23(18):3151-3171.

Gallant-Haidner et al., "Pharmacokinetics and Metabolism of Sirolimus", Therapeutic Drug Monitoring, Feb. 2000, 22(1):31-35.

Grinfeld et al., "Acid Catalyzed Functionalization of Rapamycin", Tetrahedron Letters, Sep. 12, 1994, 35(37):6835-6838.

Gura. Systems for identifying new drugs are often faulty. Science 278(5340):1041-1042 (1997).

Hallensleben, Katrin. Der In-vitro-Metabolismus von Immunsuppressiva, insbesondere Rapamycin: Charakterisierung and Identifizierung der Metabolite. PhD diss., 1999. English title: The in-vitro metabolism of immunosuppressants, in particular rapamycin: Characterization and identification of metabolites Available at https://www.deutsche-digitale-bibliothek.de/binary/A26EC7UU3H5RVSCWKHD2XW6UT4ZFOZNX/full/1.pdf; Accessed Feb. 14, 2017 (with English abstract).

Han. Targeted prodrug design to optimize drug delivery. AAPS Pharmsci 2(1):1-11 (2000).

Hensley. Zyrtec looks in mirror and sees xyzal. Blogs.wsj.com/health/2007/05/29/zyrtec-looks-in-mirror-and-sees-xyzal/. Accessed Jul. 29, 2009.

Herpes Zoster Opthalmicus from Merck manual, pp. 1-2. Accessed Mar. 23, 2011.

Hultsch, et al. The Effect of the Immunophilin Ligands Rapamycin and FK506 on Proliferation of Mast Cells and other hematopoietic cell lines. Mol. Biol. Cell, Sep. 1992, 3(9): 981-987.

Ikeda; et al., "Tacrolimus-rapamycin combination therapy for experimental autoimmune uveoretinitis. Jpn J Ophthalmol. Nov.-Dec. 1997;41(6):396-402.".

International preliminary report on patentability dated Oct. 18, 2011 for PCT/US2008/056501.

International search report and written opinion dated Jun. 24, 2008 for PCT/US2008/056501.

International search report dated Sep. 29, 2008 for PCT/US2007/078317.

Jain. Barriers to drug delivery in solid tumors. Sci Am. Jul. 1994;271(1):58-65.

Kuhnt et al., "Microbial Conversion of Rapamycin", Enzyme & Microbial Tech., Nov. 1, 1997, 21(6):405-412.

Leung et al., "Pharmacokinetics and Metabolic Disposition of Sirolimus in Healthy Male Volunteers After a Single Oral Dose", Ther. Drug Monit., Feb. 2006, 28(1):51-61.

Lhoest, et al. In vitro immunosuppressive activity of tacrolimus dihydrodiol precursors obtained by chemical oxidation and identification of a new metabolite of SDZ-RAD by electrospray and electrospray-linked scan mass spectrometry. J. Mass Spectrom., 2001, 36:889-901.

Lhoest, et al. Isolation from pig liver microsomes, identification by tandem mass spectrometry and in vitro immunosuppressive activity of an SDZ-RAD 17,18,19,20,21,22-tris-epoxide. J. Mass Spectrom., 2000, 35:454-460.

Luengo, et al. Structure-activity studies of rapamycin analogs: evidence that the C-7 methoxy group is part of the effector domain and positioned at the FKBP12-FRAP interface. Chem. & Biol., 1995, 2:471-481.

Marketletter. (Jan. 1, 2000) Drug-coated stent blocks restenosis; brief article. 0951-3175-IAC-ACC-No.68770167.

Marks, A.R., "Rapamycin: Signaling in Vascular Smooth Muscle", Transplantation Proc., 2003, 35(Suppl. 3A):231S-233S.

Marx et al. Rapamycin-FKBP inhibits cell cycle regulators of proliferation in vascular smooth muscle cells. Circ Res76(3):412-417 (1995).

Matter, et al. Effects of tacrolimus or sirolimus on proliferation of vascular smooth muscle and endothelial cells. Journal of cardiovascular pharmacology 48.6 (2006): 286-292.

Merck manual. Bowen's disease. Accessed Jun. 1, 2009.
Merck manual. Clinical aspects of cancer. Accessed Mar. 5, 2008.
Merck manual. Introduction to asthma. Accessed Jul. 28, 2009.
Merck manual. Introduction to Cancer. Accessed Mar. 5, 2008.
Merck manual. Kaposi's sarcoma. Accessed Jun. 1, 2009.
Merck manual. Rheumatoid arthritis. Accessed Jul. 29, 2009.
Merck manual. Squamous cell carcinoma. Accessed Jun. 1, 2009.
More. Xyzal: state of the art antihistamine. Accessed Jul. 29, 2009.

Morice, et al. A randomized comparison of a sirolimus-eluting stent with a standard stent for coronary revascularization. N. Engl J Med. 2002; 346(23):1773-1780.

Multiple Sclerosis Information Page from NINDS, pp. 1-4. Accessed Mar. 14, 2010.

Nickmilder, et al. Isolation and identification of new rapamycin dihydrodiol metabolites from dexamethasone-induced rat liver microsomes. Xenobiotica, 1997, 27(9):869-883.

Nishida, et al. Generation of novel rapamycin structures by microbial manipulations. Journal of Antibiotics. 1995; 48(7):657-666.

Notice of allowance dated May 21, 2015 for U.S. Appl. No. 13/302,588.

Notice of allowance dated Nov. 12, 2010 for U.S. Patent Appl. No. 11/854,312.

Office action dated Mar. 29, 2011 for U.S. Appl. No. 12/046,024.
Office action dated May 3, 2012 for U.S. Appl. No. 13/333,526.
Office action dated May 5, 2010 for U.S. Appl. No. 11/854,312.
Office action dated Jul. 25, 2012 for U.S. Appl. No. 13/333,573.
Office action dated Jul. 31, 2009 for U.S. Appl. No. 11/854,312.
Office action dated Sep. 23, 2014 for U.S. Appl. No. 13/302,588.

Onuma, et al. Mahoroba, first-in-man study: 6-month results of a biodegradable polymer sustained release tacrolimus-eluting stent in de novo coronary stenoses. Eur. Heart J., 2009, 30(12):1477-1485.

Poon, et al. Rapamycin inhibits vascular smooth muscle cell migration. J Clin Invest. 1996; 98:2277-2283.

Sedrani, et al. Dihydroxylation of the Triene Subunit of Rapamycin. J. Org. Chem., 1998, 63:10069-10073.

Simonsen, et al. Cardiology market continues rapid growth in a broad technology front. The BBI newsletter. 1999; 22(4):1049-4316.

Sousa, et al. Sustained suppression of neointimal proliferation by sirolimus-elting stents: one-year angiographic and ntravascular ultasound follow-up. Circulation. 2001; 104(17):2007-2011.

Sporn, et al. Chemoprevention of cancer. Carcinogenesis. Mar. 2000;21(3):525-30.

Sriram, et al. Experimental allergic encephalomyelitis: a misleading model of multiple sclerosis. Ann Neurol. Dec. 2005;58(6):939-45.

Steinman, et al. How to successfully apply animal studies in experimental allergic encephalomyelitis to research on multiple sclerosis. Ann Neurol. Jul. 2006;60(1):12-21.

Supplementary European Search Report dated Sep. 29, 2010 for EP 07842371.

Suzuki, et al. Stent-based delivery of sirolimus reduces neointimal formation in a porcine coronary model. Circulation 2001; 104:1188-1193.

Trepanier, et al. Rapamycin: Distribution, Pharmacokinetics and Therapeutic Range Investigations: An Update. Clin. Biochem., Jul. 1998, 31(5):345-351.

Vignot, et al. mTOR-targeted therapy of cancer with rapamycin derivatives. Annal of Oncology. 2005; 16:525-537.

(56) References Cited

OTHER PUBLICATIONS

Vippagunta et al. Crystalline Solids, Advanced Drug Delivery Reviews, 48:3-26 (2001).
Notice of Allowance dated Jun. 29, 2018 for U.S. Appl. No. 15/181,284.
Office action dated Nov. 8, 2017 for U.S. Appl. No. 15/181,284.

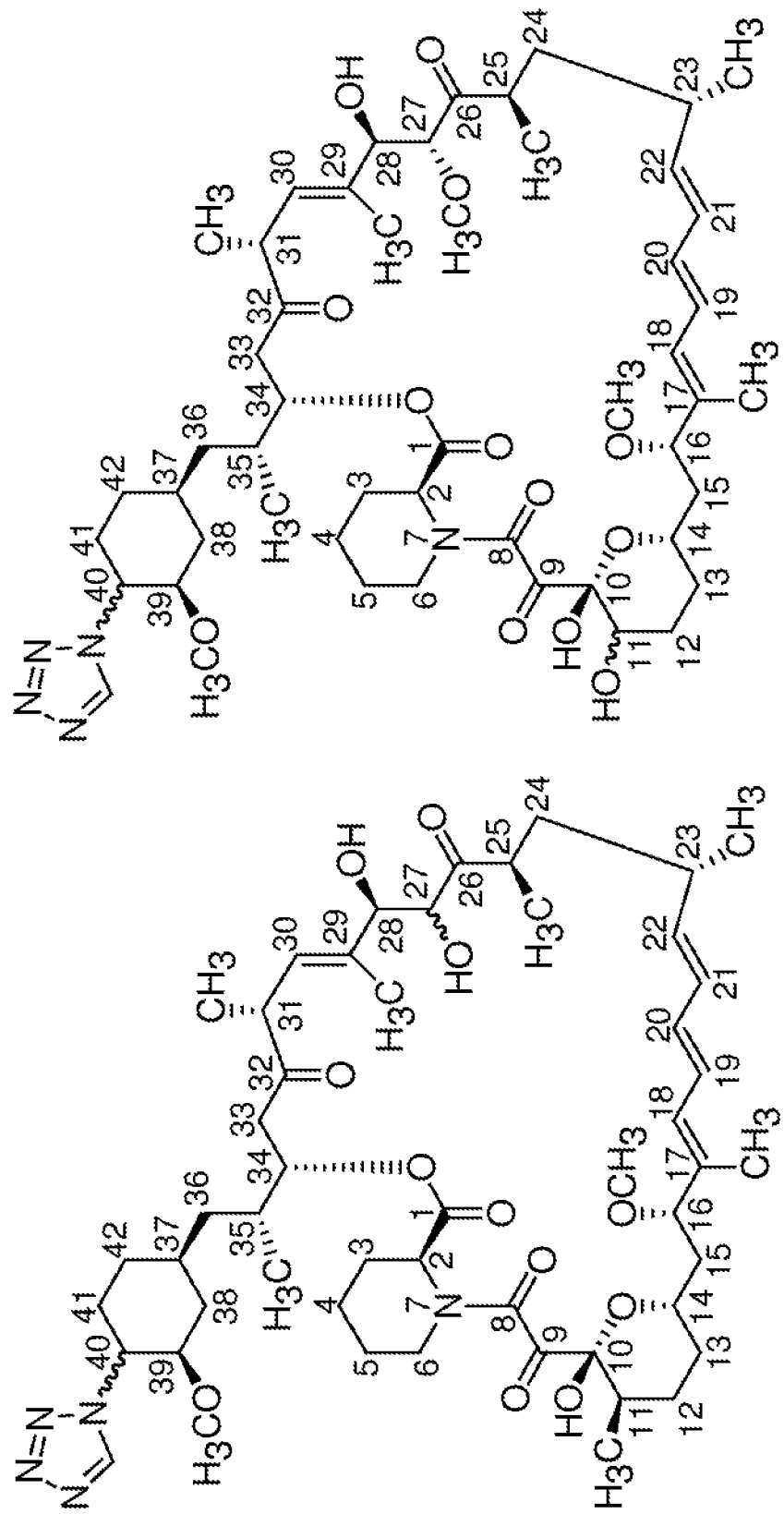

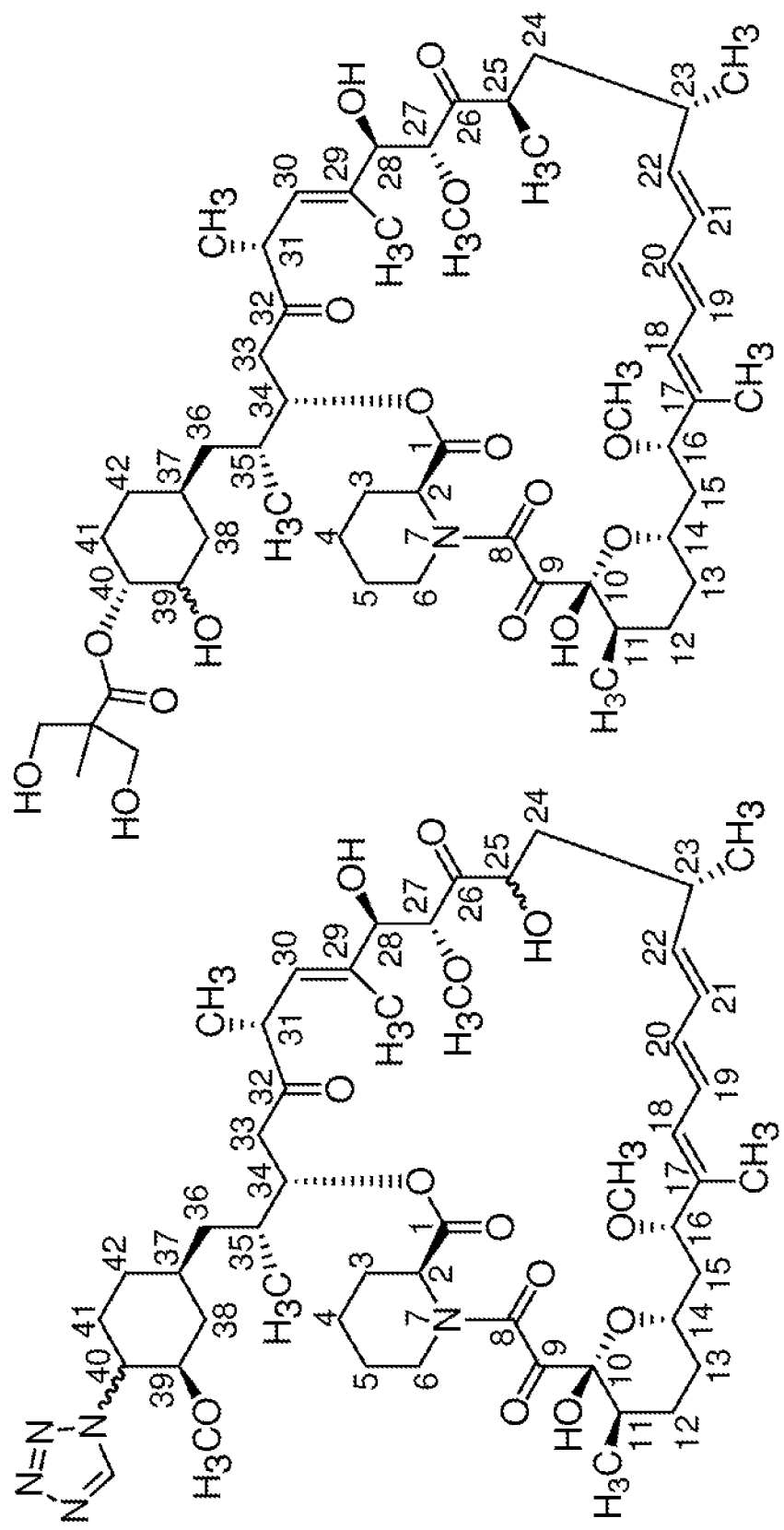

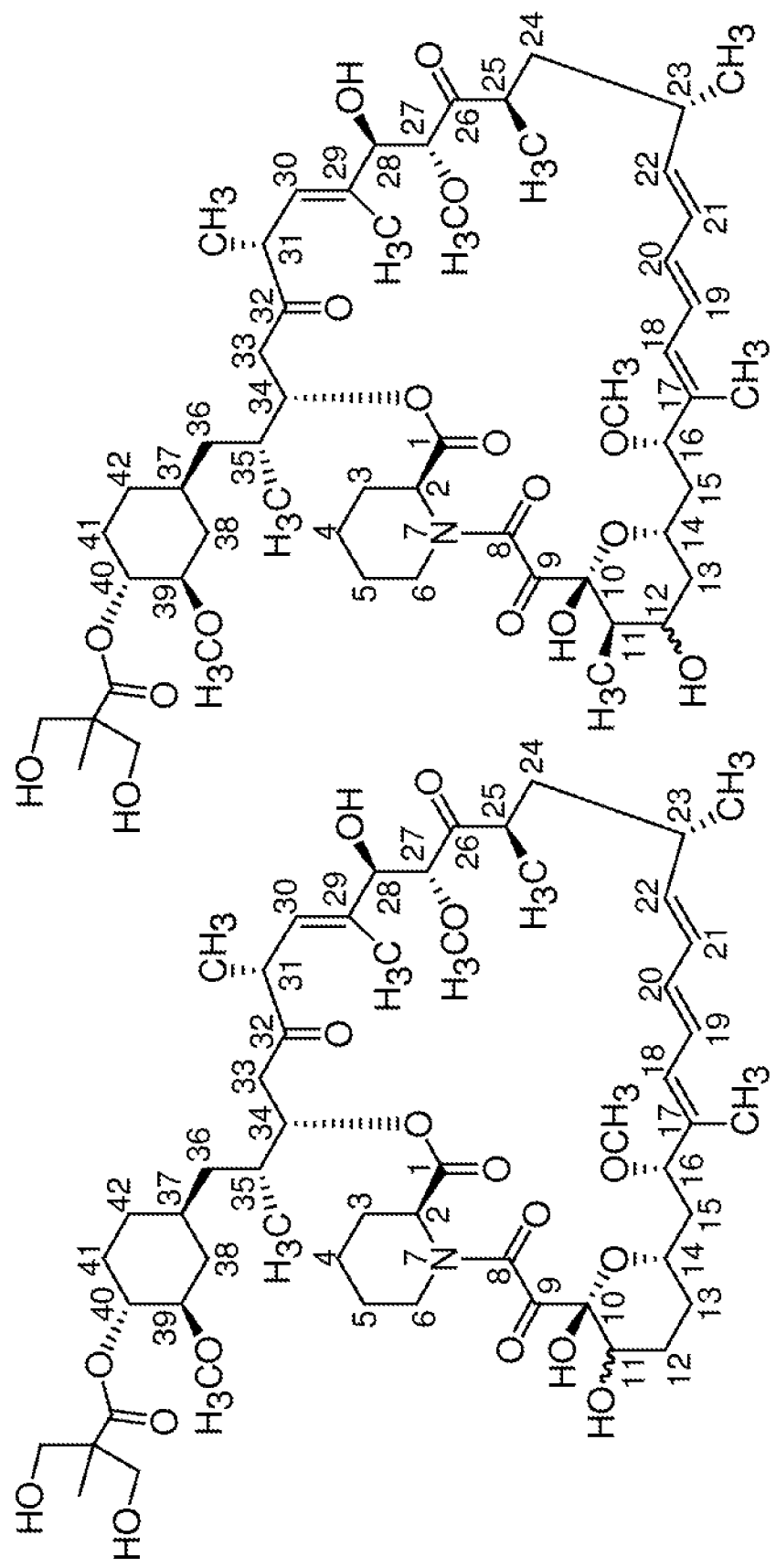

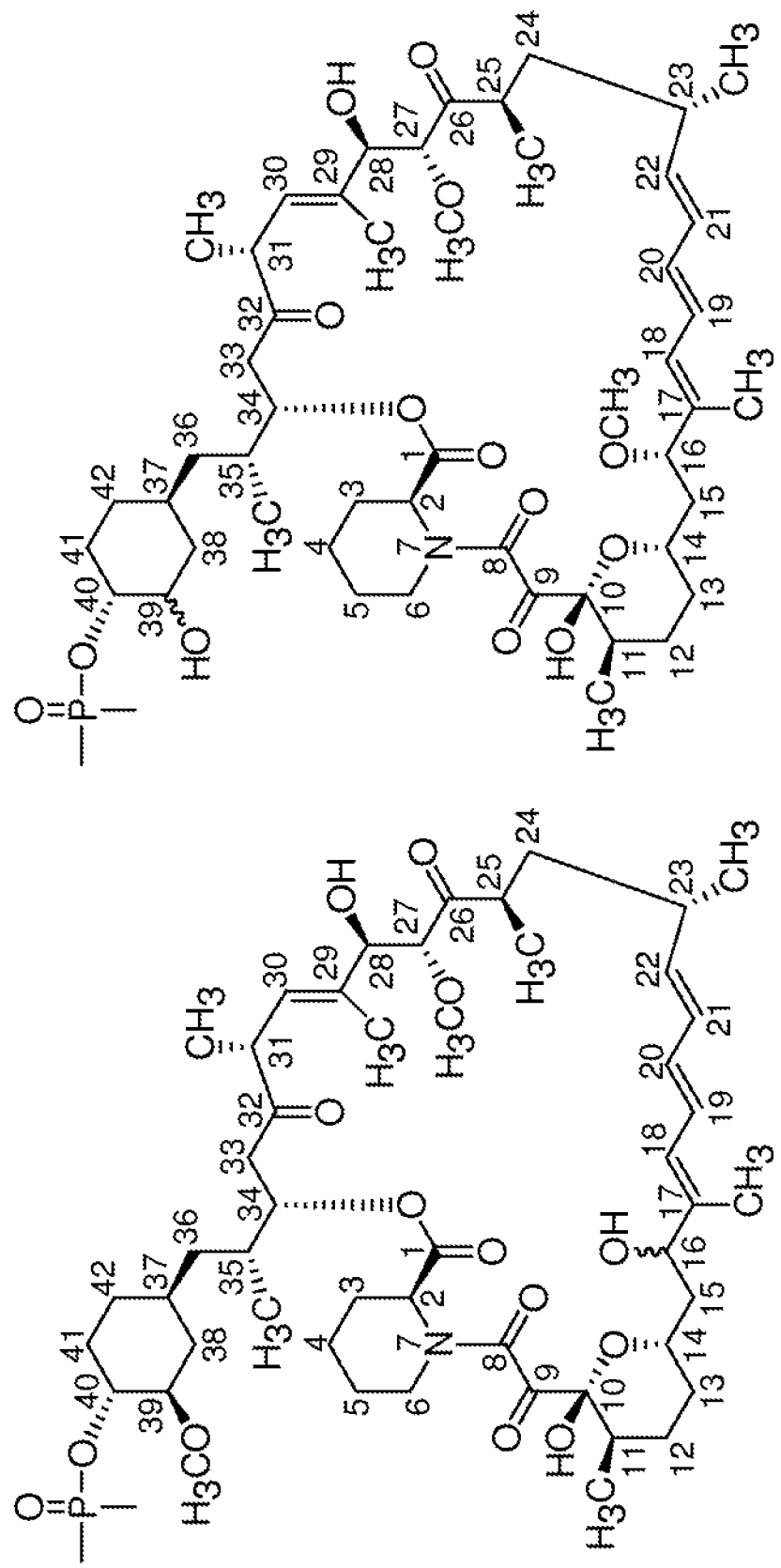

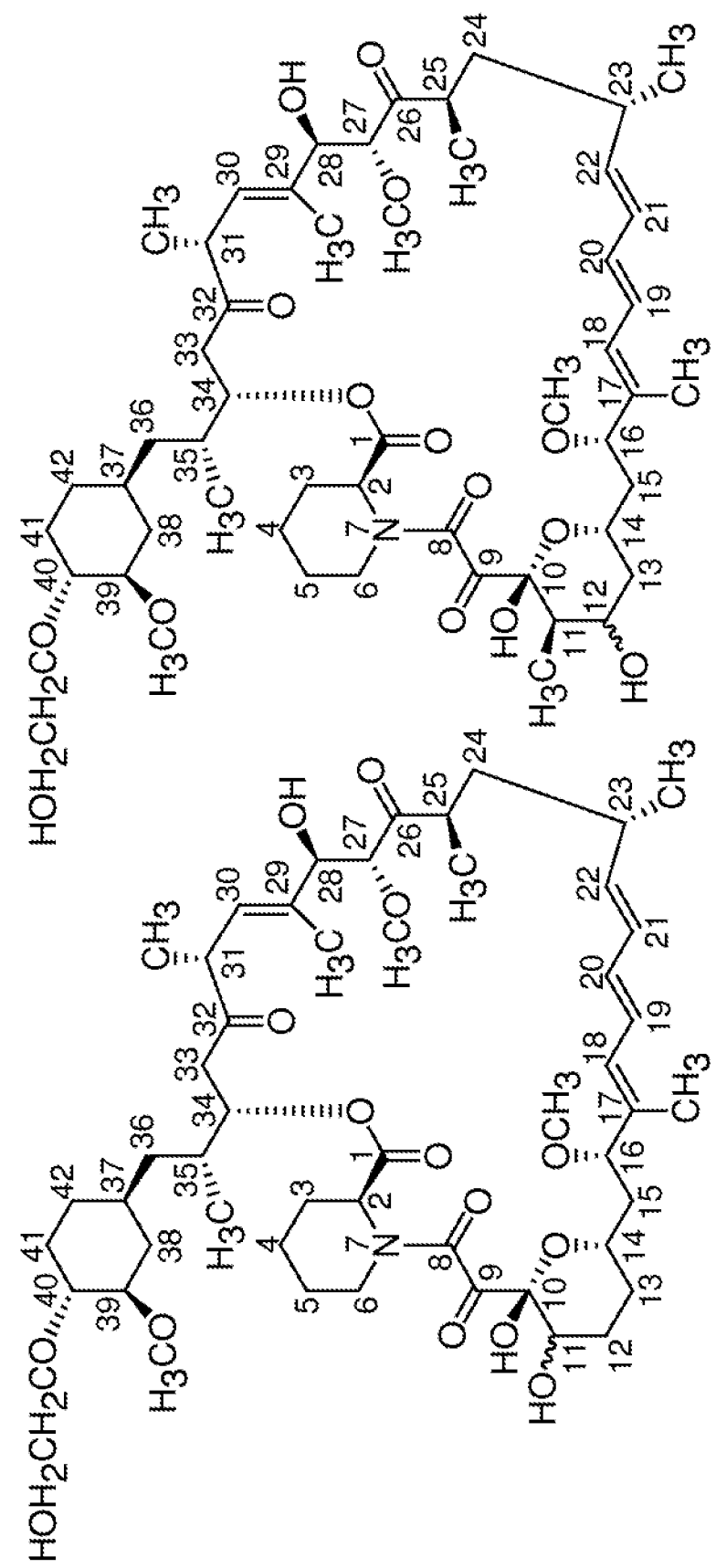

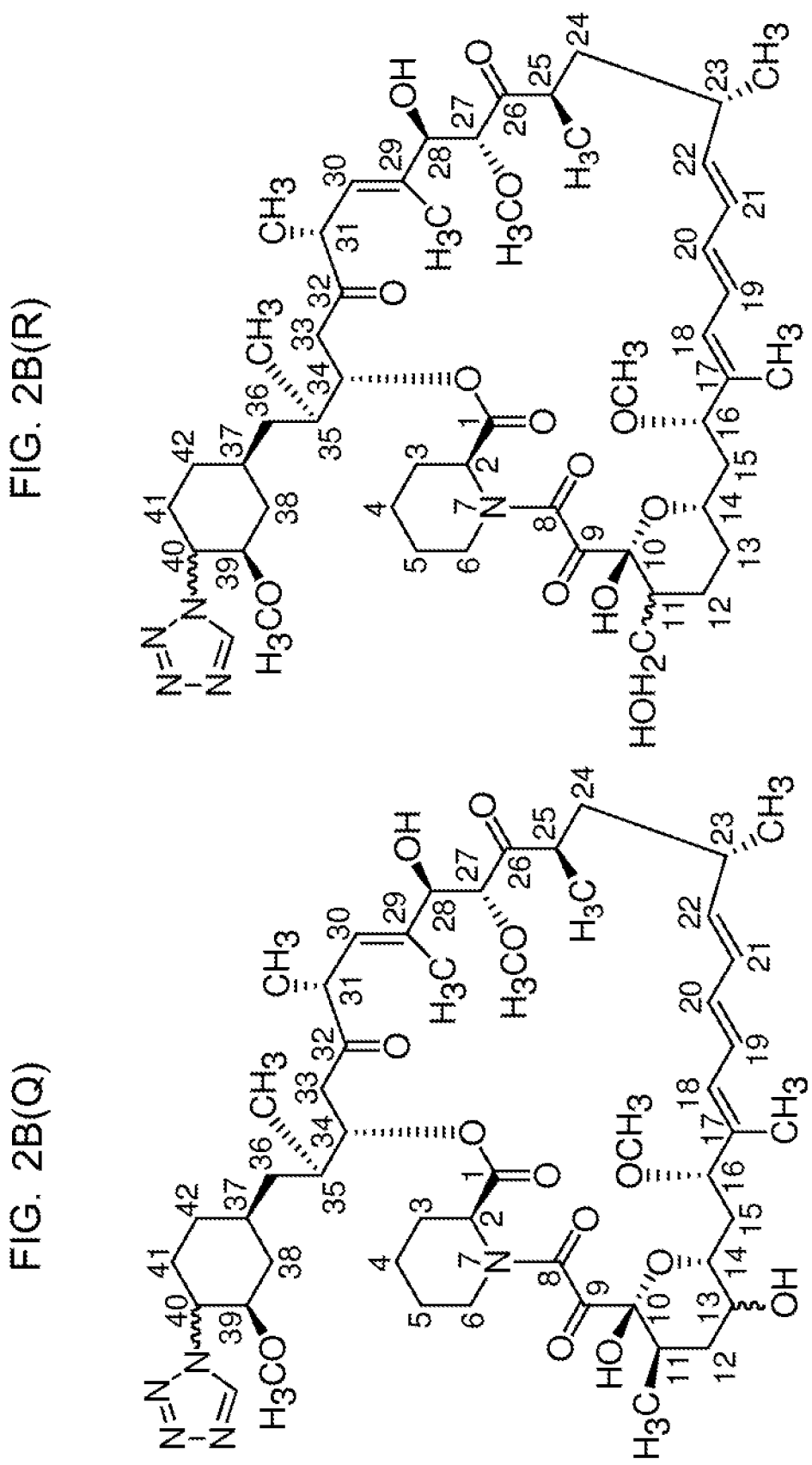

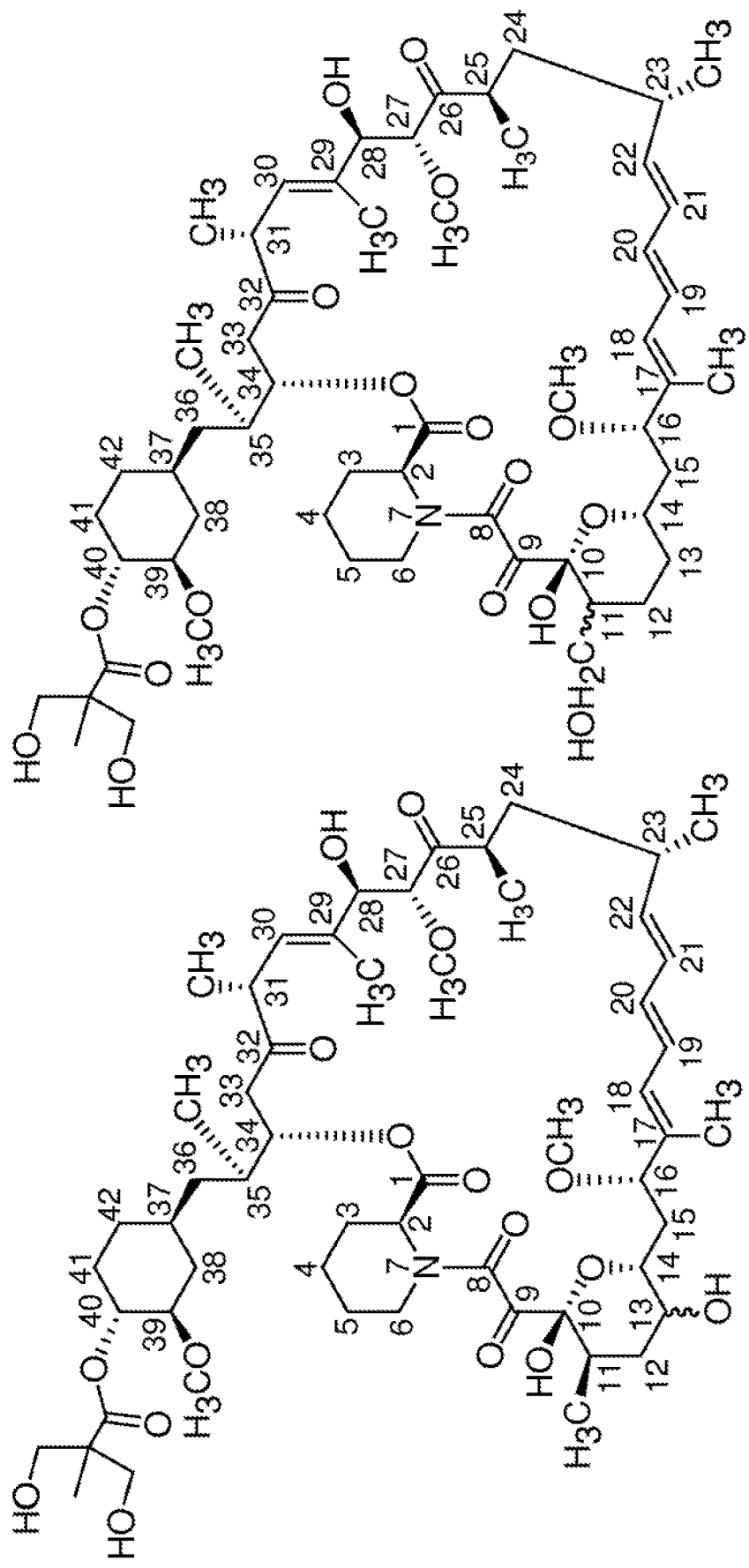

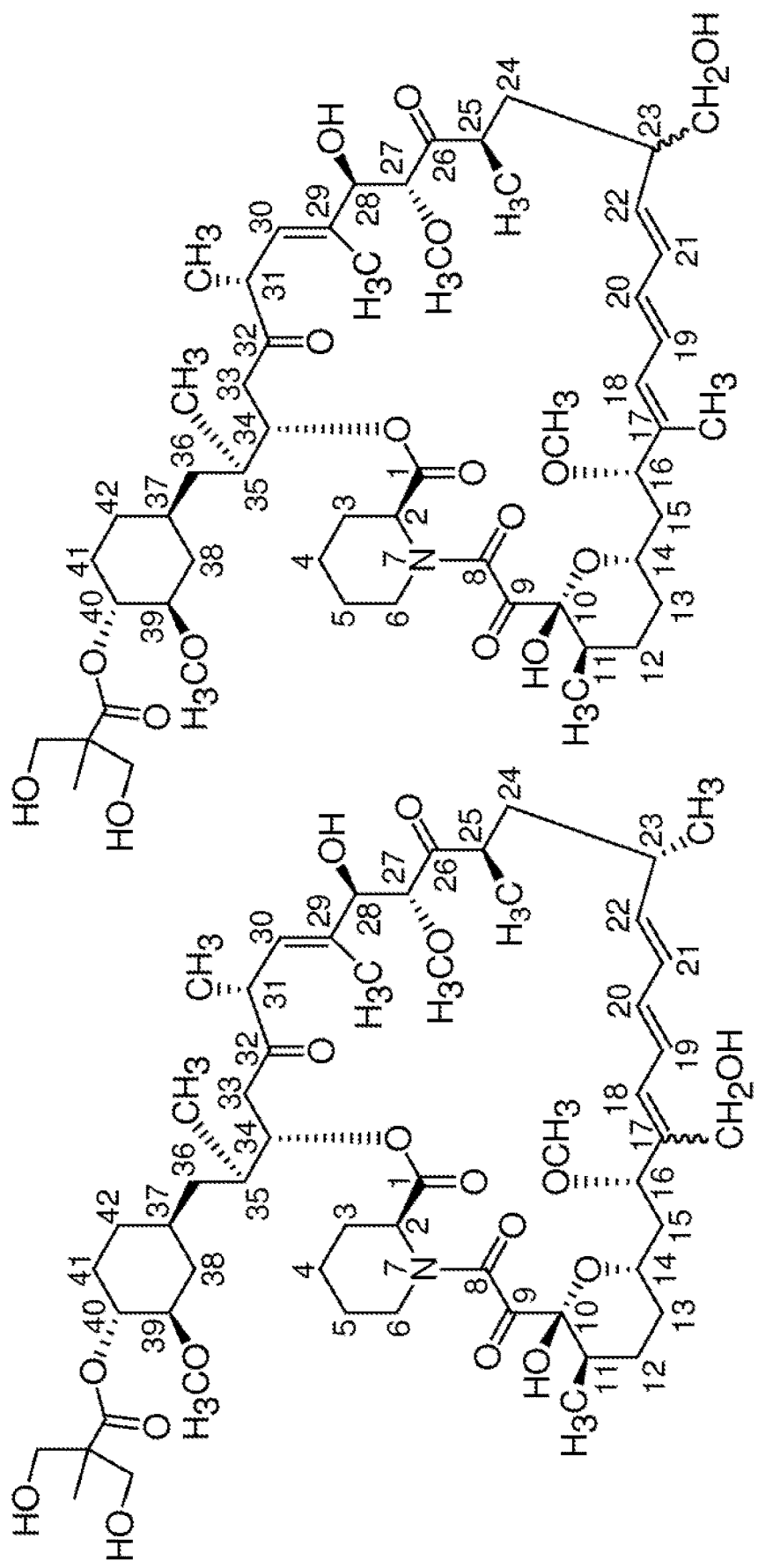

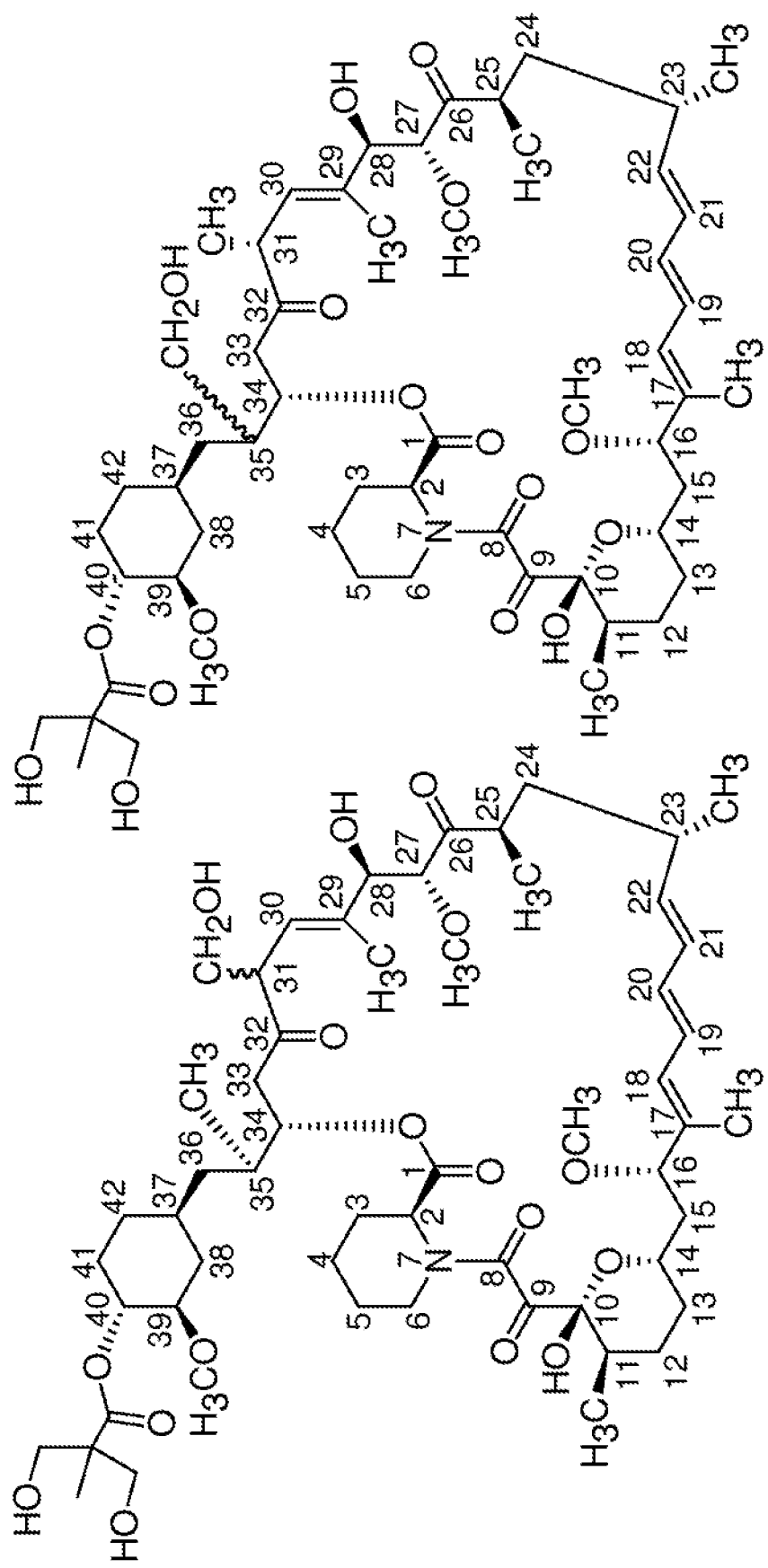

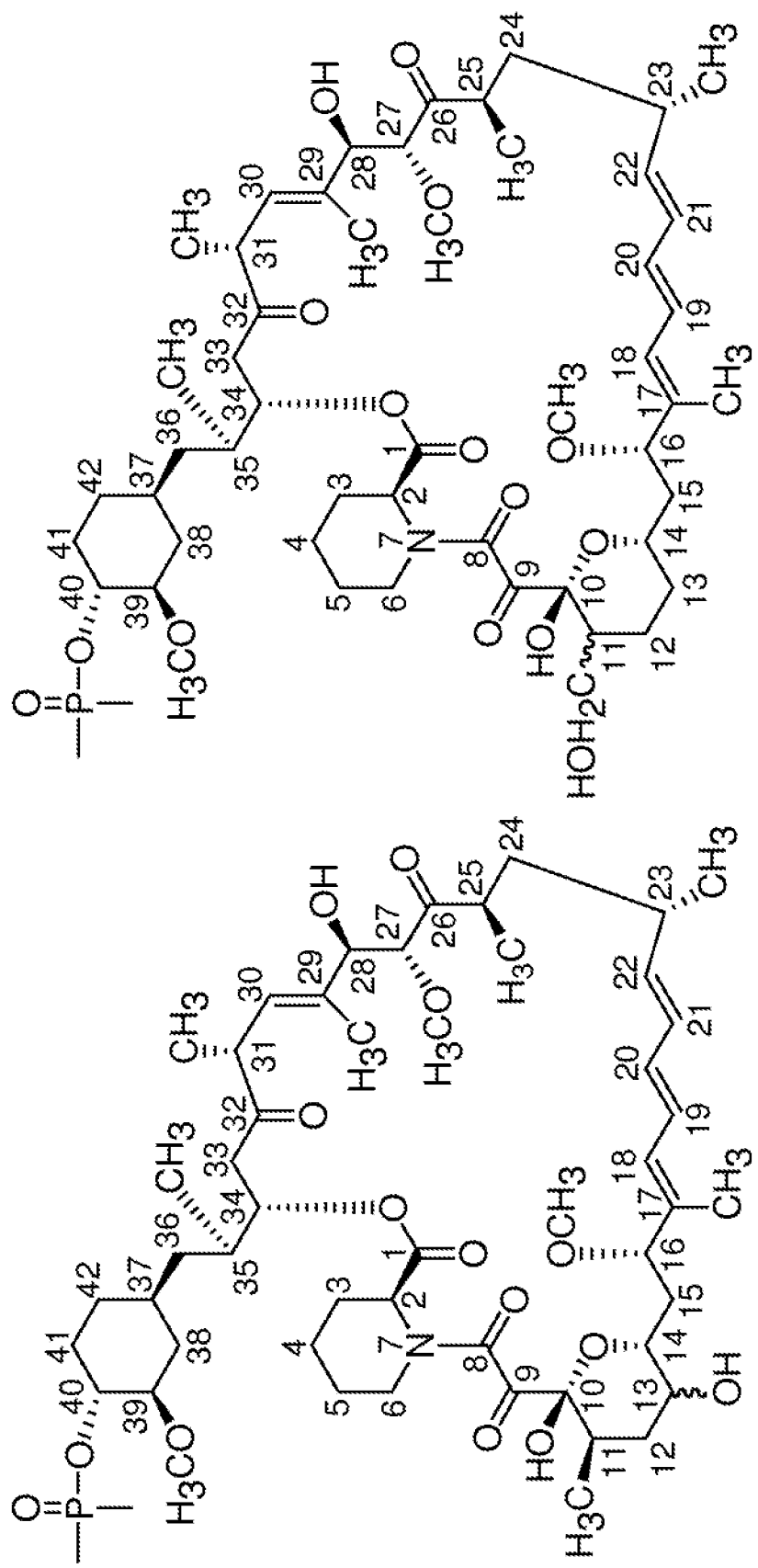

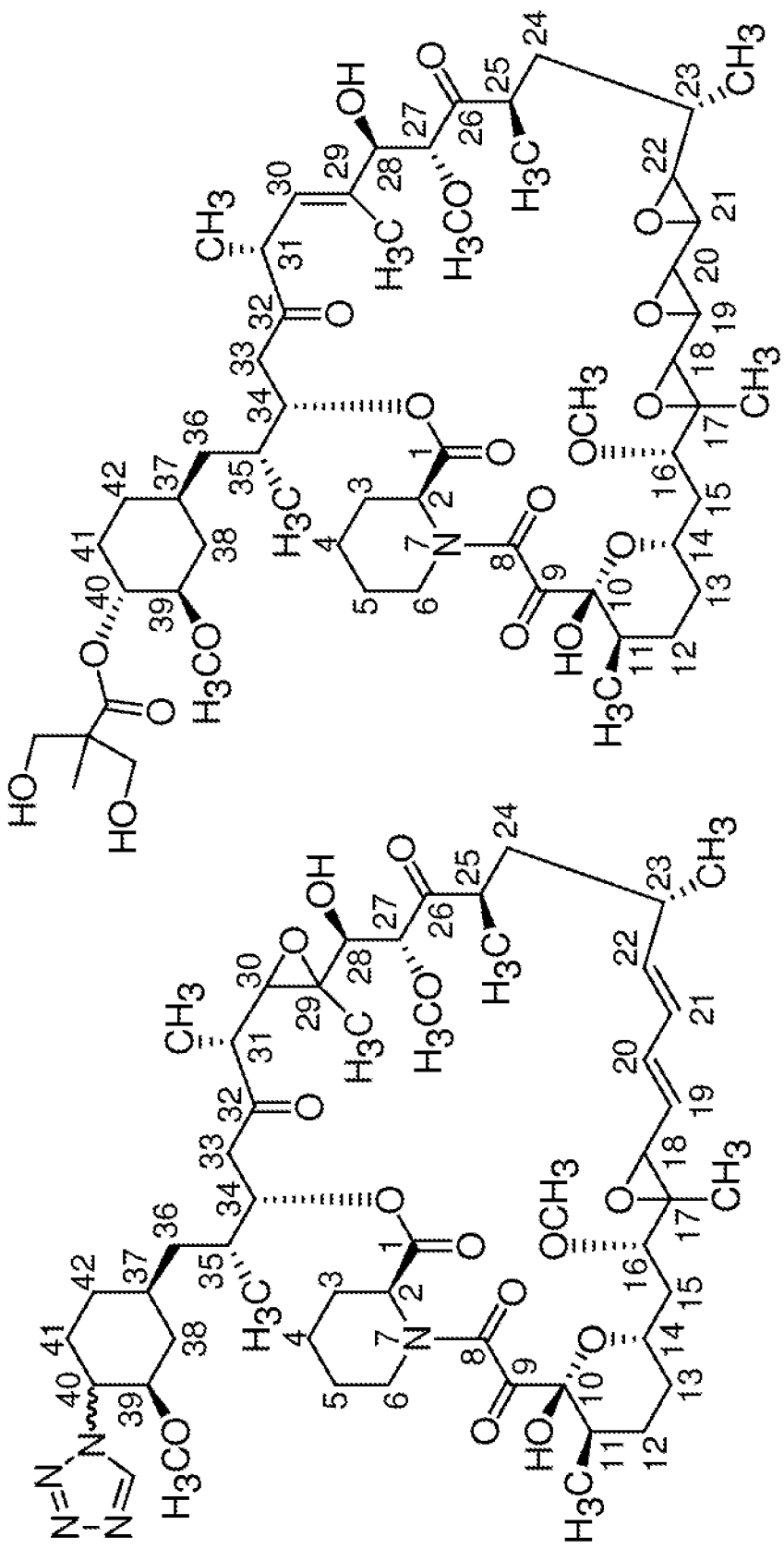

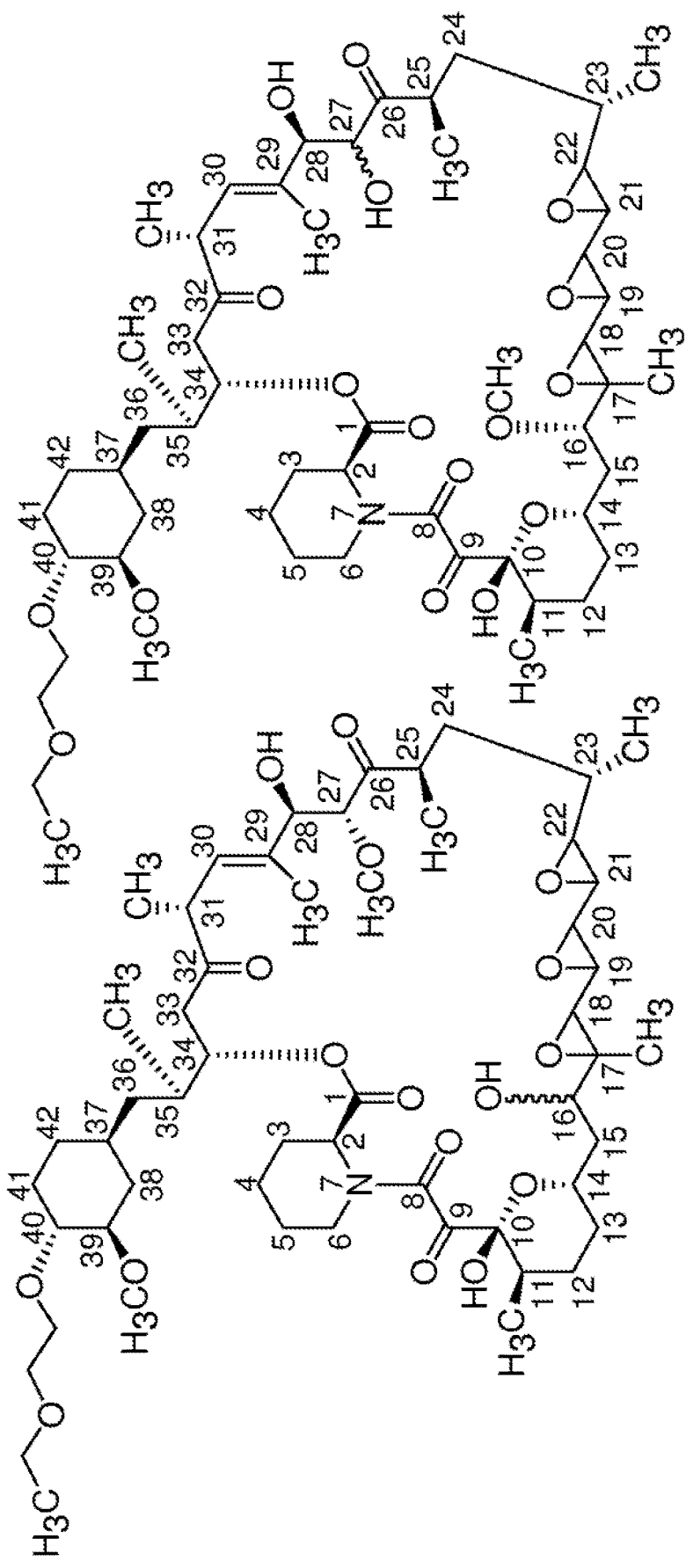

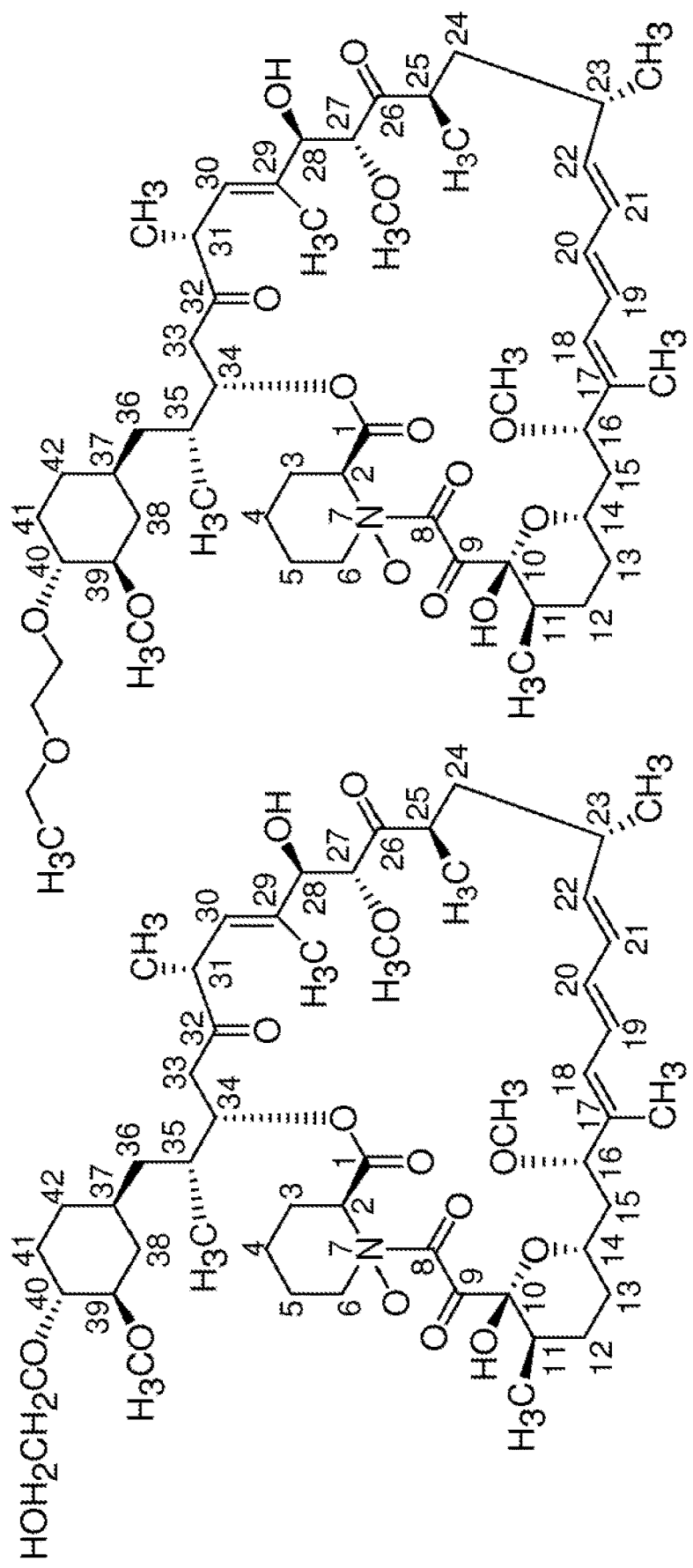

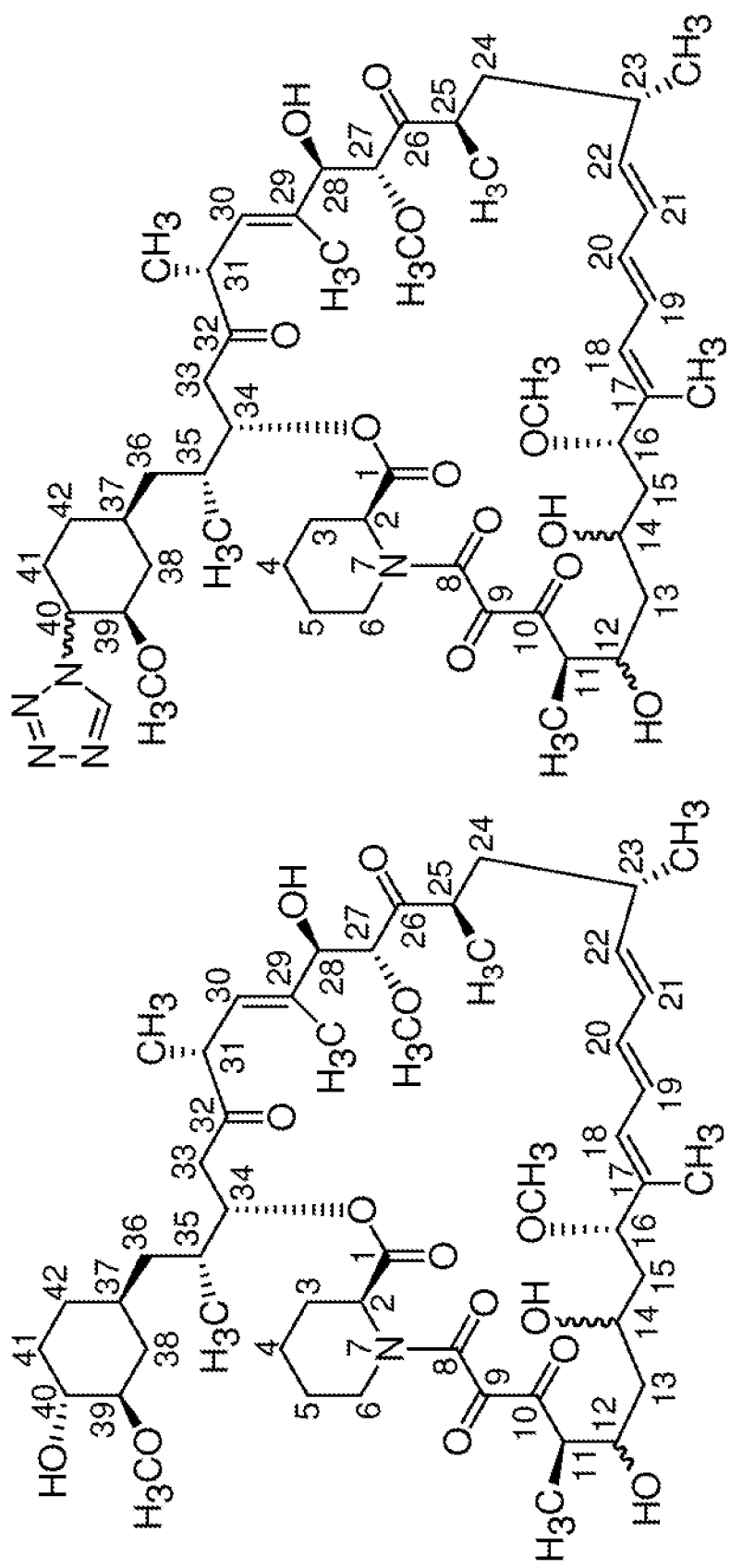

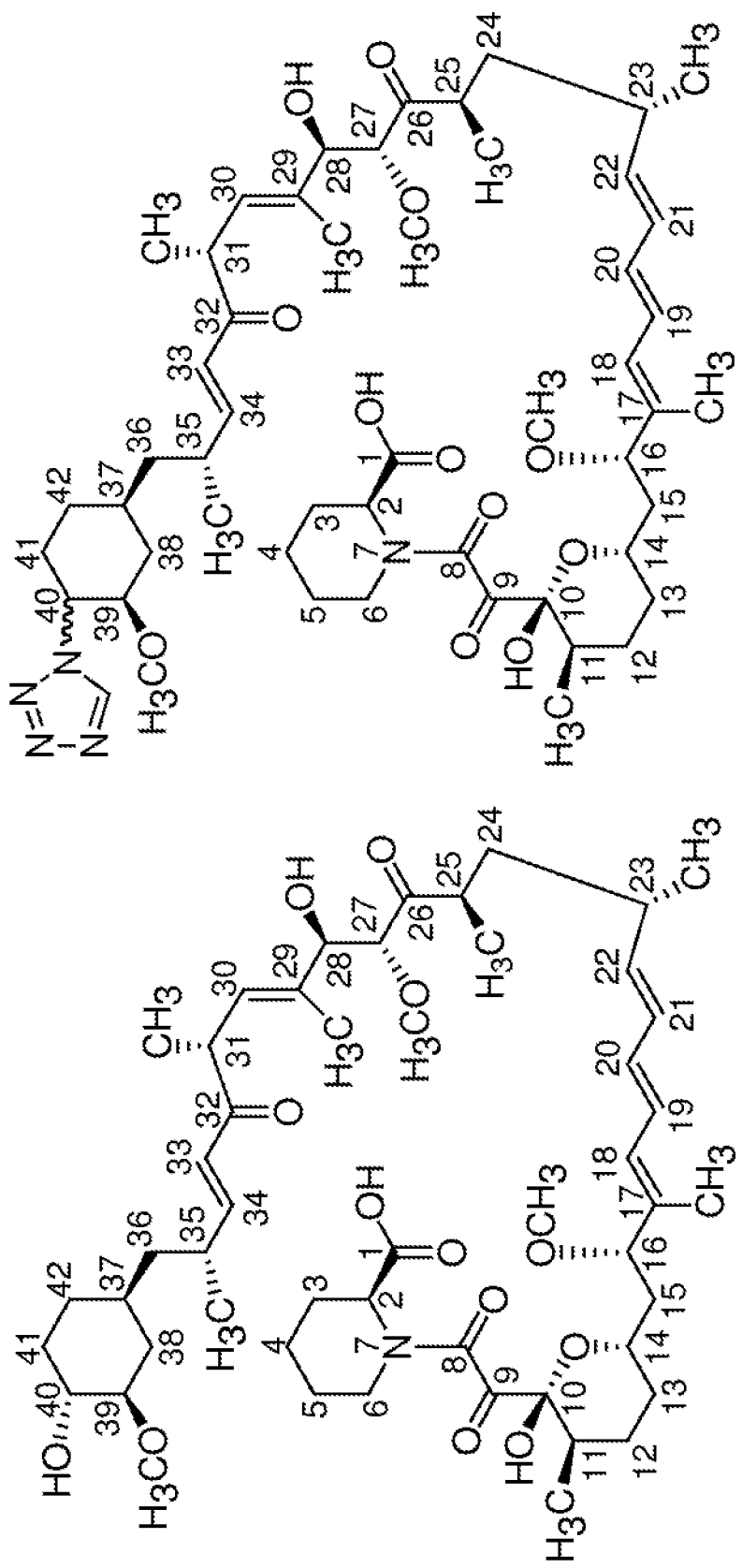

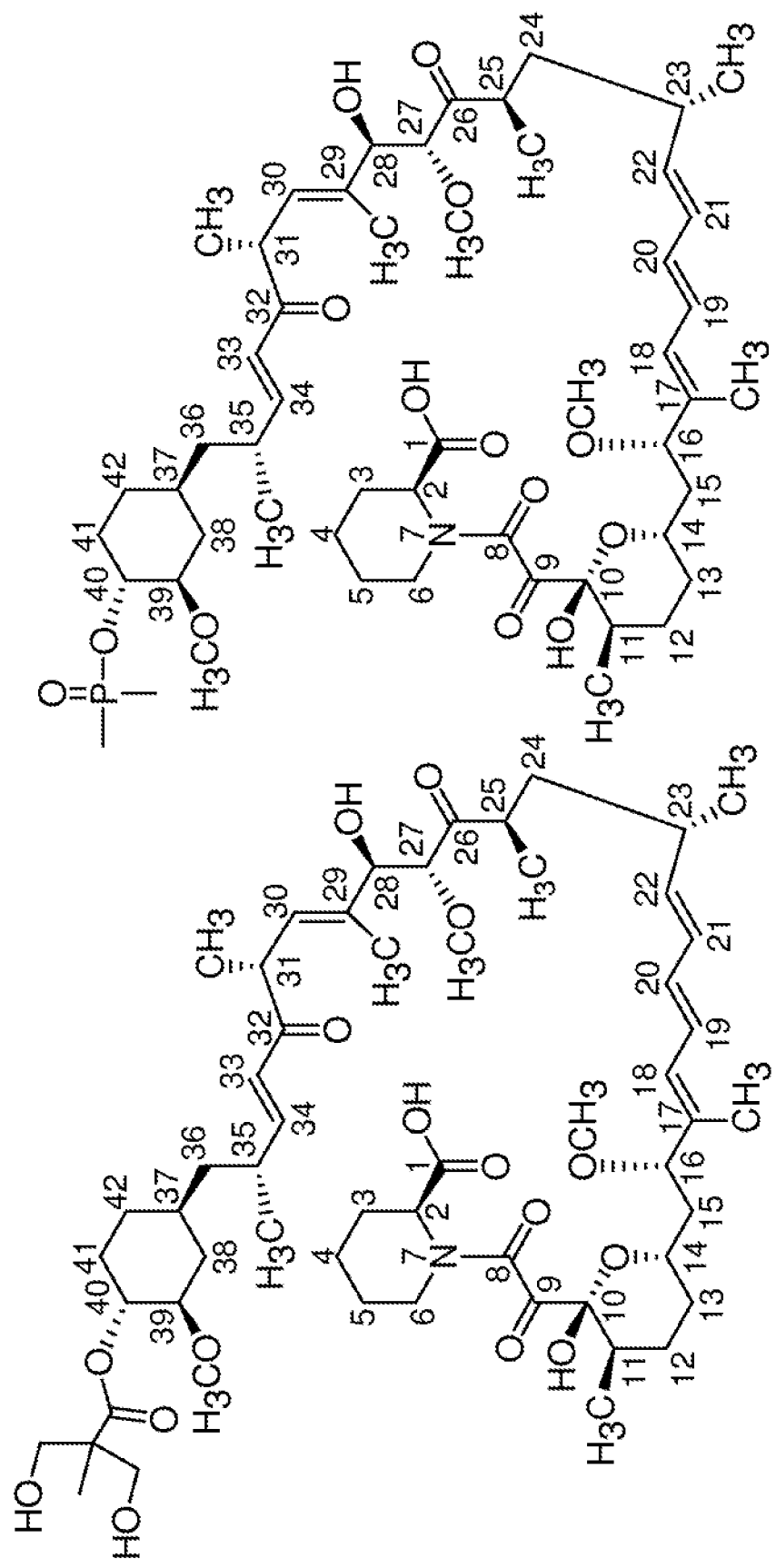

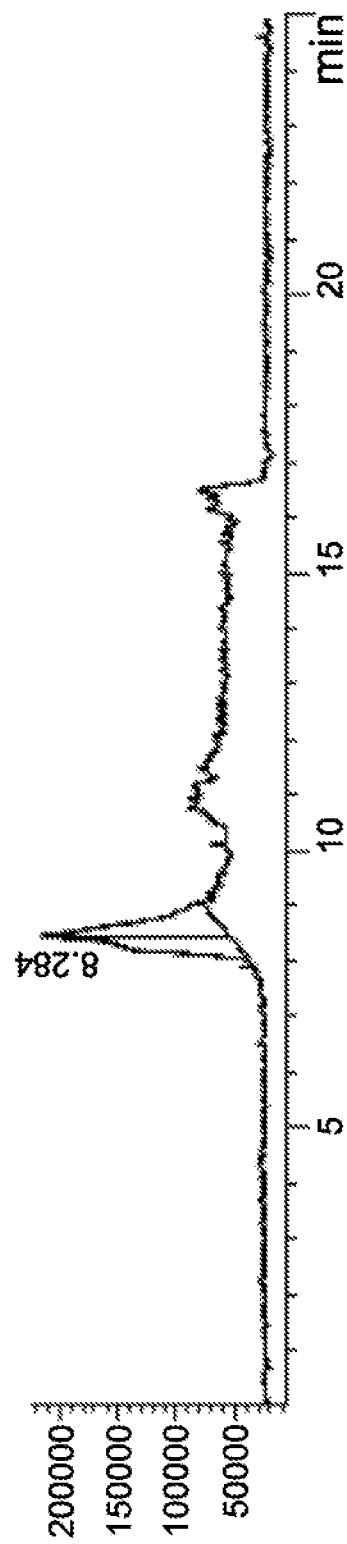
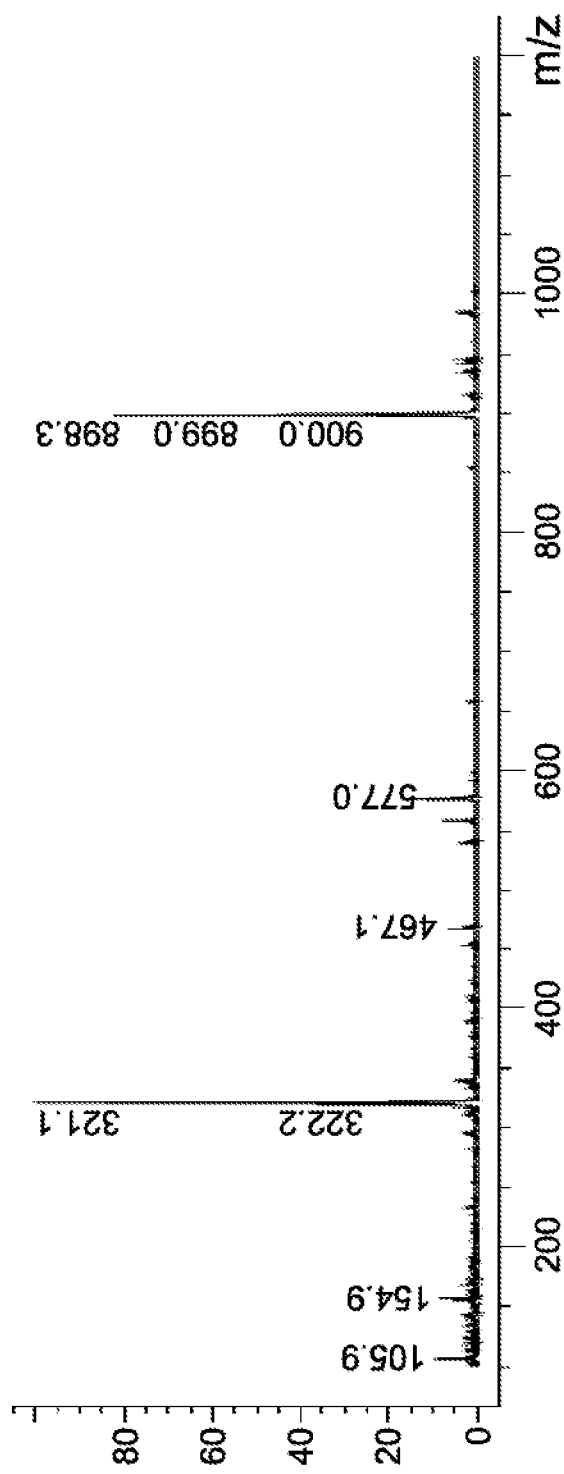
FIG. 6A
FIG. 6B

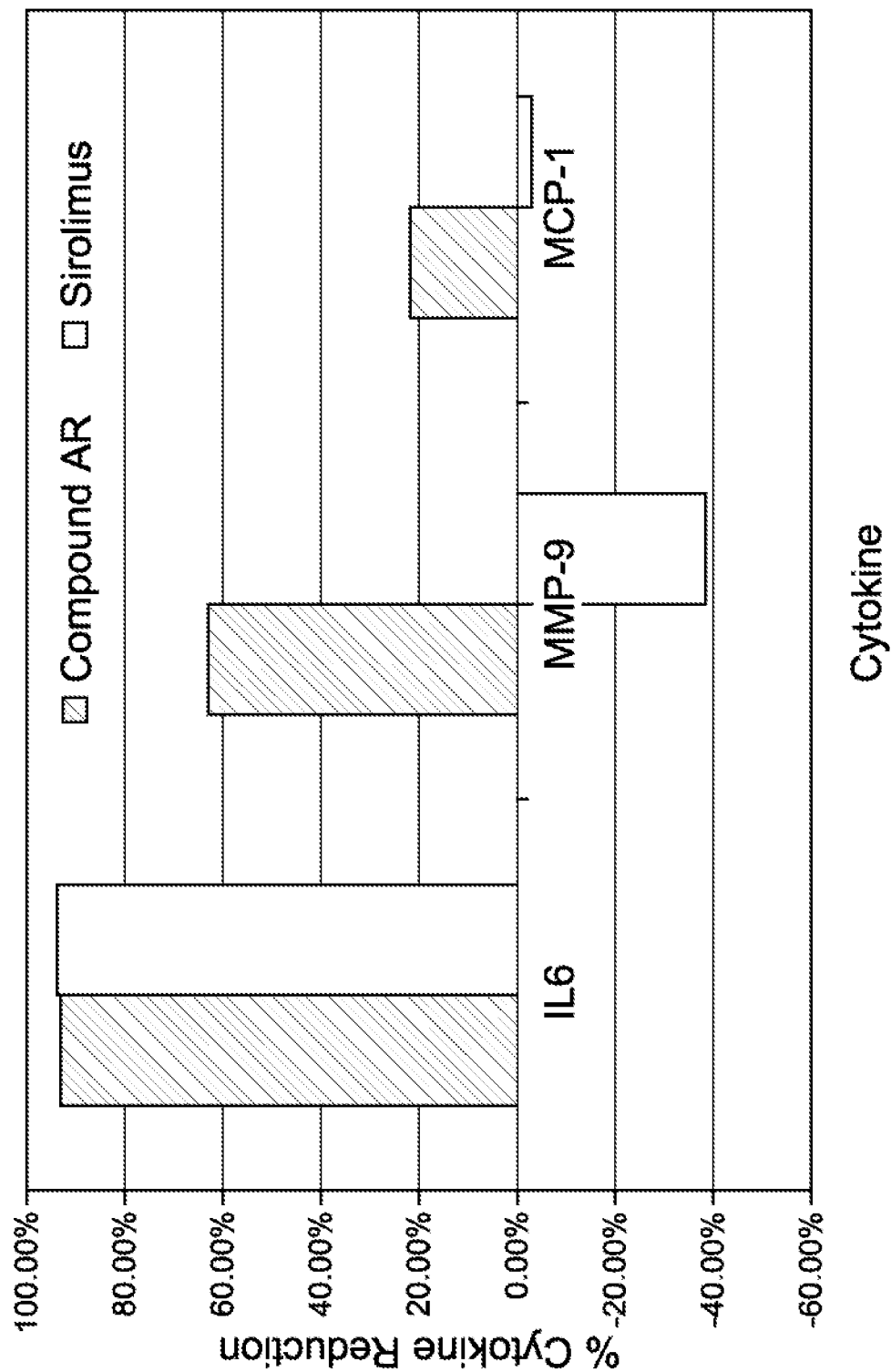

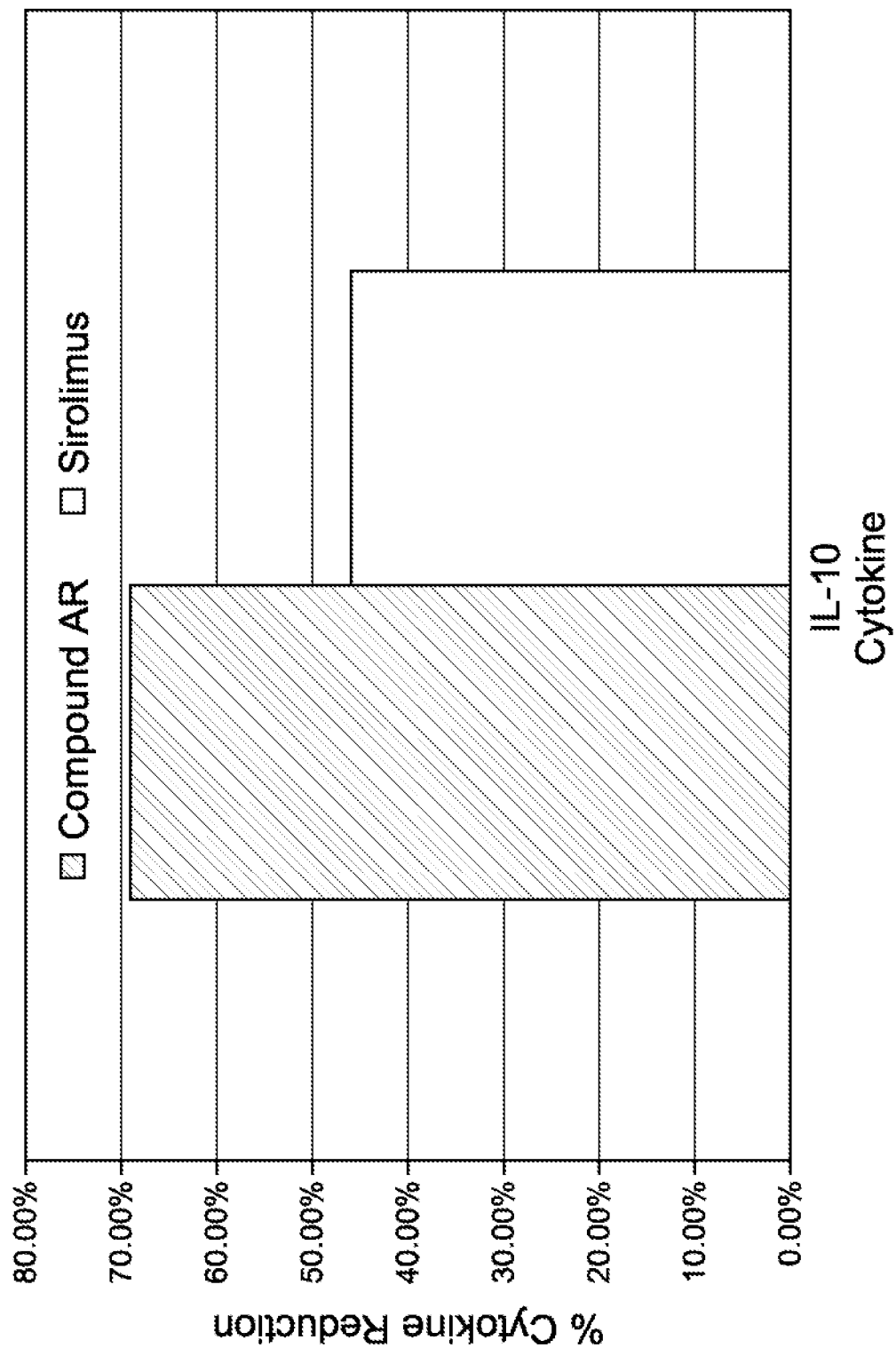

FIG. 15A

↓ Triethylchlorosilane / Imidazole
DMF
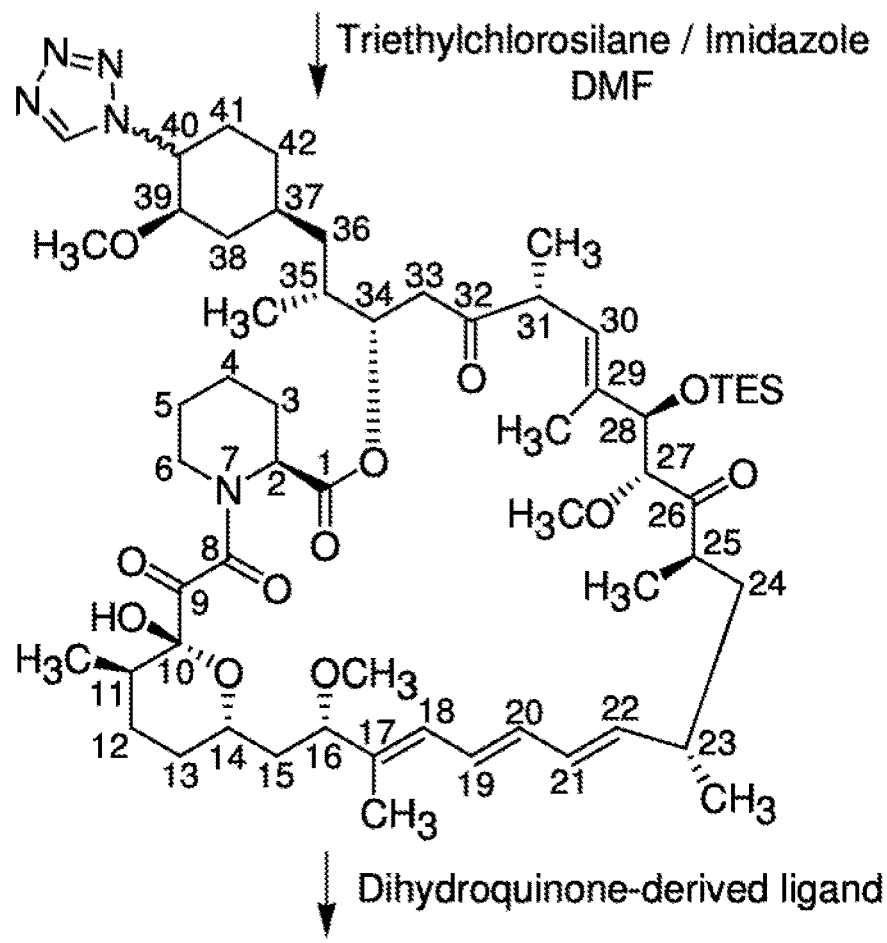
↓ Dihydroquinone-derived ligand FIG. 15B
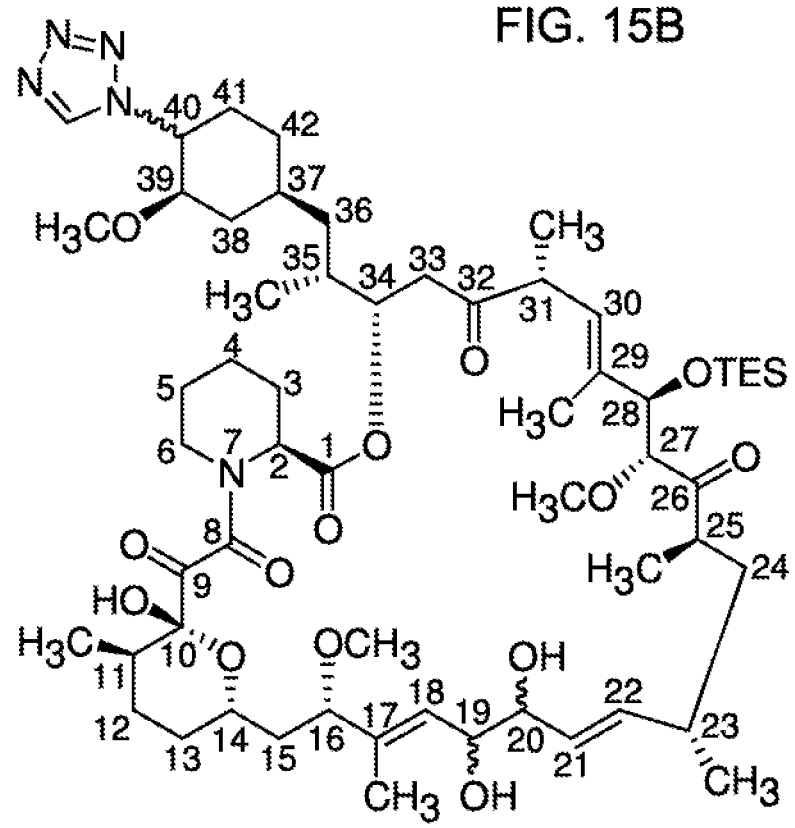
HF - Pyridine
ACN
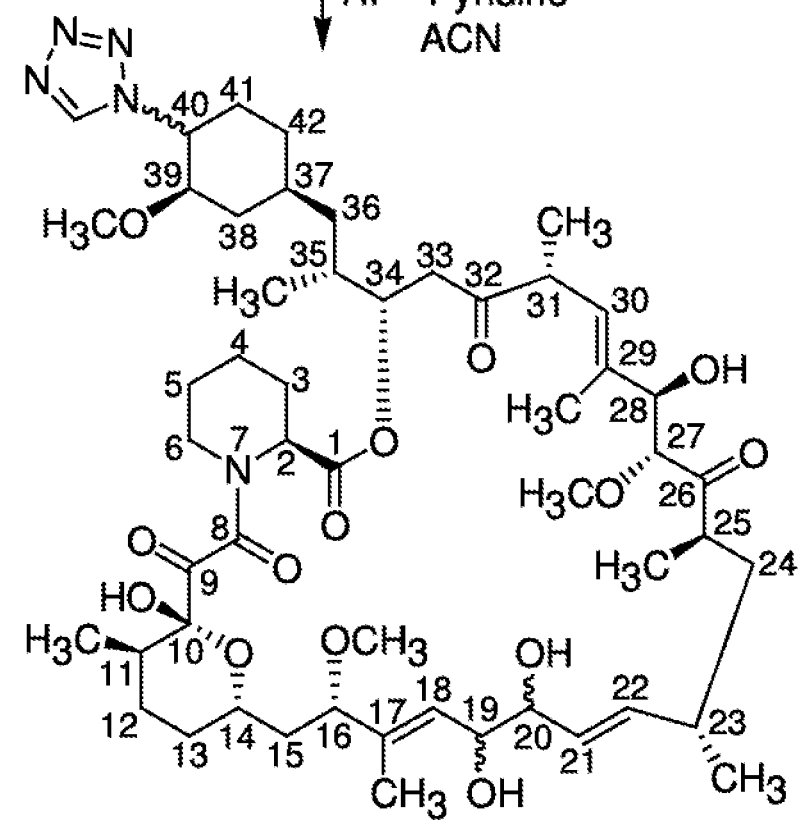

FIG. 17A
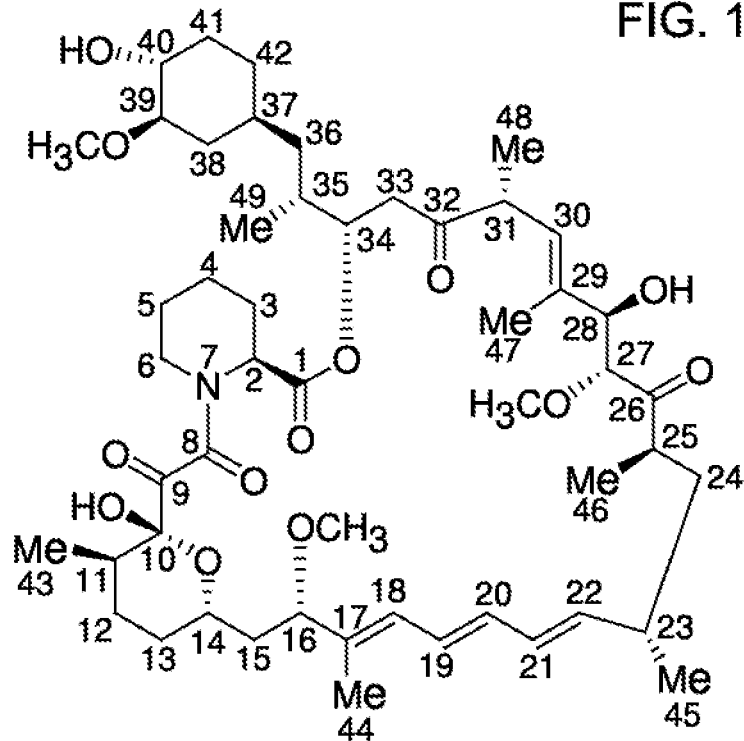
SeO₂ ↓ Protecting alkene groups or added acid if necessary
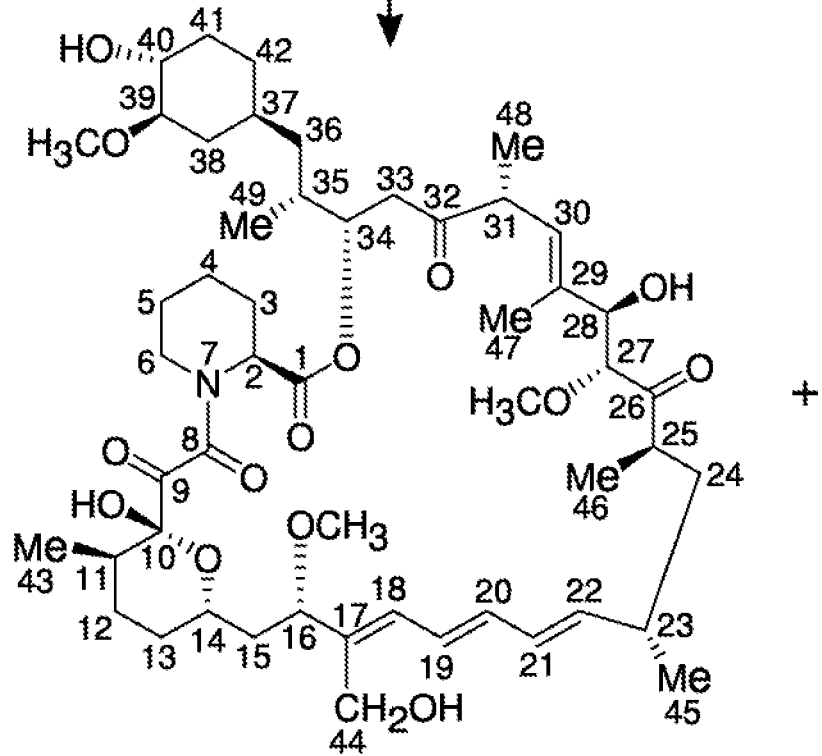
+

Preparative HPLC → Individual pure product

Preparative HPLC → Individual pure product

MACROCYCLIC LACTONE COMPOUNDS AND METHODS FOR THEIR USE

CROSS-REFERENCES TO RELATED APPLICATIONS

This application is a continuation of U.S. patent application Ser. No. 15/181,284, filed Jun. 13, 2016, (now U.S. Pat. No. 10,123,996), which is a continuation of U.S. patent application Ser. No. 14/831,747, filed Aug. 20, 2015, which is a continuation of U.S. patent application Ser. No. 13/302,588, filed Nov. 22, 2011 (now U.S. Pat. No. 9,149,470), which is a continuation of U.S. application Ser. No. 12/046,024, filed Mar. 11, 2008 (now U.S. Pat. No. 8,088,789), which claims the benefit of U.S. application Ser. No. 11/854,312, filed Sep. 12, 2007 (now U.S. Pat. No. 7,867,988), which claims the benefit of U.S. Provisional Application No. 60/825,531, filed Sep. 13, 2006, the full disclosures of which are incorporated by reference herein in their entirety.

STATEMENT AS TO RIGHTS TO INVENTIONS MADE UNDER FEDERALLY SPONSORED RESEARCH OR DEVELOPMENT

NOT APPLICABLE

REFERENCE TO A "SEQUENCE LISTING," A TABLE, OR A COMPUTER PROGRAM LISTING APPENDIX SUBMITTED ON A COMPACT DISK

NOT APPLICABLE

FIELD OF THE INVENTION

The present invention relates to structures of demethyl, hydroxyl, demethylhydroxyl, epoxide, N-oxide, opened hemiketal ring and seco-macrocyclic lactones, their synthesis, pharmaceutical compositions and use for systemic and site specific therapeutic applications.

BACKGROUND

Rapamycin (Sirolimus) is a 31-member natural macrocyclic lactone [$C_{51}H_{79}NO_{13}$; $MW_t=914.2$] produced by *Streptomyces hygroscopicus* and found in the 1970s (U.S. Pat. Nos. 3,929,992; 3,993,749). Rapamycin (structure shown below) was approved by the Food and Drug Administration (FDA) for the prophylaxis of renal transplant rejection in 1999.

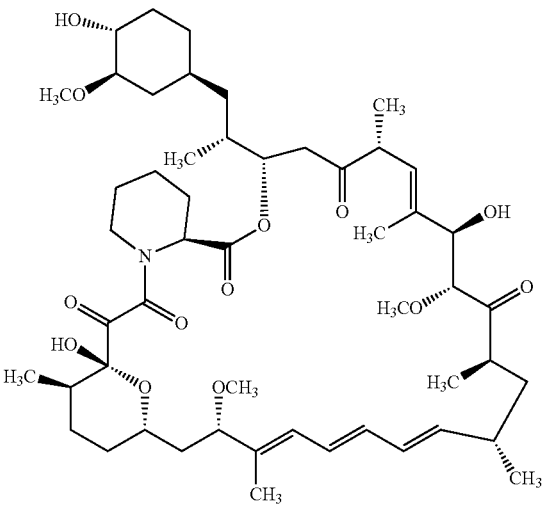

Rapamycin resembles tacrolimus (binds to the same intracellular binding protein or immunophilin known as FKBP-12) but differs in its mechanism of action. Whereas tacrolimus and cyclosporine inhibit T-cell activation by blocking lymphokine (e.g., IL2) gene transcription, sirolimus inhibits T-cell activation and T lymphocyte proliferation by binding to mammalian target of rapamycin (mTOR). Rapamycin can act in synergy with cyclosporine or tacrolimus in suppressing the immune system.

Rapamycin is also useful in preventing or treating systemic lupus erythematosus [U.S. Pat. No. 5,078,999], pulmonary inflammation [U.S. Pat. No. 5,080,899], insulin dependent diabetes mellitus [U.S. Pat. No. 5,321,009], skin disorders, such as psoriasis [U.S. Pat. No. 5,286,730], bowel disorders [U.S. Pat. No. 5,286,731], smooth muscle cell proliferation and intimal thickening following vascular injury [U.S. Pat. Nos. 5,288,711 and 5,516,781], adult T-cell leukemia/lymphoma [European Patent Application 525,960 A1], ocular inflammation [U.S. Pat. No. 5,387,589], malignant carcinomas [U.S. Pat. No. 5,206,018], cardiac inflammatory disease [U.S. Pat. No. 5,496,832], anemia [U.S. Pat. No. 5,561,138] and increase neurite outgrowth [Parker, E. M. et al, Neuropharmacology 39, 1913-1919, 2000].

Although rapamycin can be used to treat various disease conditions, the utility of the compound as a pharmaceutical drug has been limited by its very low and variable bioavailability and its high immunosuppressive potency and potential high toxicity. Also, rapamycin is only very slightly soluble in water. To overcome these problems, prodrugs and analogues of the compound have been synthesized. Water soluble prodrugs prepared by derivatizing rapamycin positions 31 and 42 (formerly positions 28 and 40) of the rapamycin structure to form glycinate, propionate, and pyrrolidino butyrate prodrugs have been described (U.S. Pat. No. 4,650,803). Some of the analogues of rapamycin described in the art include monoacyl and diacyl analogues (U.S. Pat. No. 4,316,885), acetal analogues (U.S. Pat. No. 5,151,413), silyl ethers (U.S. Pat. No. 5,120,842), hydroxyesters (U.S. Pat. No. 5,362,718), as well as alkyl, aryl, alkenyl, and alkynyl analogues (U.S. Pat. Nos. 5,665,772; 5,258,389; 6,384,046; WO 97/35575).

Prodrugs and analogues of rapamycin are synthesized by chemical synthesis, where additional synthetic steps are required to protect and deprotect certain positions. Analogues can also be synthesized biologically, where the Streptomyces strain is genetically modified to produce these analogues of rapamycin. The analogues need to maintain necessary positions for protein binding or other cellular interactions and not generate steric hindrance in order to preserve its activity. The safety of these analogues requires extensively testing by series of preclinical and clinical experimentations.

The present invention comprises novel macrocyclic lactones and novel uses for macrocyclic lactones, where the compositions can be synthesized chemically or biologically and which preserve at least some immunosuppressive, anti-proliferative, anti-fungal and anti-tumor properties for use in systemic and site specific applications.

BRIEF SUMMARY OF THE INVENTION

In one embodiment, the present invention provides a pharmaceutical composition comprising a pharmaceutically acceptable excipient and a compound of the formula:

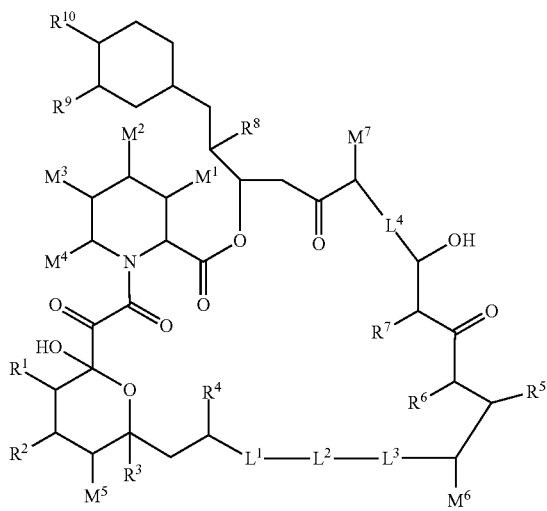

wherein $R^1$, $R^2$, $R^3$, $R^5$, $R^6$, $R^8$, $M^1$, $M^2$, $M^3$, $M^4$, $M^5$, $M^6$ and $M^7$ are each independently a member selected from the group consisting of H, $C_{1-6}$ alkyl, OH and $C_{1-6}$ hydroxyalkyl; $R^4$, $R^7$ and $R^9$ are each independently selected from the group consisting of $C_{1-6}$ alkoxy and OH; $R^{10}$ is a member selected from the group consisting of H, —OH, —OP(O)Me$_2$,

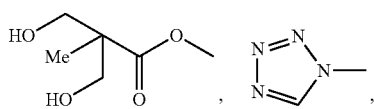

—O—$(CH_2)_n$—OH and —O—$(CH_2)_m$—O—$(CH_2)_o$—$CH_3$, wherein subscripts n and m are each independently from 2 to 8 and subscript o is from 1 to 6; each of $L^1$ and $L^4$ are independently selected from the group consisting of:

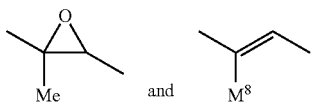

wherein each $M^8$ is independently a member selected from the group consisting of $C_{1-6}$ alkyl, OH and $C_{1-6}$ hydroxyalkyl; each of $L^2$ and $L^3$ are independently selected from the group consisting of:

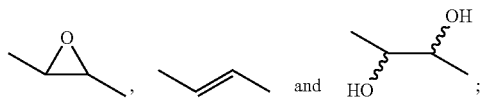

and salts, hydrates, isomers, metabolites, N-oxides and prodrugs thereof.

In a second embodiment, the present invention provides a device for intracorporeal use, the device comprising an implant; and at least one source of a compound of the present invention.

In a third embodiment, the present invention provides a method of inhibiting cell proliferation by administering to a subject in need thereof, a therapeutically effective amount of a compound of the present invention.

In a fourth embodiment, the present invention provides macrocyclic lactone compounds of the following formula:

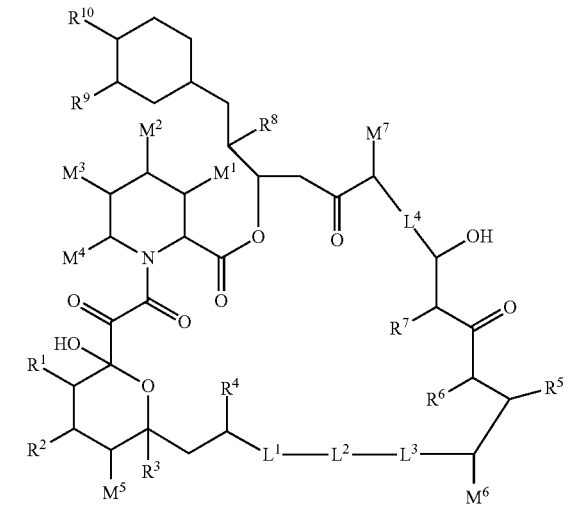

wherein $R^1$, $R^2$, $R^3$, $R^4$, $R^5$, $R^6$, $R^7$, $R^8$, $R^9$, $R^{10}$, $M^1$, $M^2$, $M^3$, $M^4$, $M^5$, $M^6$, $M^7$, $L^1$, $L^2$, $L^3$ and $L^4$ are as described above; with the proviso that when $R^1$, $R^6$, $R^8$, $M^6$ and $M^7$ are Me, $R^3$, $R^5$, $M^1$, $M^2$, $M^3$, $M^4$ and $M^5$ are H, $R^4$, $R^7$ and $R^9$ are OMe, $R^{10}$ and $M^8$ are OH, $L^2$ and $L^3$ are —CH=CH—, and $L^1$ and $L^4$ are

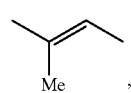

$R^2$ is other than OH;

with the proviso that when $R^1$, $R^6$, $R^8$, $M^6$ and $M^7$ are Me, $R^2$, $R^3$, $R^5$, $M^1$, $M^2$, $M^3$, $M^4$ and $M^5$ are H, $R^7$ and $R^9$ are OMe, $R^{10}$ and $M^8$ are OH, $L^2$ and $L^3$ are —CH=CH—, and $L^1$ and $L^4$ are $R^4$ is other than OH;

with the proviso that when $R^1$, $R^6$, $R^8$, $M^6$ and $M^7$ are Me, $R^2$, $R^3$, $R^5$, $M^1$, $M^2$, $M^3$, $M^4$ and $M^5$ are H, $R^4$ and $R^7$ are OMe, $R^{10}$ and $M^8$ are OH, $L^2$ and $L^3$ are —CH=CH—, and $L^1$ and $L^4$ are

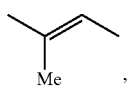

$R^9$ is other than OH;

with the proviso that when $R^1$, $R^6$, $R^8$, $M^6$ and $M^7$ are Me, $R^2$, $R^3$, $R^5$, $M^1$, $M^2$, $M^3$, $M^4$ and $M^5$ are H, $R^4$, $R^7$ and $R^9$ are OMe, $M^8$ is OH, $L^2$ and $L^3$ are —CH=CH—, and $L^1$ and $L^4$ are

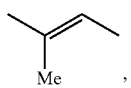

$R^{10}$ is other than OH, —OP(O)Me$_2$,

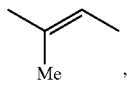

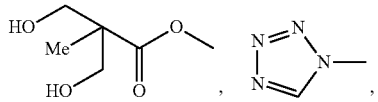

—O—(CH$_2$)$_n$—OH and —O—(CH$_2$)$_m$—O—(CH$_2$)$_o$—CH$_3$; and salts, hydrates, isomers, metabolites, N-oxides and prodrugs thereof.

In a fifth embodiment, the present invention provides a method of making a compound of the present invention, the method comprising contacting a macrocyclic lactone with an acid to replace an alkoxy group with a nucleophile, thereby making a compound of the present invention.

In a sixth embodiment, the present invention provides a method of making a compound of the present invention, the method comprising contacting a macrocyclic lactone with an epoxidation agent to modify an alkene group to an epoxide, thereby making a compound of the present invention.

In a seventh embodiment, the present invention provides a pharmaceutical composition including a pharmaceutically acceptable excipient and a compound of the formula:

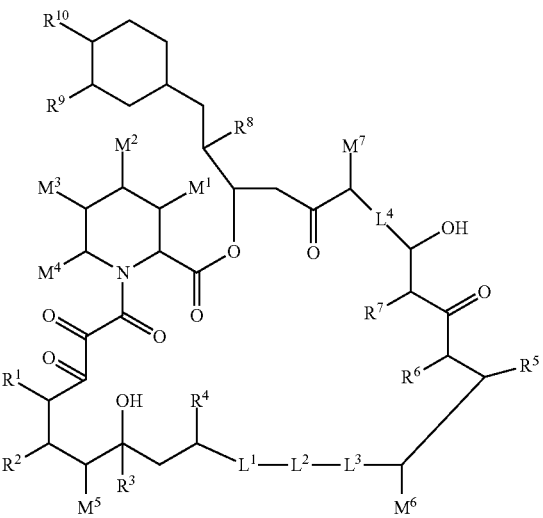

wherein $R^1$, $R^2$, $R^3$, $R^4$, $R^5$, $R^6$, $R^7$, $R^8$, $R^9$, $R^{10}$, $M^1$, $M^2$, $M^3$, $M^4$, $M^5$, $M^6$, $M^7$, $L^1$, $L^2$, $L^3$ and $L^4$ are as described above; and salts, hydrates, isomers, metabolites, N-oxides and prodrugs thereof.

In an eighth embodiment, the present invention provides a pharmaceutical composition including a pharmaceutically acceptable excipient and a compound of the formula:

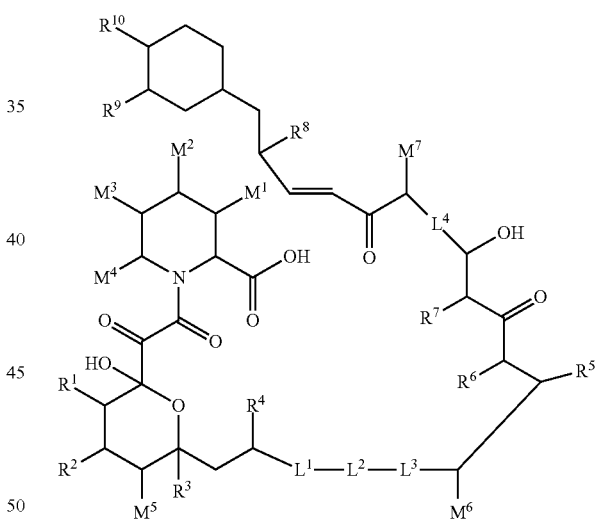

wherein $R^1$, $R^2$, $R^3$, $R^4$, $R^5$, $R^6$, $R^7$, $R^8$, $R^9$, $R^{10}$, $M^1$, $M^2$, $M^3$, $M^4$, $M^5$, $M^6$, $M^7$, $L^1$, $L^2$, $L^3$ and $L^4$ are as described above; and salts, hydrates, isomers, metabolites, N-oxides and prodrugs thereof.

In a ninth embodiment, the present invention provides a method of treating an ophthalmic condition or disease by administering to a subject in need thereof, a therapeutically effective amount of a compound of the present invention.

BRIEF DESCRIPTION OF THE DRAWINGS

FIGS. 6A and 6B show results of liquid chromatography and mass spectra of Compound AR.

FIG. 12A shows inhibition of IL-6, MMP-9 and MCP-1 released by activated macrophages by exposure to macrocyclic lactone Compound AR and Sirolimus at 10 nM concentration.

FIG. 12B shows inhibition of IL-10 released by activated macrophages by exposure to macrocyclic lactone Compound AR and Sirolimus at 10 nM concentration

FIGS. 15A-15B show the synthesis of 19, 20 bis-hydroxy macrocyclic lactone.

FIGS. 17A-17B show the synthesis of 31-hydroxyl, 44-hydroxyl and 47-hydroxyl macrocyclic lactones.

DETAILED DESCRIPTION OF THE INVENTION

I. Definitions

Figure 1:
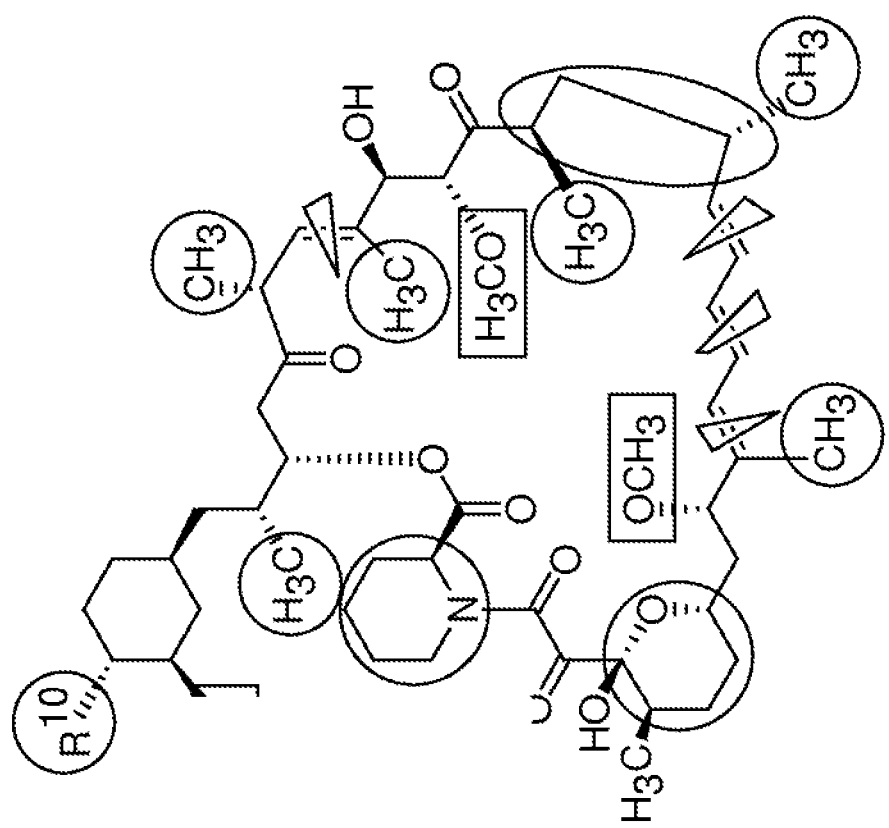
FIG. 1 shows the structure of macrocyclic lactones with some potential sites for chemical modifications to provide compounds of the present invention. Areas marked with a square are sites for demethylation, and areas marked by A circle are sites for hydroxylation and C=C sites (C17=C18, C19=C20=, C21=C22, C29=C30) are sites for epoxidation.
Figure 2A:
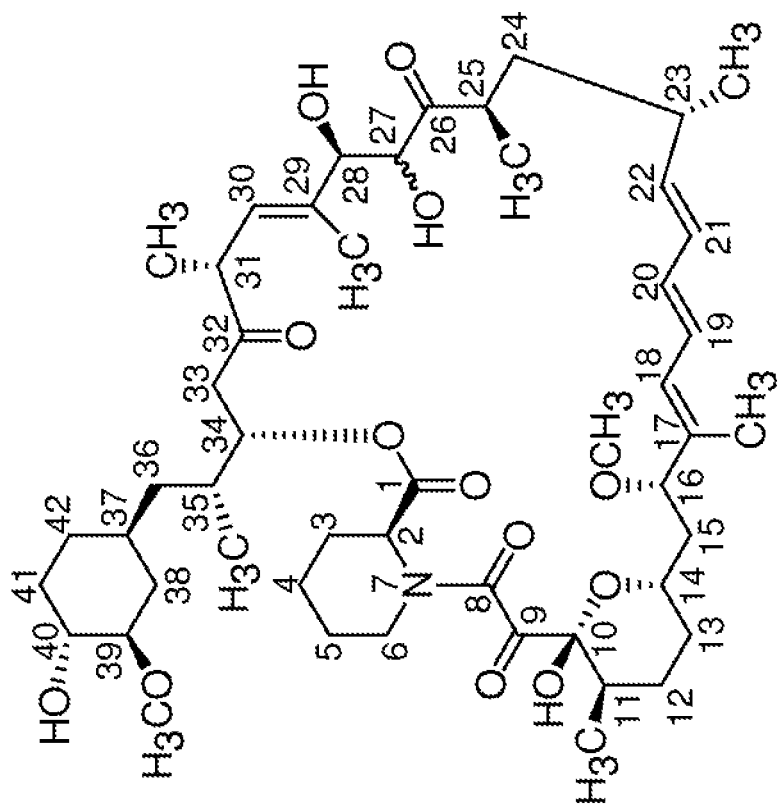
FIGS. 2A-2F(V) show compounds of the present invention.
Figure 2B:
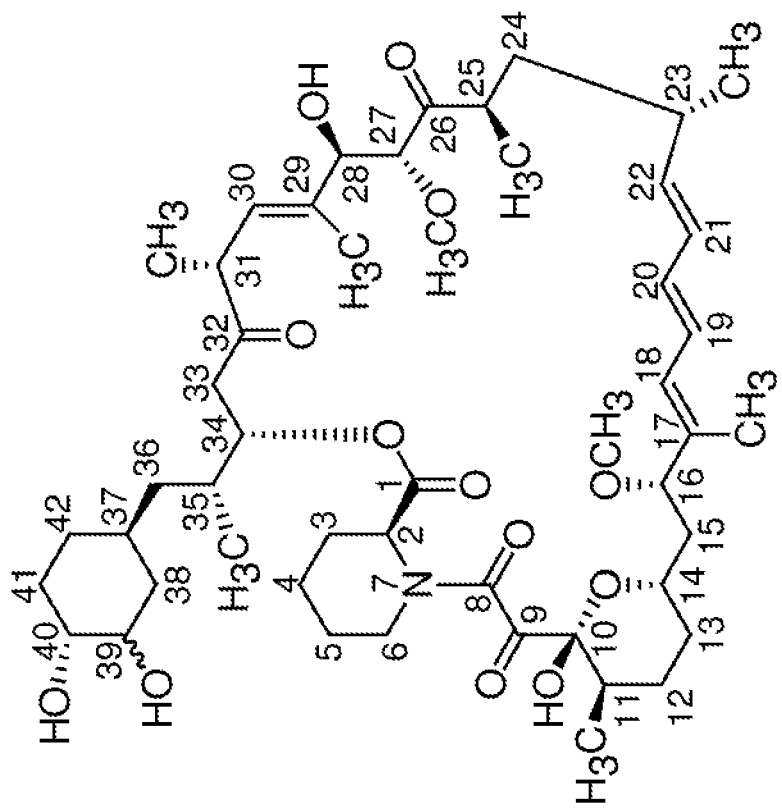
Figure 2C:
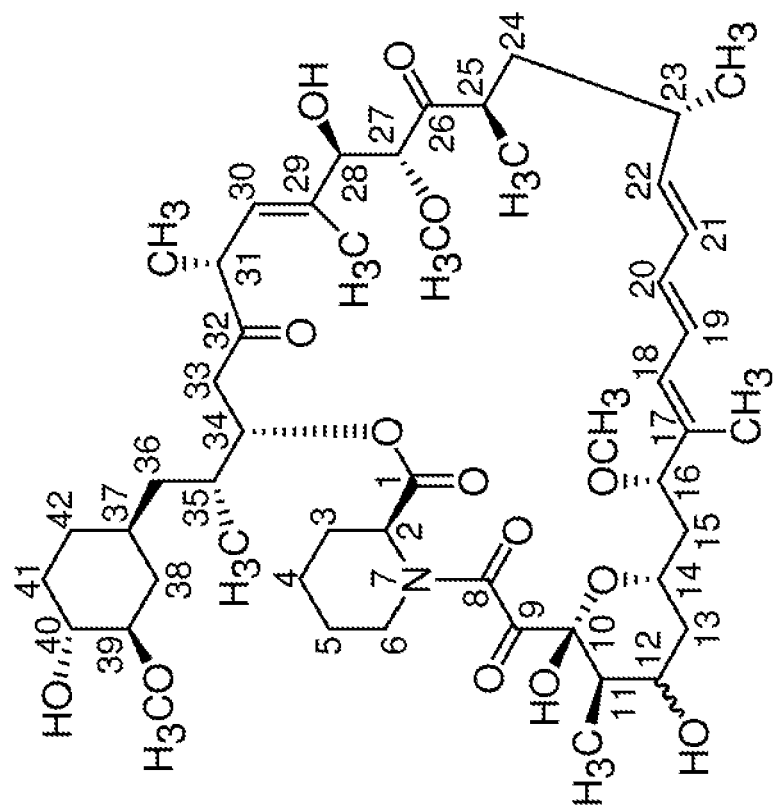
Figure 2D:
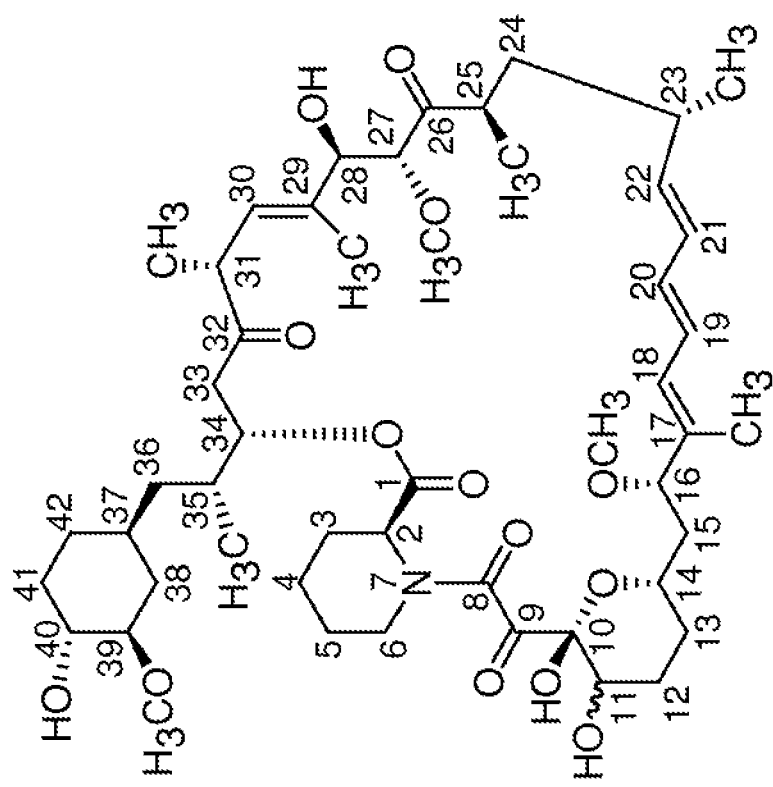
Figure 2E:
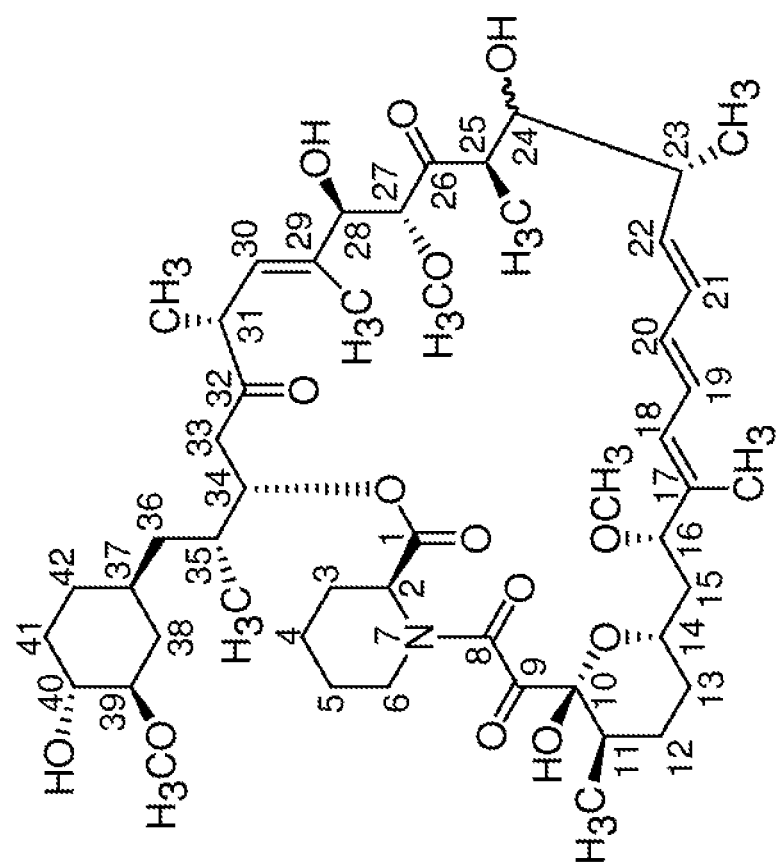
Figure 2F:
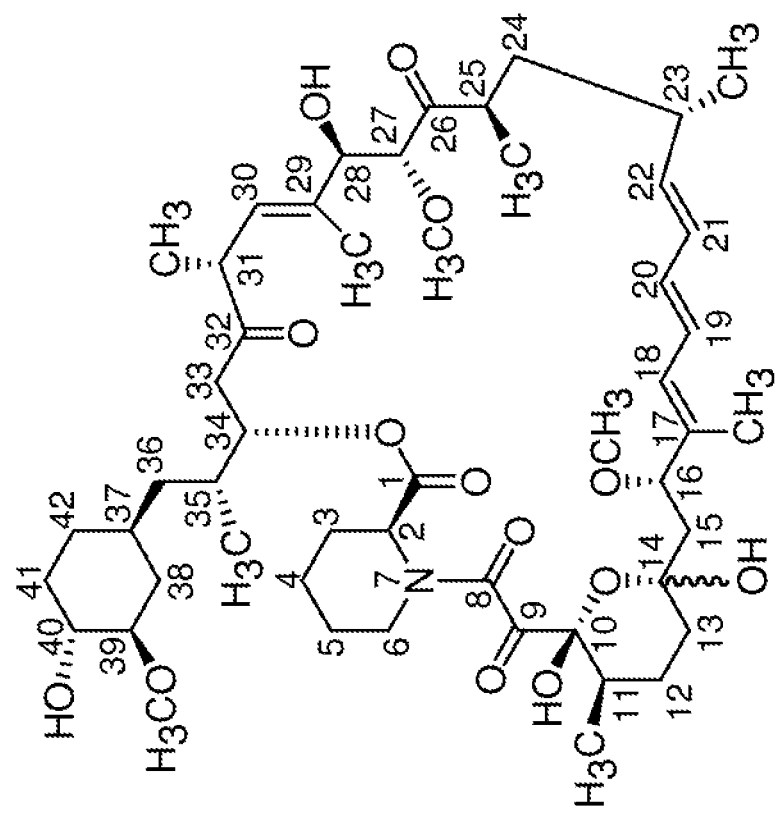
Figure 2H:
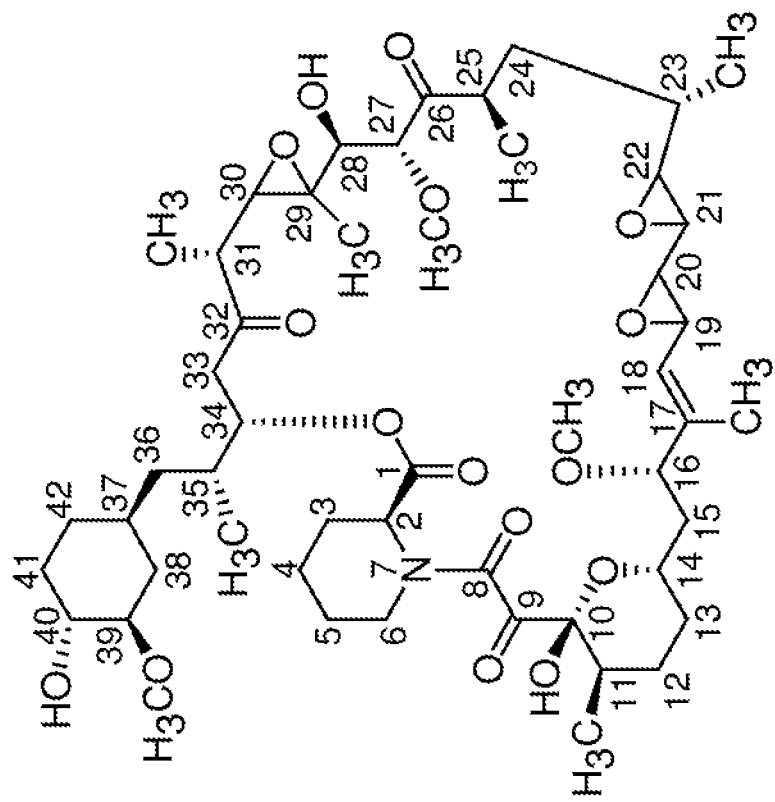
Figure 2G:
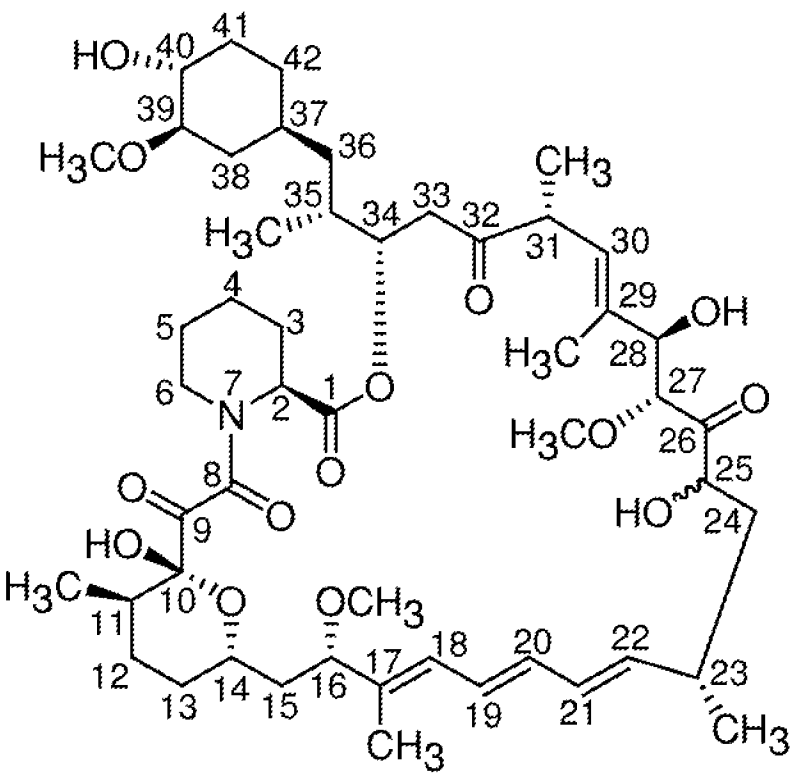
Figures 2I, 2J:
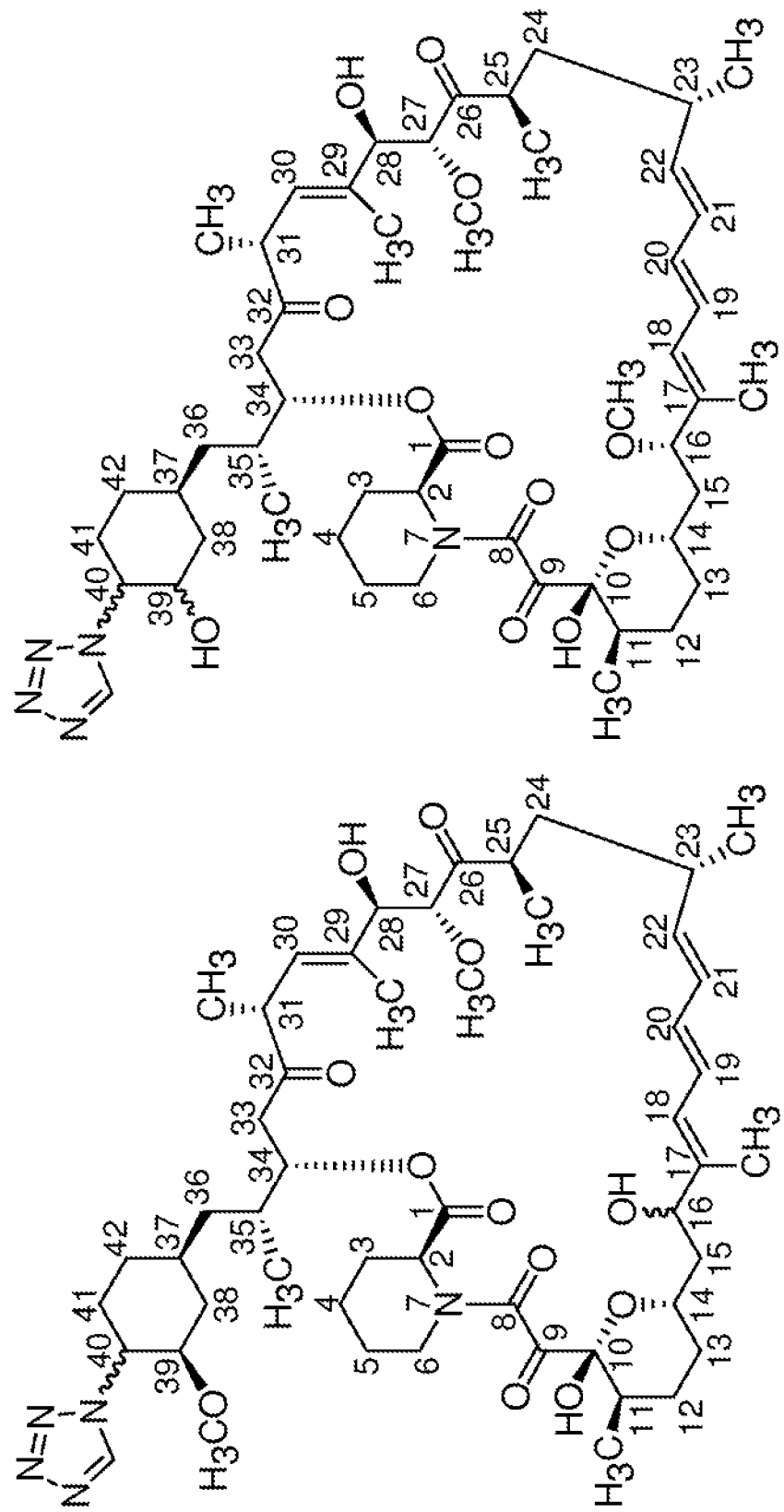
Figure 2N:
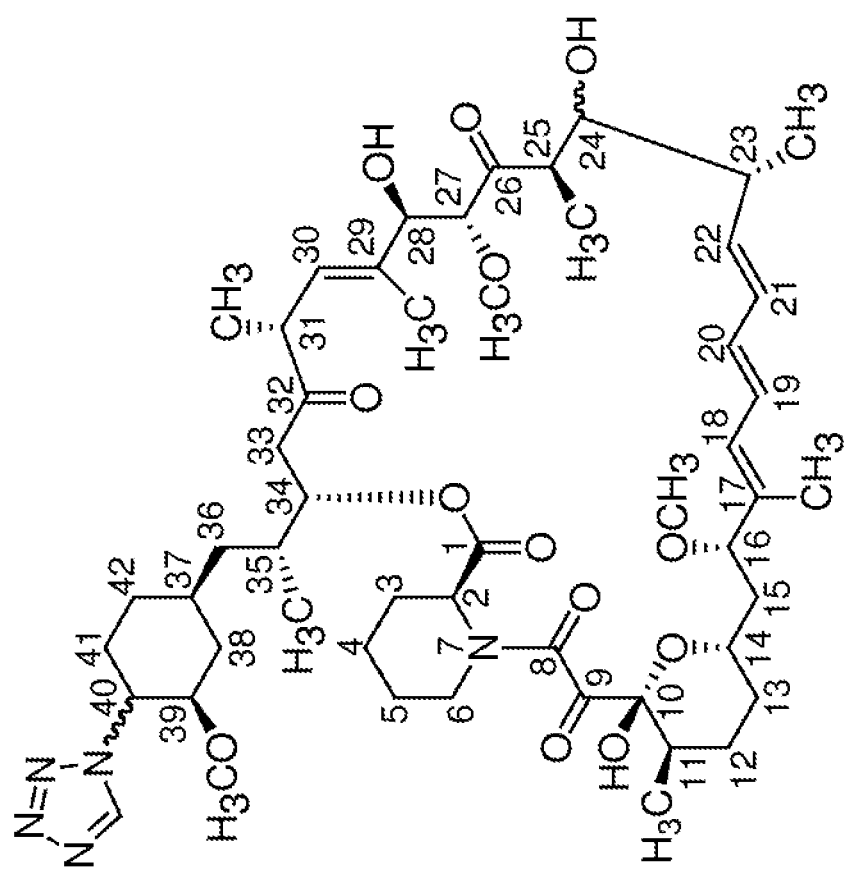
Figure 2M:
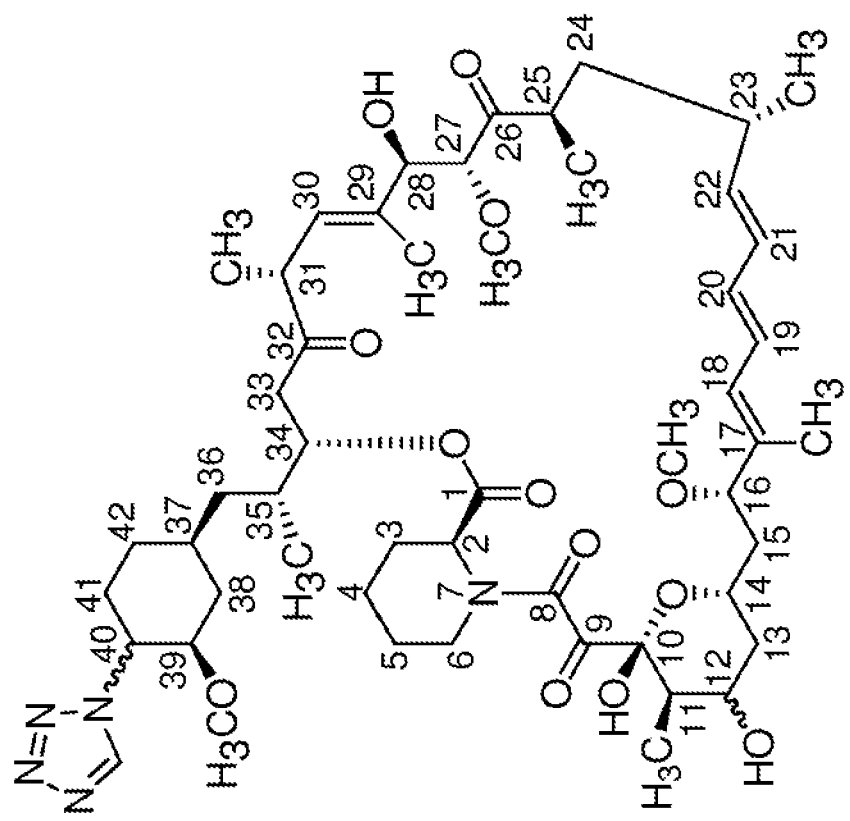
Figures 2Q, 2R:
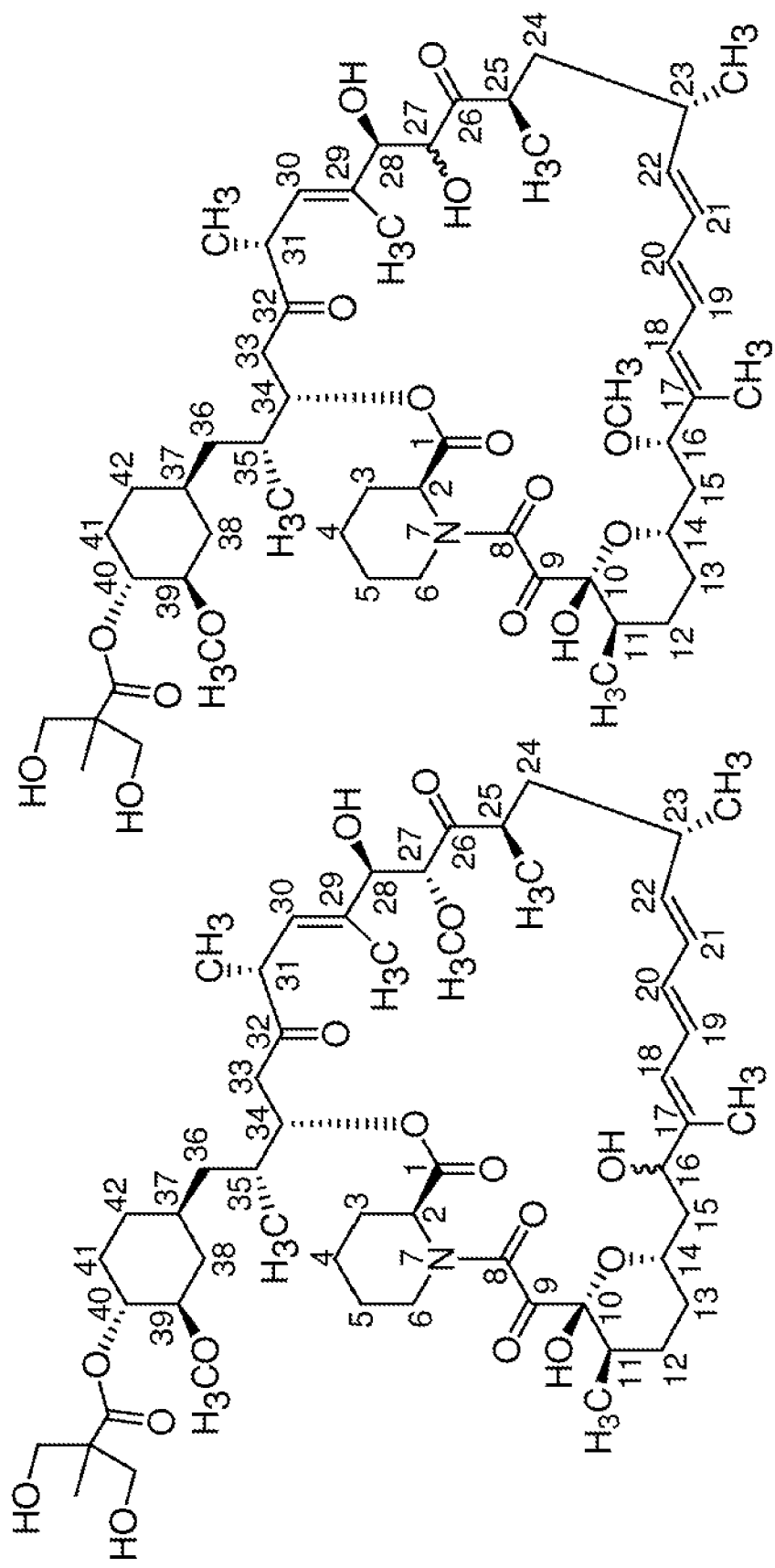
Figures 2U, 2V:
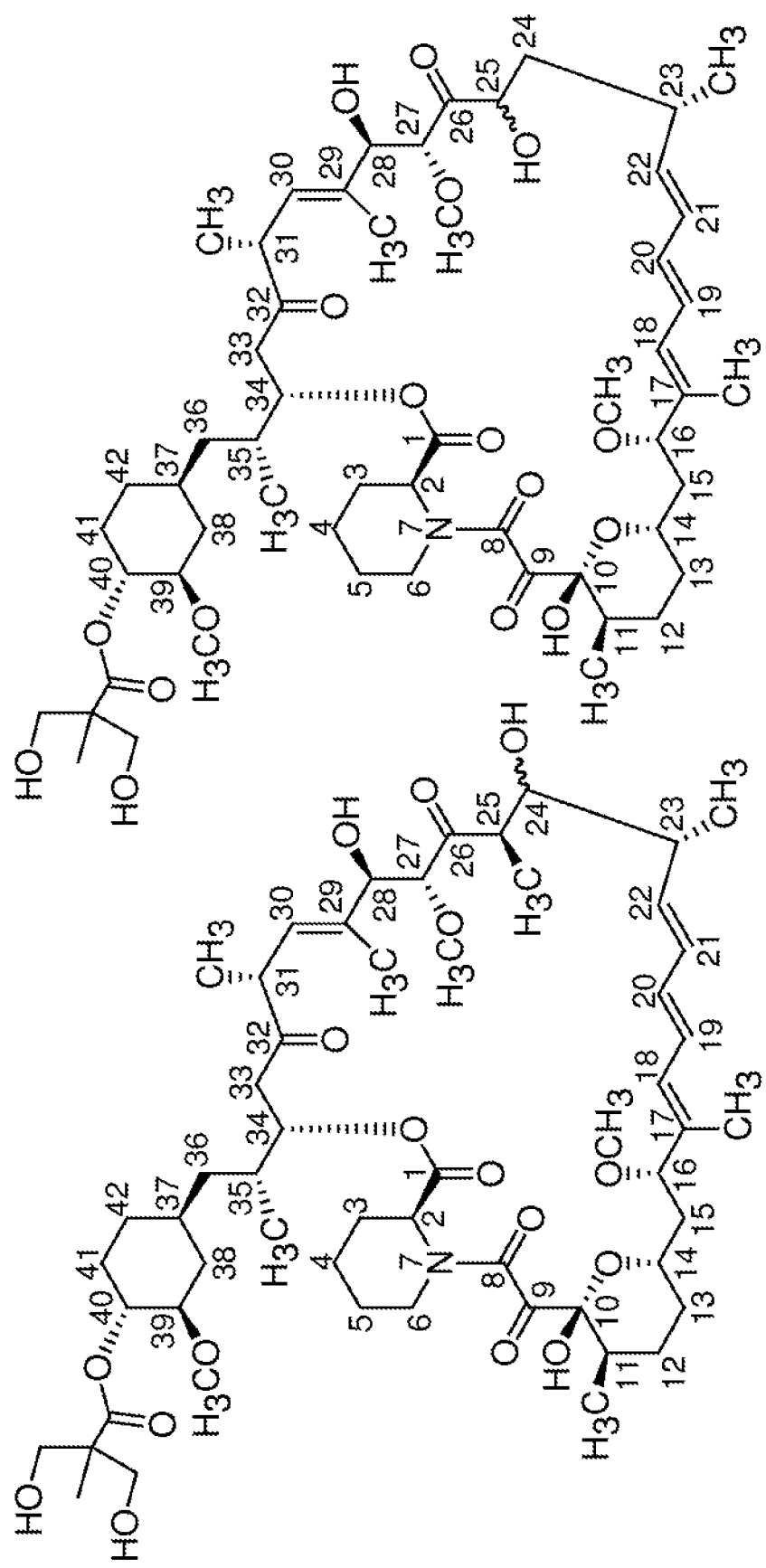
Figure 2Y:
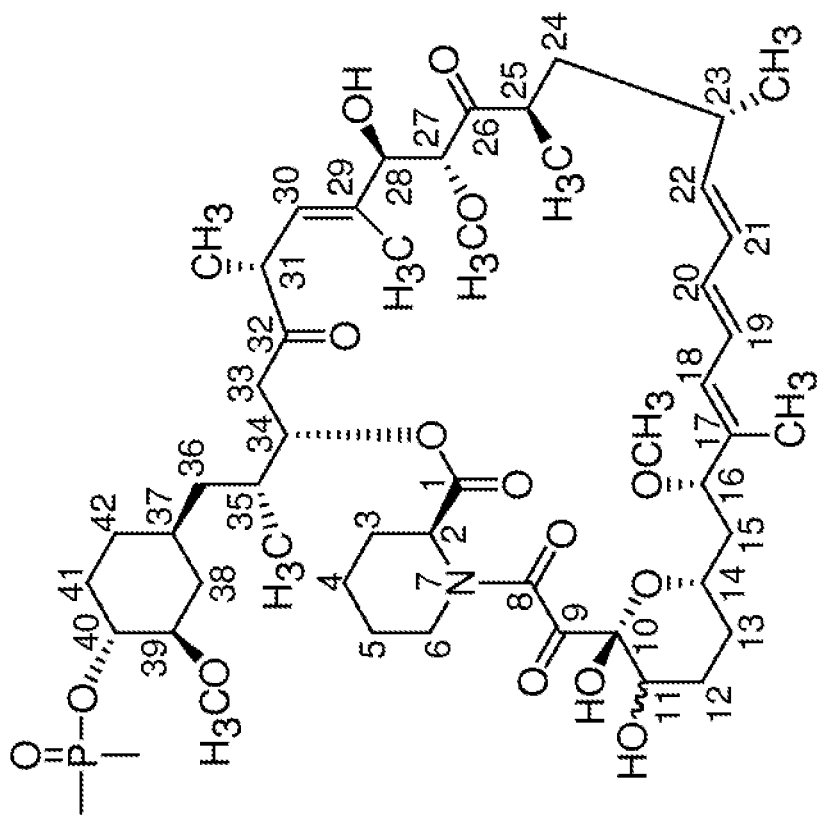
Figure 2Z:
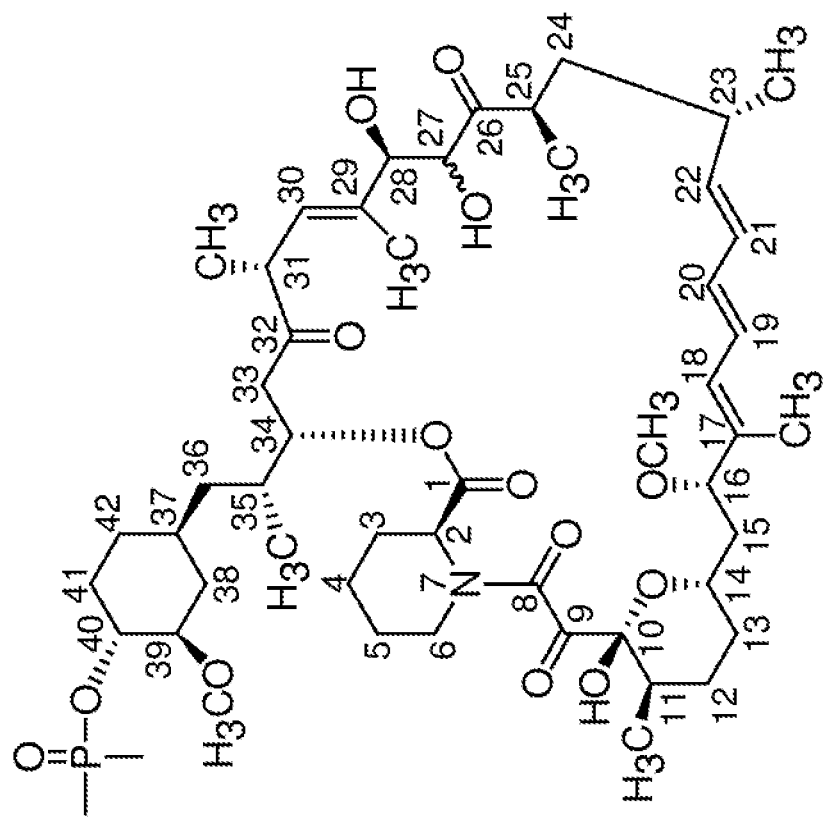
Figure 2A:
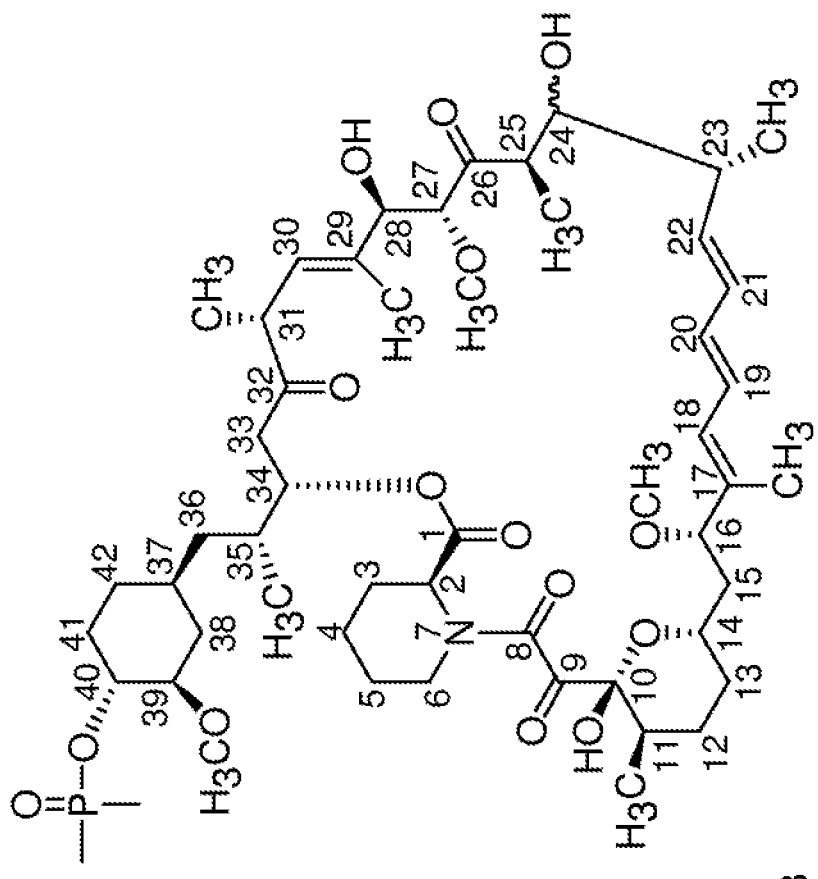
Figure 2A:
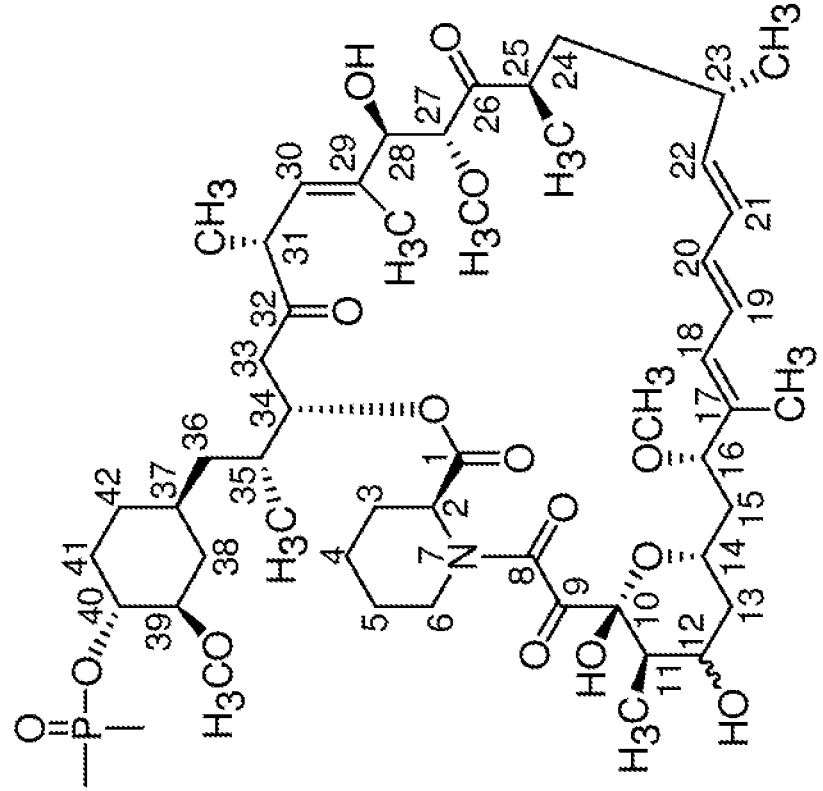
Figure 2A:
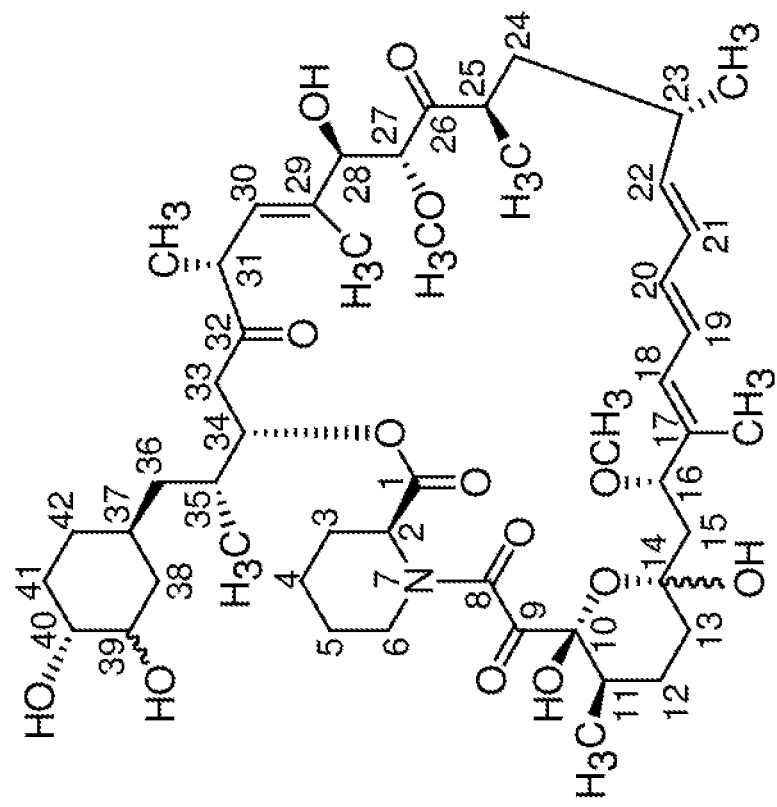
Figure 2A:
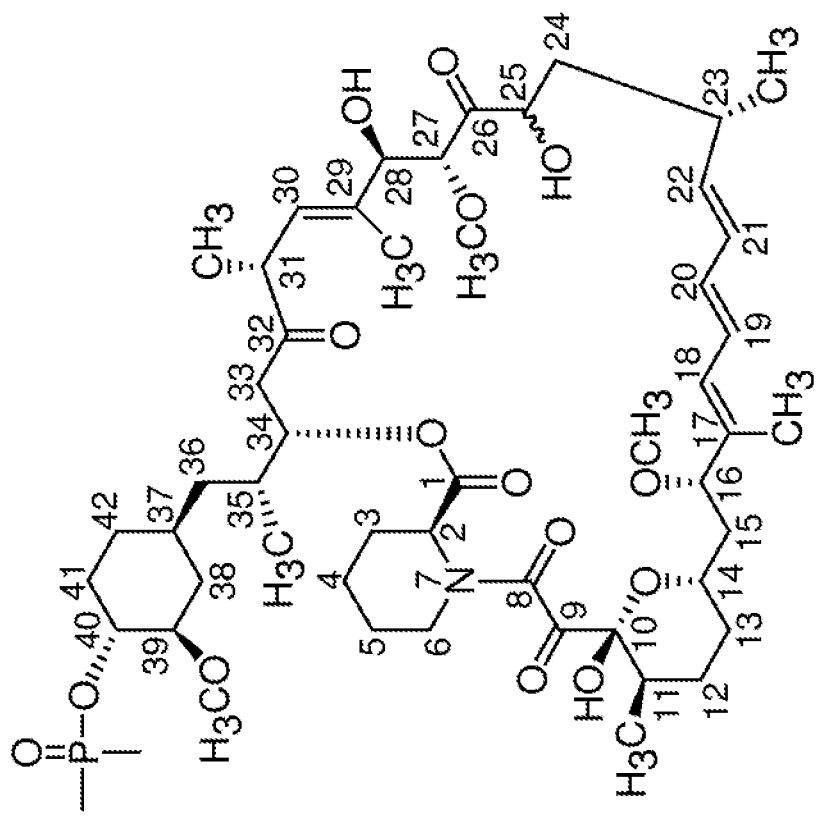
Figure 2A:
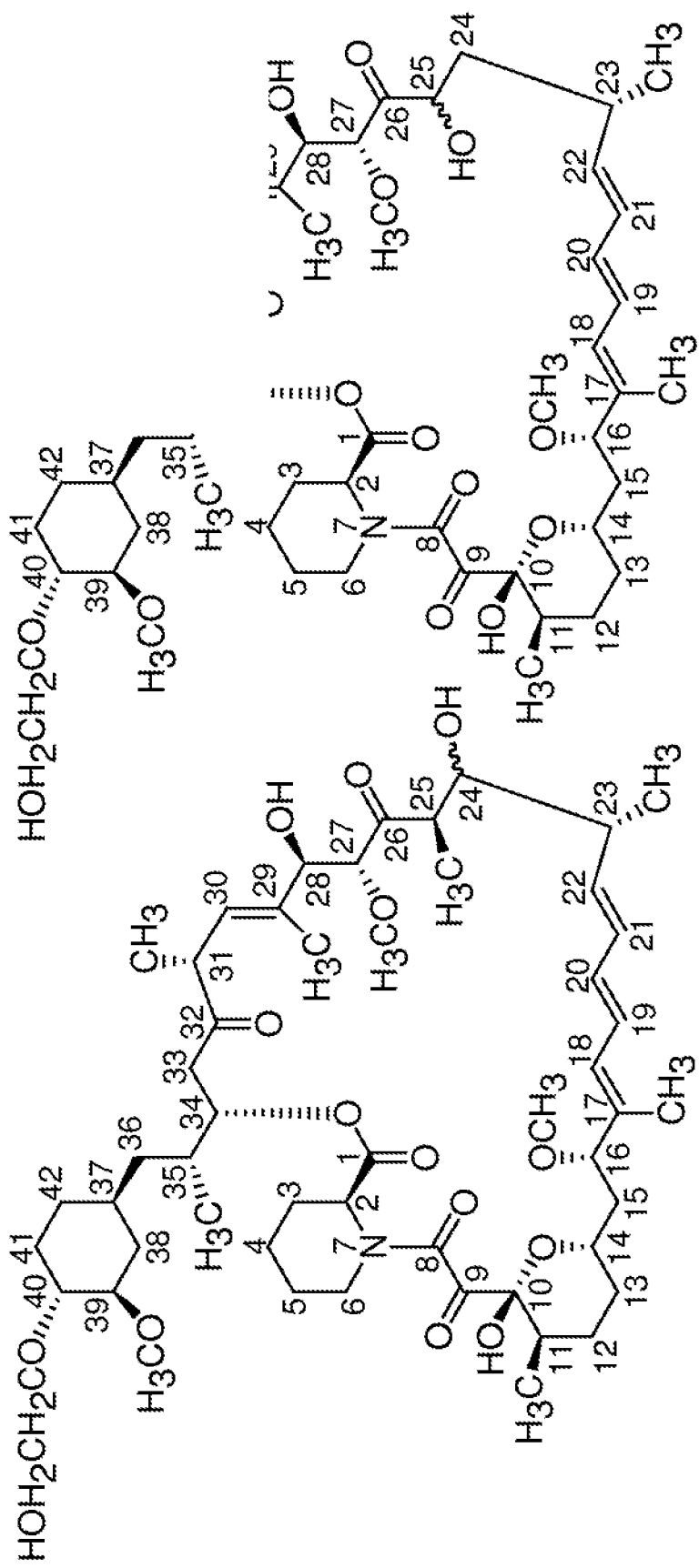
Figure 2A:
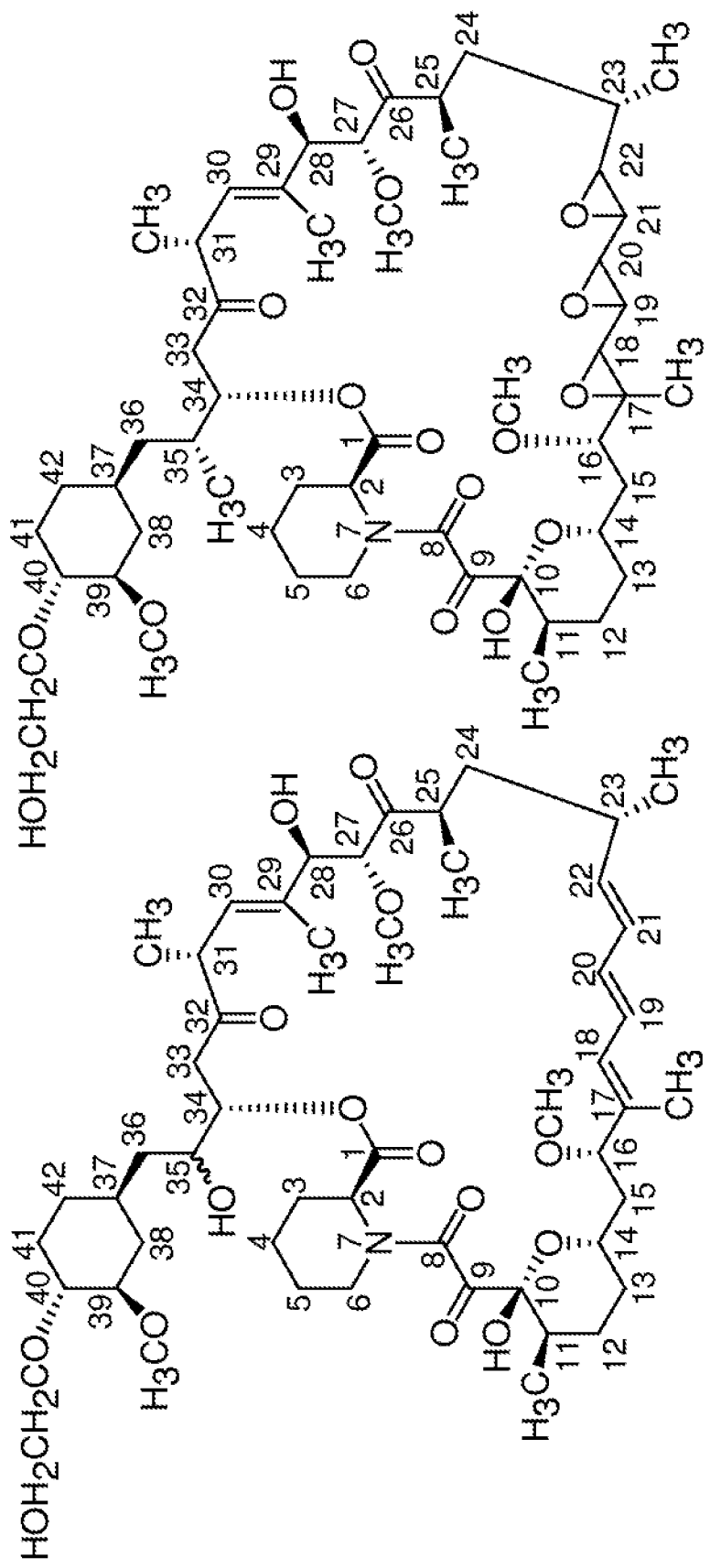
Figure 2A:
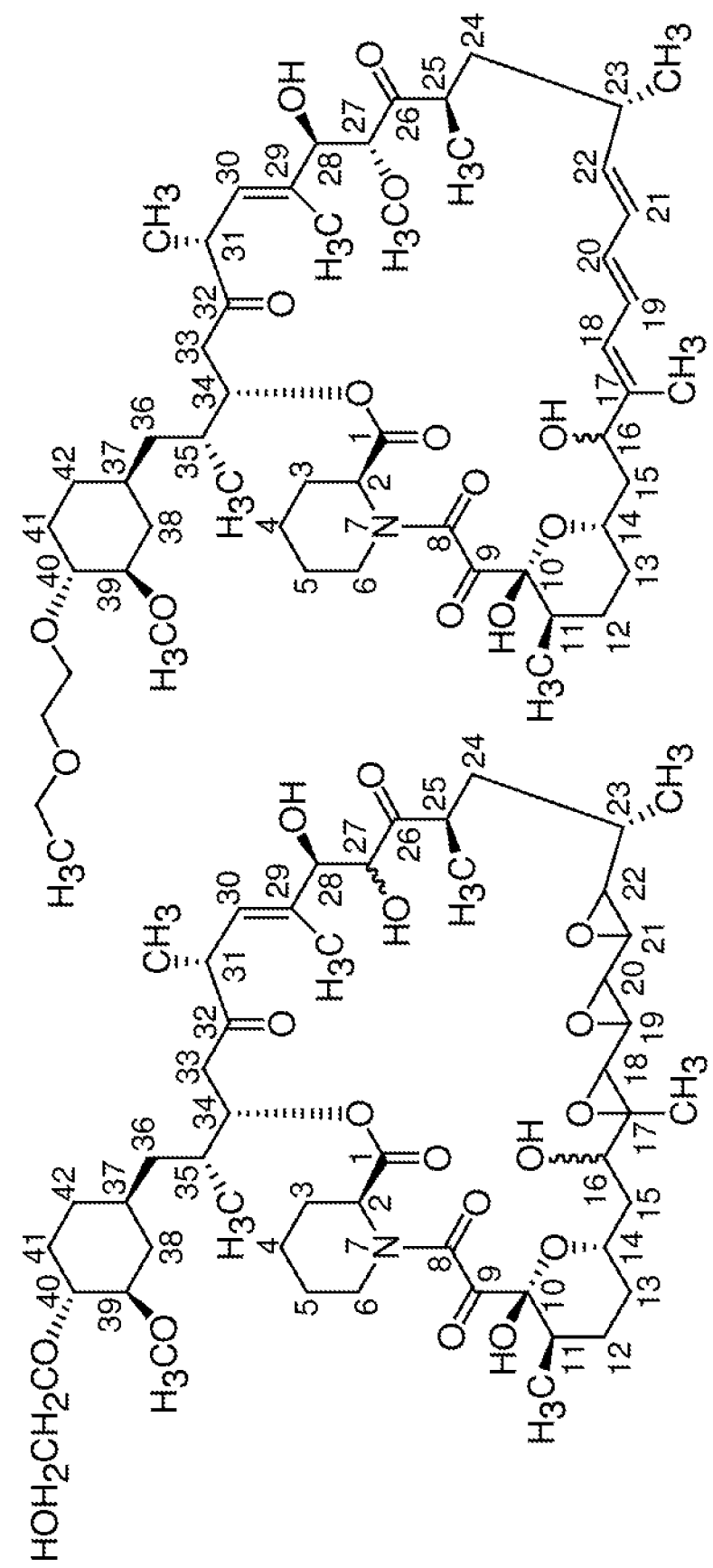
Figure 2A:
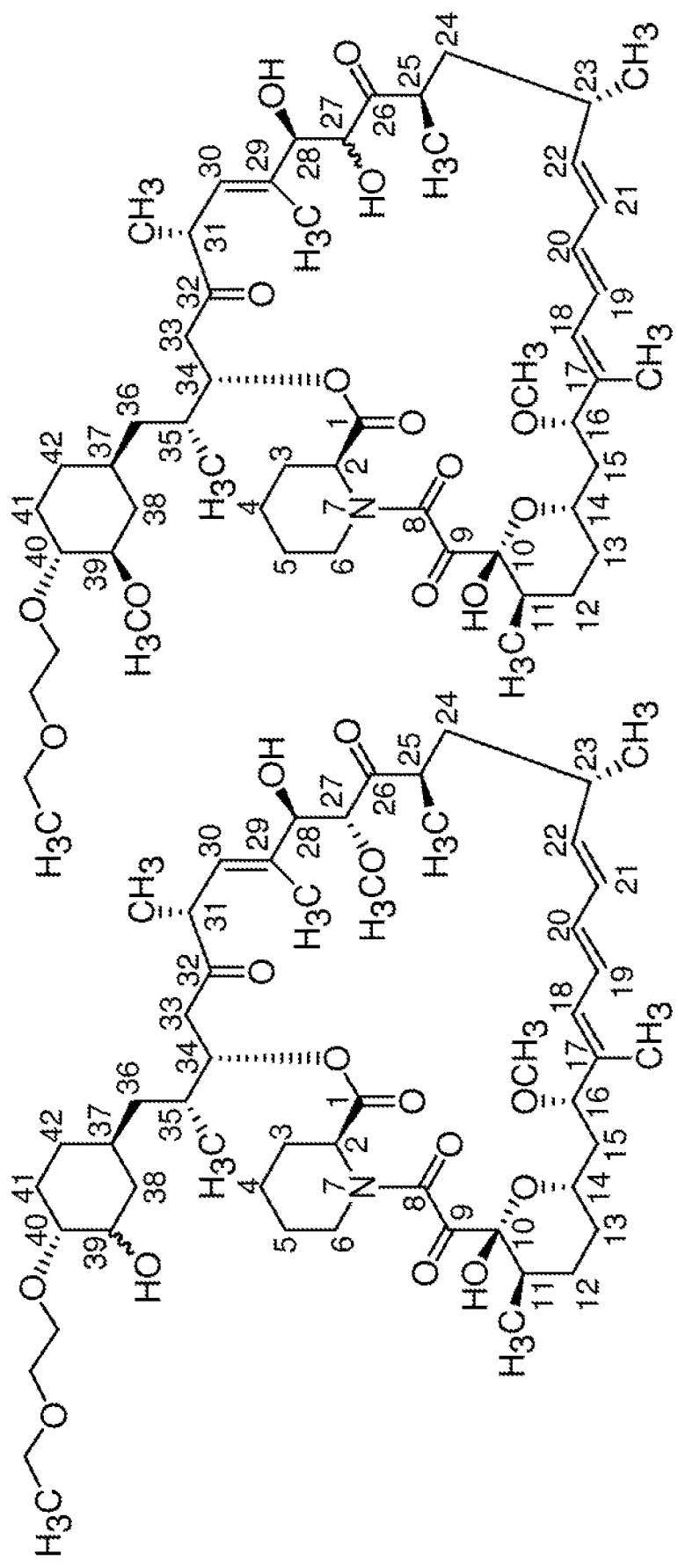
Figure 2A:
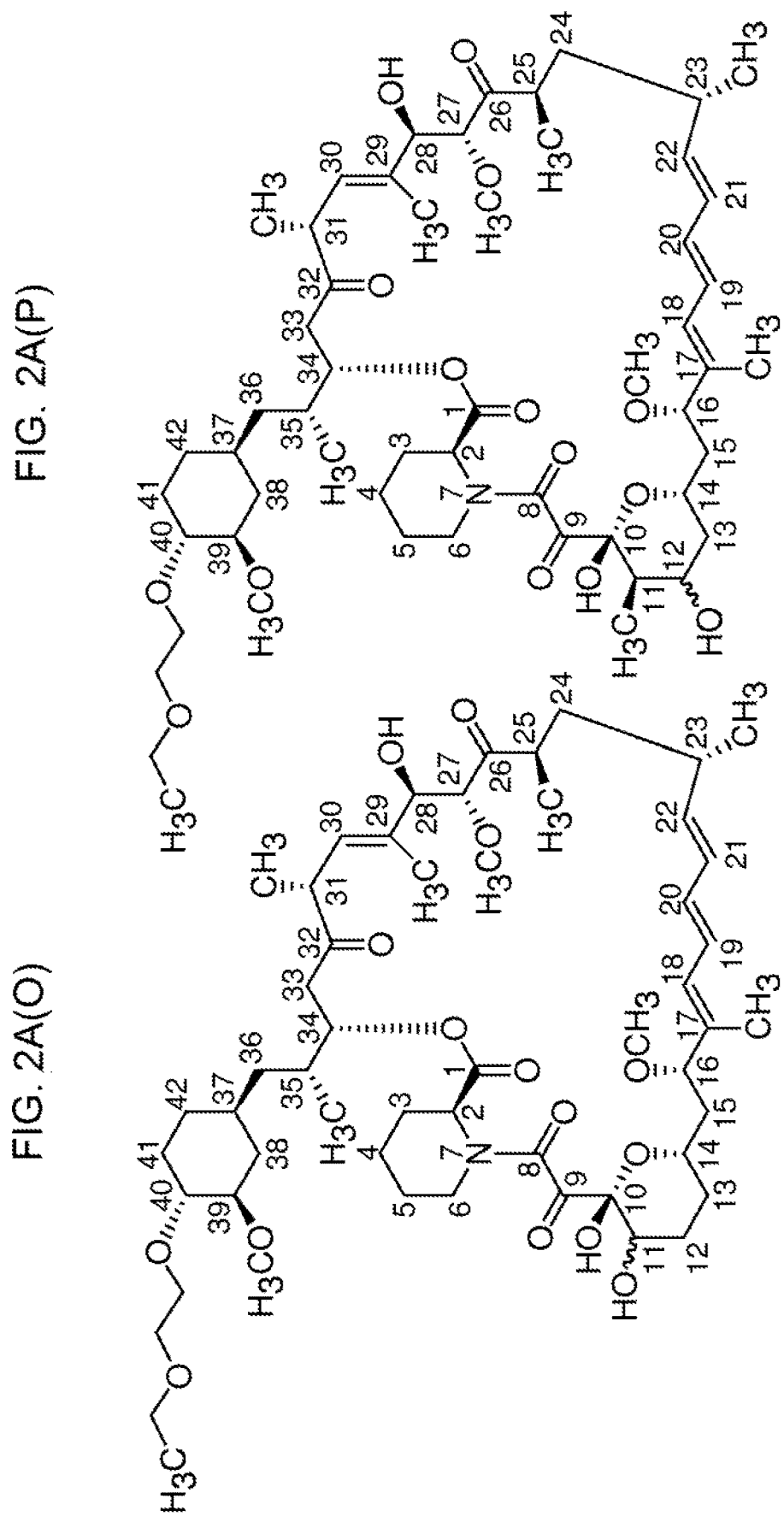
Figure 2A:
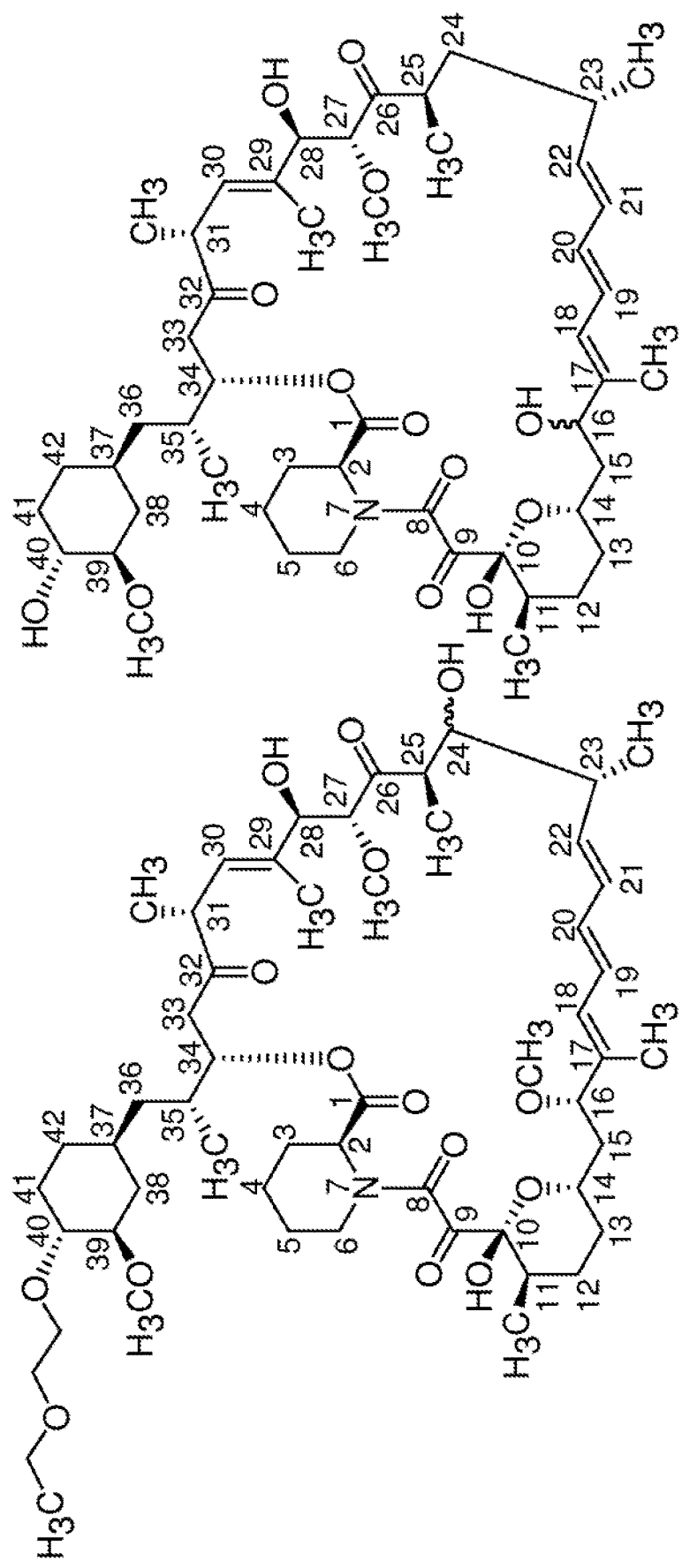
Figure 2A:
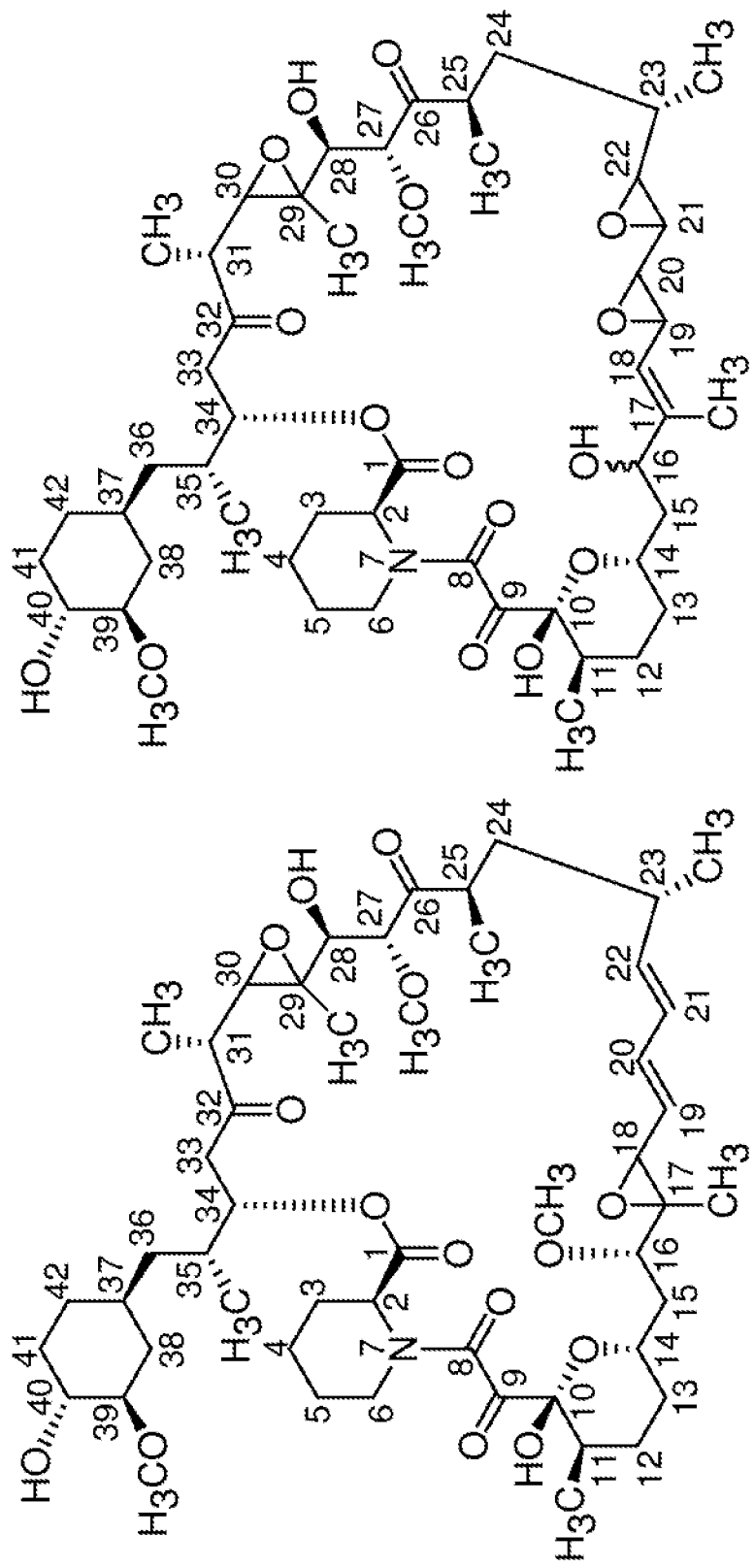
Figure 2A:
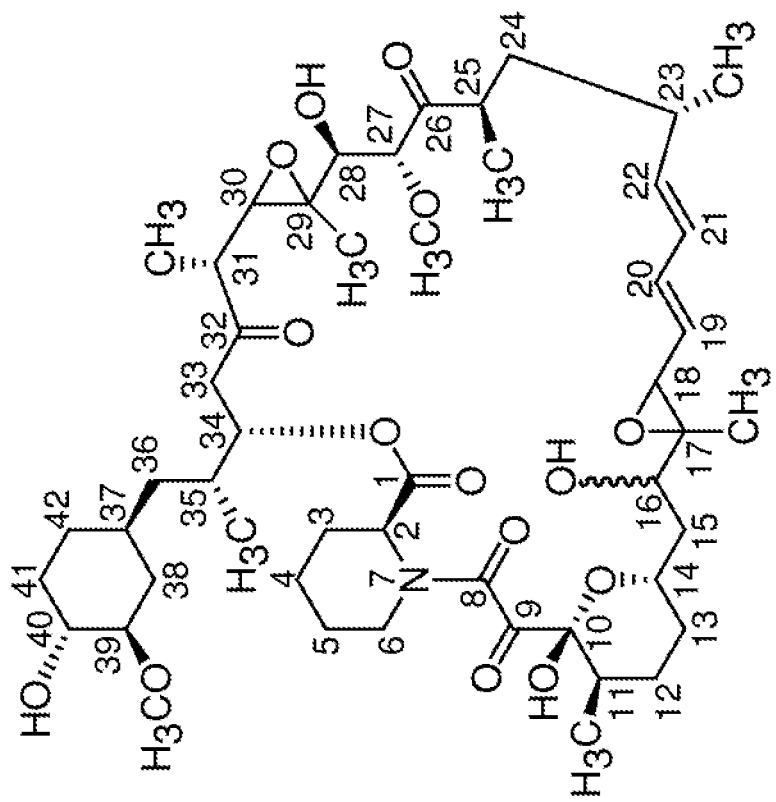
Figure 2A:
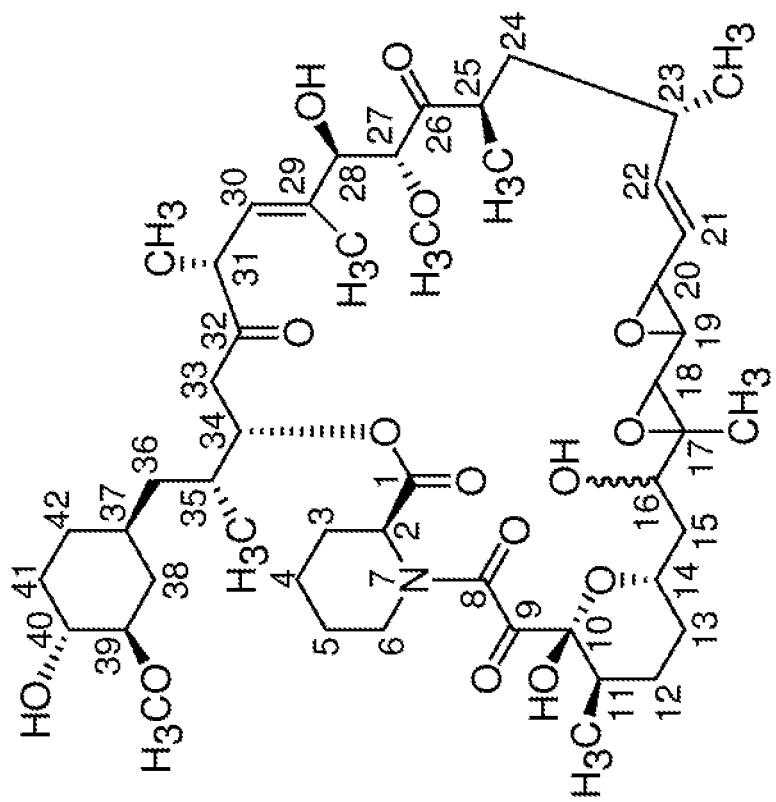
Figure 2A:
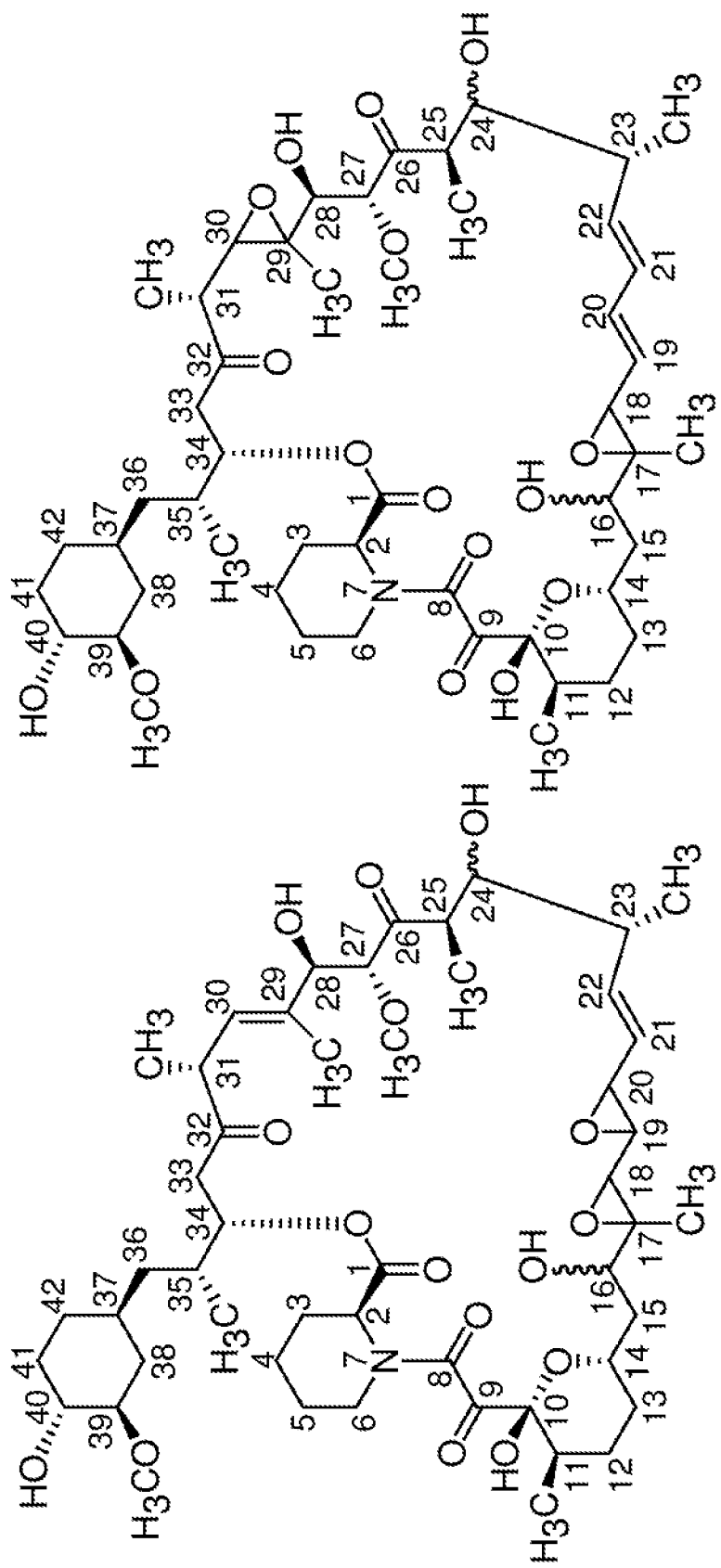
Figure 2A:
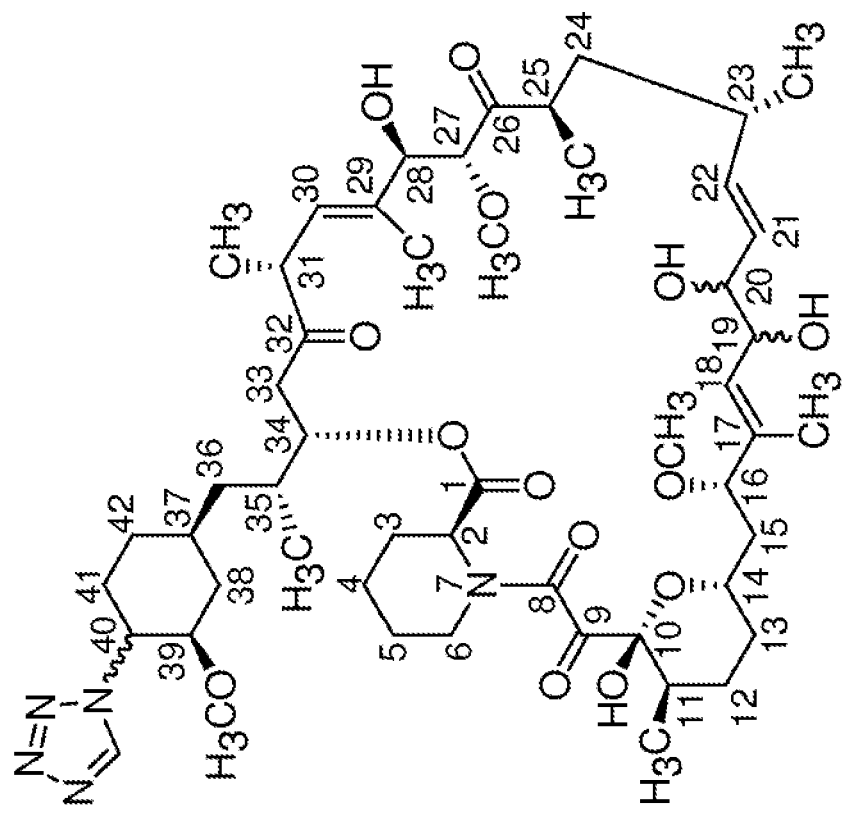
Figure 2A:
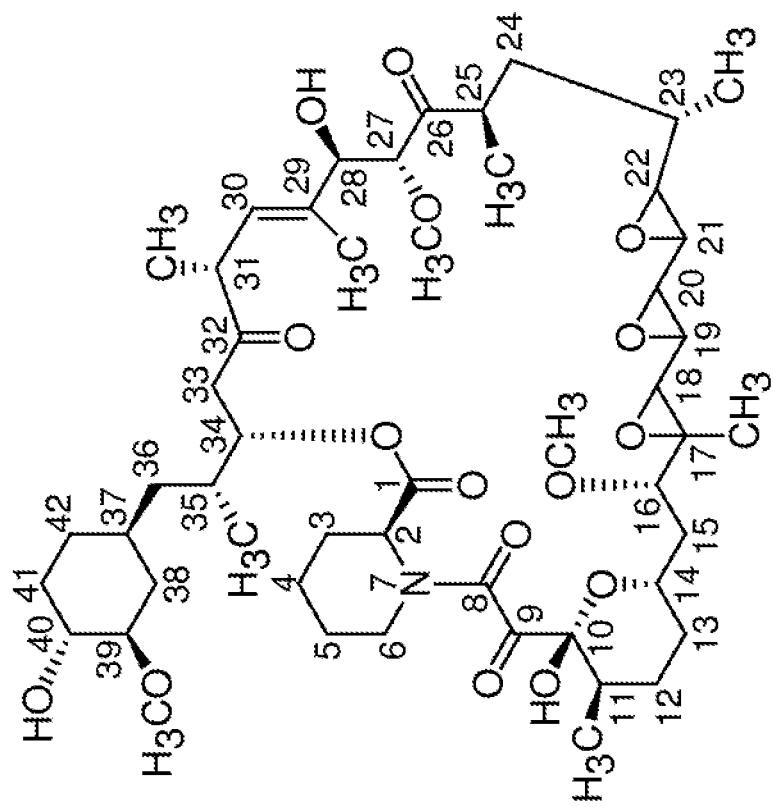
Figure 2B:
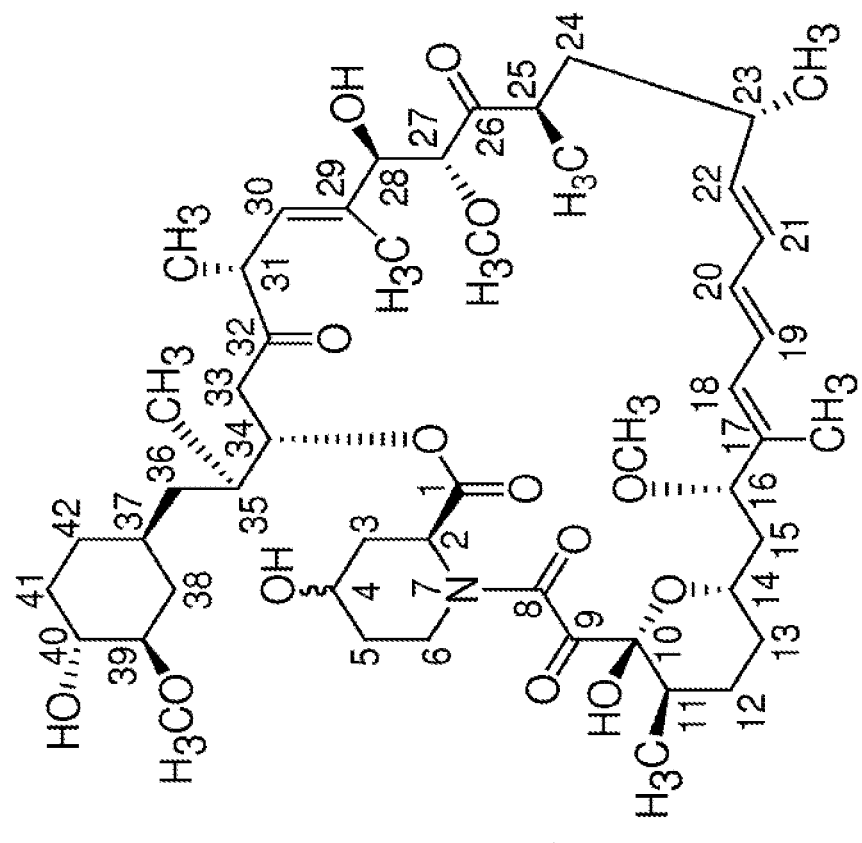
Figure 2B:
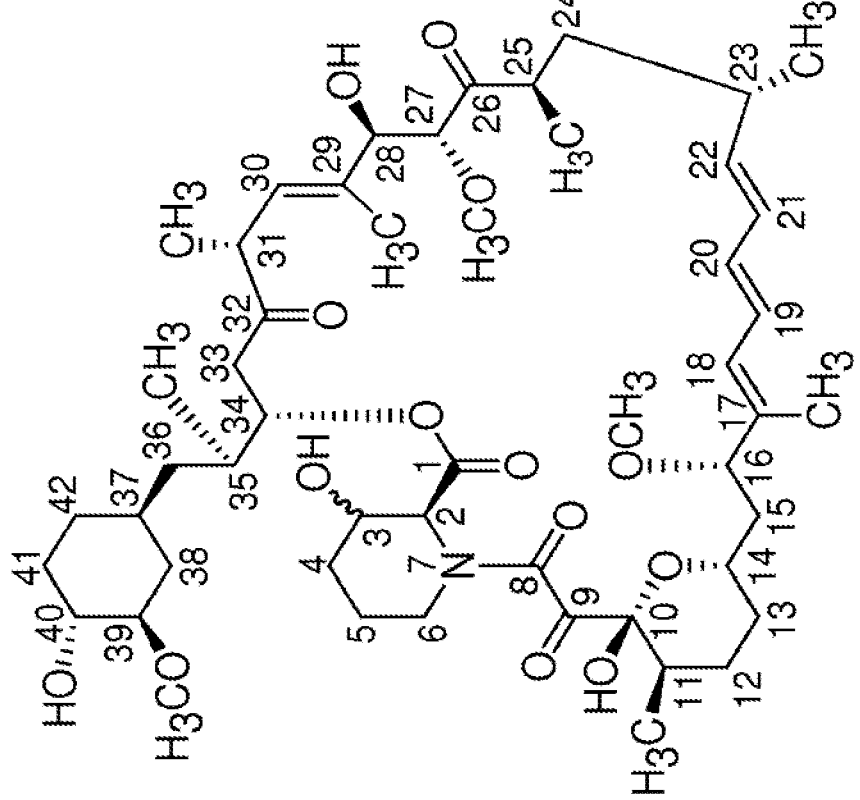
Figure 2B:
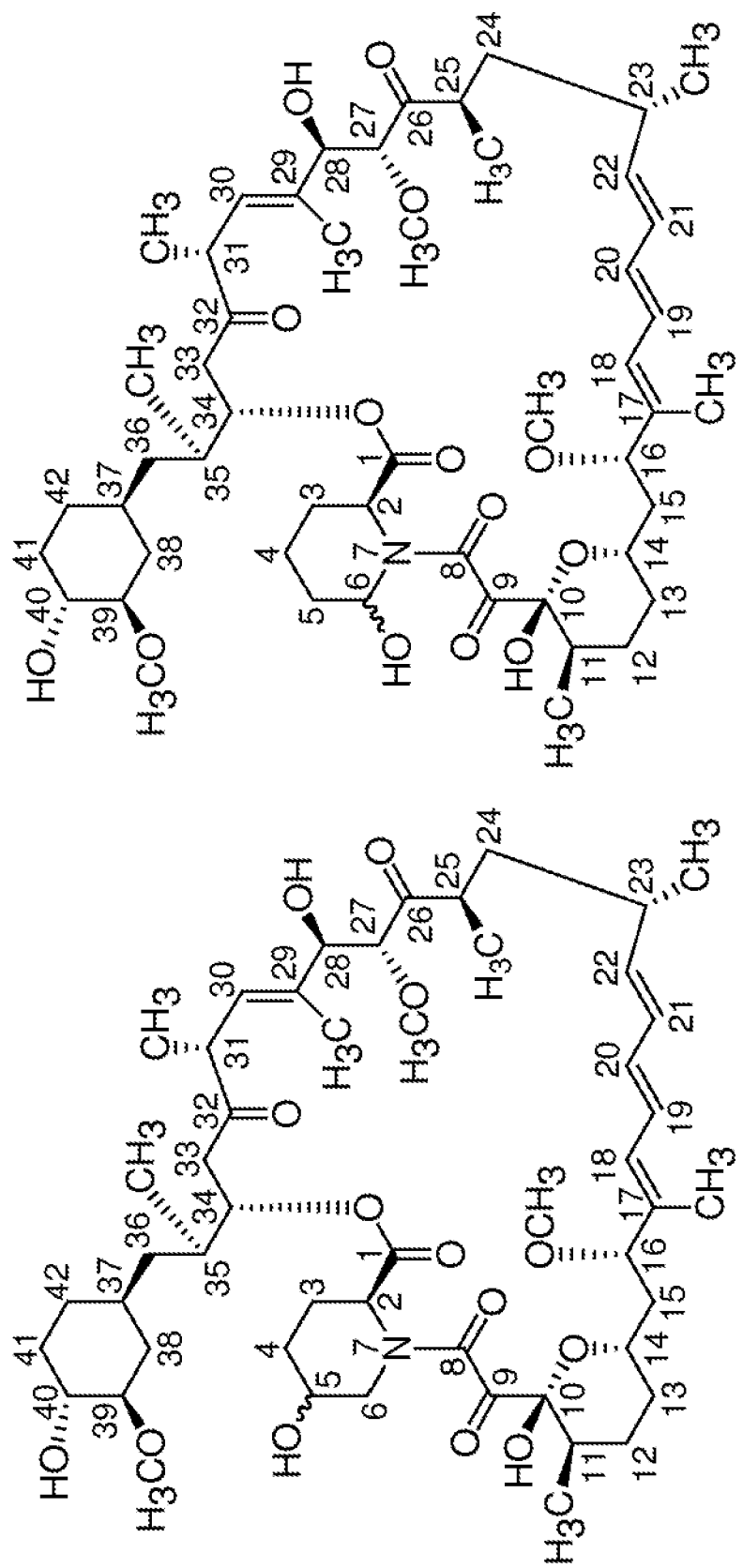
Figure 2B:
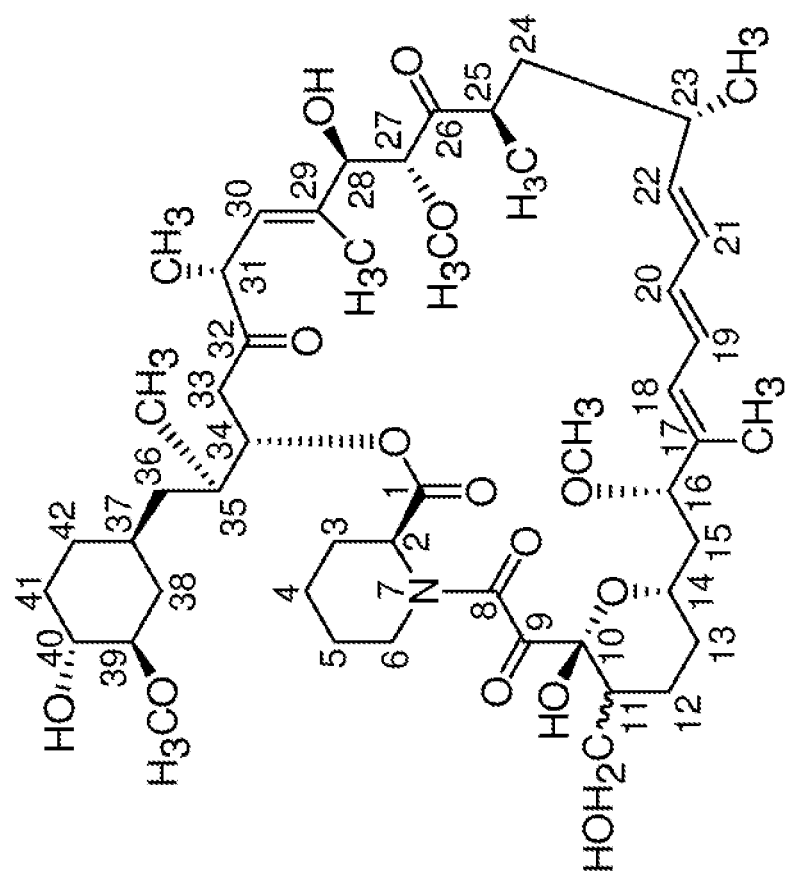
Figure 2B:
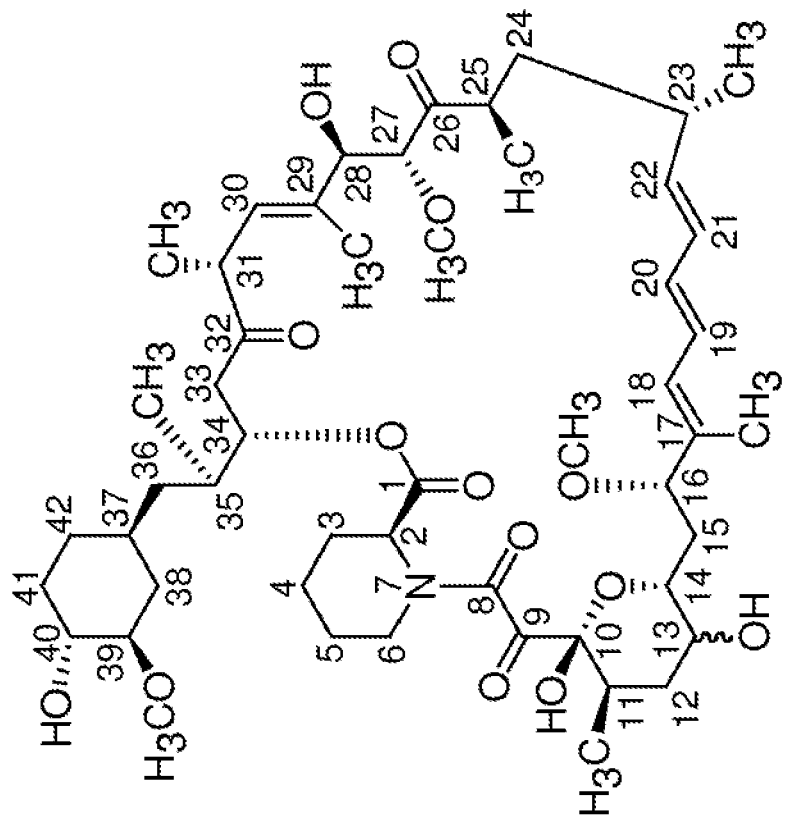
Figure 2B:
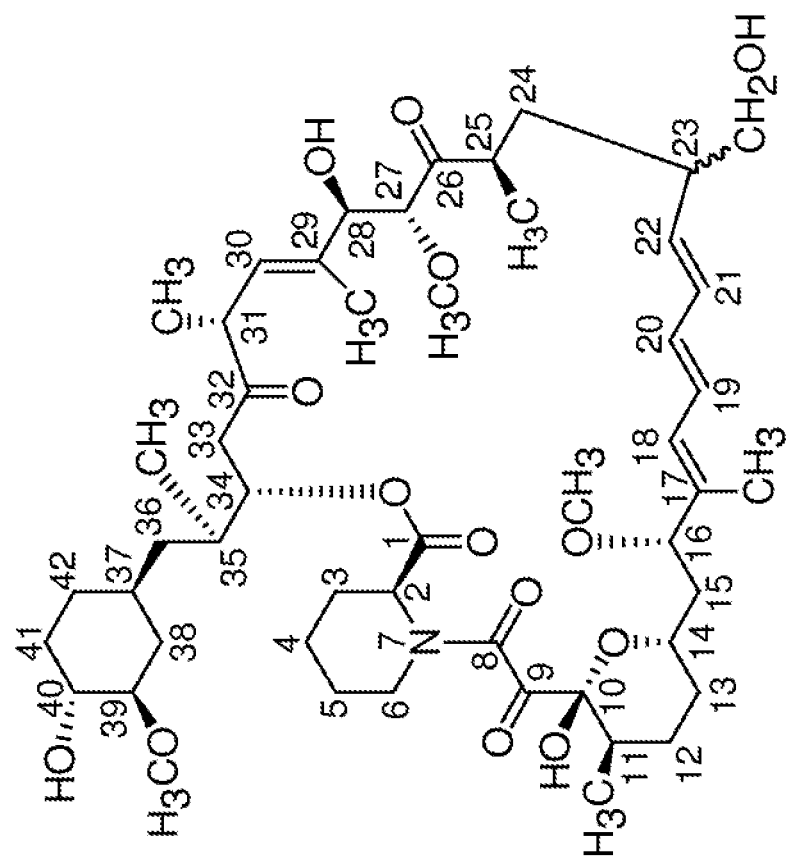
Figure 2B:
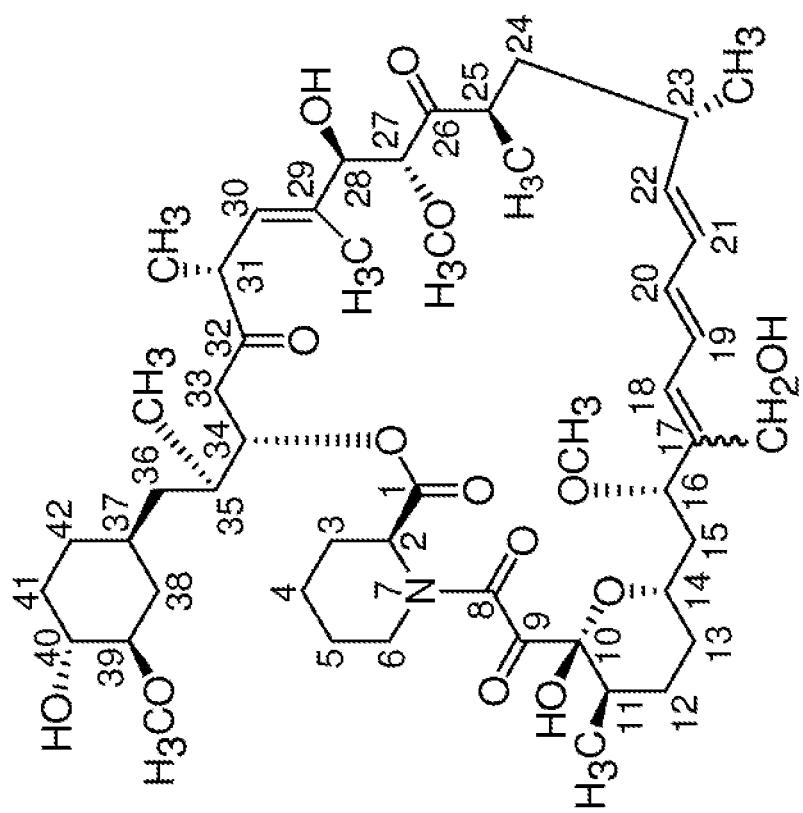
Figure 2B:
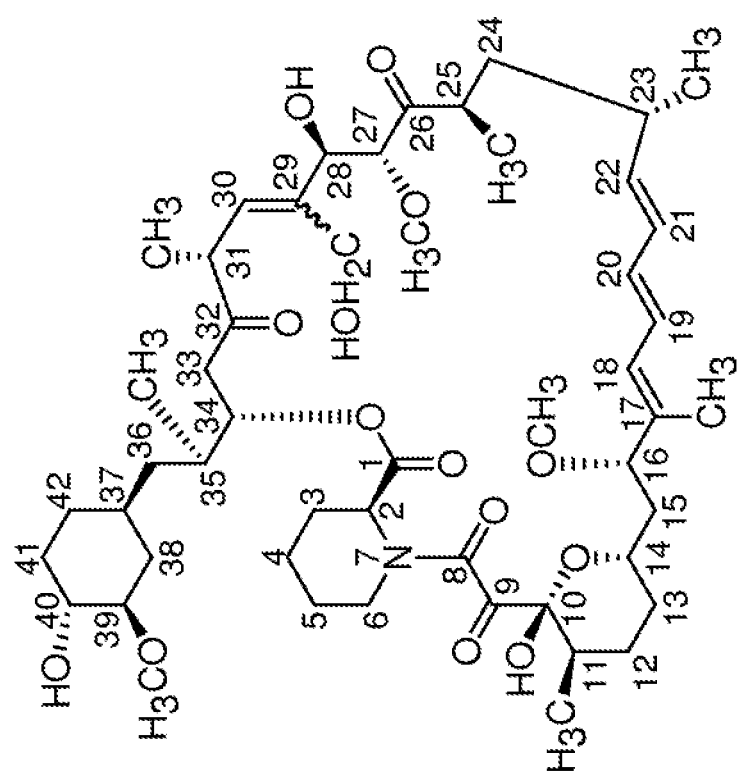
Figure 2B:
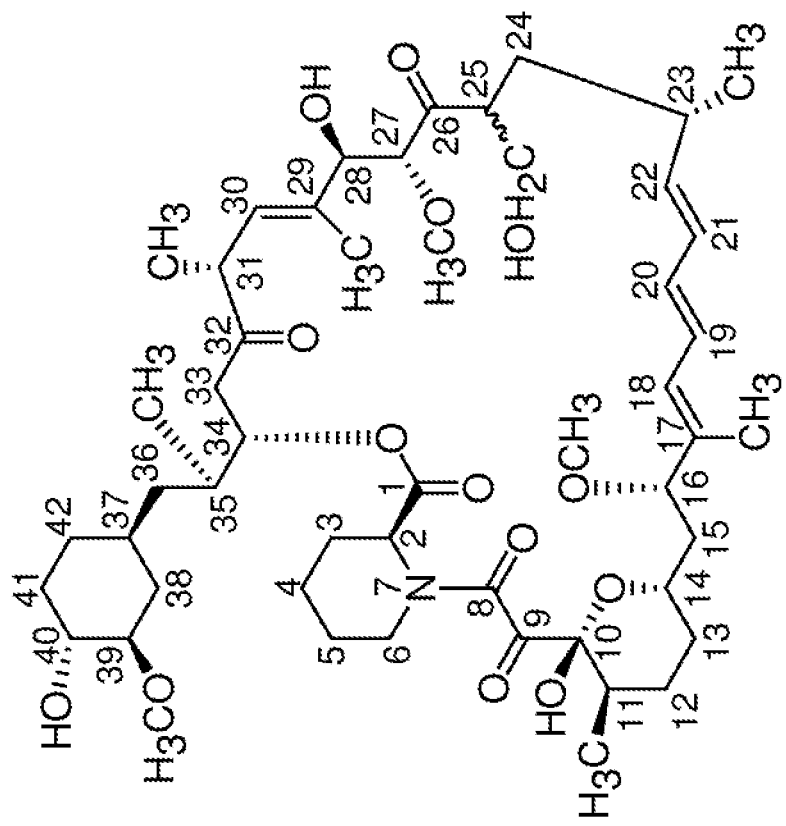
Figure 2B:
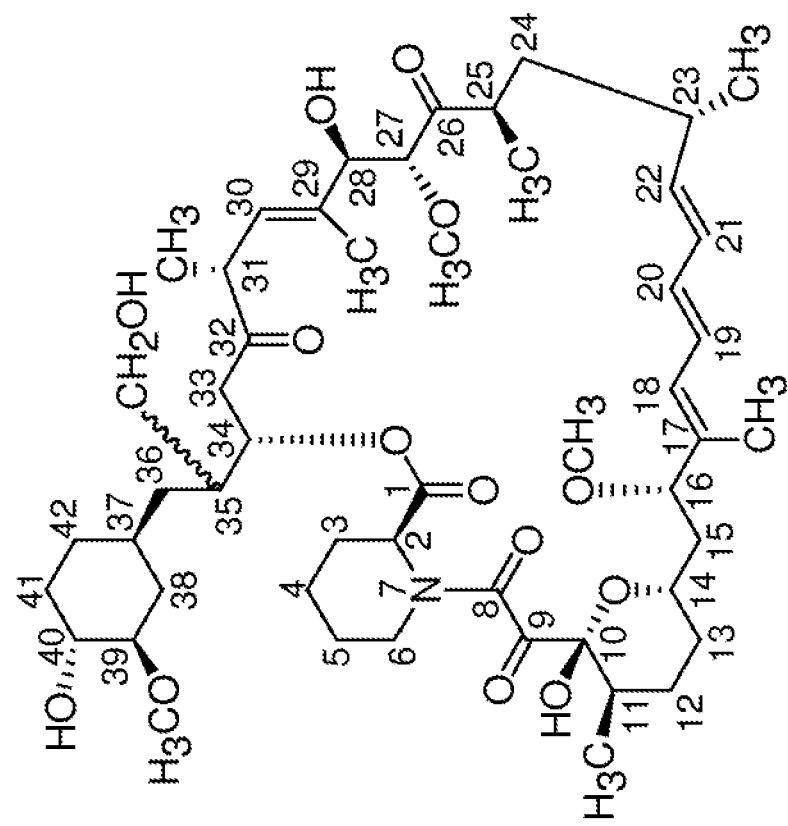
Figure 2B:
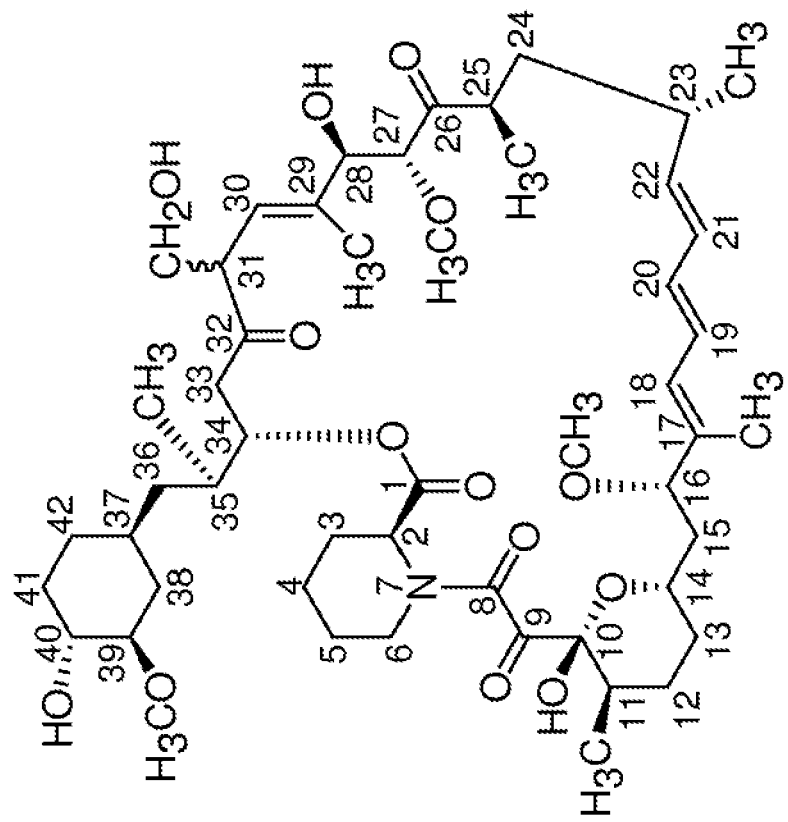
Figure 2B:
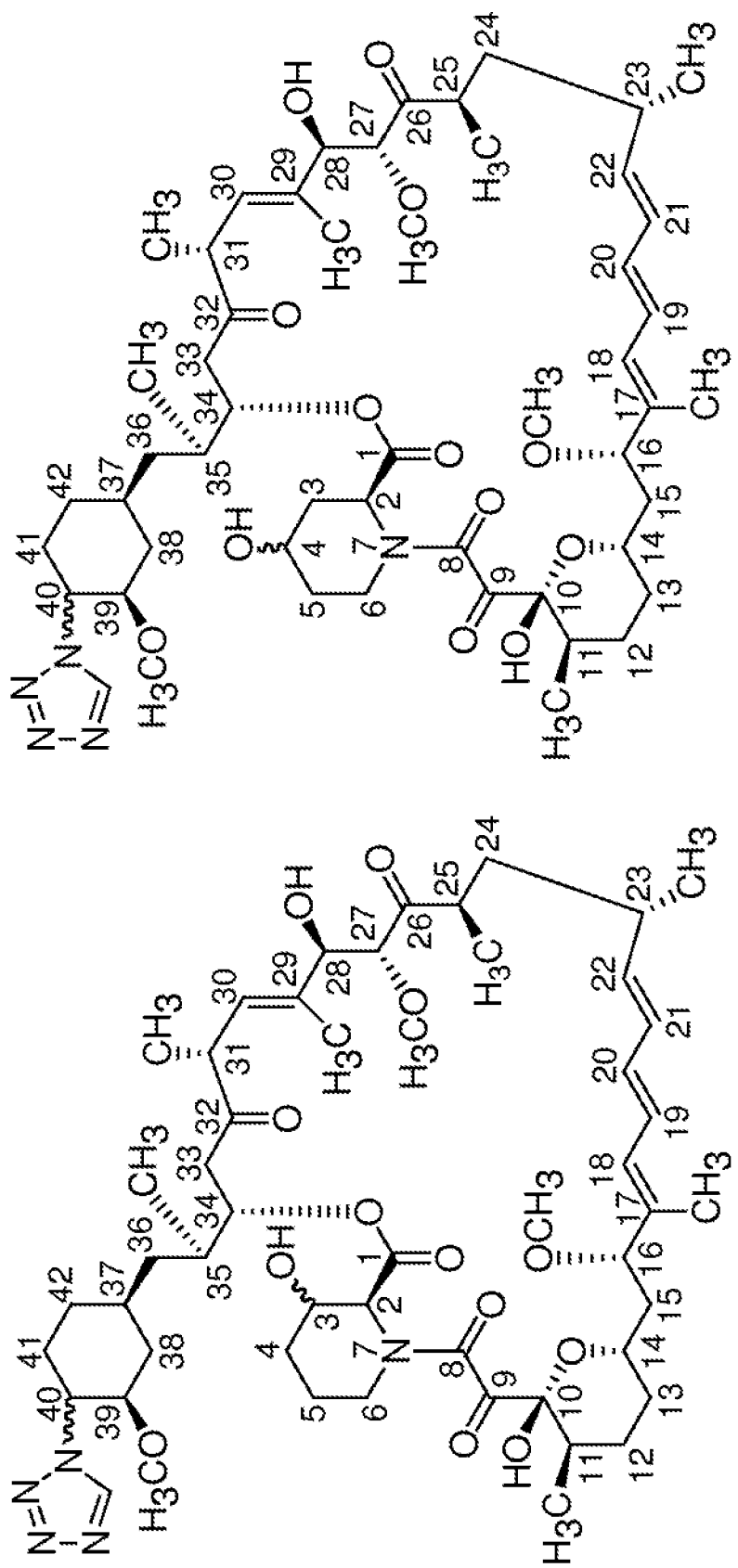
Figure 2B:
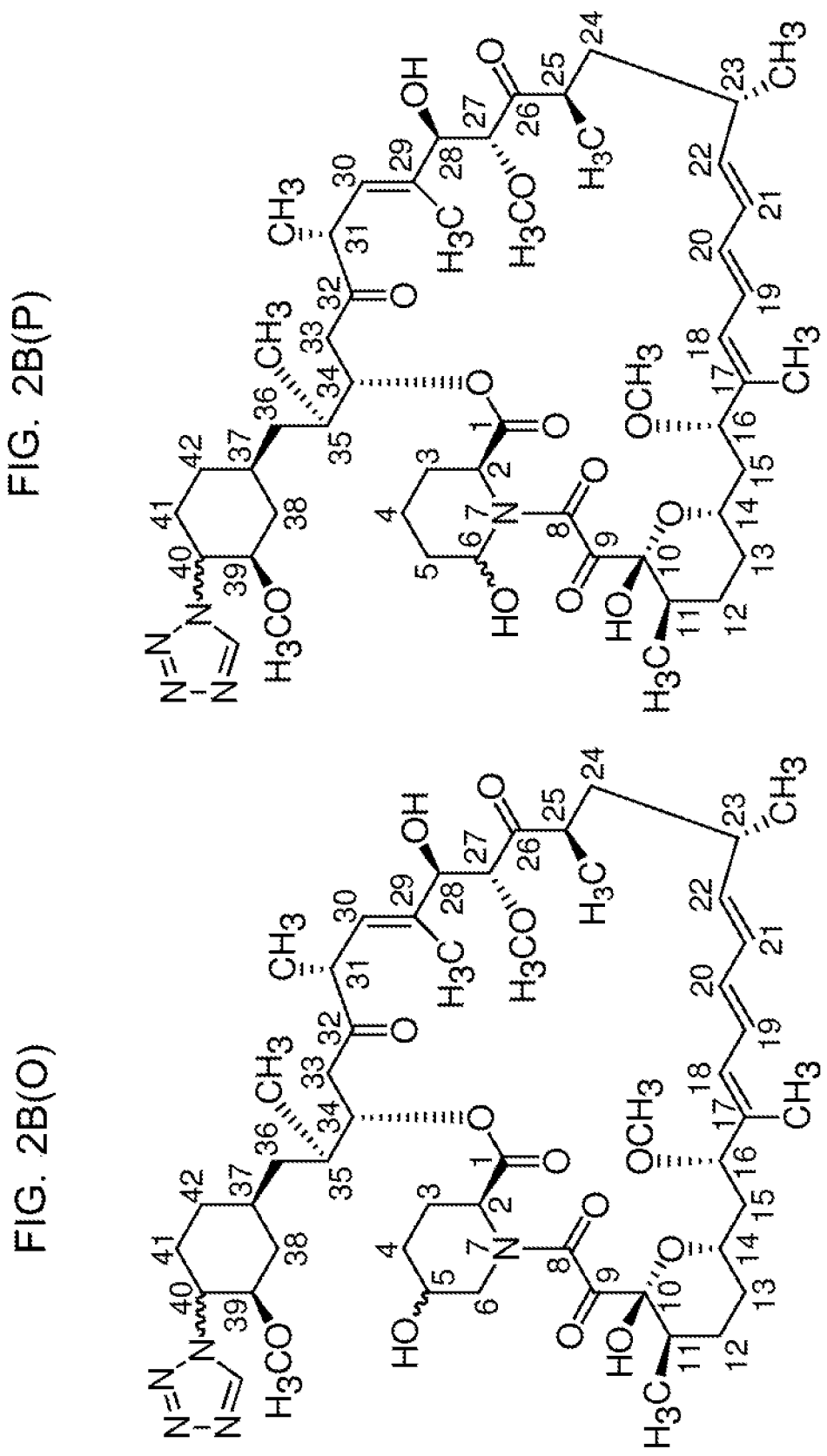
Figure 2B:
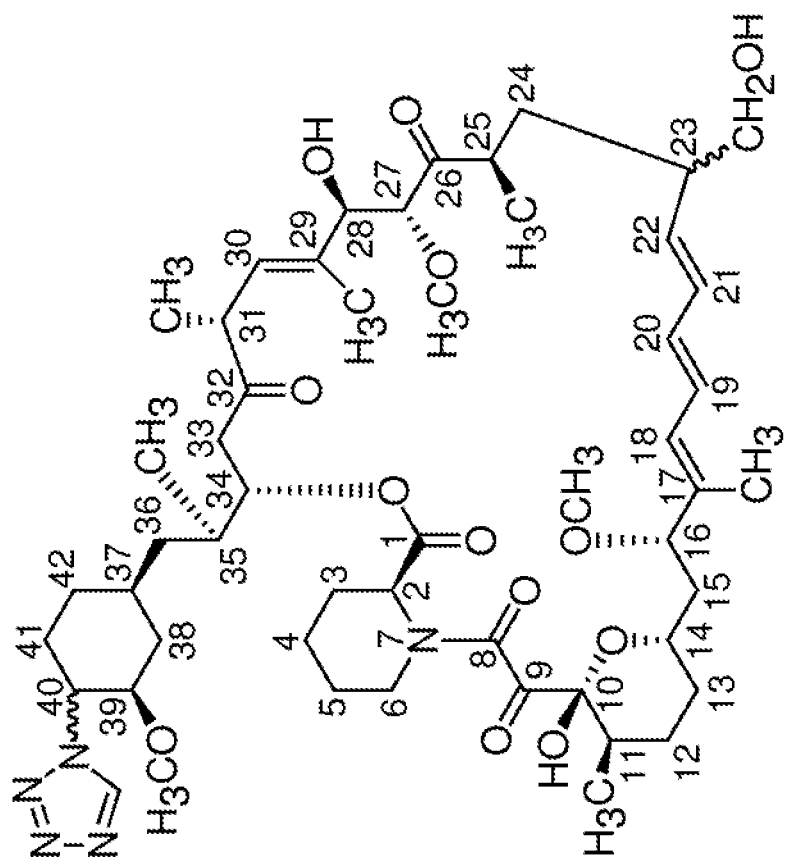
Figure 2B:
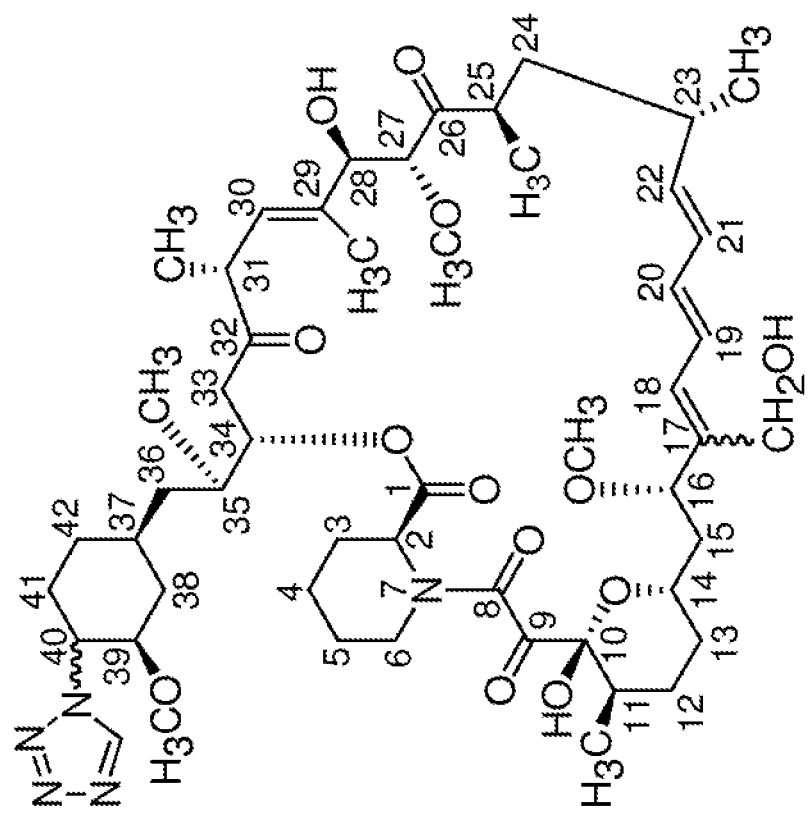
Figure 2B:
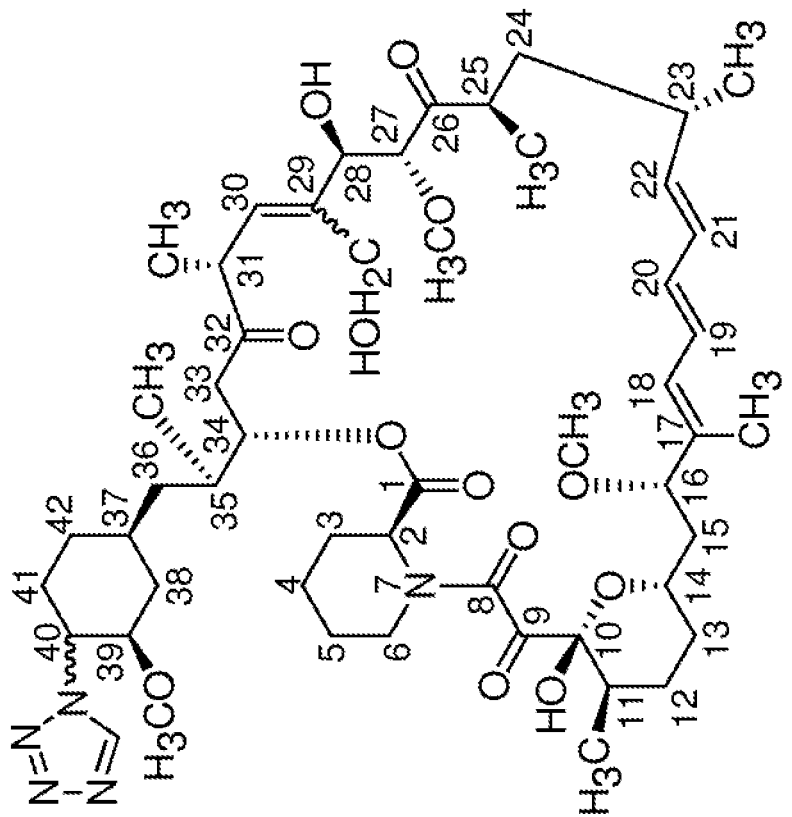
Figure 2B:
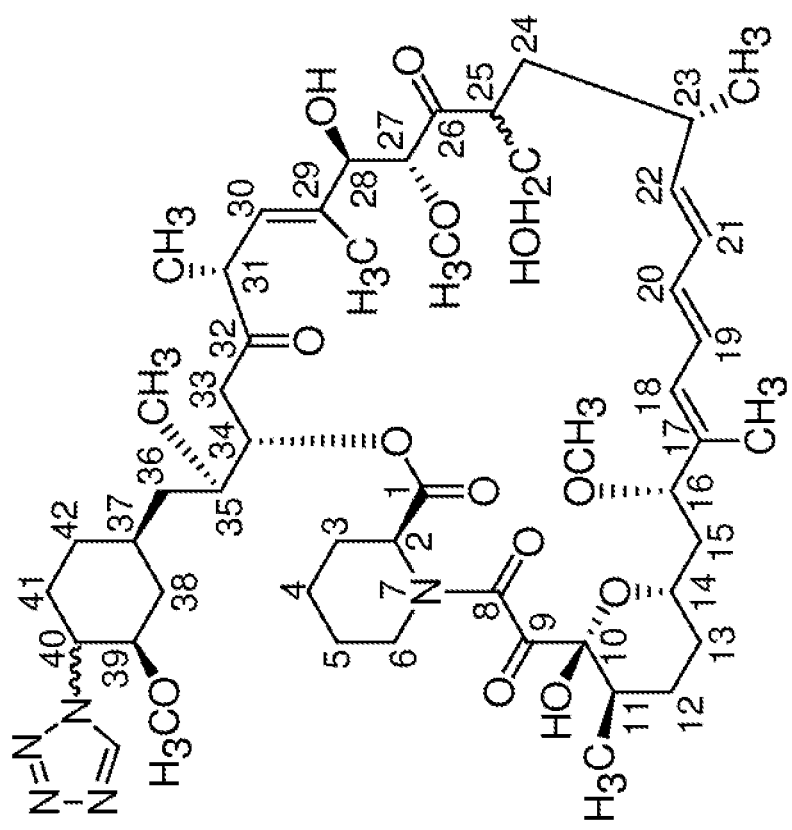
Figure 2B:
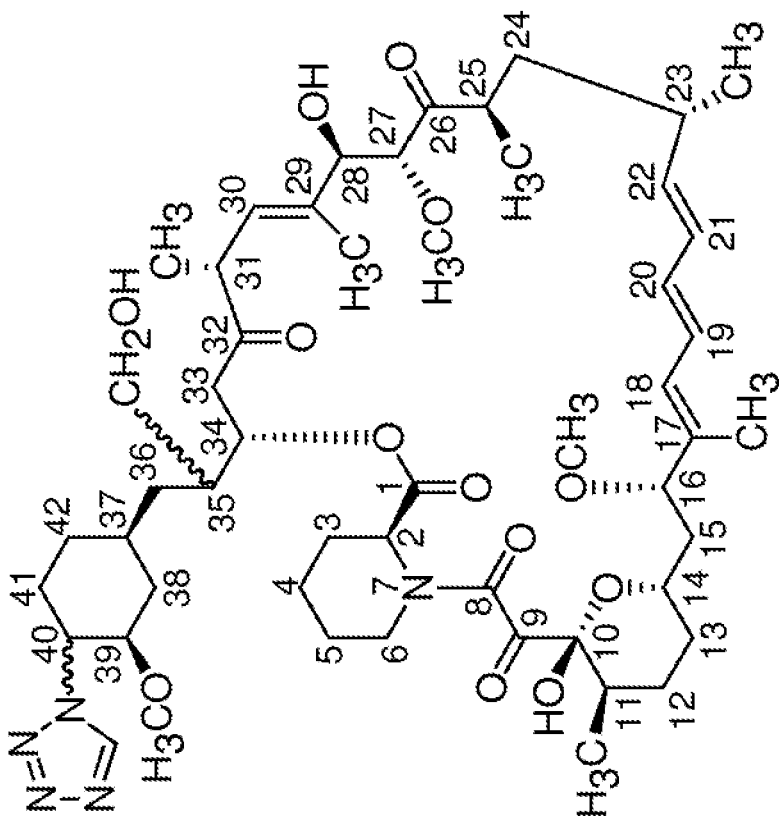
Figure 2B:
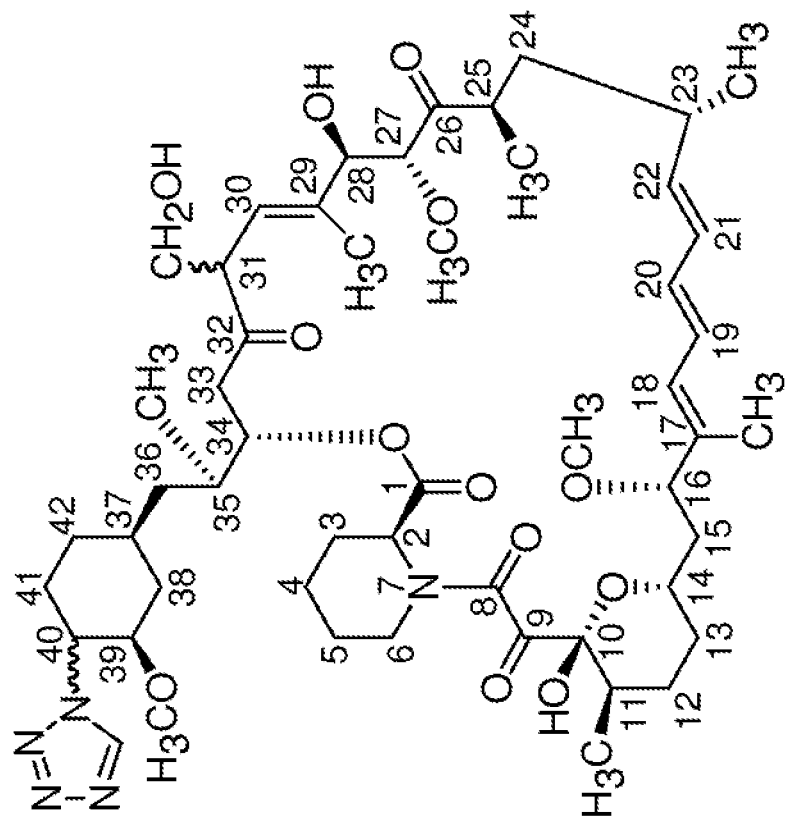
Figure 2B:
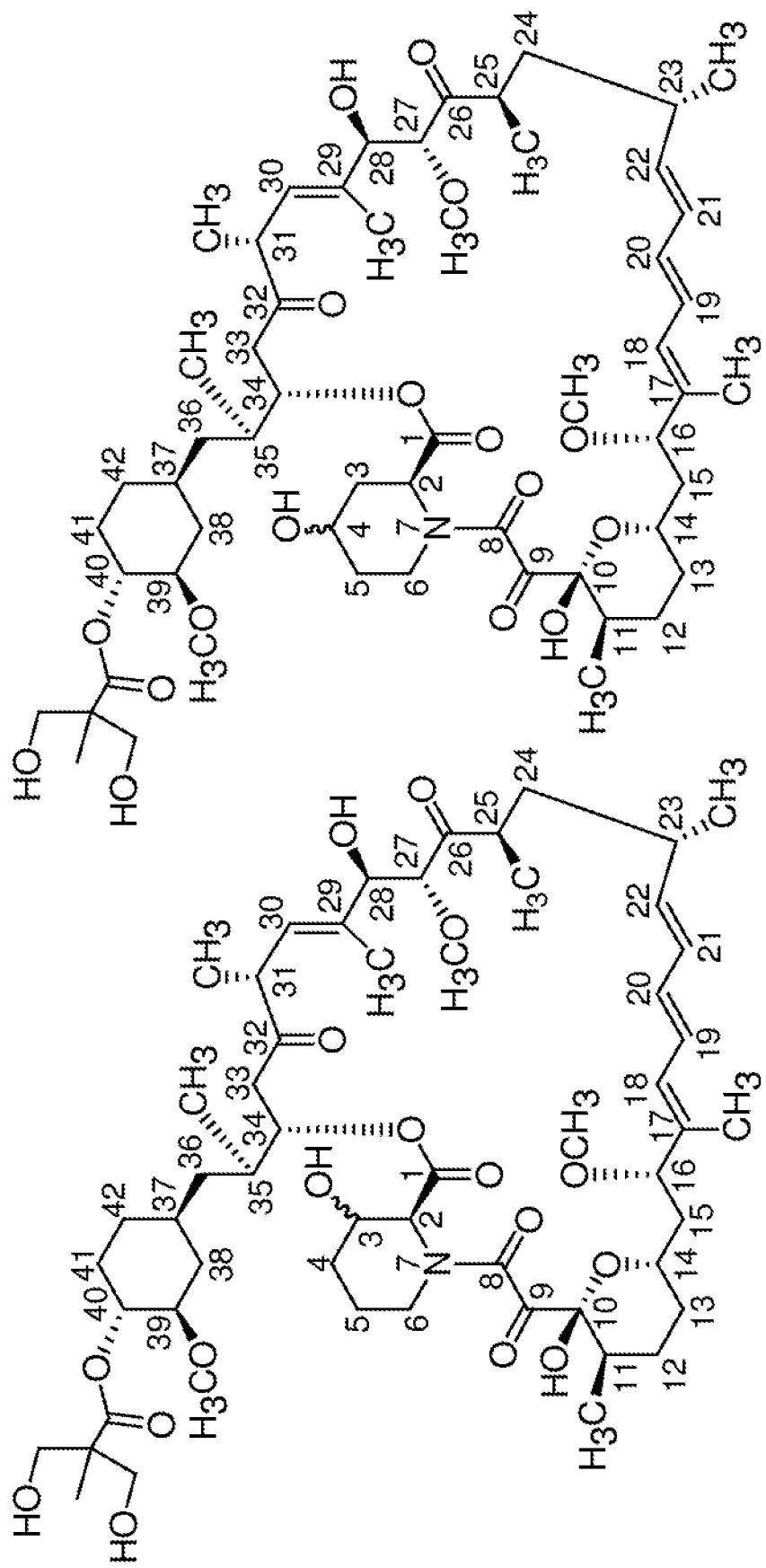
Figure 2C:
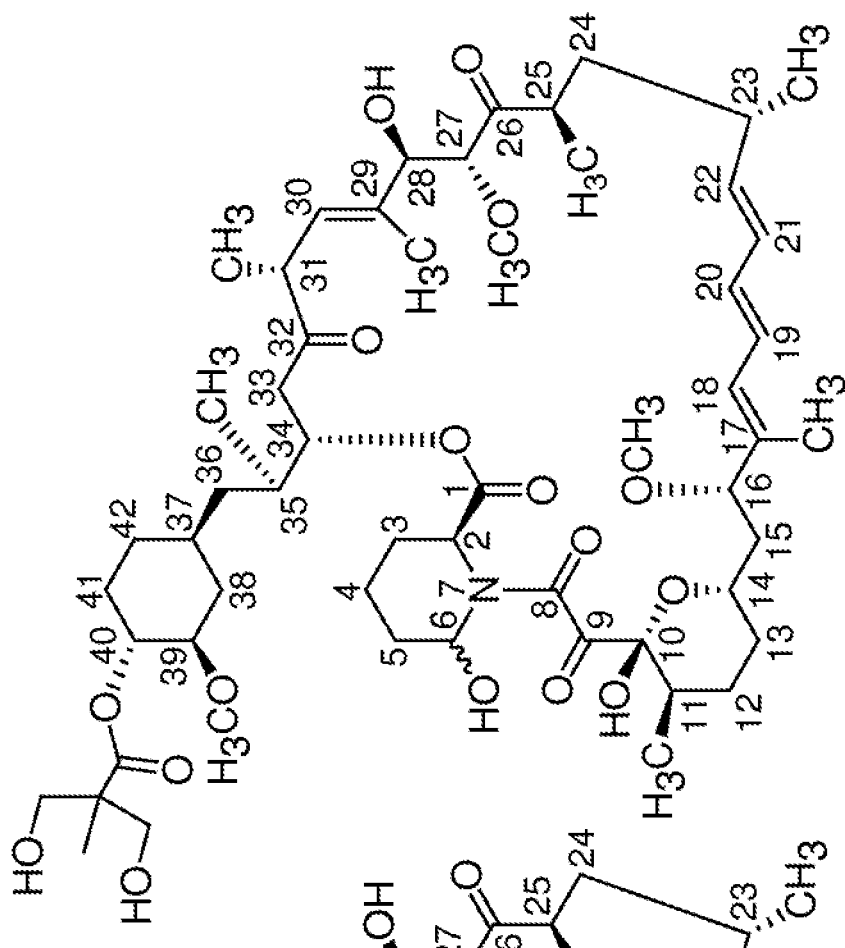
Figure 2C:
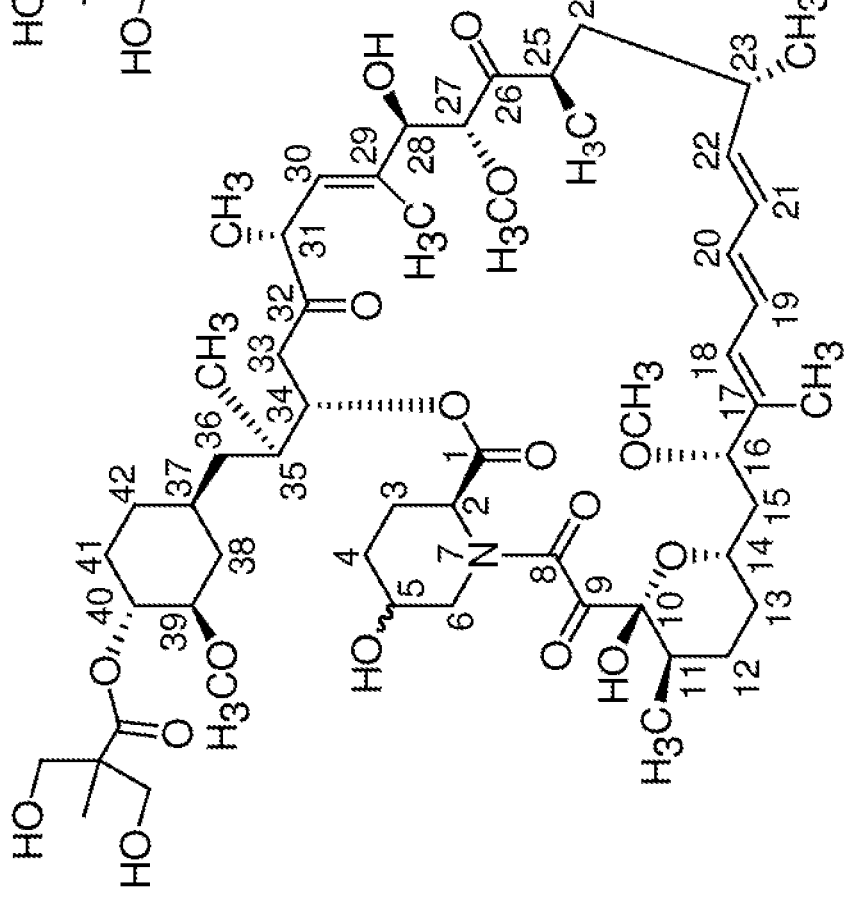
Figure 2C:
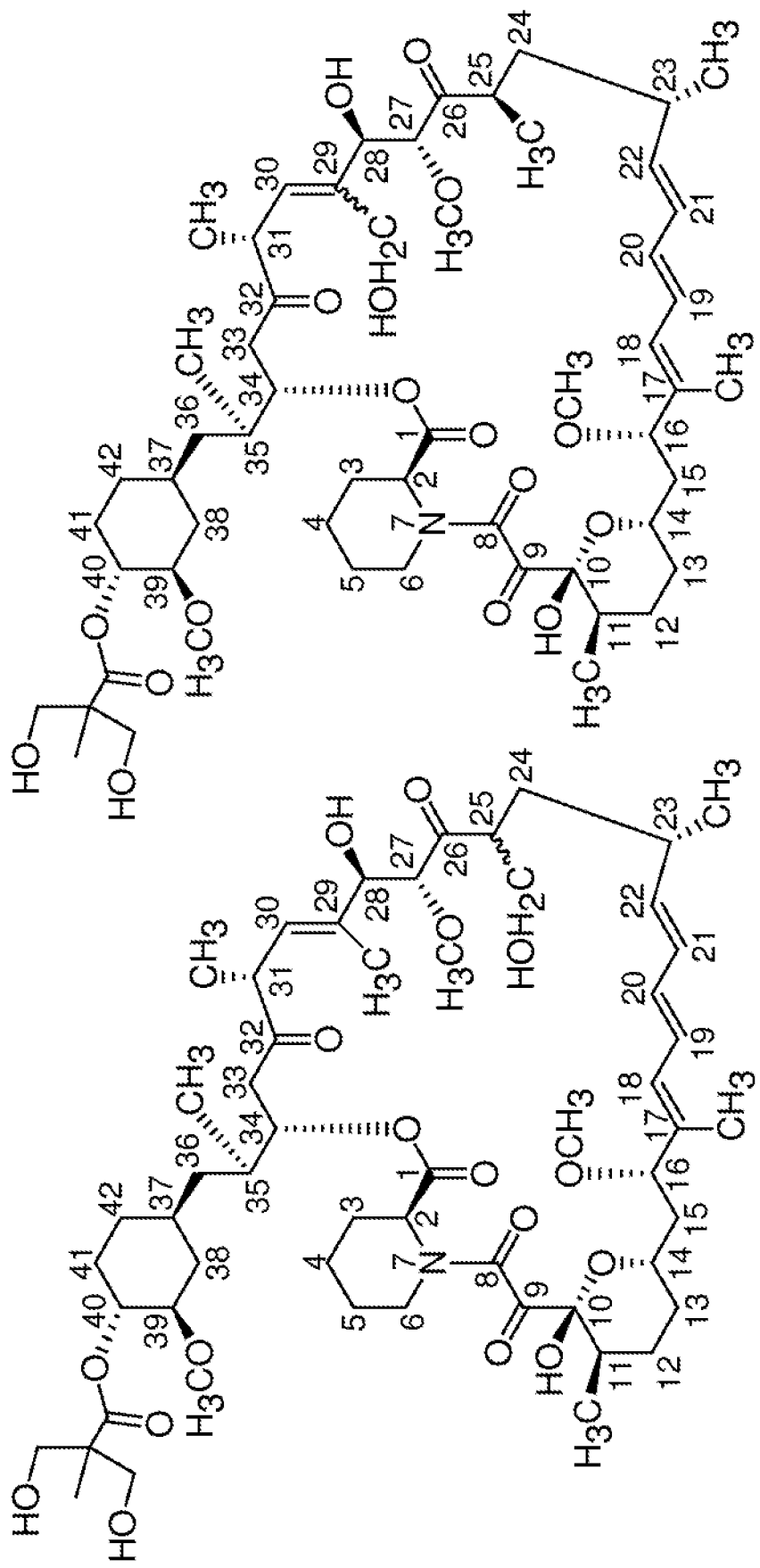
Figure 2C:
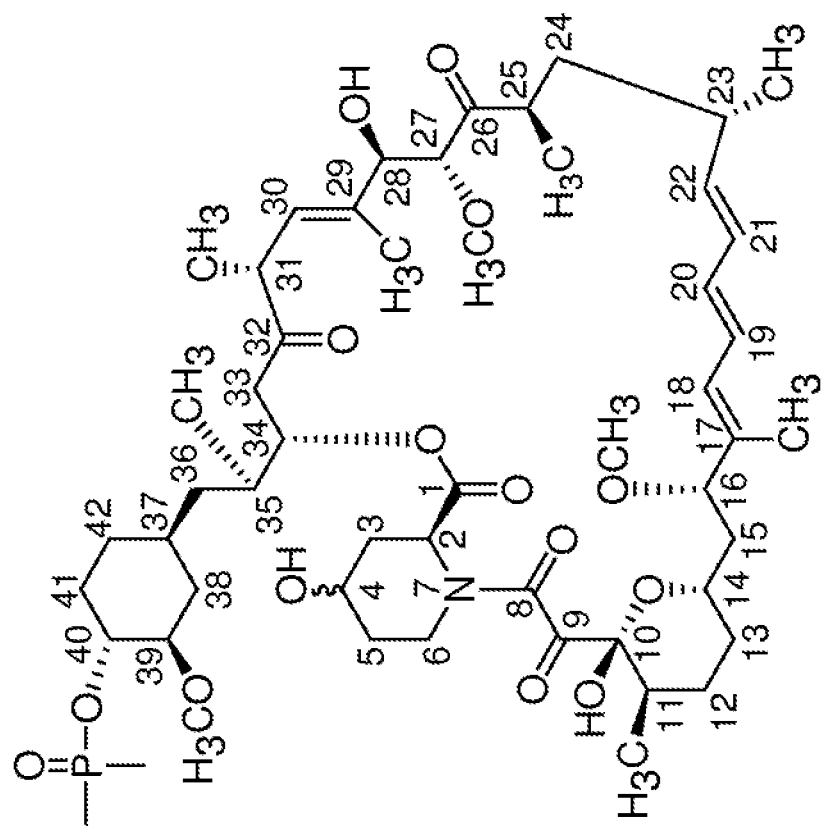
Figure 2C:
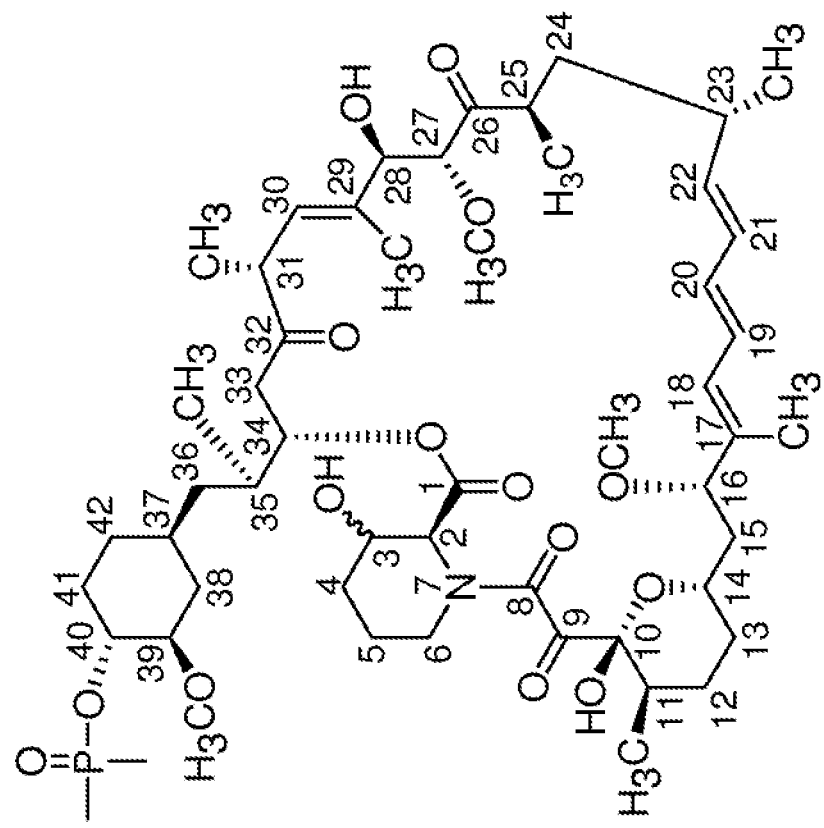
Figure 2C:
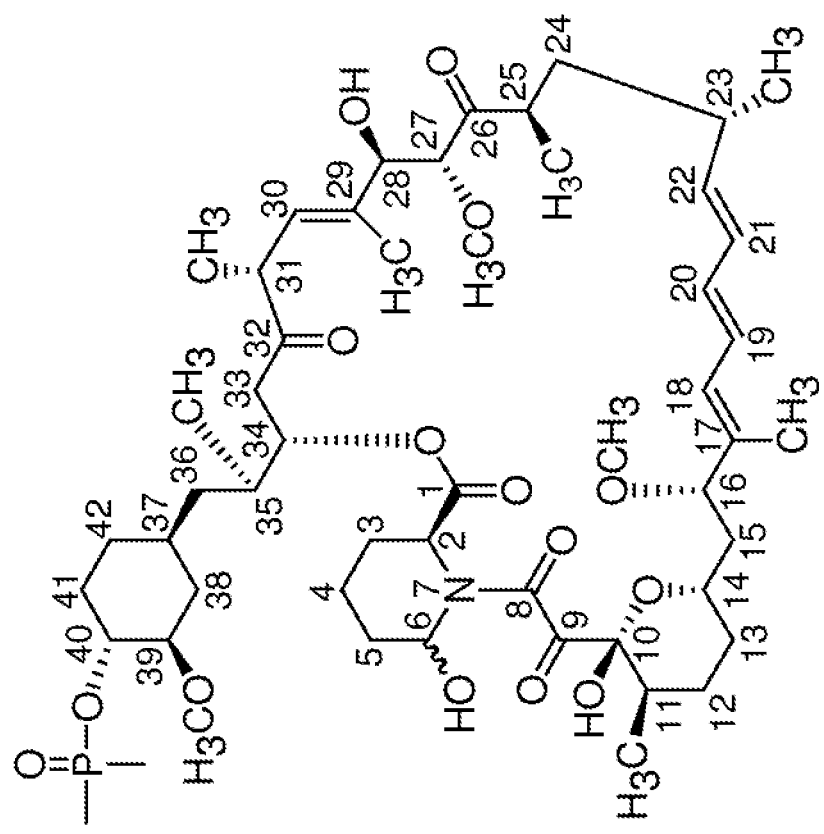
Figure 2C:
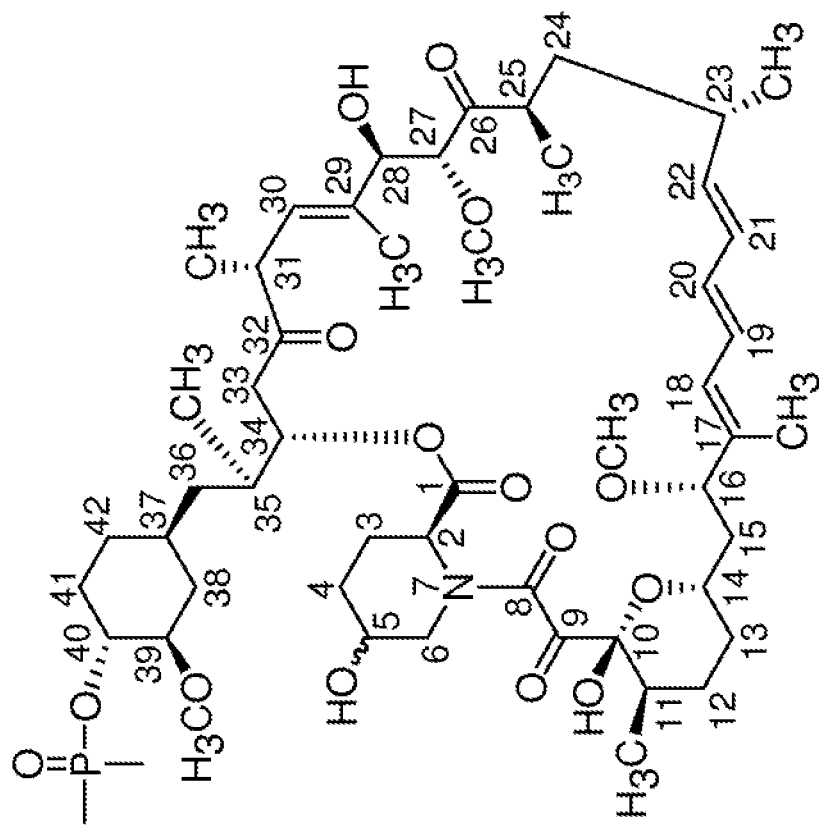
Figure 2C:
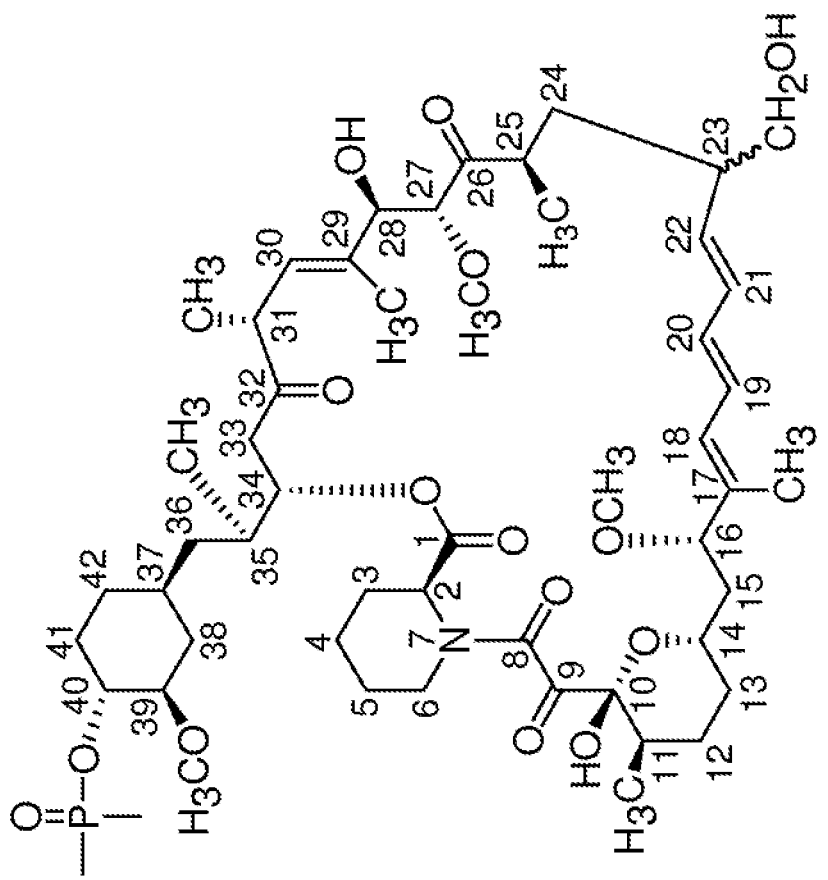
Figure 2C:
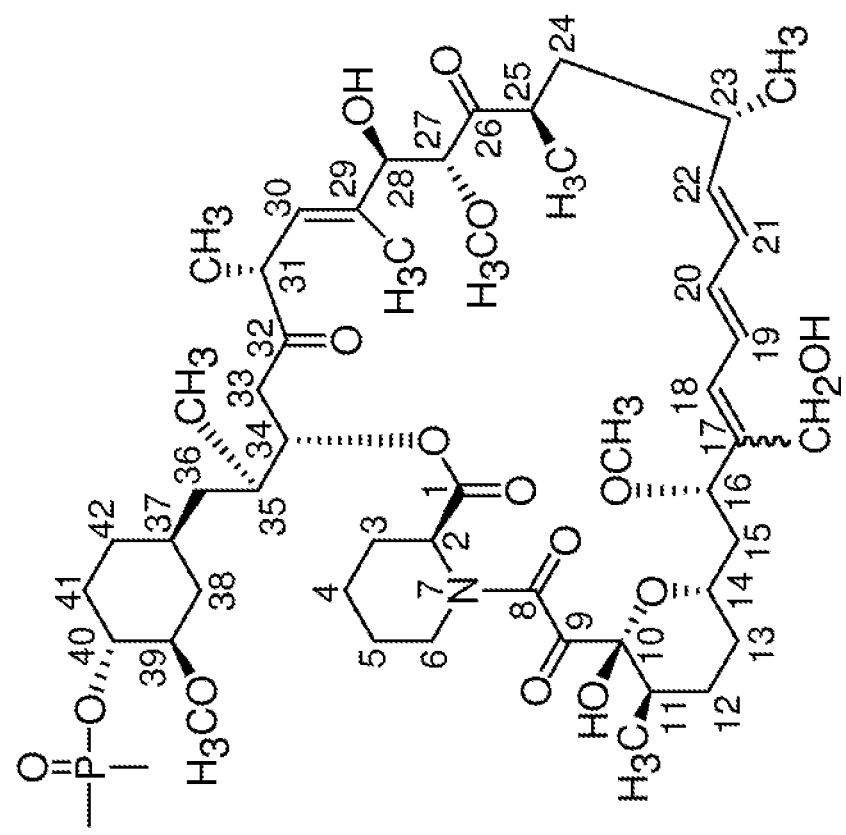
Figure 2C:
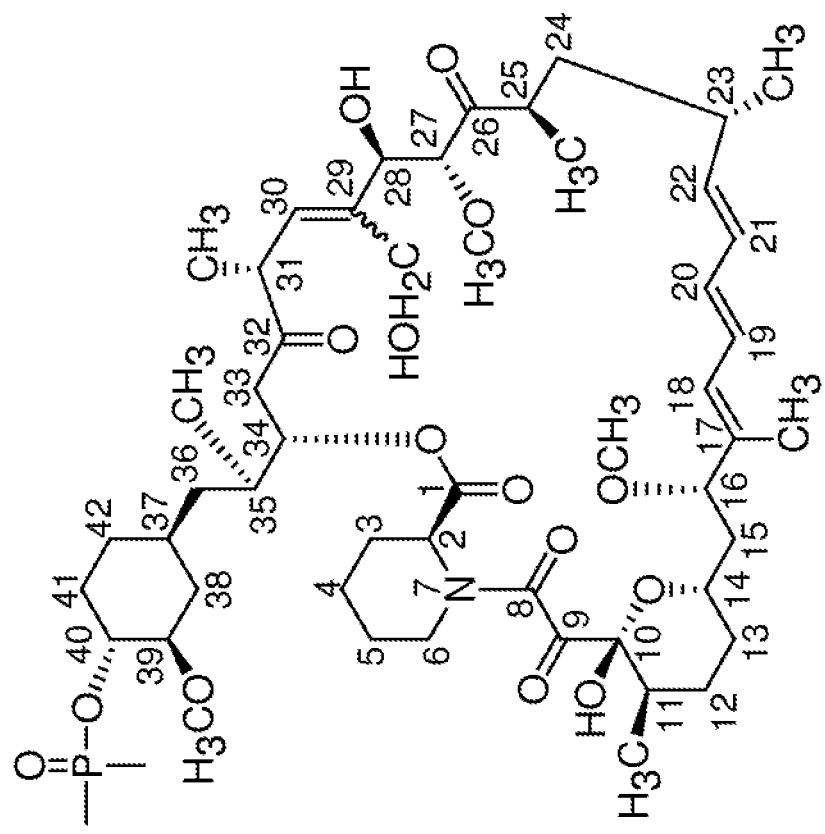
Figure 2C:
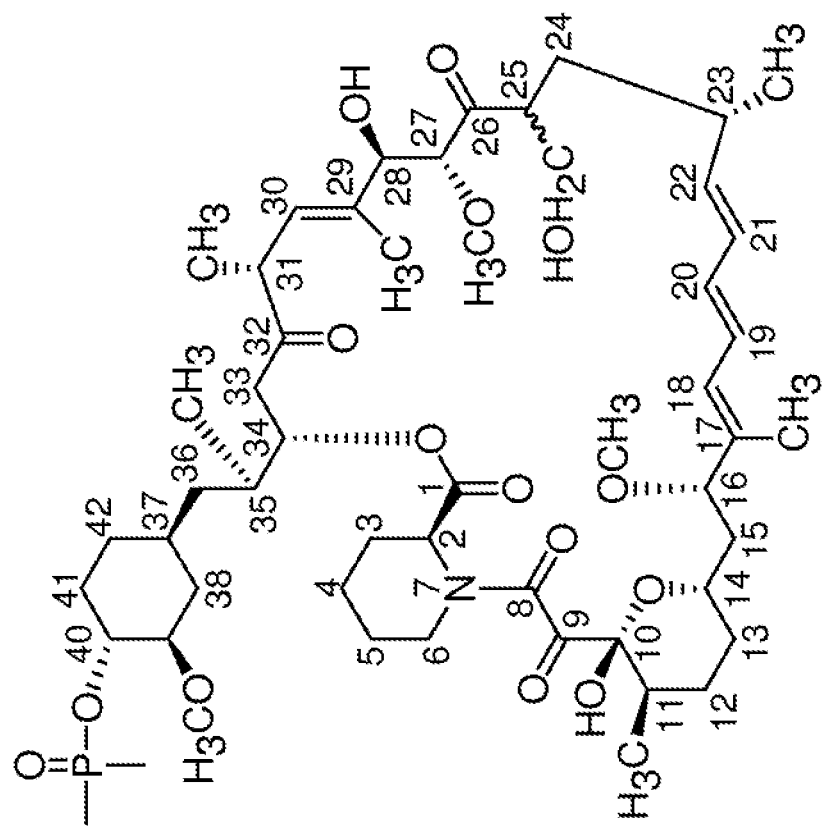
Figure 2C:
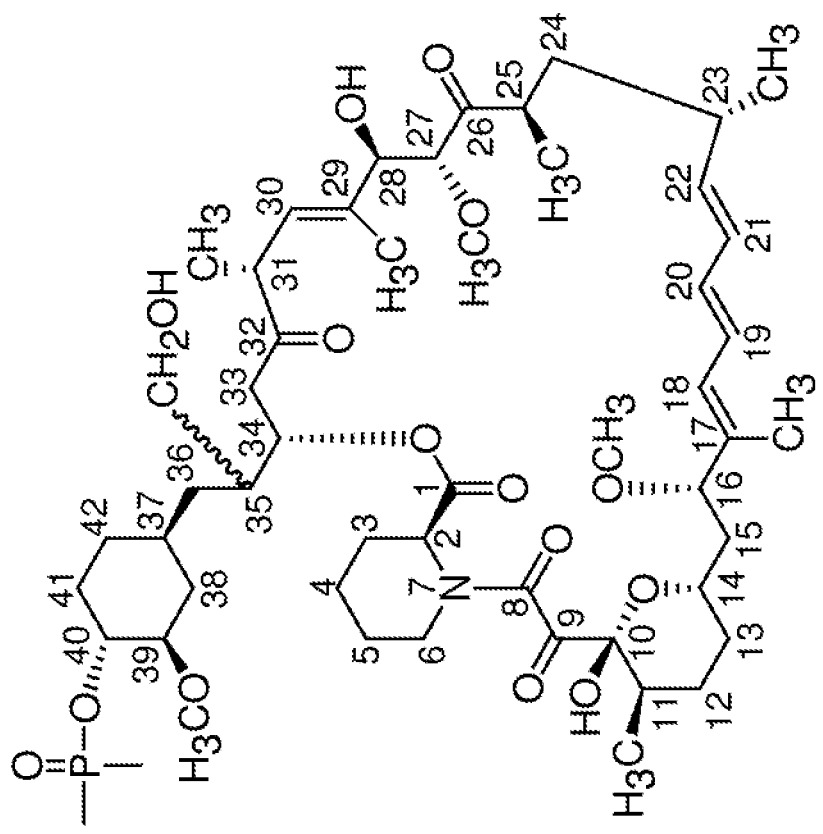
Figure 2C:
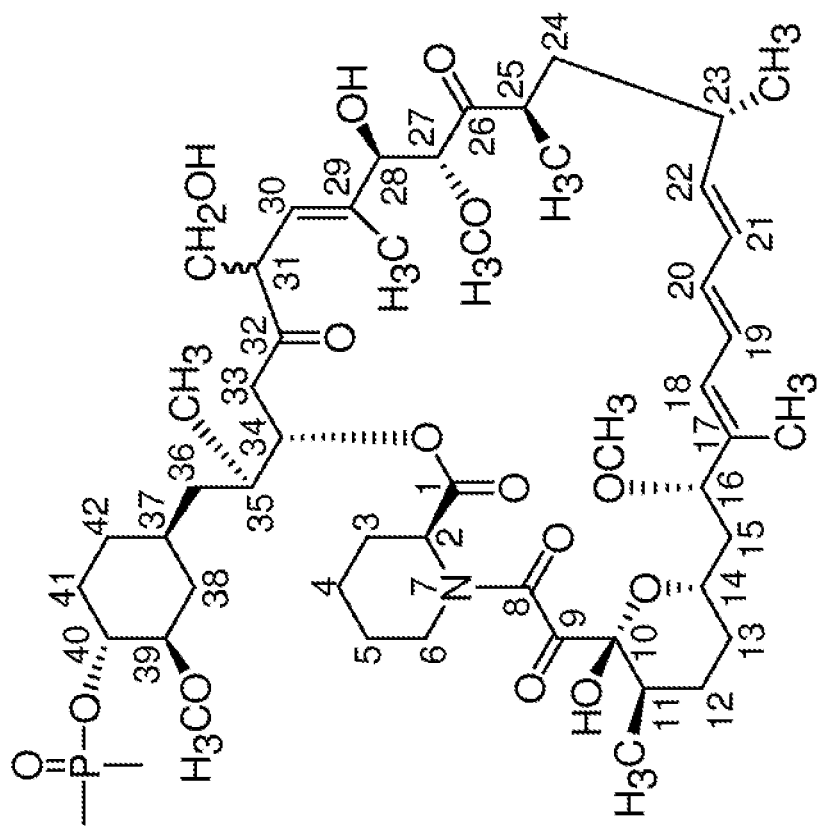
Figure 2C:
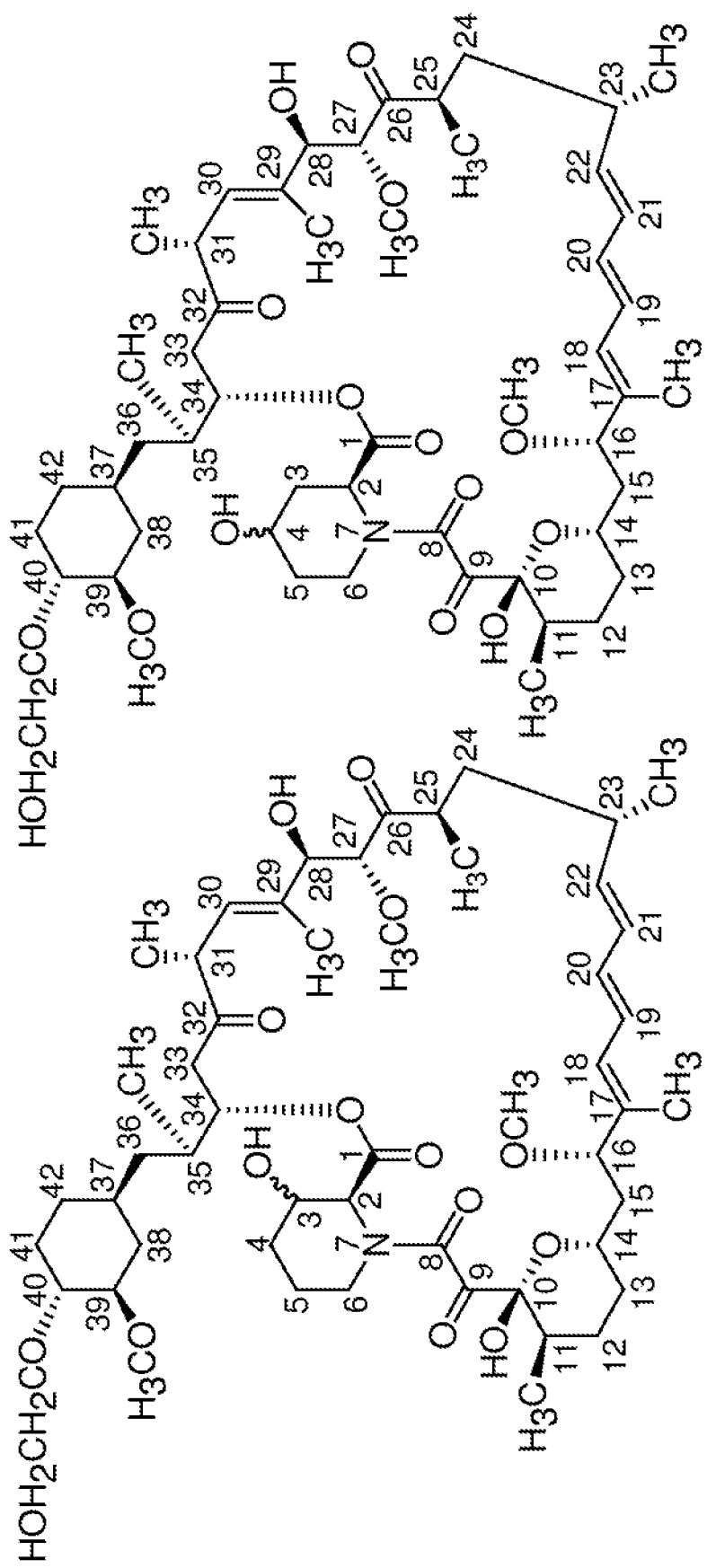
Figure 2C:
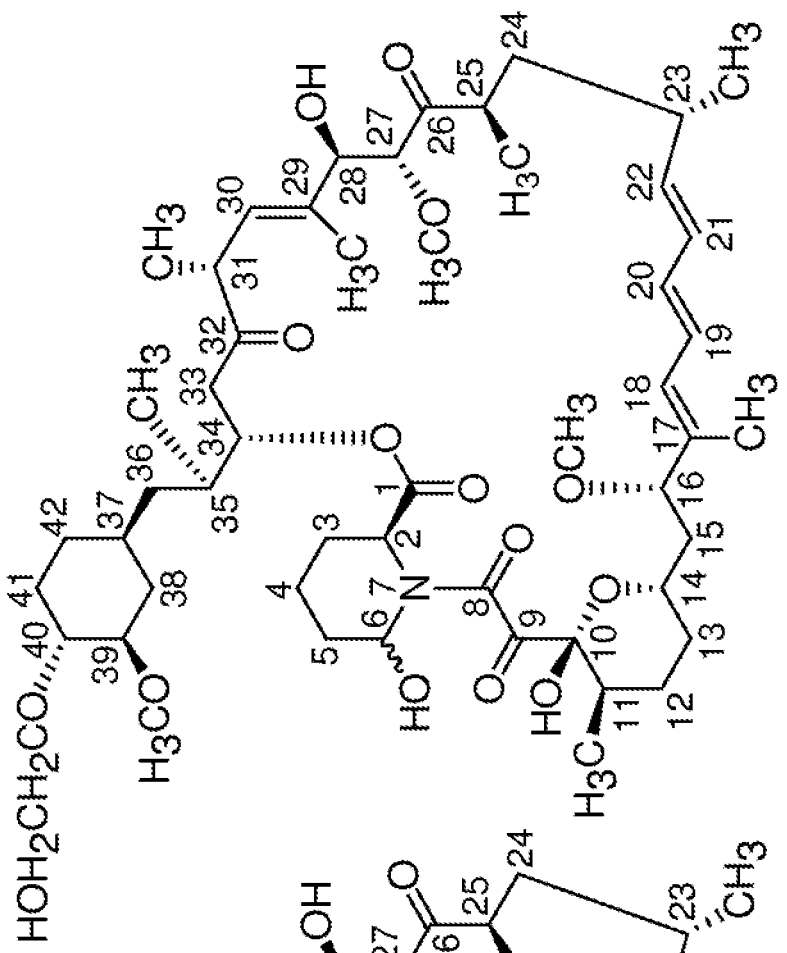
Figure 2C:
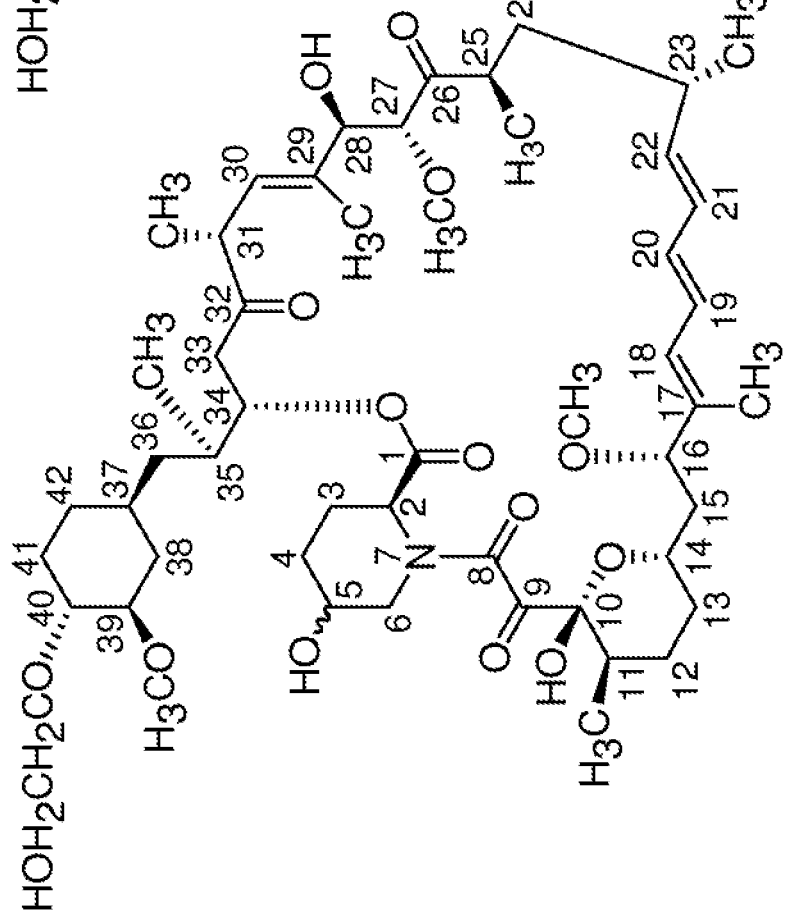
Figure 2D:
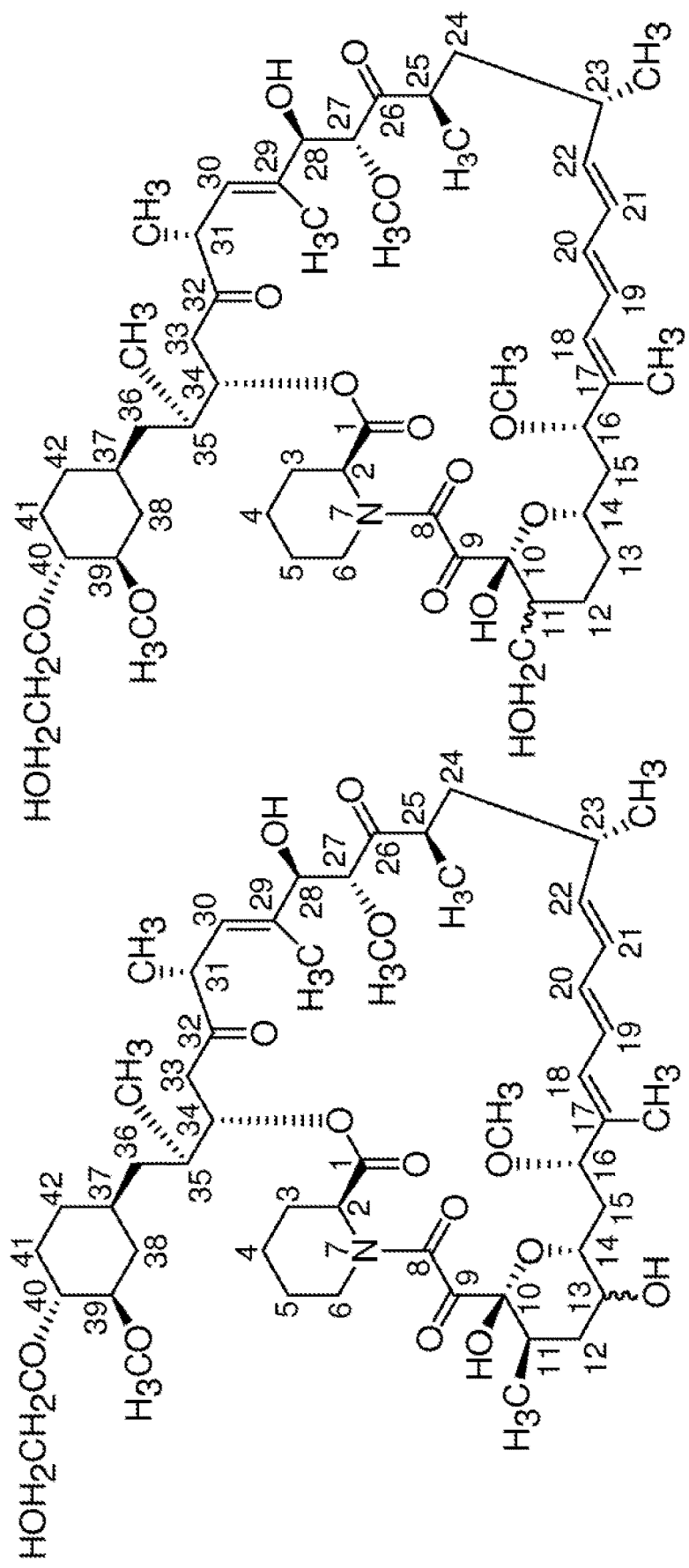
Figure 2D:
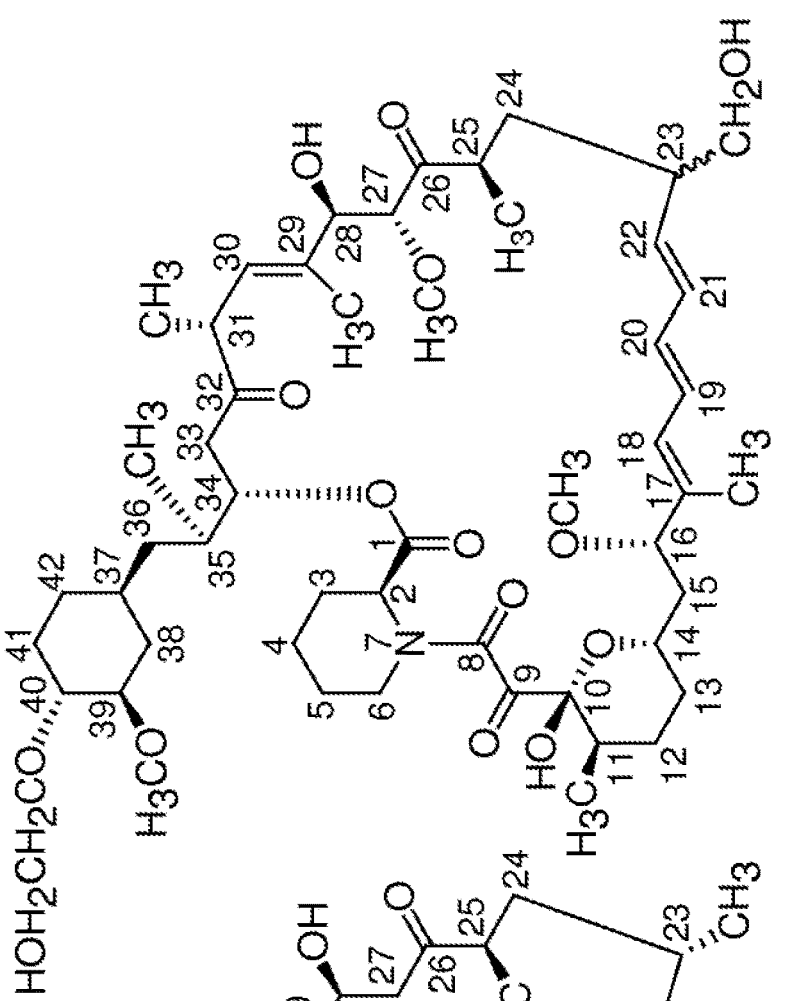
Figure 2D:
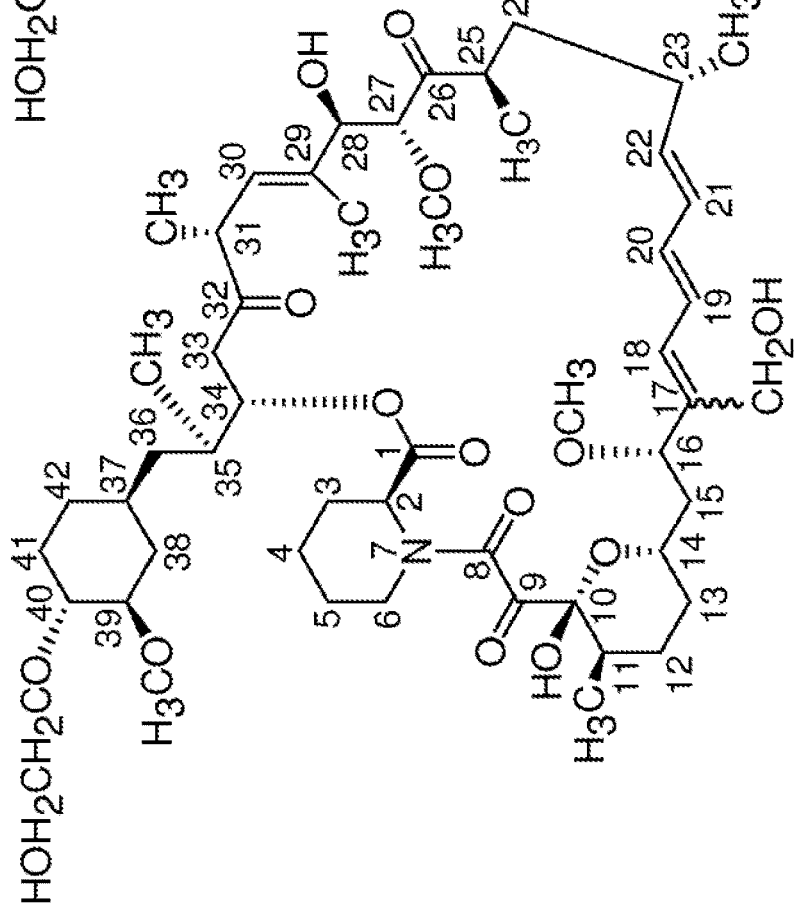
Figure 2D:
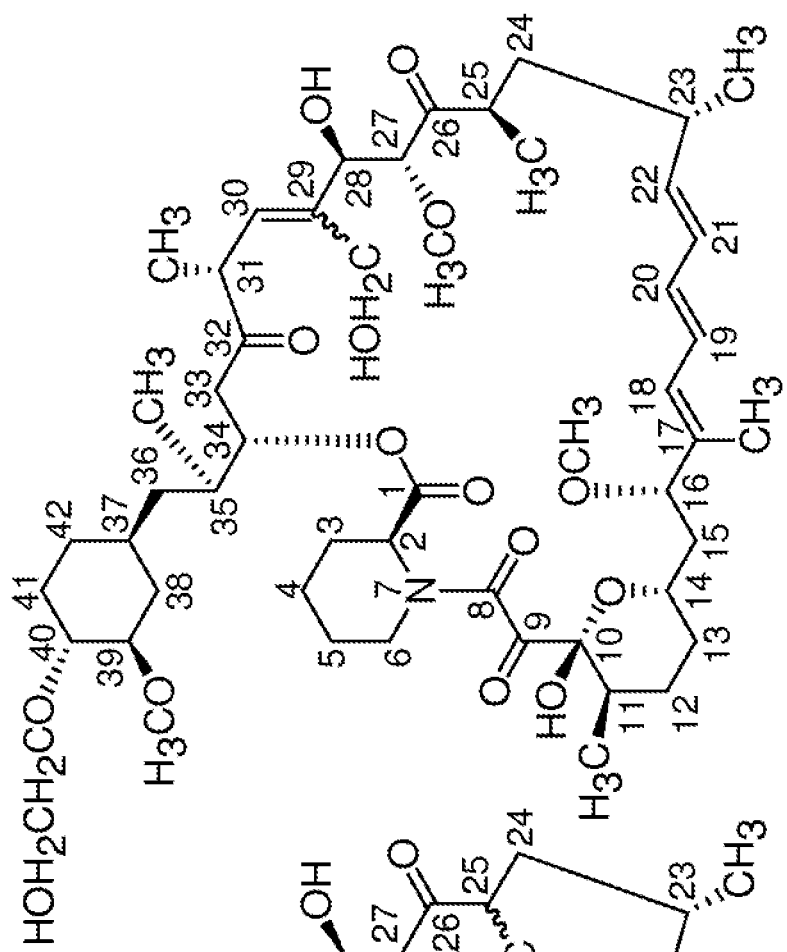
Figure 2D:
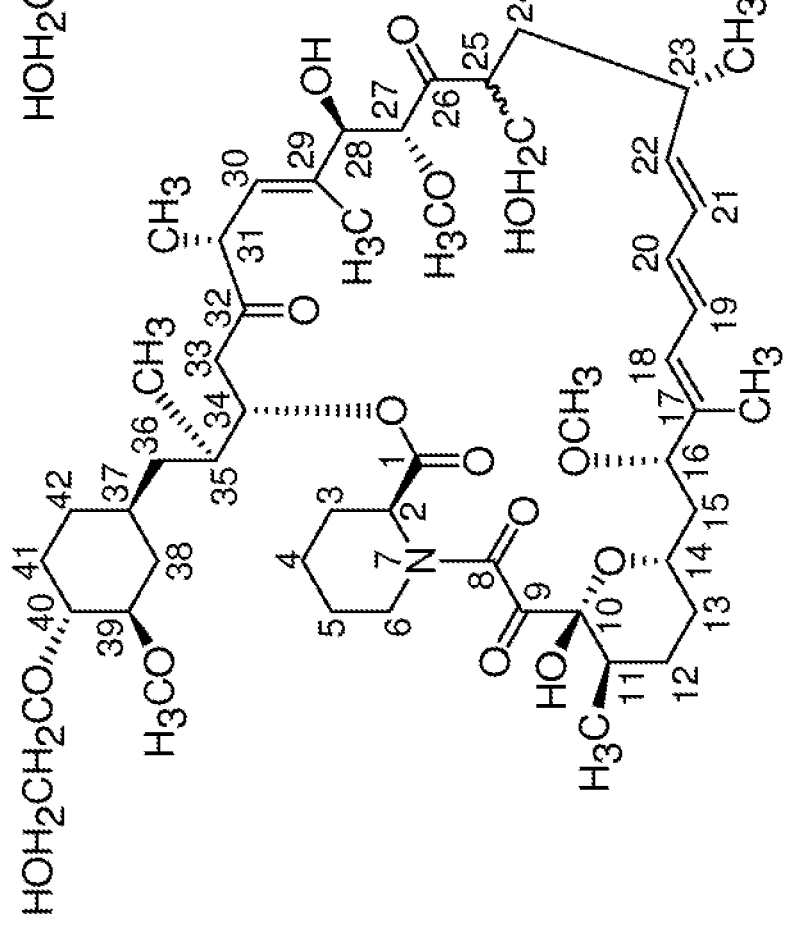
Figure 2D:
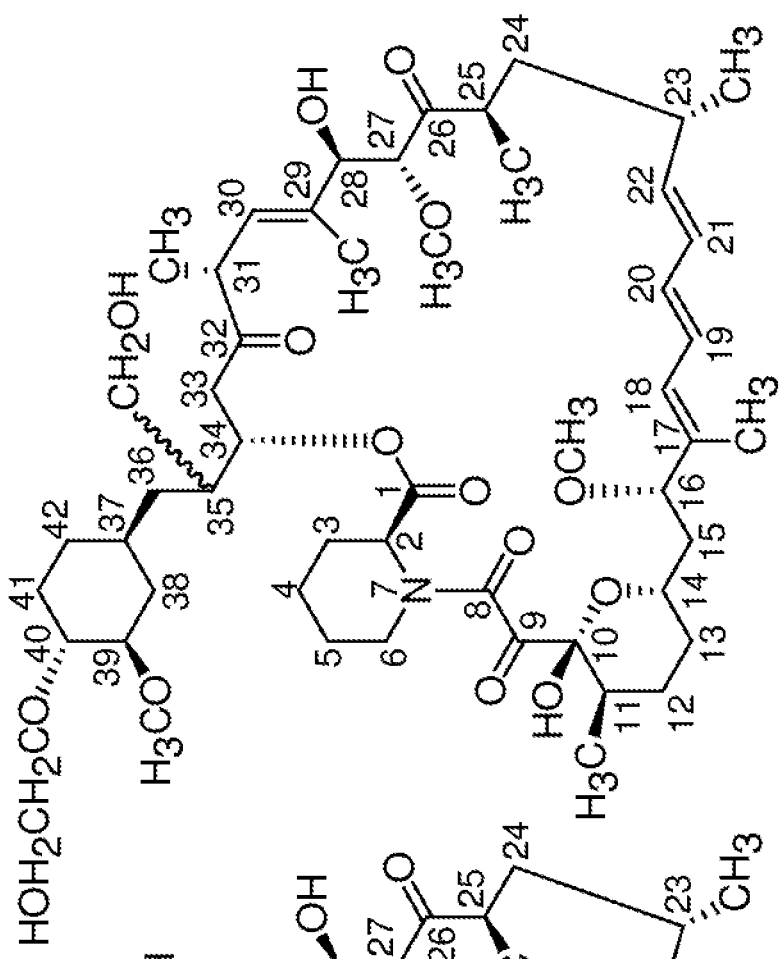
Figure 2D:
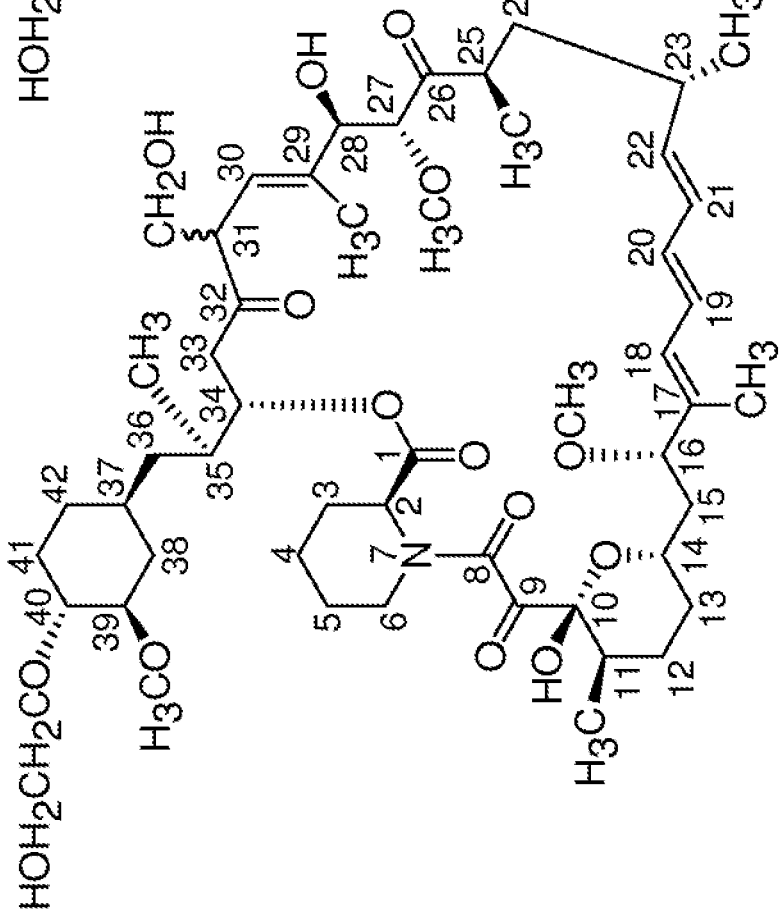
Figure 2D:
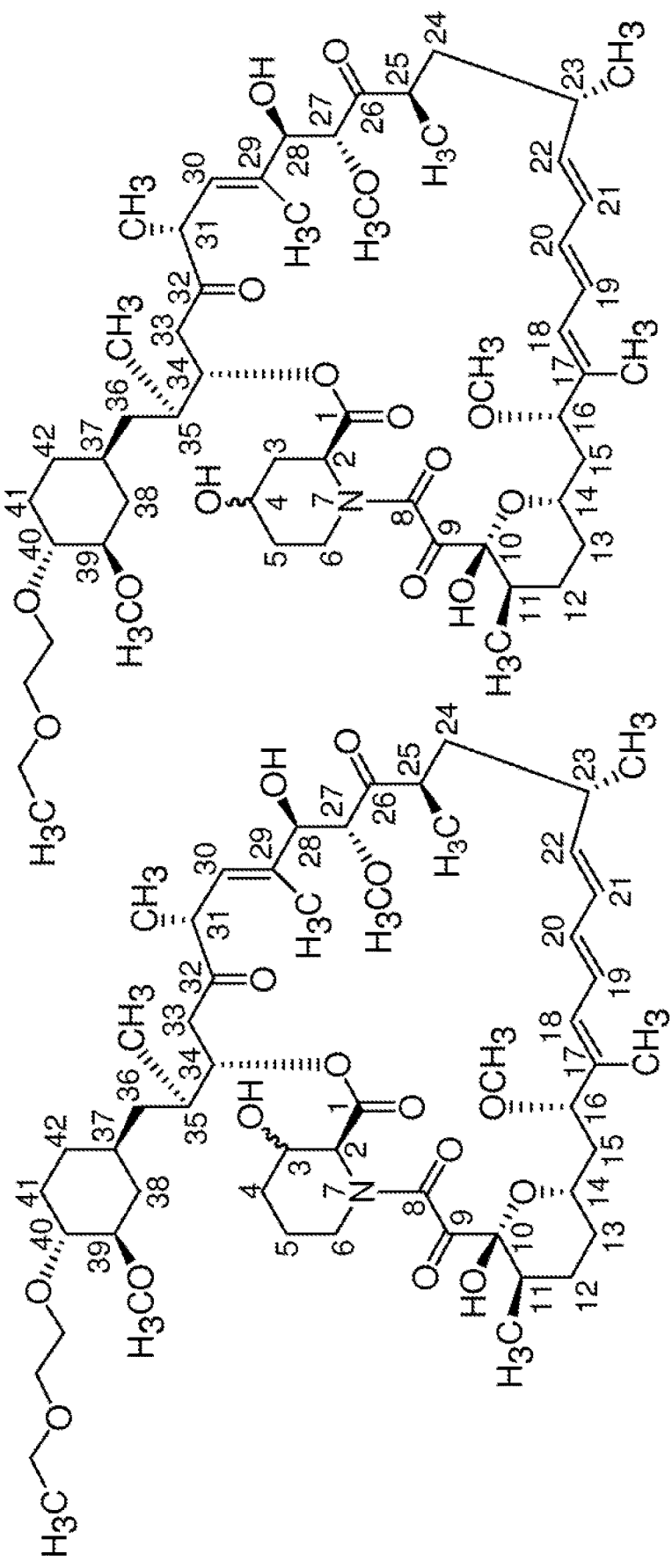
Figure 2D:
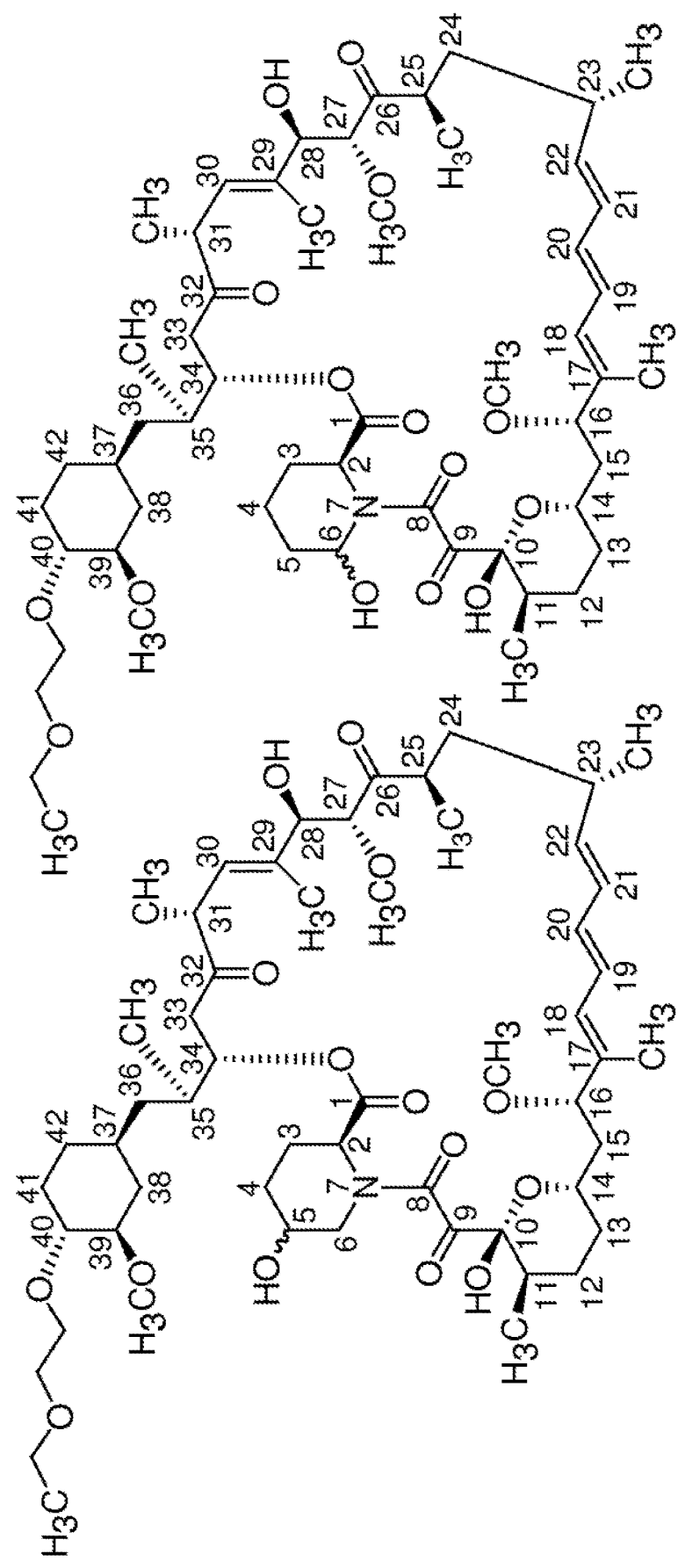
Figure 2D:
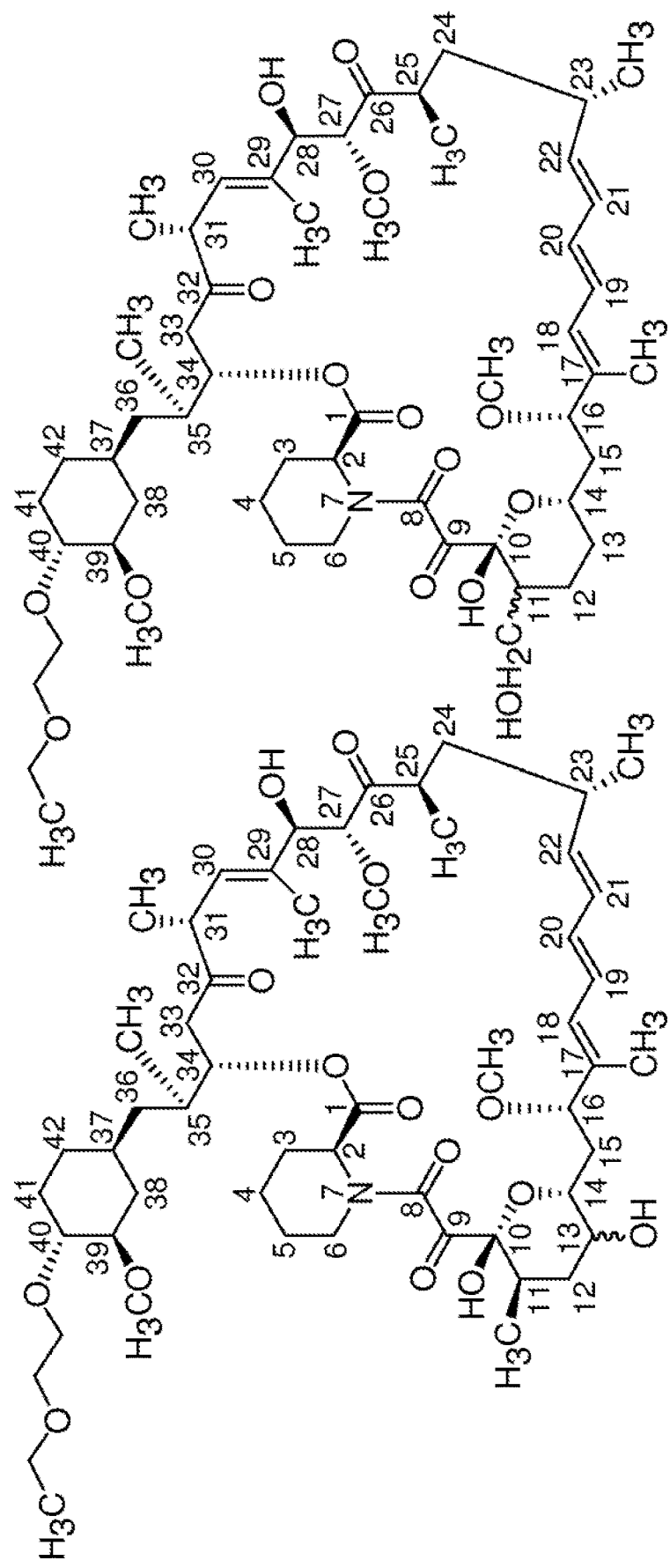
Figure 2D:
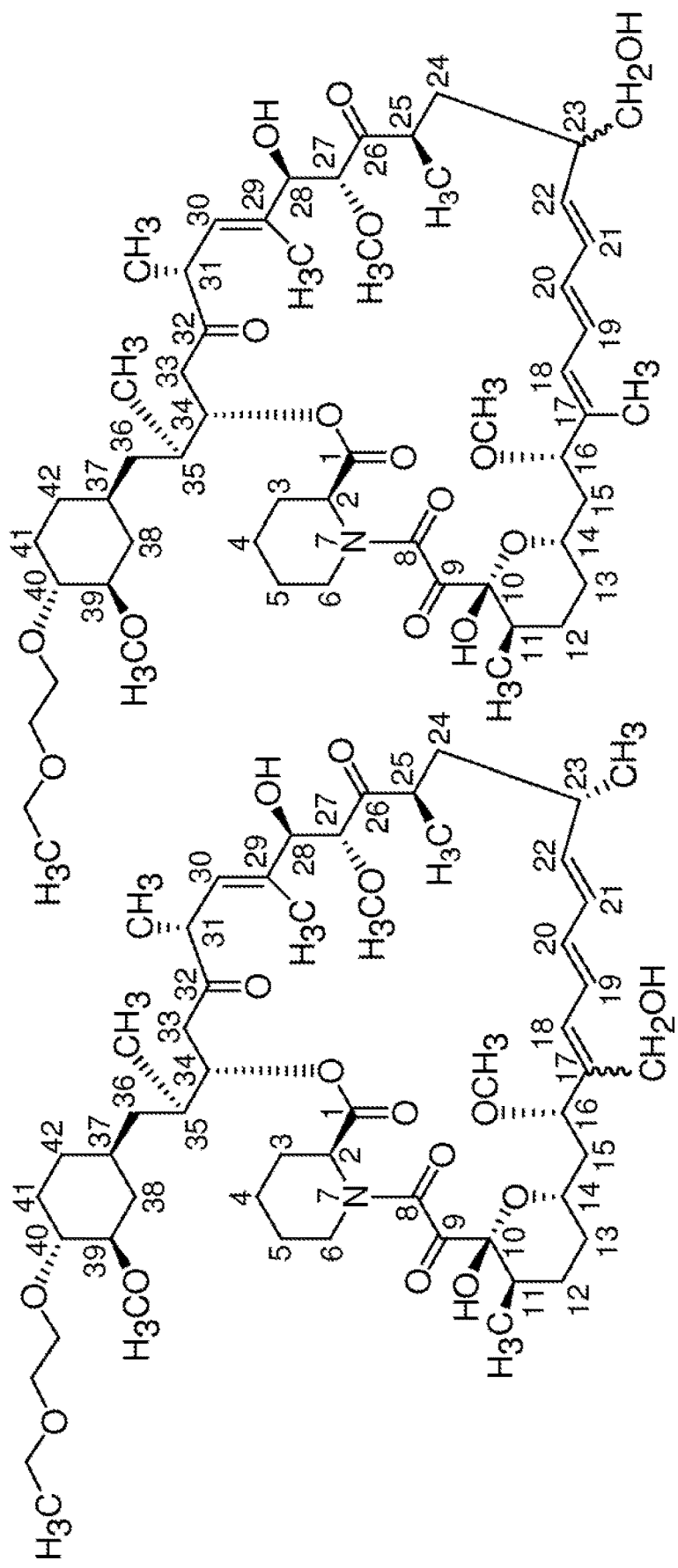
Figure 2D:
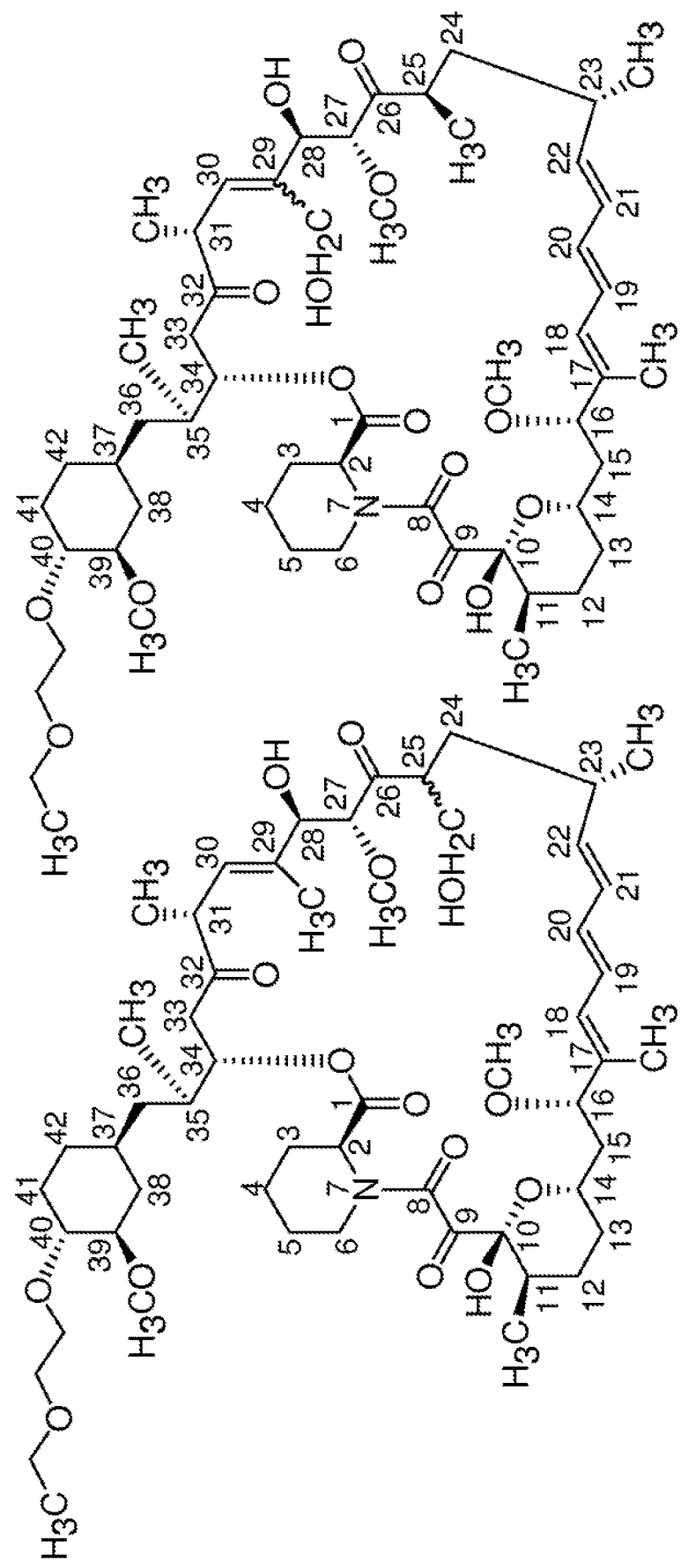
Figure 2D:
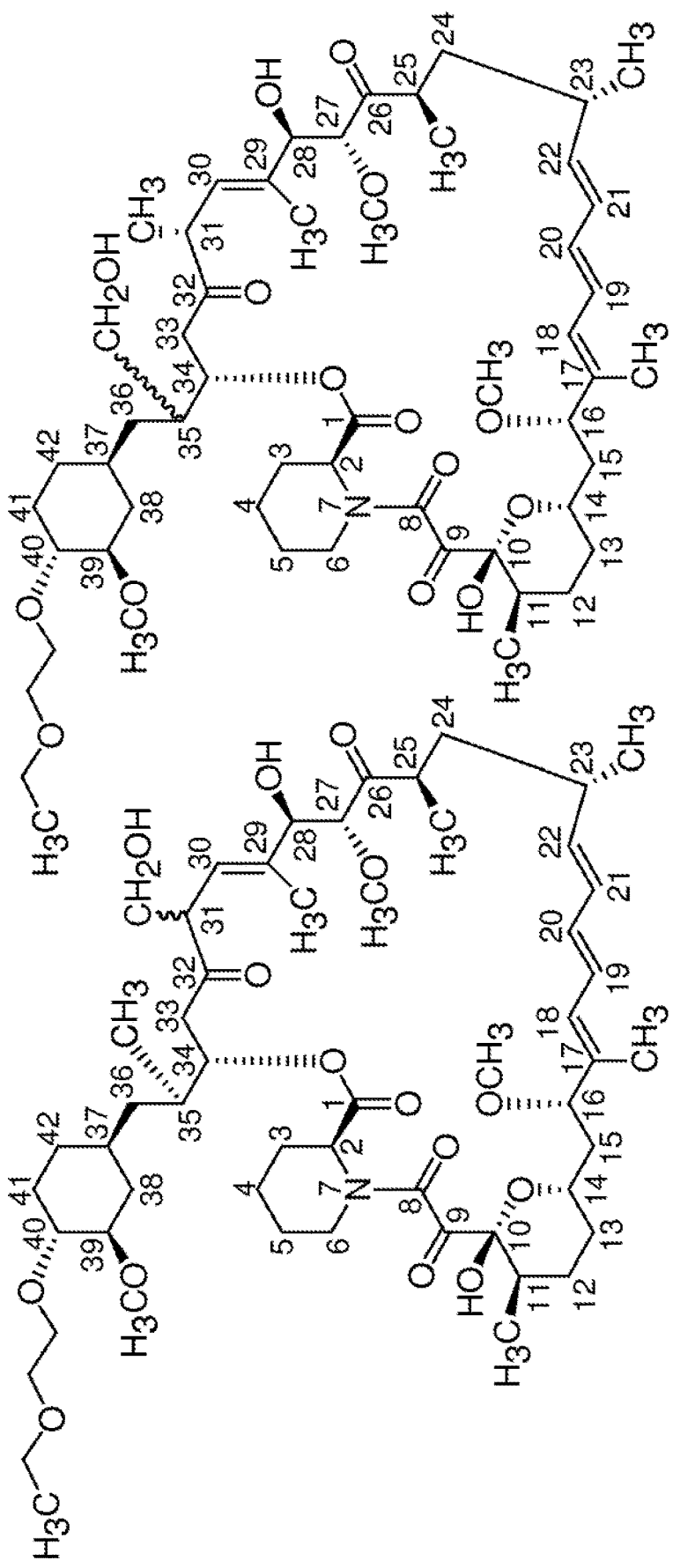
Figure 2D:
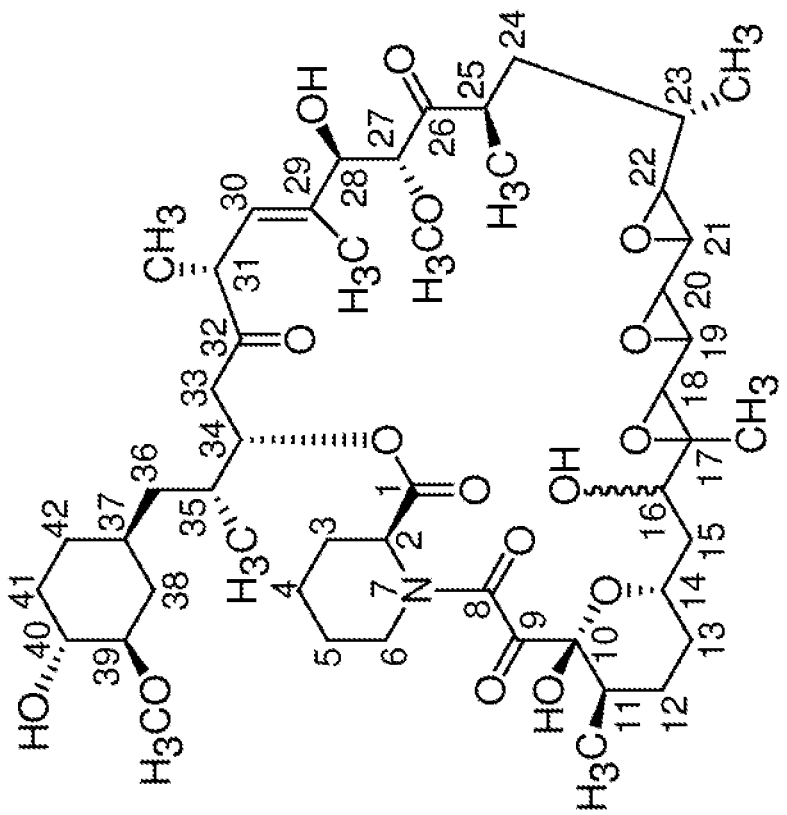
Figure 2D:
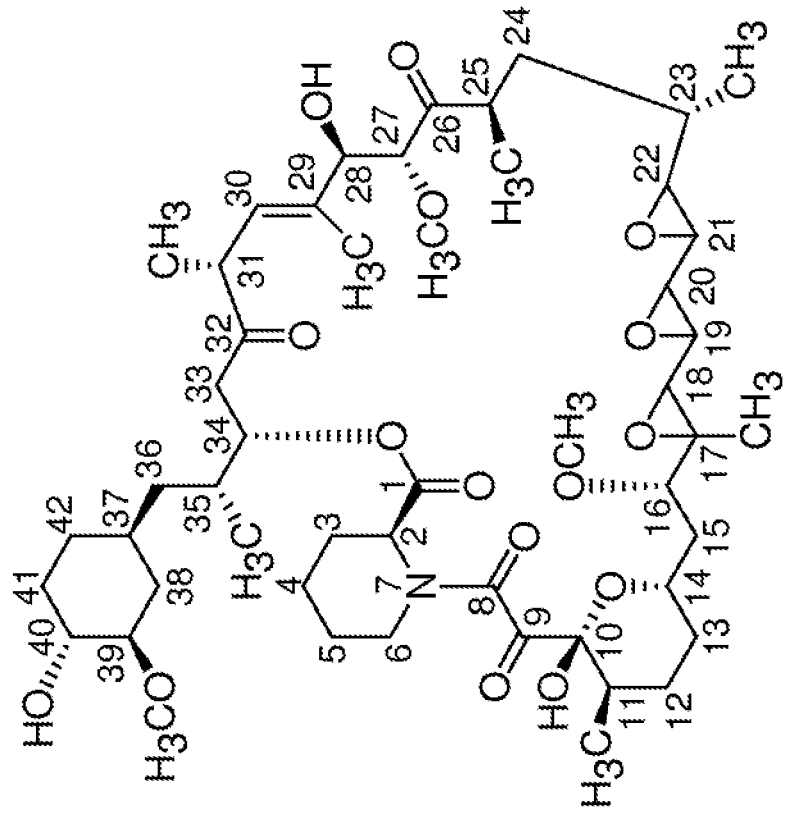
Figure 2D:
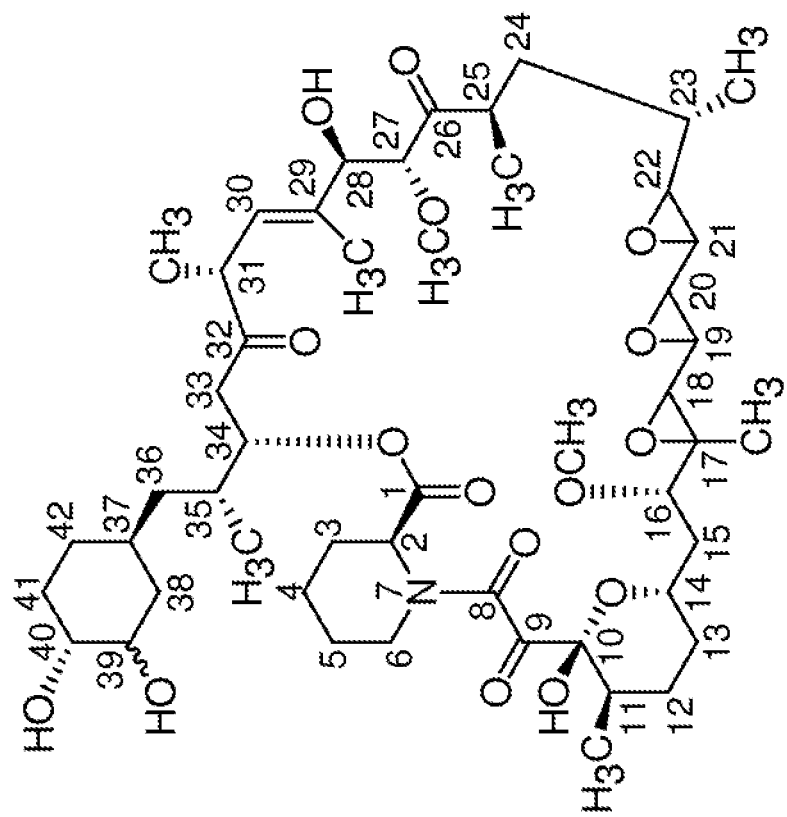
Figure 2D:
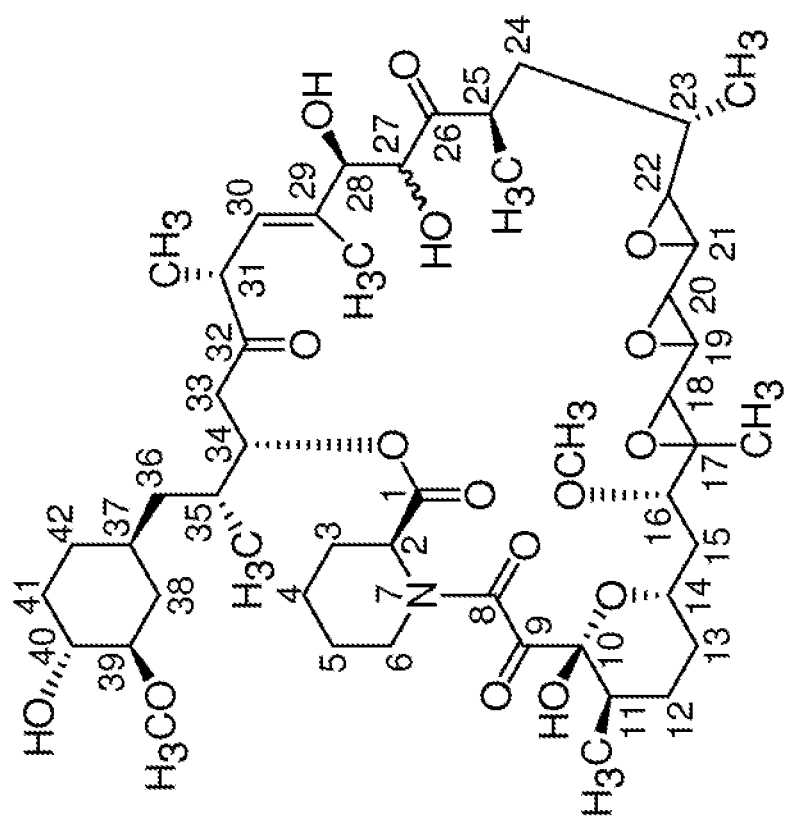
Figure 2D:
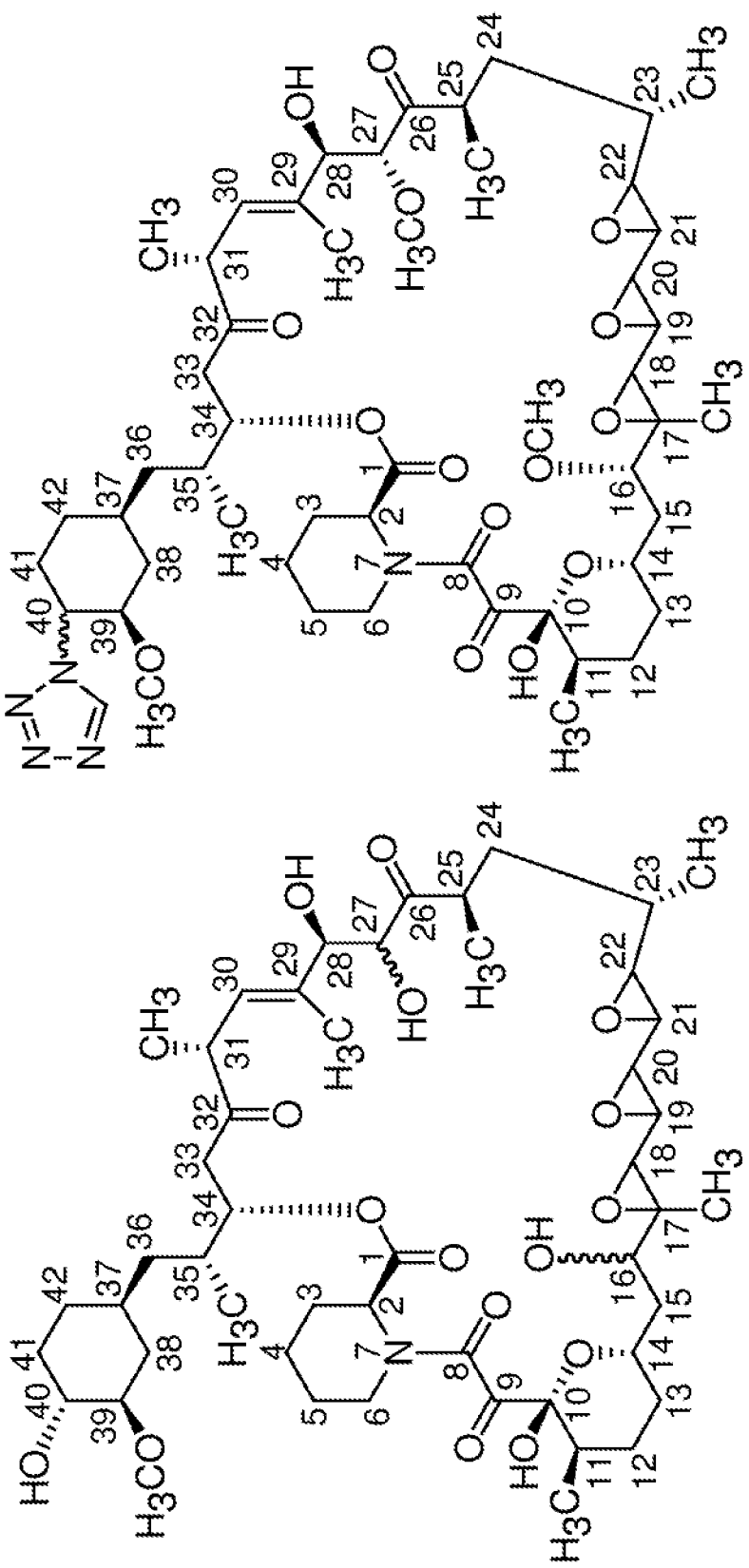
Figure 2E:
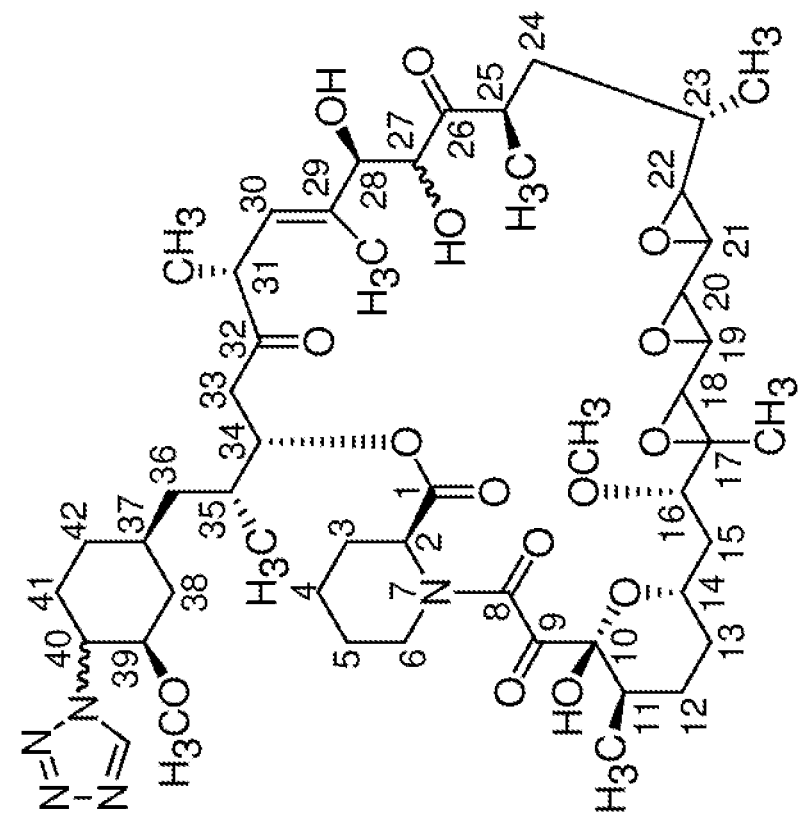
Figure 2E:
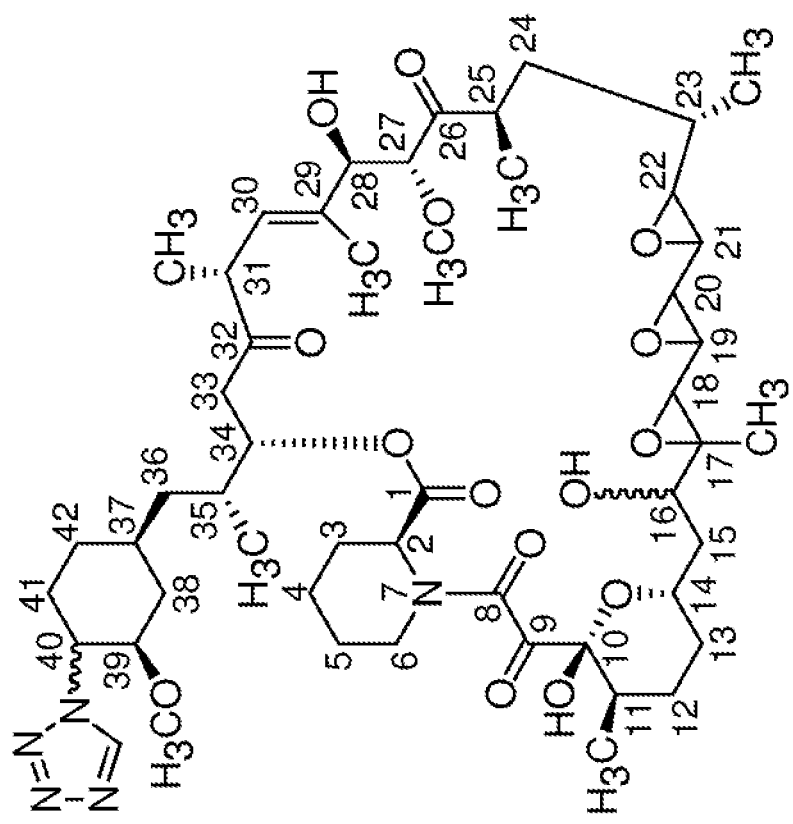
Figure 2E:
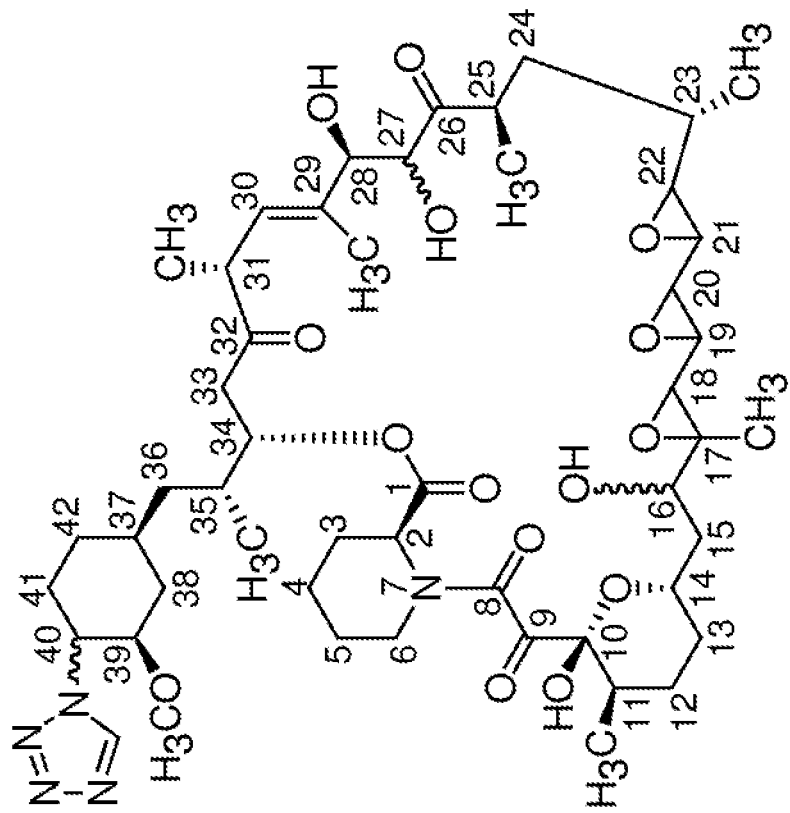
Figure 2E:
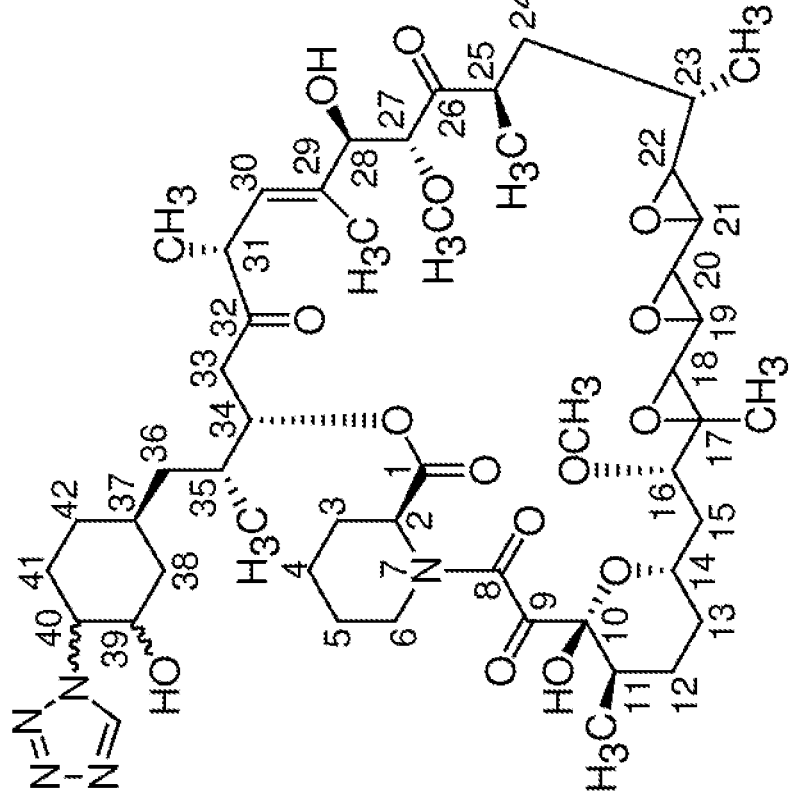
Figure 2E:
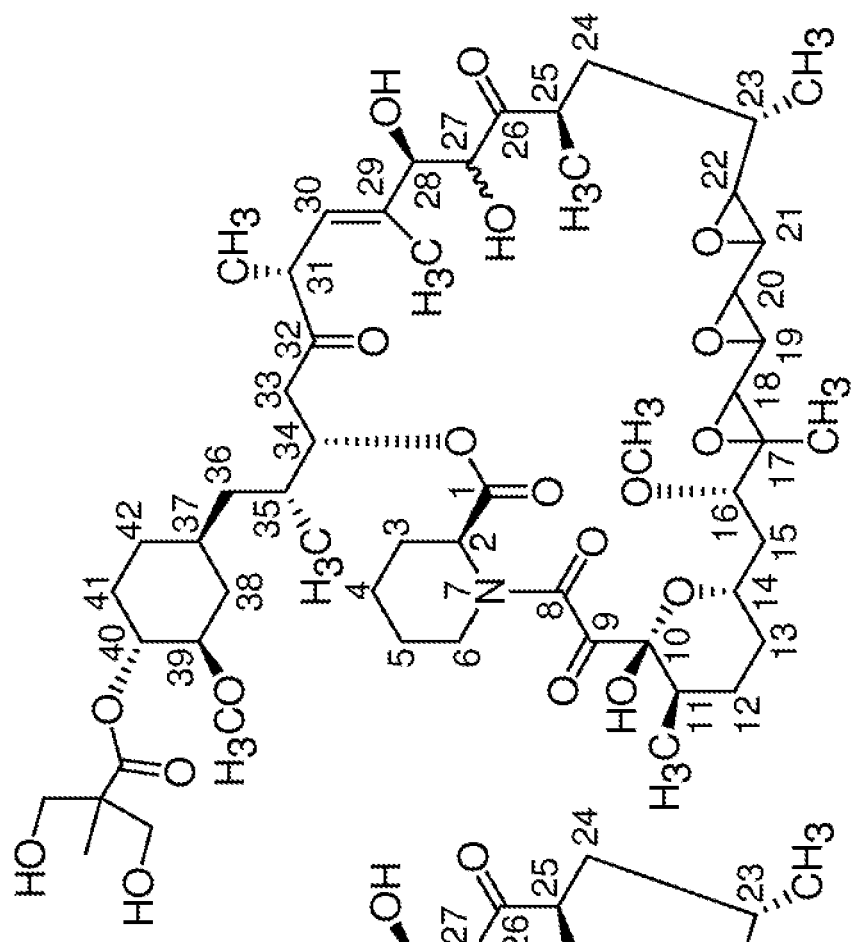
Figure 2E:
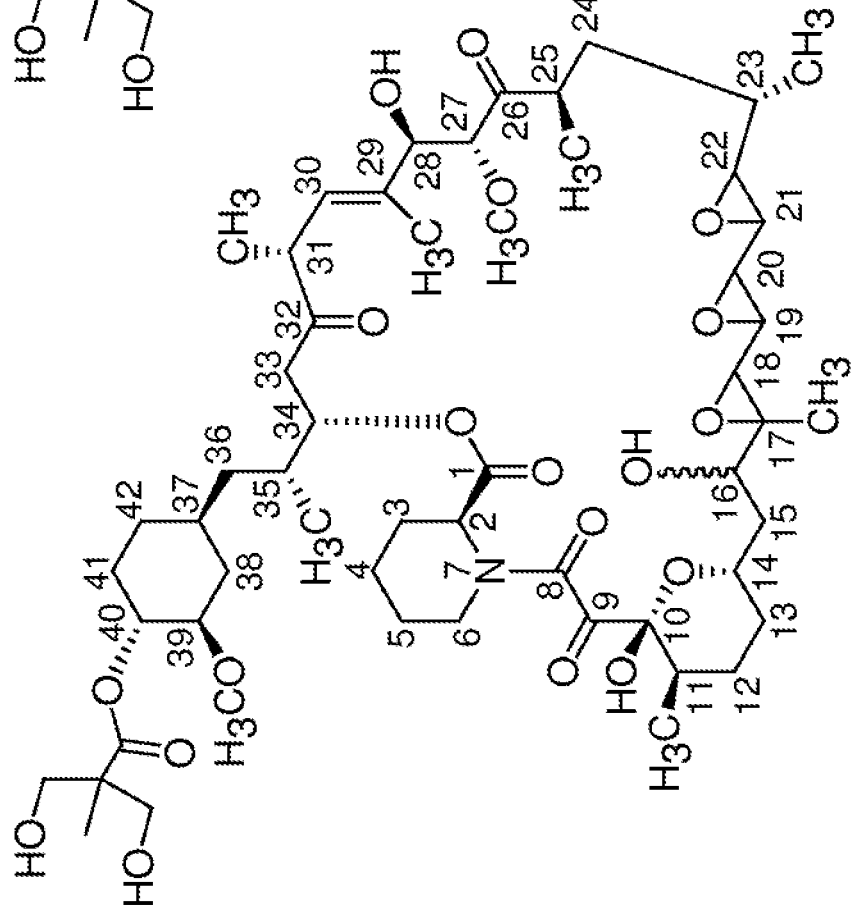
Figure 2E:
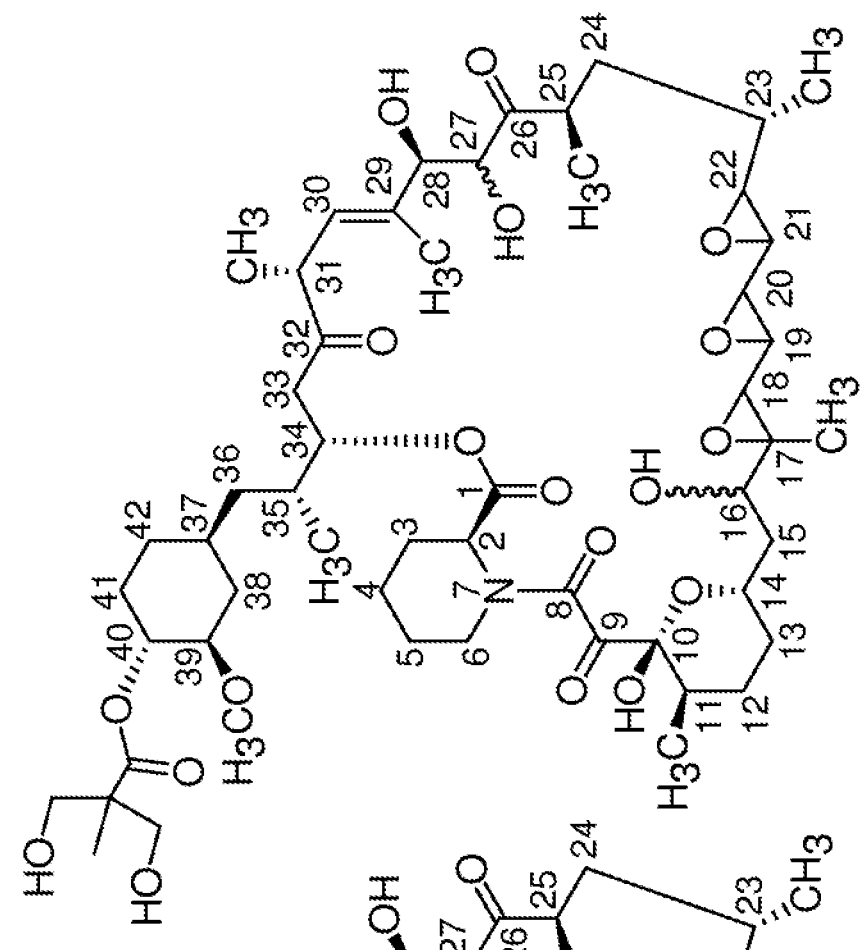
Figure 2E:
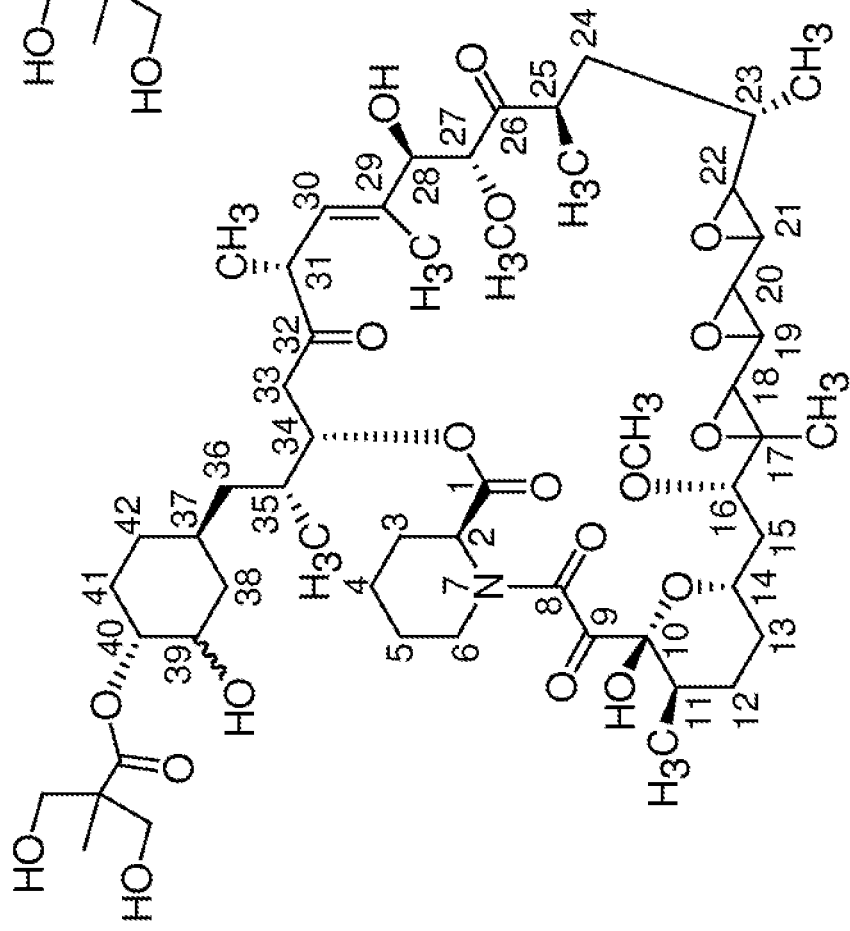
Figure 2E:
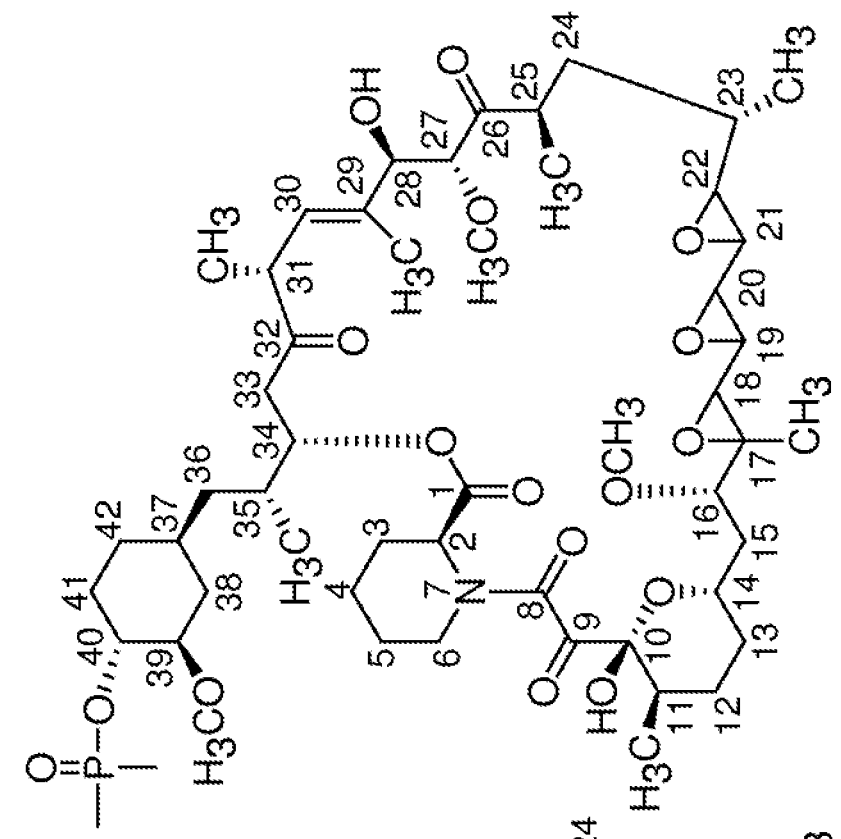
Figure 2E:
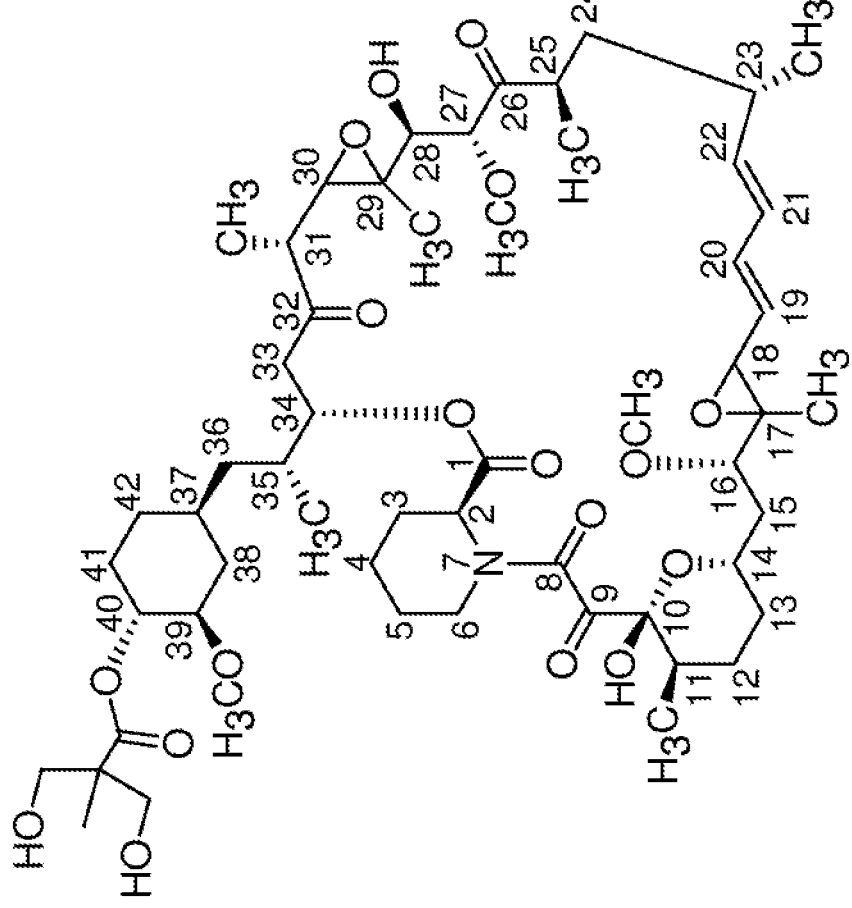
Figure 2E:
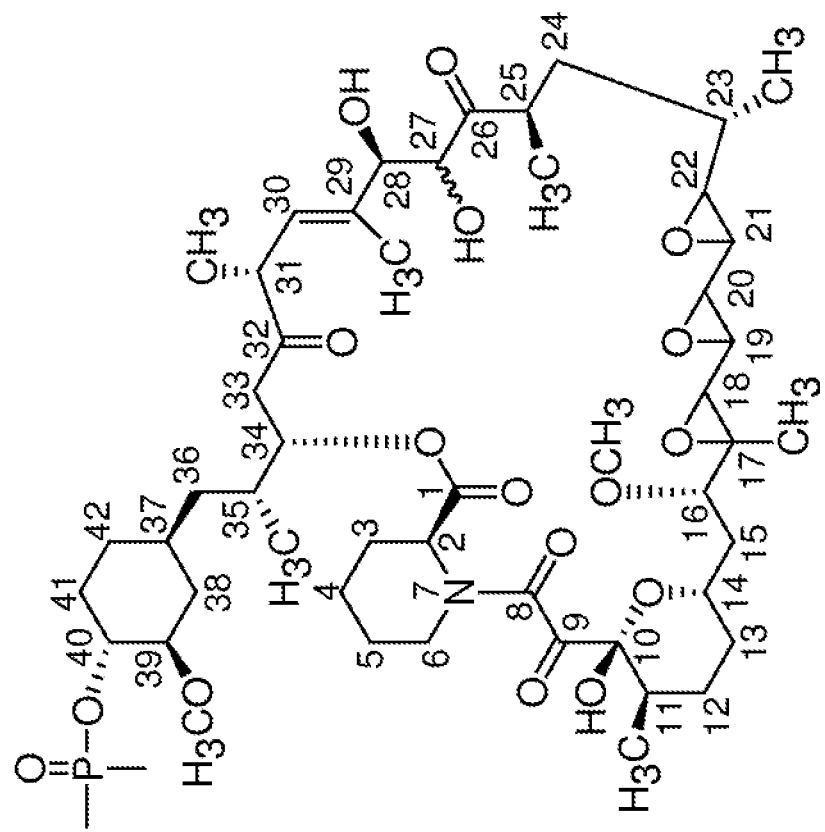
Figure 2E:
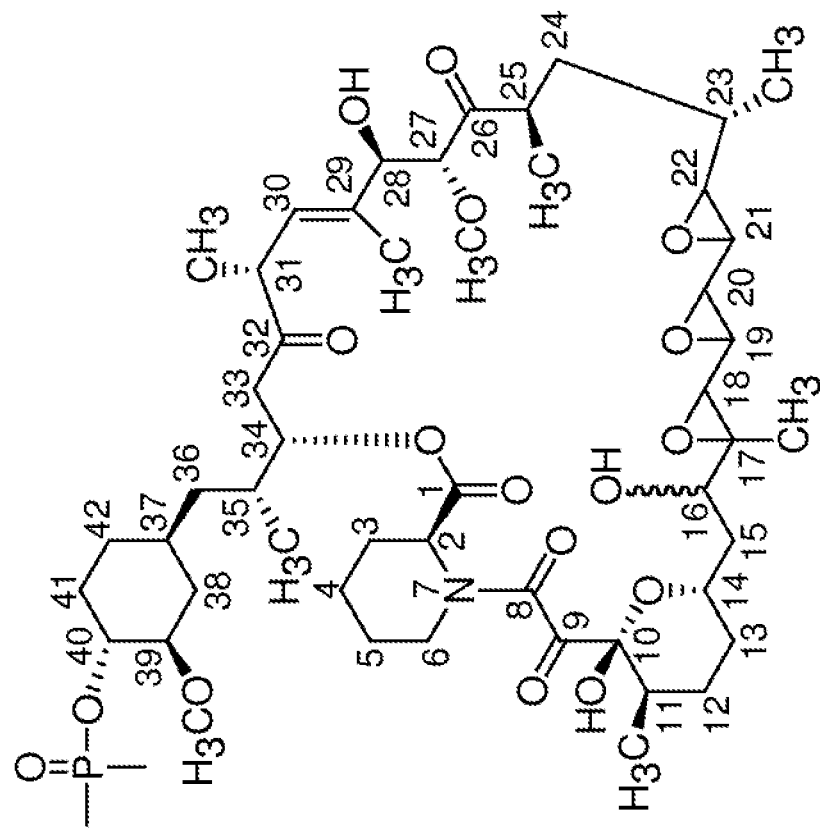
Figure 2E:
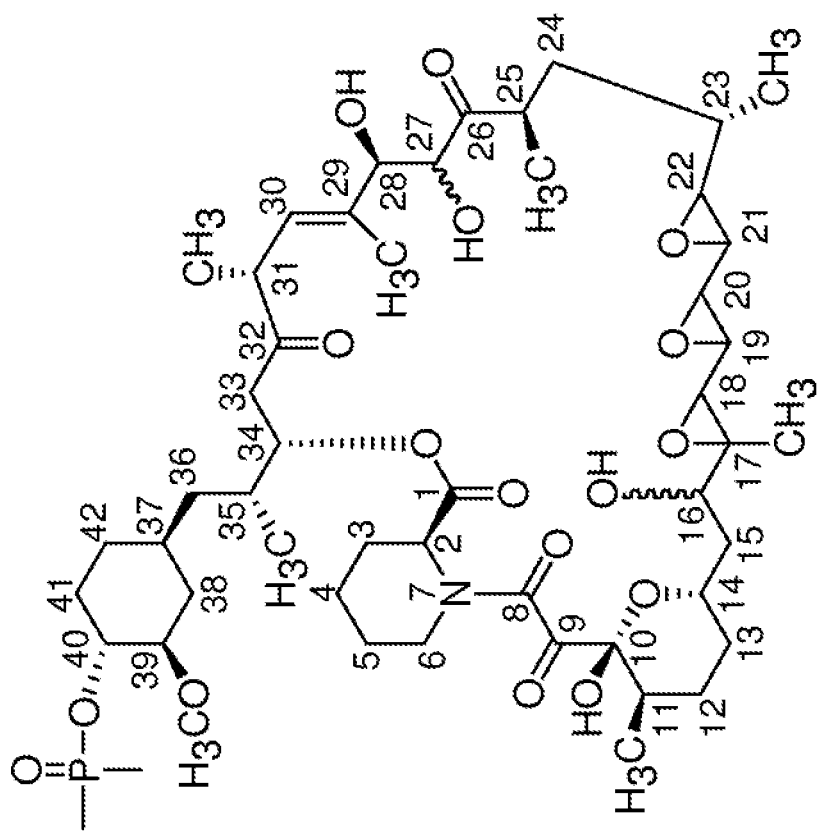
Figure 2E:
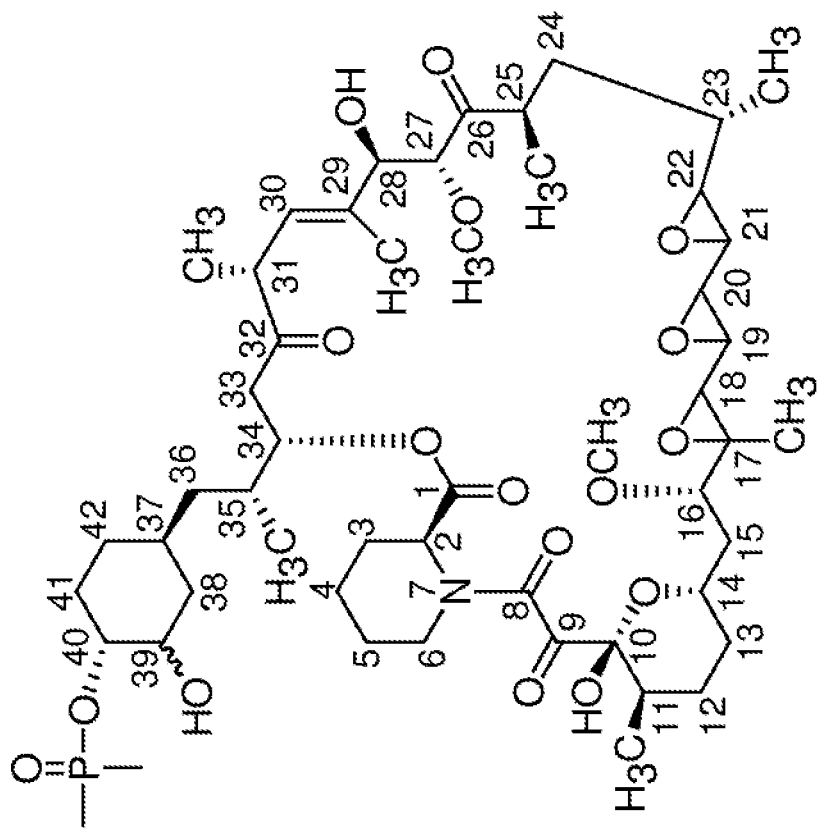
Figure 2E:
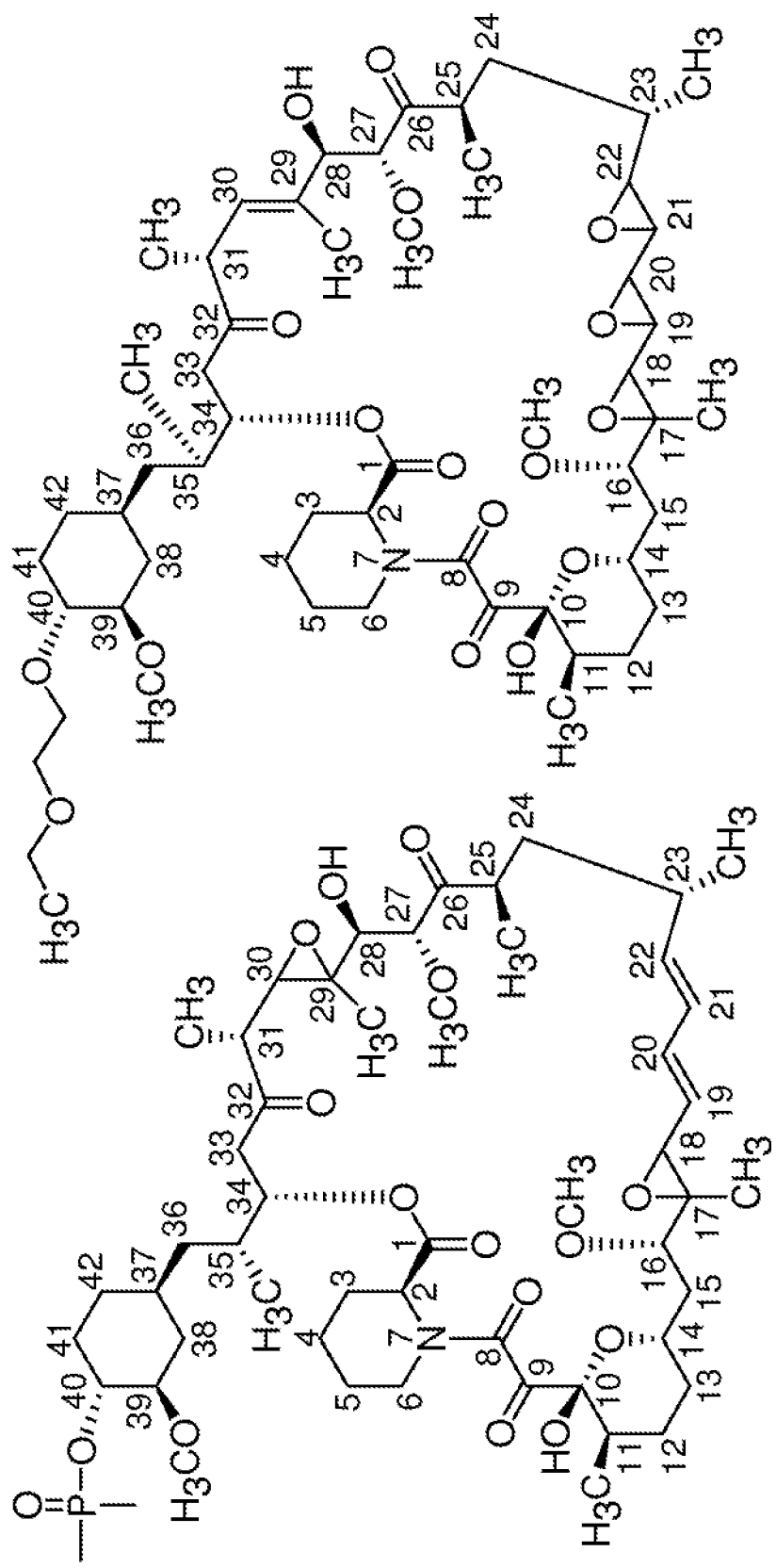
Figure 2E:
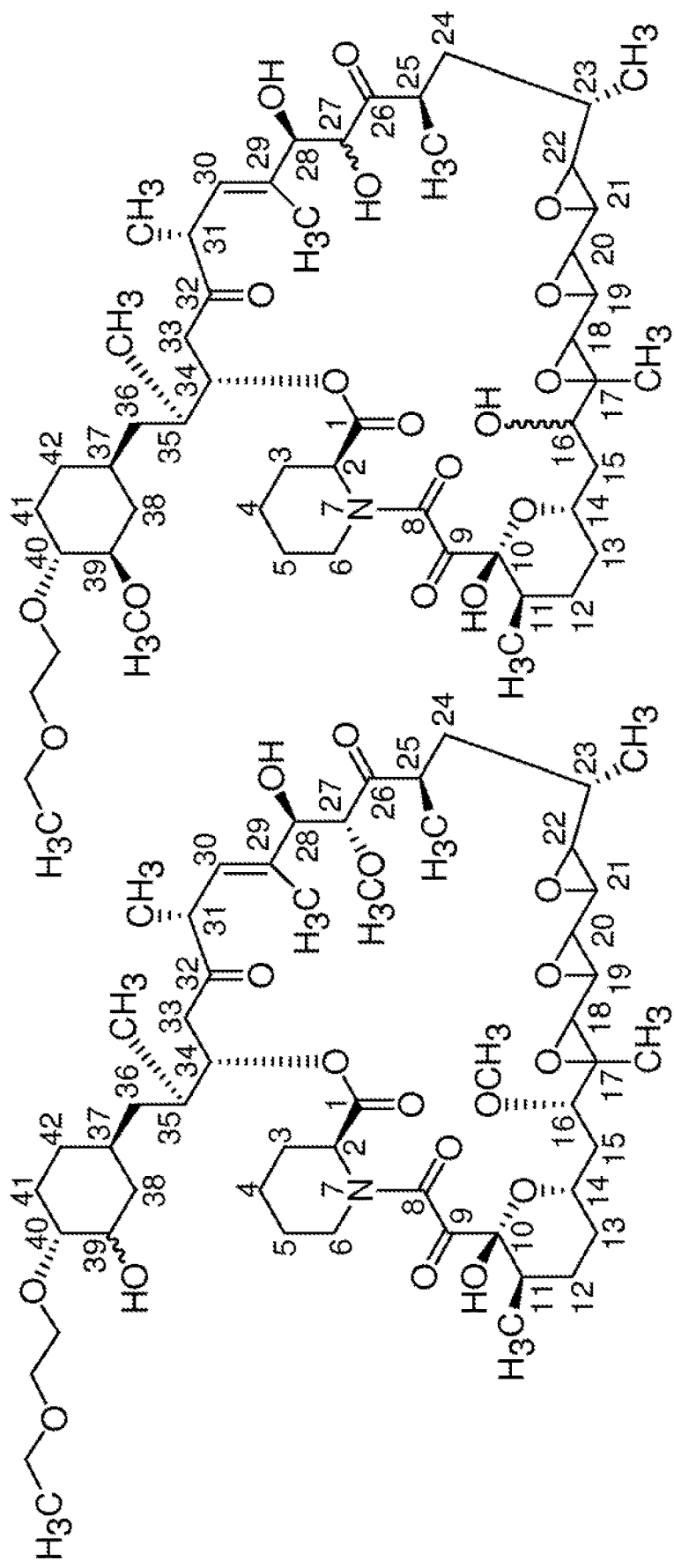
Figure 2E:
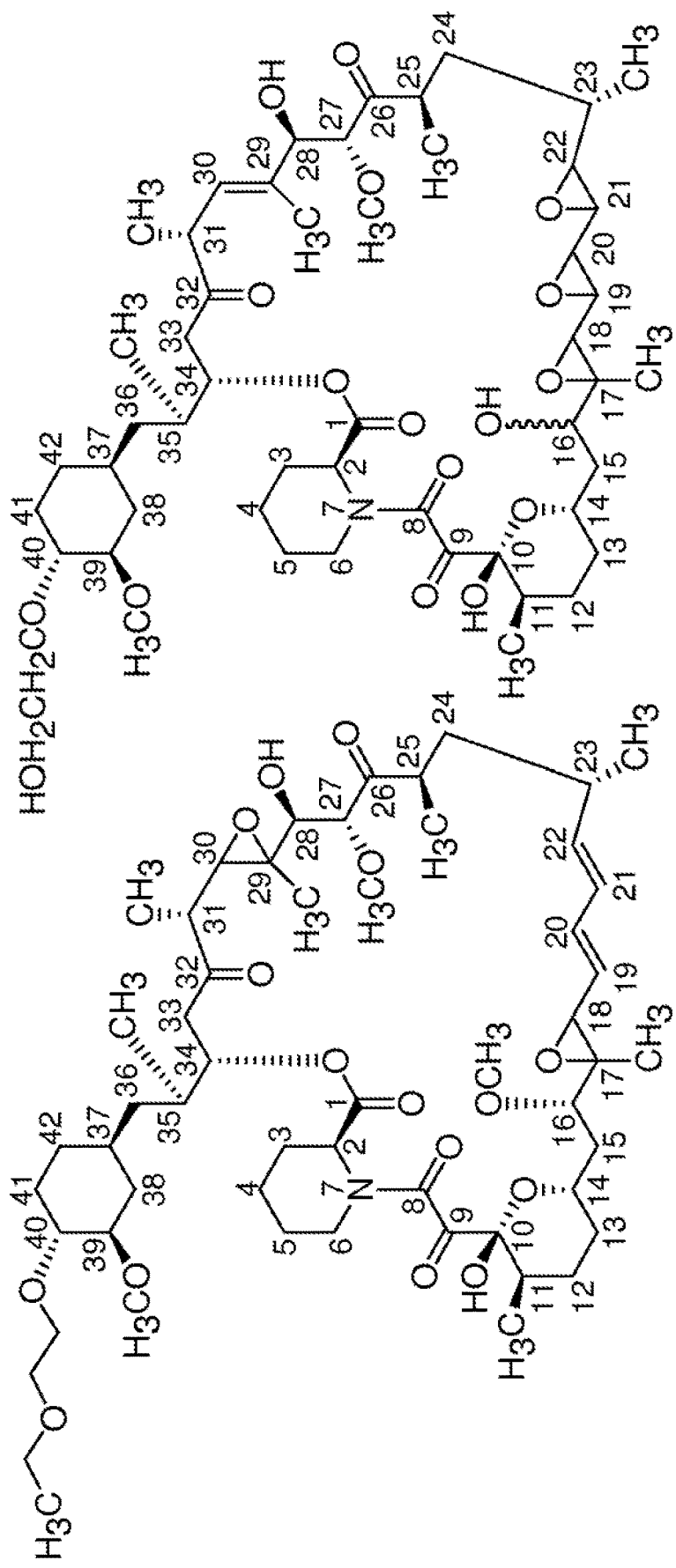
Figure 2E:
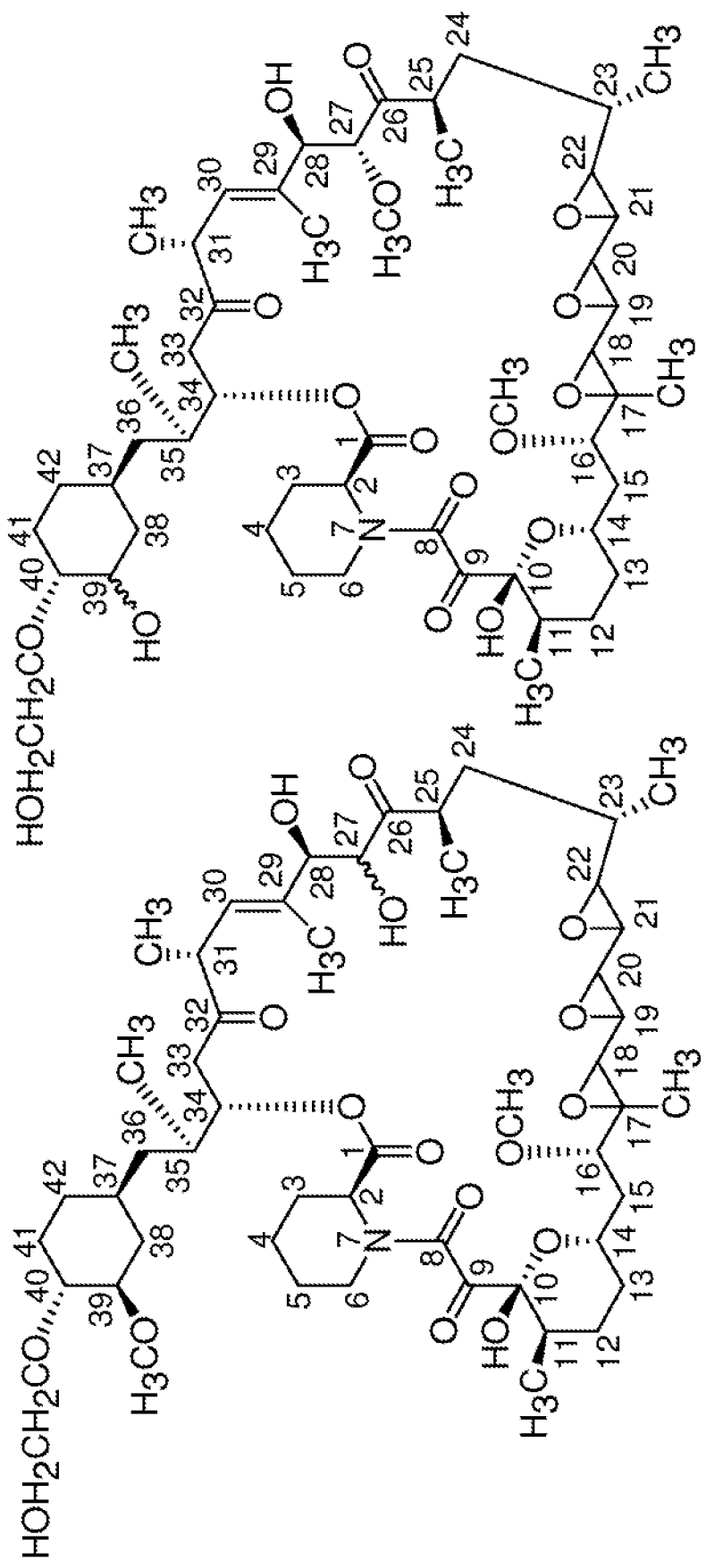
Figure 2F:
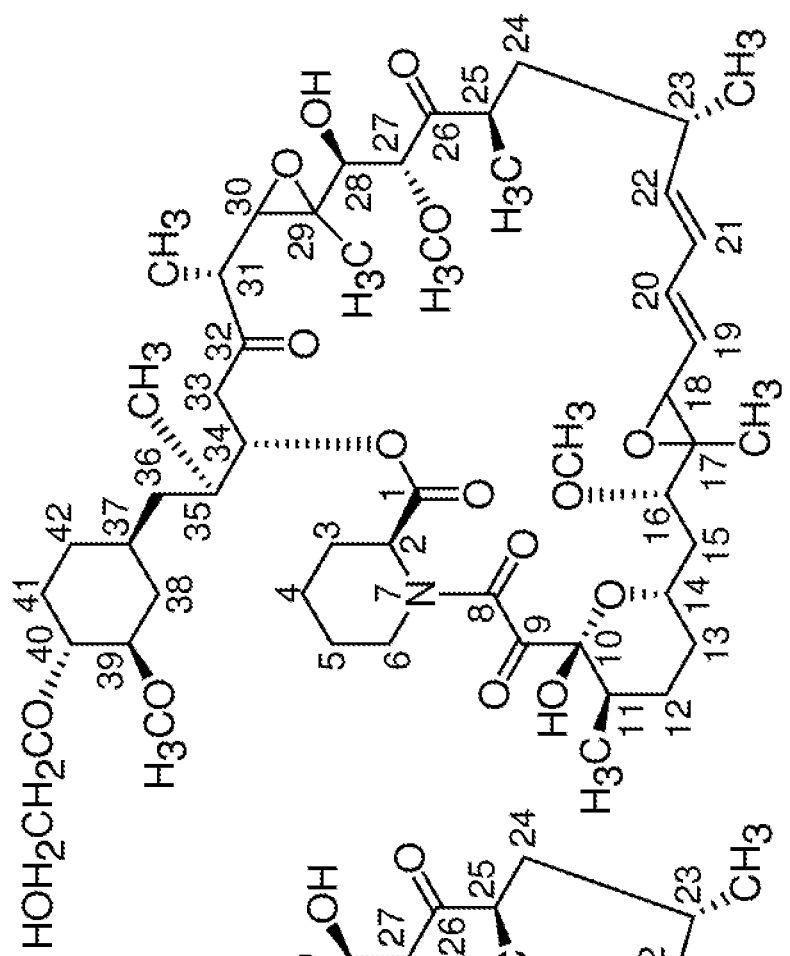
Figure 2F:
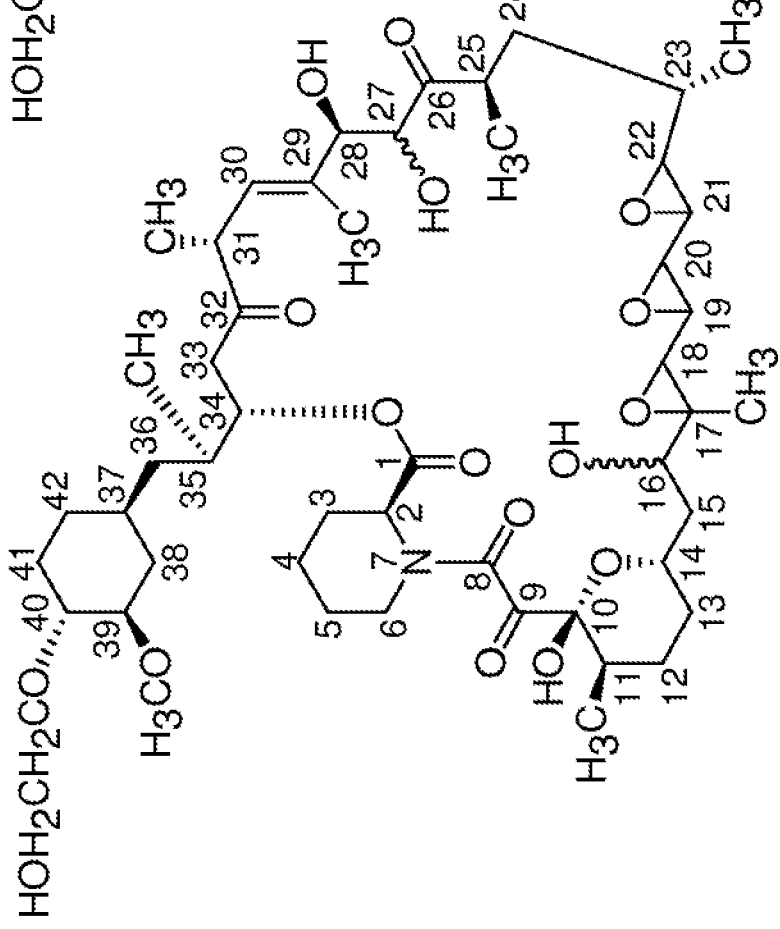
Figure 2F:
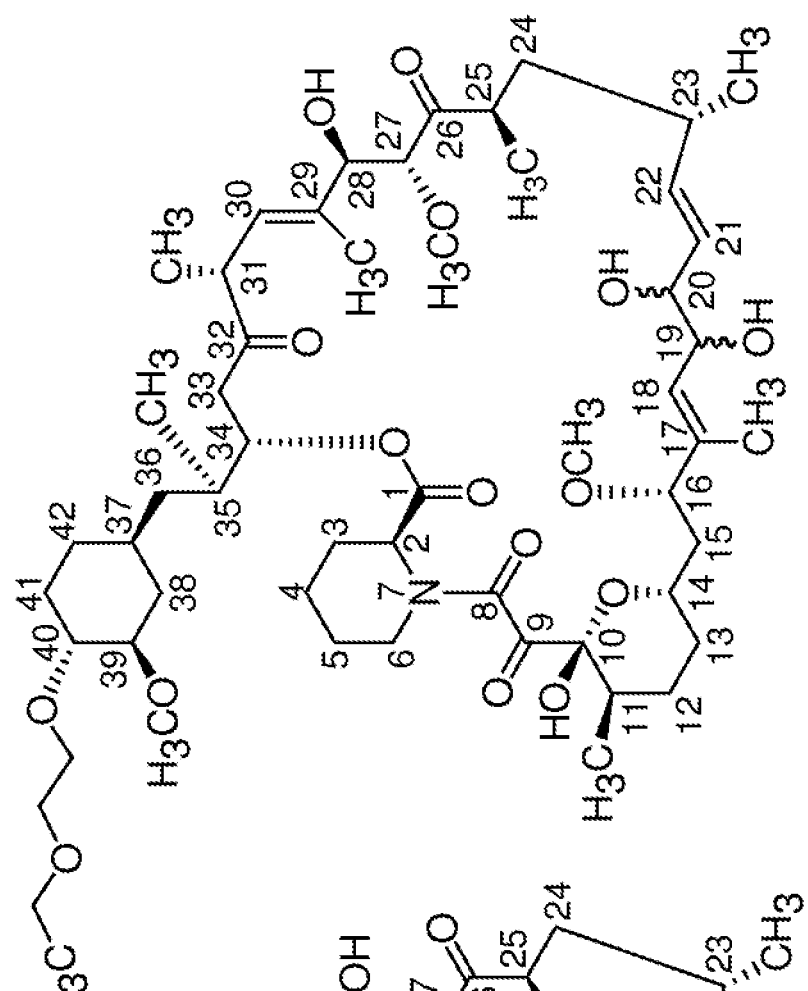
Figure 2F:
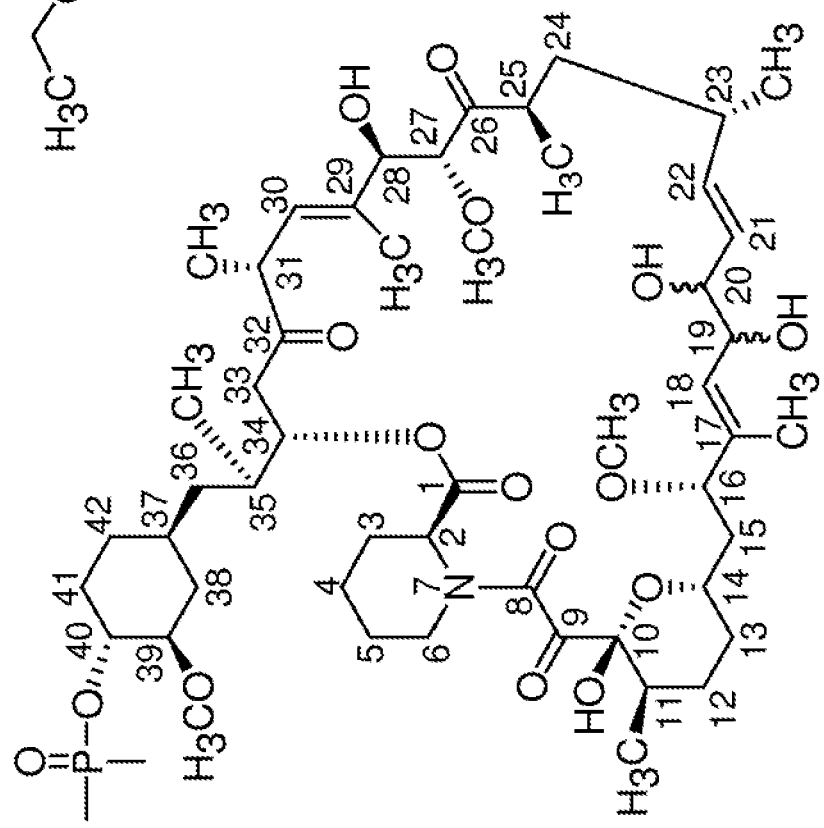
Figure 2F:
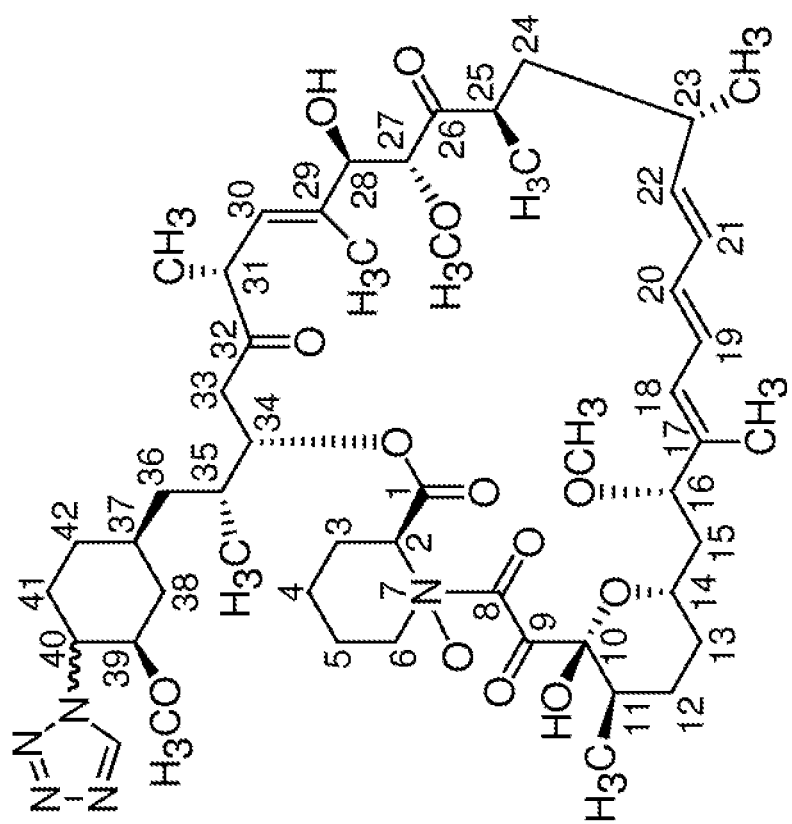
Figure 2F:
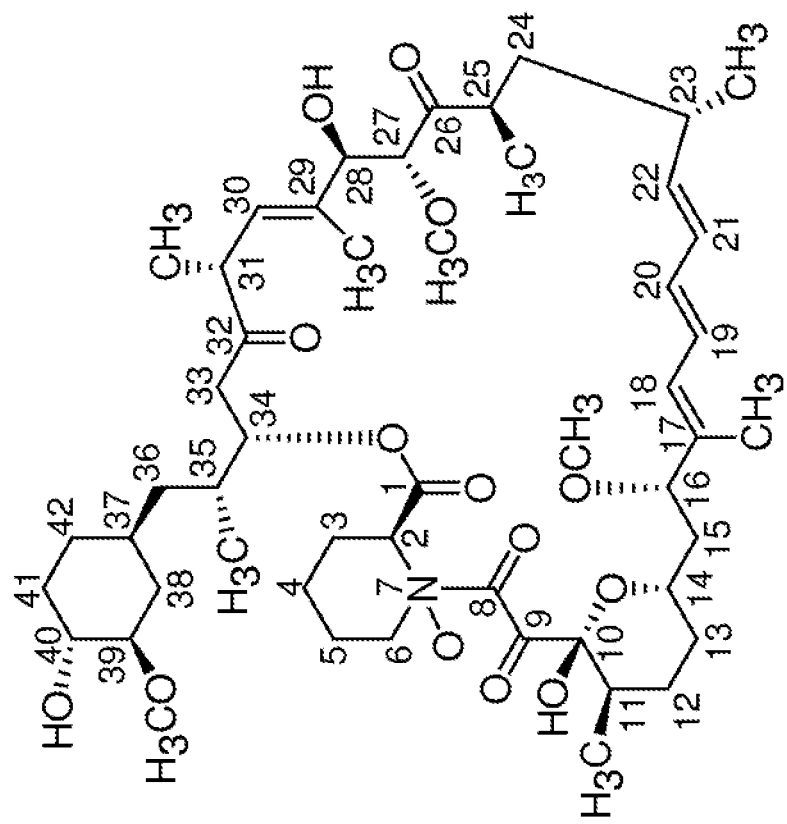
Figure 2F:
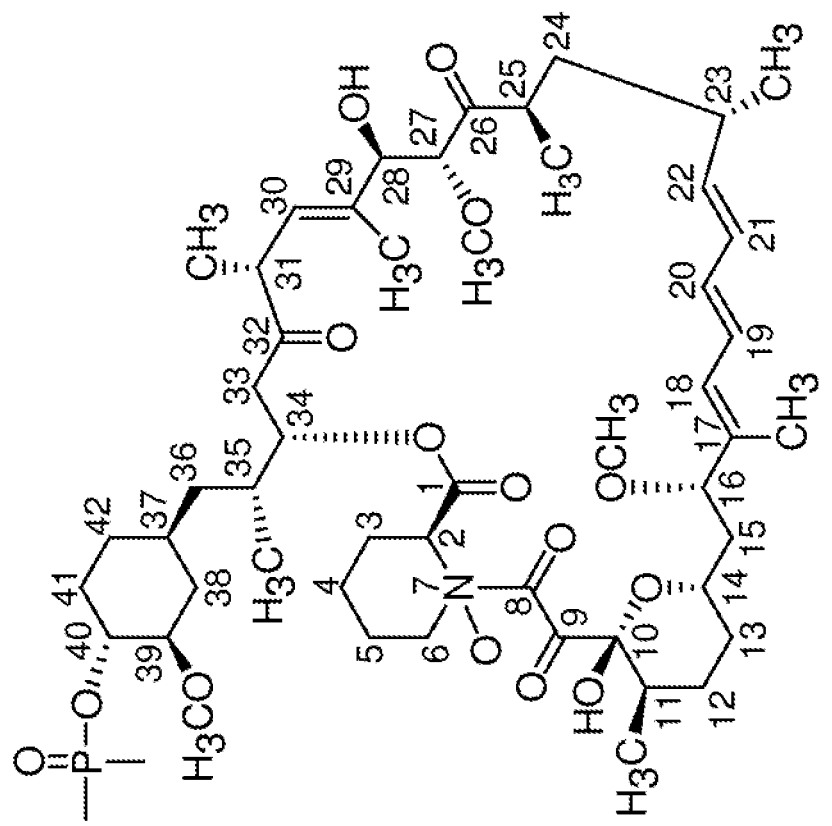
Figure 2F:
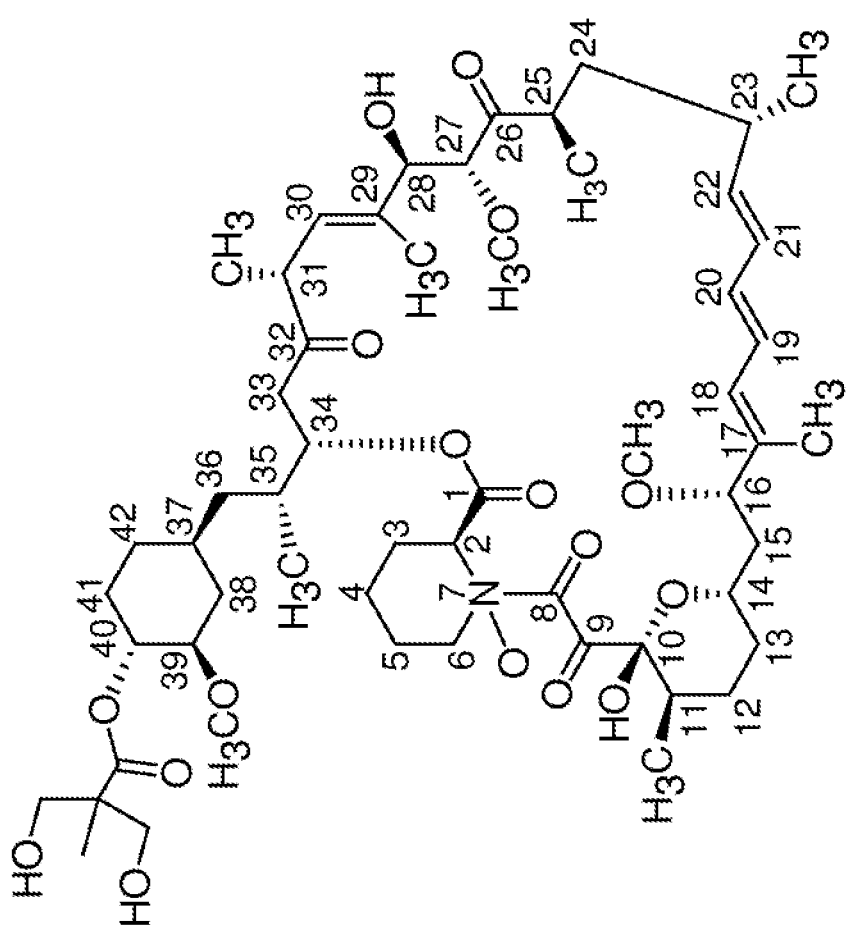
Figure 2F:
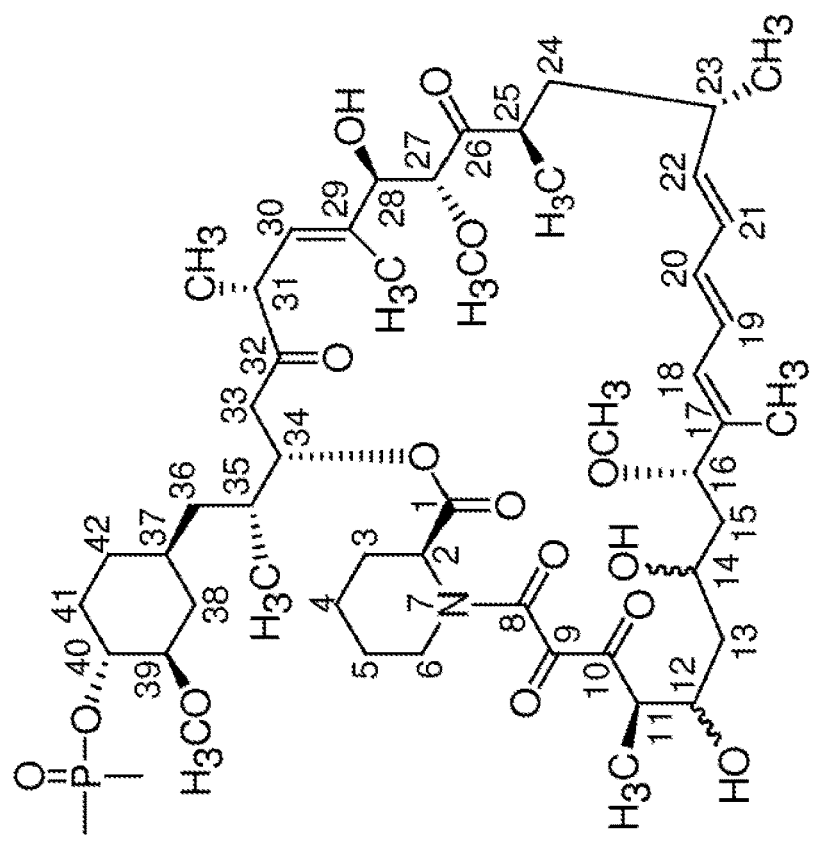
Figure 2F:
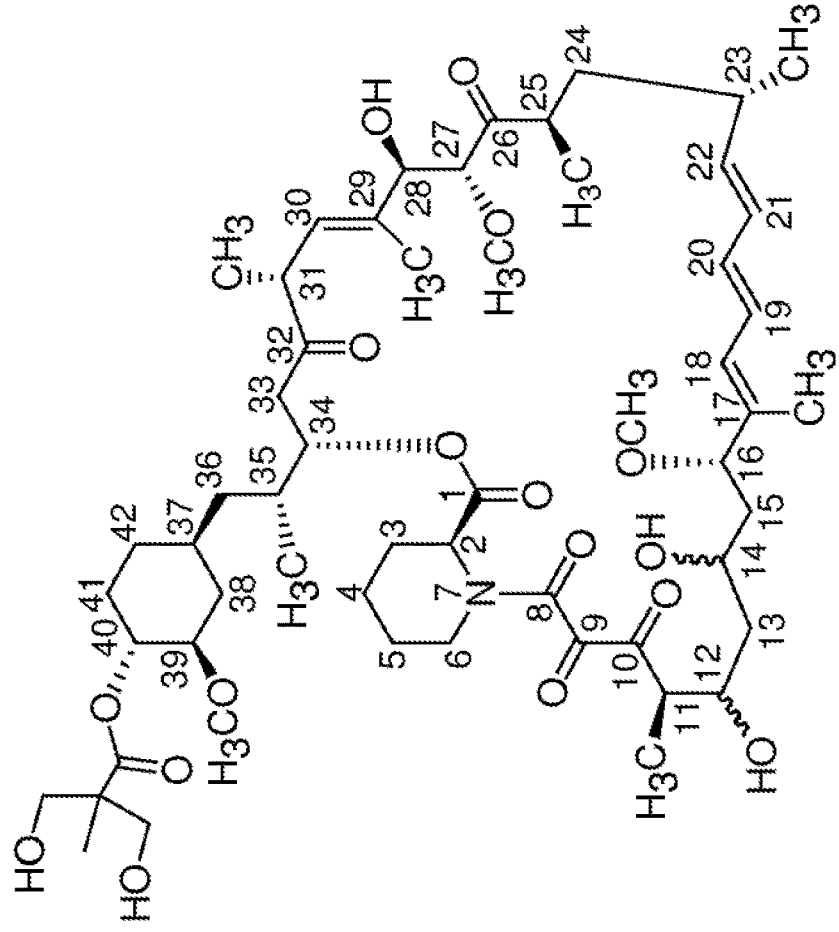
Figure 2F:
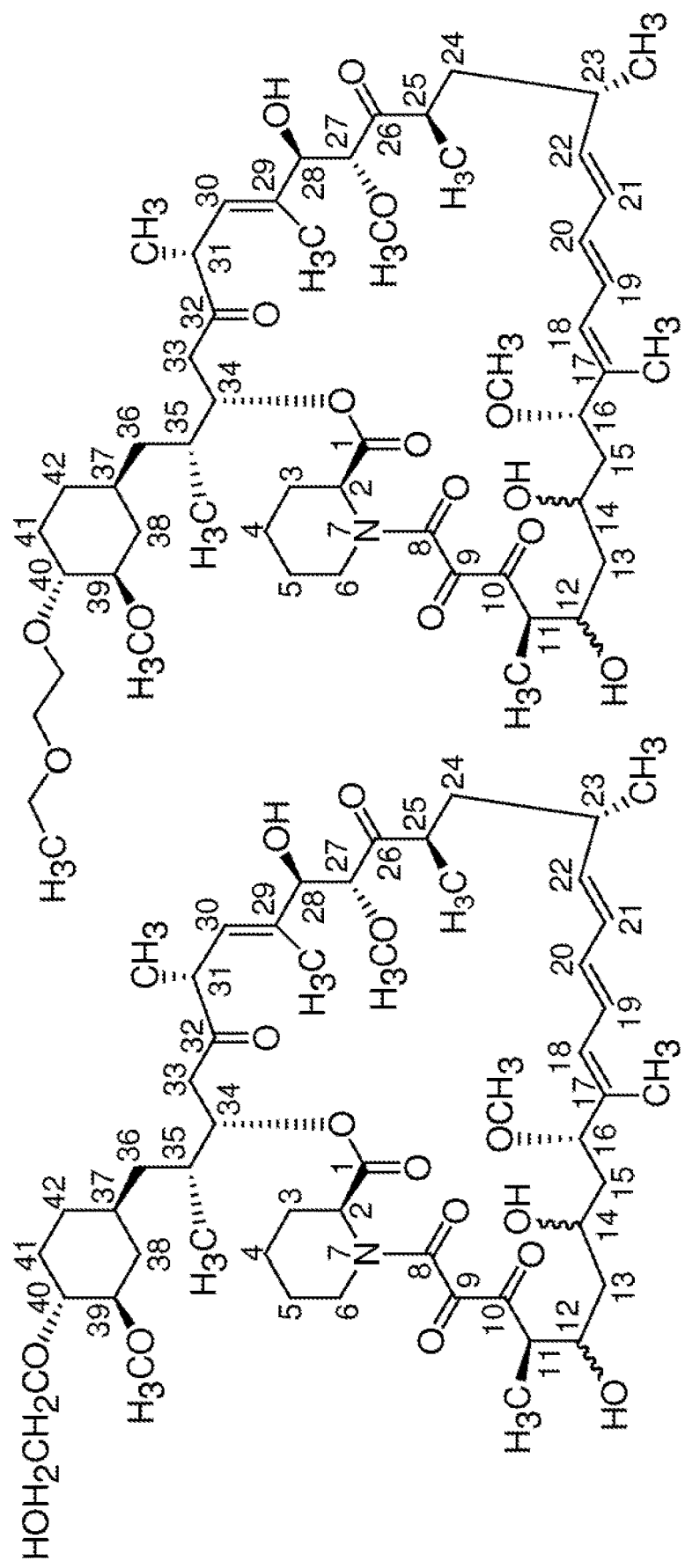
Figure 2F:
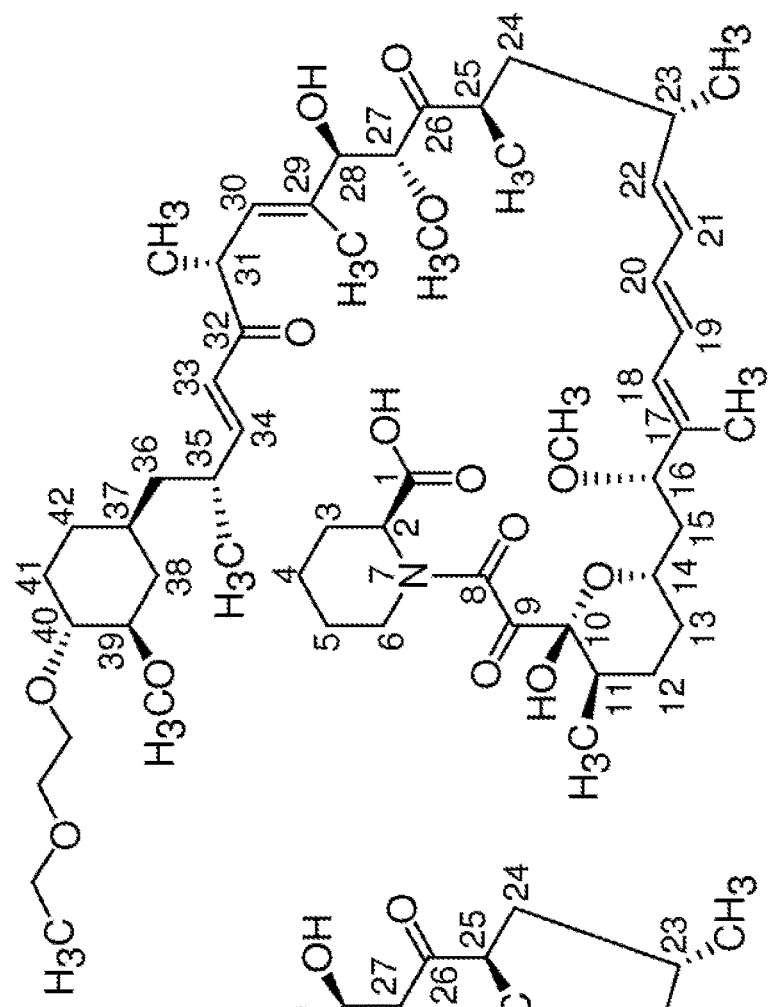
Figure 2F:
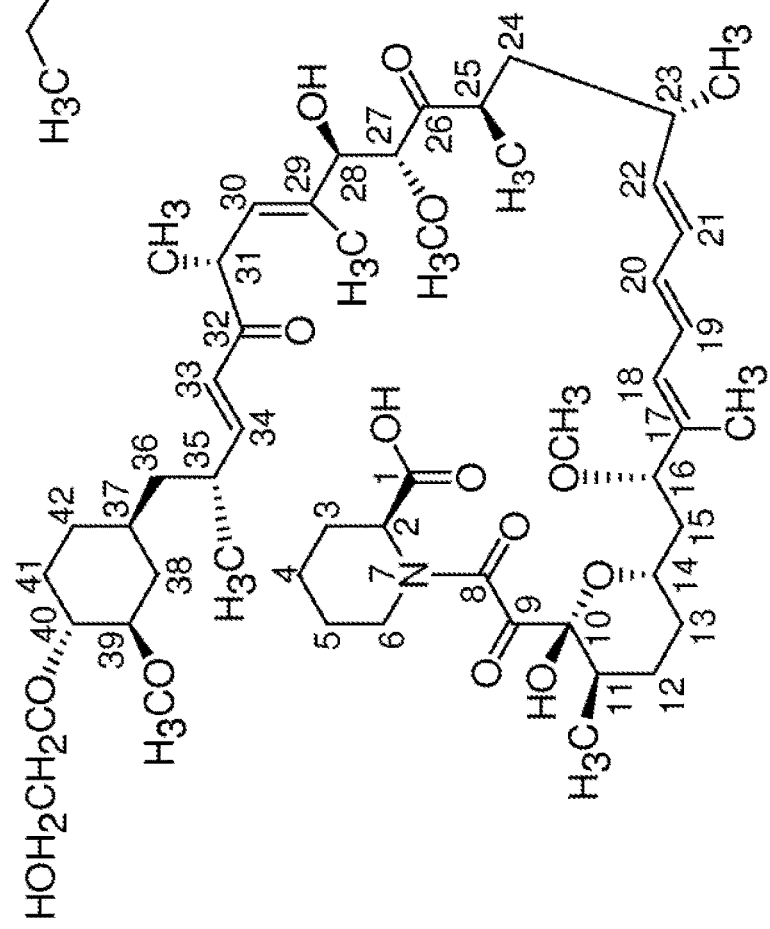

As used herein, the term "acid" refers to any chemical compound that, when dissolved in water, gives a solution with a pH less than 7.0. Acids are generally described as a compound which donates a hydrogen ion (H+) (Bronsted-Lowry) or as an electron-pair acceptor (Lewis acid). Acids useful in the present invention include, but are not limited to, HCl, $H_2SO_4$, $HNO_3$ and acetic acid. One of skill in the art will appreciate that other acids are useful in the present invention.

As used herein, "administering" refers to systemic and local administration or a combination thereof such as oral administration, administration as a suppository, topical contact, parenteral, intravascular, intravenous, intraperitoneal, intramuscular, intralesional, intranasal, pulmonary, mucosal, transdermal, subcutaneous administration, intrathecal, intraocular, intravitreal administration, delivery through a temporary device such as catheter, porous balloon, delivery through implant such as polymeric implant, osmotic pump, prosthesis such as drug eluting stents or others to the subject. One of skill in the art will appreciate that other modes and methods of administering the compounds of the present invention are useful in the present invention.

As used herein, the term "alkoxy" refers to alkyl with the inclusion of an oxygen atom, for example, methoxy, ethoxy, etc. "Halo-substituted-alkoxy" is as defined for alkoxy where some or all of the hydrogen atoms are substituted with halogen atoms. For example, halo-substituted-alkoxy includes trifluoromethoxy, etc. One of skill in the art will appreciate that other alkoxy groups are useful in the present invention.

As used herein, the term "alkyl" refers to a straight or branched, saturated, aliphatic radical having the number of carbon atoms indicated. For example, $C_1$-$C_6$ alkyl includes, but is not limited to, methyl, ethyl, propyl, butyl, pentyl, hexyl, iso-propyl, iso-butyl, sec-butyl, tert-butyl, etc. One of skill in the art will appreciate that other alkyl groups are useful in the present invention.

As used herein, the term "hydroxyalkyl" refers to alkyl as defined above where at least one of the hydrogen atoms is substituted with a hydroxy group. For example, hydroxyalkyl includes hydroxy-methyl, hydroxy-ethyl (1- or 2-), hydroxy-propyl (1-, 2- or 3-), hydroxy-butyl (1-, 2-, 3- or 4-), hydroxy-pentyl (1-, 2-, 3-, 4- or 5-), hydroxy-hexyl (1-, 2-, 3-, 4-, 5- or 6-), 1,2-dihydroxyethyl, and the like. One of skill in the art will appreciate that other hydroxyalkyl groups are useful in the present invention.

As used herein, the term "body lumen" refers to the lining or cavity of an artery, vein or an organ.

As used herein, the term "contacting" refers to the process of bringing into contact at least two distinct species such that they can react. It should be appreciated, however, that the resulting reaction product can be produced directly from a reaction between the added reagents or from an intermediate from one or more of the added reagents which can be produced in the reaction mixture.

As used herein, the term "hydrate" refers to a compound that is complexed to at least one water molecule. The compounds of the present invention can be complexed with from 1 to 100 water molecules.

As used herein, the term "implant" refers to a medical device inserted into a body in order to treat a condition. Implants include, but are not limited to, drug-eluting devices.

As used herein, the terms "inhibition", "inhibits" and "inhibitor" refer to a compound that prohibits, reduces, diminishes or lessens, or to a method of prohibiting, reducing, diminishing or lessening a specific action or function.

As used herein, the term "intracorporeal" refers to an mammalian body.

As used herein, the term "isomer" refers to compounds of the present invention that possess asymmetric carbon atoms (optical centers) or double bonds, the racemates, diastereomers, enantiomers, geometric isomers, structural isomers and individual isomers are all intended to be encompassed within the scope of the present invention.

As used herein, the term "organ" refers to any organ of a mammal, such as, but not limited to, heart, lungs, brain, eye, stomach, spleen, bones, pancreas, kidneys, liver, intestines, uterus, colon, ovary, blood, skin, muscle, tissue, prostate, mammary and bladder. One of skill in the art will appreciate that other organs are useful in the present invention.

As used herein, the term "peracid" refers to an acid in which an acidic —OH group has been replaced by an —OOH group. Peracids can be peroxy-carboxylic acids of the formula R—C(O)—OOH, where the R group can be groups such as H, alkyl, alkene or aryl. Peracids include, but are not limited to, peroxy-acetic acid and meta-chloroperoxybenzoic acid (MCPBA). One of skill in the art will appreciate that other peracids are useful in the present invention.

As used herein, the term "peroxide" refers to a compound containing an oxygen-oxygen single bond. Examples of peroxides include, but are not limited to, hydrogen peroxide. One of skill in the art will appreciate that other peroxides are useful in the present invention.

As used herein, the term "pharmaceutically acceptable excipient" refers to a substance that aids the administration of an active agent to and absorption by a subject. Pharmaceutical excipients useful in the present invention include, but are not limited to, polymers, solvents, antioxidants, binders, fillers, disintegrants, lubricants, coatings, sweeteners, flavors, stabilizers, colorants, metals, ceramics and semi-metals. See below for additional discussion of pharmaceutically acceptable excipients. One of skill in the art will recognize that other pharmaceutical excipients are useful in the present invention.

As used herein, the term "polymer" refers to a molecule composed of repeating structural units, or monomers, connected by covalent chemical bonds. Polymers useful in the present invention are described below. One of skill in the art will appreciate that other polymers are useful in the present invention.

As used herein, the term "prodrug" refers to compounds which are capable of releasing the active agent of the methods of the present invention, when the prodrug is administered to a mammalian subject. Release of the active ingredient occurs in vivo. Prodrugs can be prepared by techniques known to one skilled in the art. These techniques generally modify appropriate functional groups in a given compound. These modified functional groups however regenerate original functional groups by routine manipulation or in vivo. Prodrugs of the active agents of the present invention include active agents wherein a hydroxy, amidino, guanidino, amino, carboxylic or a similar group is modified.

As used herein, the term "salt" refers to acid or base salts of the compounds used in the methods of the present invention. Illustrative examples of pharmaceutically acceptable salts are mineral acid (hydrochloric acid, hydrobromic acid, phosphoric acid, and the like) salts, organic acid (acetic acid, propionic acid, glutamic acid, citric acid and the like) salts, quaternary ammonium (methyl iodide, ethyl iodide, and the like) salts. Additional information on suitable pharmaceutically acceptable salts can be found in Remington's Pharmaceutical Sciences, 17th ed., Mack Publishing Company, Easton, Pa., 1985, which is incorporated herein by reference.

Pharmaceutically acceptable salts of the acidic compounds of the present invention are salts formed with bases, namely cationic salts such as alkali and alkaline earth metal salts, such as sodium, lithium, potassium, calcium, magnesium, as well as ammonium salts, such as ammonium, trimethyl-ammonium, diethylammonium, and tris-(hydroxymethyl)-methyl-ammonium salts.

Similarly acid addition salts, such as of mineral acids, organic carboxylic and organic sulfonic acids, e.g., hydrochloric acid, methanesulfonic acid, maleic acid, are also possible provided a basic group, such as pyridyl, constitutes part of the structure.

The neutral forms of the compounds may be regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the present invention.

As used herein, the term "source" refers to a location on the device of the present invention providing a supply of the compound of the present invention or a supply of a therapeutic agent. The device of the present invention can have more than one source, such as a first and second. Each source can have a different compound and composition and be used to treat a different indication.

As used herein, the term "subject" refers to animals such as mammals, including, but not limited to, primates (e.g., humans), cows, sheep, goats, horses, pigs, dogs, cats, rabbits, rats, mice and the like. In certain embodiments, the subject is a human.

As used herein, the term "therapeutic agent" refers to any agent, compound or biological molecule that has a therapeutic effect on the patient to whom the therapeutic agent is administered.

As used herein, the terms "therapeutically effective amount or dose" or "therapeutically sufficient amount or dose" or "effective or sufficient amount or dose" refer to a dose that produces therapeutic effects for which it is administered. The exact dose will depend on the purpose of the treatment, and will be ascertainable by one skilled in the art using known techniques (see, e.g., Lieberman, *Pharmaceutical Dosage Forms* (vols. 1-3, 1992); Lloyd, *The Art, Science and Technology of Pharmaceutical Compounding* (1999); Pickar, *Dosage Calculations* (1999); and *Remington: The Science and Practice of Pharmacy,* 20th Edition, 2003, Gennaro, Ed., Lippincott, Williams & Wilkins). In sensitized cells, the therapeutically effective dose can often be lower than the conventional therapeutically effective dose for non-sensitized cells.

As used herein, the term "vascular prosthesis" refers to a prosthesis for the circulatory system of a mammal.

II. Compounds of the Present Invention

Macrocyclic lactones, their salts, prodrugs, tautomers and isomers will be referred to collectively as "macrocyclic lactones" in this invention.

The compounds of the present invention are macrocyclic lactone compounds of the following formula:

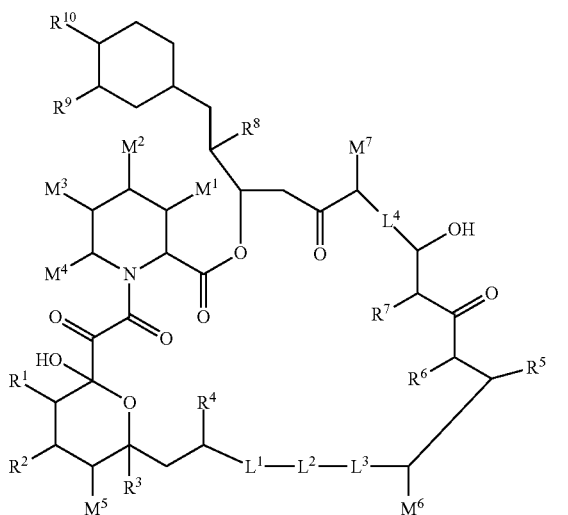

wherein $R^1, R^2, R^3, R^5, R^6, R^8, M^1, M^2, M^3, M^4, M^5, M^6$ and $M^7$ are each independently a member selected from the group consisting of H, $C_{1-6}$ alkyl, OH and $C_{1-6}$ hydroxyalkyl; $R^4, R^7$ and $R^9$ are each independently selected from the group consisting of $C_{1-6}$ alkoxy and OH; $R^{10}$ is a member selected from the group consisting of H, —OH, —OP(O)Me$_2$,

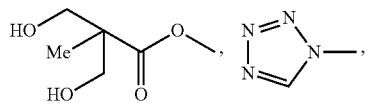

—O—(CH$_2$)$_n$—OH and —O—(CH$_2$)$_m$—O—(CH$_2$)$_o$—CH$_3$, wherein subscripts n and m are each independently from 2 to 8 and subscript o is from 1 to 6; each of $L^1$ and $L^4$ are independently selected from the group consisting of:

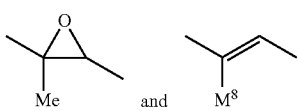

wherein each $M^8$ is independently a member selected from the group consisting of $C_{1-6}$ alkyl, OH and $C_{1-6}$ hydroxyalkyl; each of $L^2$ and $L^3$ are independently selected from the group consisting of:

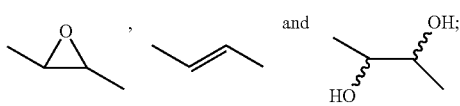

and
with the proviso that when $R^1, R^6, R^8, M^6$ and $M^7$ are Me, $R^3, R^5, M^1, M^2, M^3, M^4$ and $M^5$ are H, $R^4, R^7$ and $R^9$ are OMe, $R^{10}$ and $M^8$ are OH, $L^2$ and $L^3$ are —CH=CH—, and $L^1$ and $L^4$ are

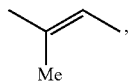

$R^2$ is other than OH;
with the proviso that when $R^1, R^6, R^8, M^6$ and $M^7$ are Me, $R^2, R^3, R^5, M^1, M^2, M^3, M^4$ and $M^5$ are H, $R^7$ and $R^9$ are OMe, $R^{10}$ and $M^8$ are OH, $L^2$ and $L^3$ are —CH=CH—, and $L^1$ and $L^4$ are

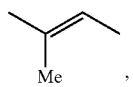

$R^4$ is other than OH;
with the proviso that when $R^1, R^6, R^8, M^6$ and $M^7$ are Me, $R^2, R^3, R^5, M^1, M^2, M^3, M^4$ and $M^5$ are H, $R^4$ and $R^7$ are OMe, $R^{10}$ and $M^8$ are OH, $L^2$ and $L^3$ are —CH=CH—, and $L^1$ and $L^4$ are

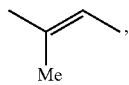

$R^9$ is other than OH;
with the proviso that when $R^1, R^6, R^8, M^6$ and $M^7$ are Me, $R^2, R^3, R^5, M^1, M^2, M^3, M^4$ and $M^5$ are H, $R^4, R^7$ and $R^9$ are OMe, $M^8$ is OH, $L^2$ and $L^3$ are —CH=CH—, and $L^1$ and $L^4$ are

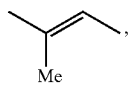

$R^{10}$ is other than OH, —OP(O)Me$_2$,

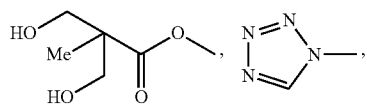

—O—(CH$_2$)$_n$—OH and —O—(CH$_2$)$_m$—O—(CH$_2$)$_o$—CH$_3$; and salts, hydrates, isomers, metabolites, N-oxides and prodrugs thereof.

In some embodiments, $R^{10}$ is

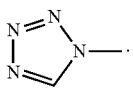

In some other embodiments, $R^{10}$ is

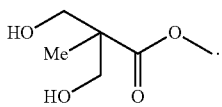

In other embodiments, $R^{10}$ is —OP(O)Me$_2$.
In still other embodiments, $R^{10}$ is

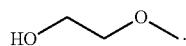

In another embodiment, $R^{10}$ is

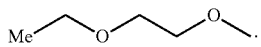

In a further embodiment, the compound is a compound of FIGS. 2A-2F(V). In other embodiments, at least one of $R^1$, $R^2$, $R^3$, $R^4$, $R^5$, $R^6$, $R^7$, $R^8$ and $R^9$ is OH. In still other embodiments, $R^4$ is OH. In yet other embodiments, $R^1$, $R^6$ and $R^8$ are each methyl, $R^2$, $R^3$ and $R^5$ are each H, $R^4$ and $R^{10}$ are each OH, $R^7$ and $R^9$ are each OMe, $M^1$, $M^2$, $M^3$, $M^4$ and $M^5$ are each H, $M^6$ and $M^7$ are each methyl, $L^1$ and $L^4$ are each

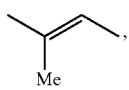

and $L^2$ and $L^3$ are each

The invention provides macrocyclic lactone compounds which are described in detail with Formula IA, IB, IC and ID.

In one embodiment, the composition contains macrocyclic lactones which include hydroxy, demethyl, hydroxydemethyl and epoxide macrocyclic lactones.

The structure of certain macrocyclic lactones with some potential sites for chemical modifications to provide compounds of the present invention is shown below.

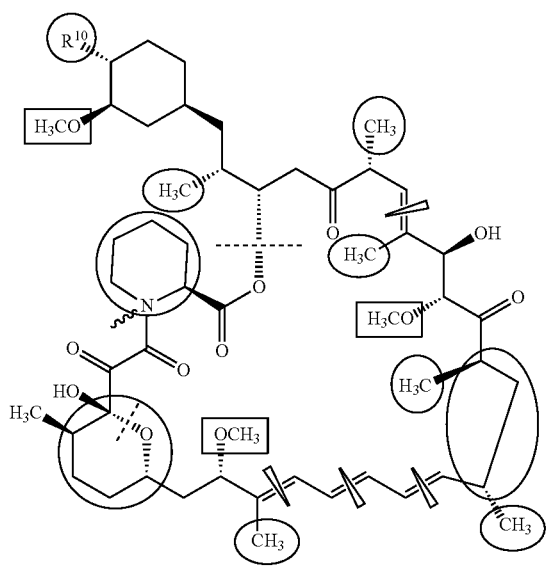

wherein squares represent the demethylation positions; circles represent the hydroxylation positions; triangles represent the epoxidation positions; curved lines represent the N-oxidation position; dashed lines represent the position for ring-opening position; $R^{10}$ is a member selected from the group consisting of —OH,

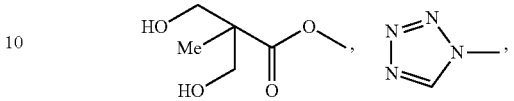

—OP(O)Me$_2$, —R$^a$OH, where R$^a$ is alkyl, such as —(CH$_2$)$_2$ to (CH$_2$)$_7$ and —R$^b$OR$^c$, where R$^b$ is C$_{2-6}$ alkylene and R$^c$ is C$_{1-5}$ alkyl, such as 40-O-(ethoxyethyl) rapamycin.

In some embodiments, the compounds of the present invention include certain demethyl macrocyclic lactones, such as 16-O-demethyl macrocyclic lactone, 39-O-demethyl macrocyclic lactone, 27-O-demethyl macrocyclic lactone, 16, 27-bis-O-demethyl macrocyclic lactone, 27, 39-bis-O-demethyl macrocyclic lactone, 16, 39-bis-O-demethyl macrocyclic lactone, individually or in combination with each other, as shown in Formula IA.

Formula IA

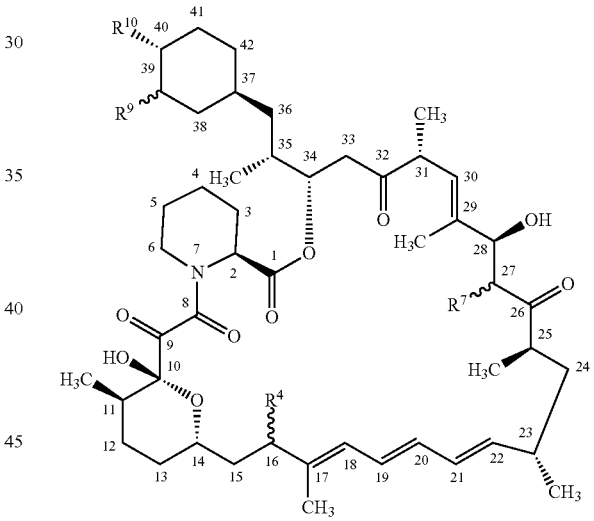

wherein
Each of $R^4$, $R^7$ and $R^9$ are selected from the group of consisting of —OCH$_3$ and —OH.
$R^4$ and $R^7$ are both, independently, selected from the group of consisting of —OH and —OCH$_3$.
$R^7$ and $R^9$ are both, independently, selected from the group of consisting of —OH and —OCH$_3$.
$R^4$ and $R^9$ are both, independently, selected from the group of consisting of —OH and —OCH$_3$.
$R^4$, $R^7$ and $R^9$ are each, independently, selected from the group of consisting of —OH and —OCH$_3$.
And wherein $R^{10}$ is as described above.

In another embodiment, the compounds of the present invention includes compositions of hydroxyl macrocyclic lactone, such as 11-hydroxyl macrocyclic lactone, 12-hydroxyl macrocyclic lactone, 14-hydroxyl macrocyclic lactone, 24-hydroxyl macrocyclic lactone, 25-hydroxyl macrocyclic lactone, 25-methyl alcohol macrocyclic lactone, 31-methyl alcohol macrocyclic lactone, 35-methyl alcohol macrocyclic lactone, 13-methyl alcohol macrocyclic lactone, individually or in combination with each other, as shown in Formula IB.

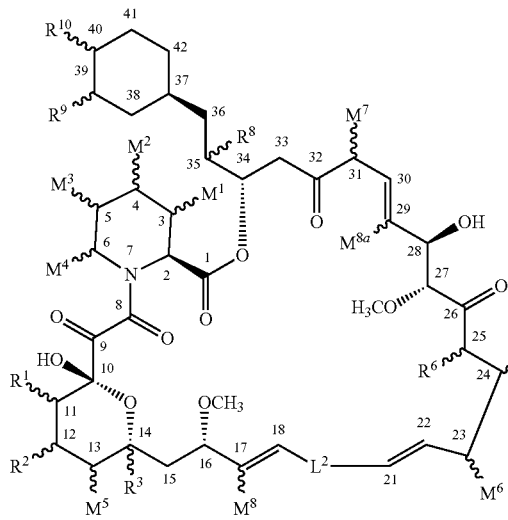

Formula IB wherein
Each of $R^1$, $R^6$, $R^8$, $M^6$, $M^7$, $M^8$ and $M^{8a}$ are selected from the group of consisting of —$CH_3$, —$CH_2OH$ and —OH. Each of $R^2$, $R^3$, $R^5$, $M^1$, $M^2$, $M^3$, $M^4$ and $M^5$ are selected from the group of consisting of —H and —OH. $R^9$ is selected from the group of consisting of —OH and —$OCH_3$ $L_2$ is selected from the group of consisting of

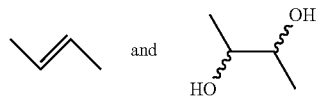

And wherein $R^{10}$ is as described above.

In another embodiment, the compounds of the present invention include compositions of epoxide macrocyclic lactone, such as 19, 20-21, 22-29, 30 tris epoxide macrocyclic lactone, 17, 18-19, 20-21, 22 tris epoxide macrocyclic lactone and 17, 18-29, 30 bis epoxide macrocyclic lactone, as shown in Formula IC.

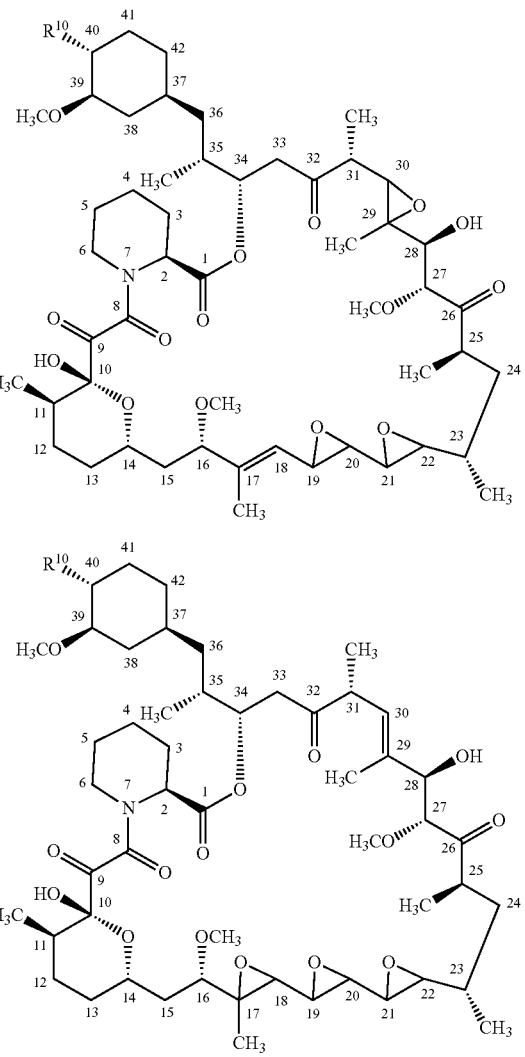

Formula IC

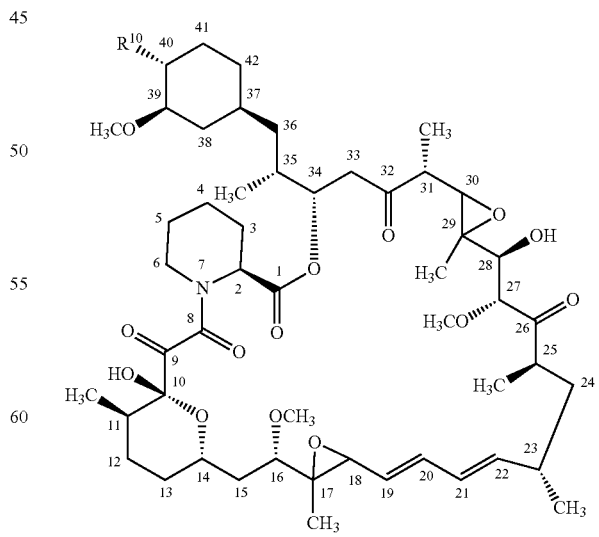

And wherein $R^{10}$ is as described above.

Formula ID

In another embodiment, the compounds of the present invention include compositions of N-oxidized macrocyclic lactone, 11-hydroxyl with 10,14 ring opening macrocyclic lactone, seco-macrocyclic lactone (with 1, 34 ring opened), as shown in Formula ID

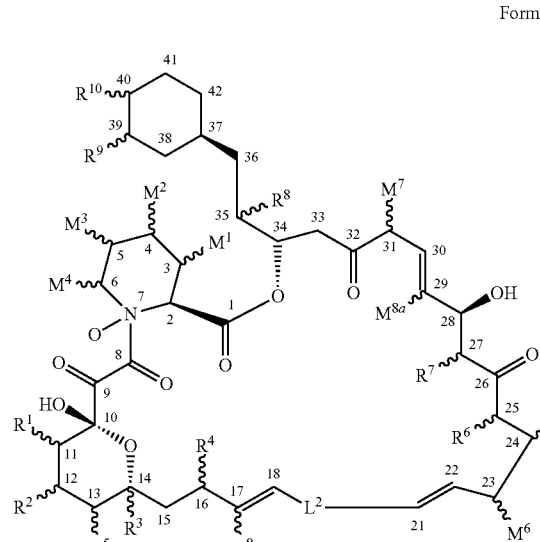

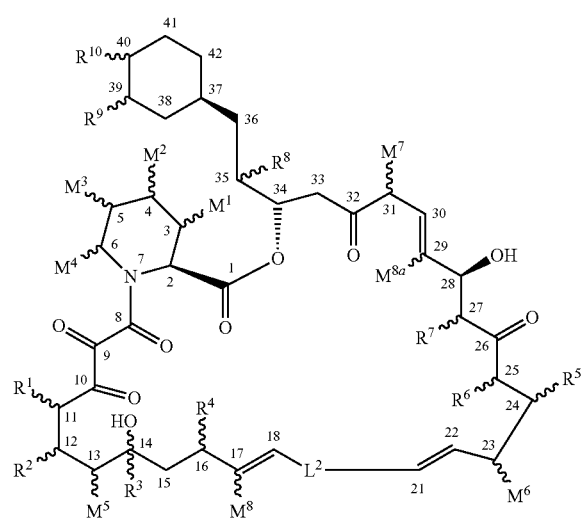

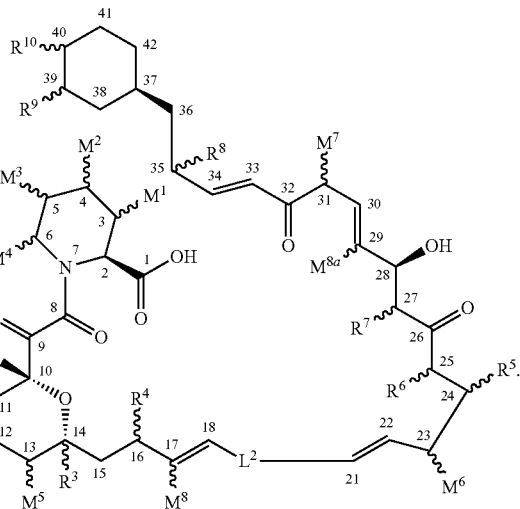

Wherein each of $R^1$, $R^6$, $R^8$, $M^6$, $M^7$, $M^8$ and $M^{8a}$ are independently selected from the group of consisting of —$CH_3$, —OH and $C_{1-6}$ hydroxyalkyl. Each of $R^2$, $R^3$, $R^5$, $M^1$, $M^2$, $M^3$, $M^4$ and $M^5$ are independently selected from the group of consisting of —H and —OH. $R^4$, $R^7$, $R^9$ are independently selected from the group of consisting of —OH and —$OCH_3$. $L^2$ is selected from the group of consisting of

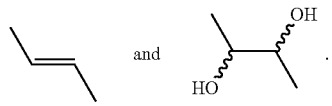

In another embodiment, the compounds of the present invention are a combination of Formula IA and Formula IB, including composition of demethylhydroxy macrocyclic lactone such as 14-hydroxy-39-O-demethyl macrocyclic lactone, 16,39-bis-O-demethyl-24-hydroxy macrocyclic lactone, 16,27-bis-O-demethyl-24-hydroxy macrocyclic lactone, 27,39-bis-O-demethyl-24-hydroxy macrocyclic lactone individually or in combination with each other.

In another embodiment, the compounds of the present invention are a combination of Formula IA and Formula IC, including composition of epoxide demethyl macrocyclic lactone such as 17,18-19,20-bis-epoxide-16-O-demethyl macrocyclic lactone, 17,18-29,30-bis-epoxide-16-O-demethyl macrocyclic lactone, individually or in combination with each other.

In yet another embodiment, the compounds of the present invention are a combination of Formula IA, Formula IB and Formula IC, including composition of epoxide demethylhydroxyl macrocyclic lactone such as 17,18-19,20-bis-epoxide-16-O-demethyl-24-hydroxy-macrocyclic lactone, 17,18-29,30-bis-epoxide-16-O-demethyl-24-hydroxy-macrocyclic lactone, individually or in combination with each other.

This invention also covers the compositions of salts, hydrates, isomers, tautomers, metabolites, N-oxides and prodrugs of compounds of the present invention of Formula IA, IB, IC and ID.

Structures of preferred embodiments (A, B, C, . . . AA, AB, AC, . . . FB, FC, FD) amongst compounds of the present invention of Formula IA, IB, IC and ID, and their combinations, are shown in Table 1, along with some in FIGS. 2A-2F(V).
 include both sterocenter:  and ⁞⁞⁞⁞⁞)

TABLE 1
Table of preferred compounds.
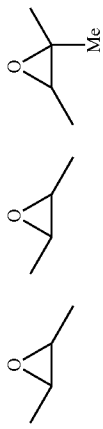
| * | R¹ | R² | R³ | R⁴ | R⁵ | R⁶ | R⁷ | R⁸ | R⁹ | R¹⁰ | M¹ | M² | M³ | M⁴ | M⁵ | M⁶ | M⁷ | L¹ | L² | L³ | L⁴ |
|---|----|----|----|----|----|----|----|----|----|-----|----|----|----|----|----|----|----|----|----|----|----|
| A | Me | H  | H  | OMe| H  | Me | OMe| Me | OMe| OH  | H  | H  | H  | H  | H  | H  | Me | L¹ | L² | L³ | L⁴ |
| B | OH |    |    |    |    |    |    |    |    |     |    |    |    |    |    |    |    |    |    |    |    |
| C |    | OH |    |    |    |    |    |    |    |     |    |    |    |    |    |    |    |    |    |    |    |
| D |    |    | OH |    |    |    |    |    |    |     |    |    |    |    |    |    |    |    |    |    |    |
| E |    |    |    |    | OH |    |    |    |    |     |    |    |    |    |    |    |    |    |    |    |    |
| F |    |    |    |    |    | OH |    |    |    |     |    |    |    |    |    |    |    |    |    |    |    |
| G |    |    |    |    |    |    | OH |    |    |     |    |    |    |    |    |    |    |    |    |    |    |
| H |    |    |    |    |    |    |    |    | OH |     |    |    |    |    |    |    |    |    |    |    |    |
| I |    |    |    |    |    |    |    |    |    | OH  |    |    |    |    |    |    |    |    |    |    |    |
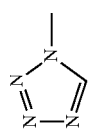

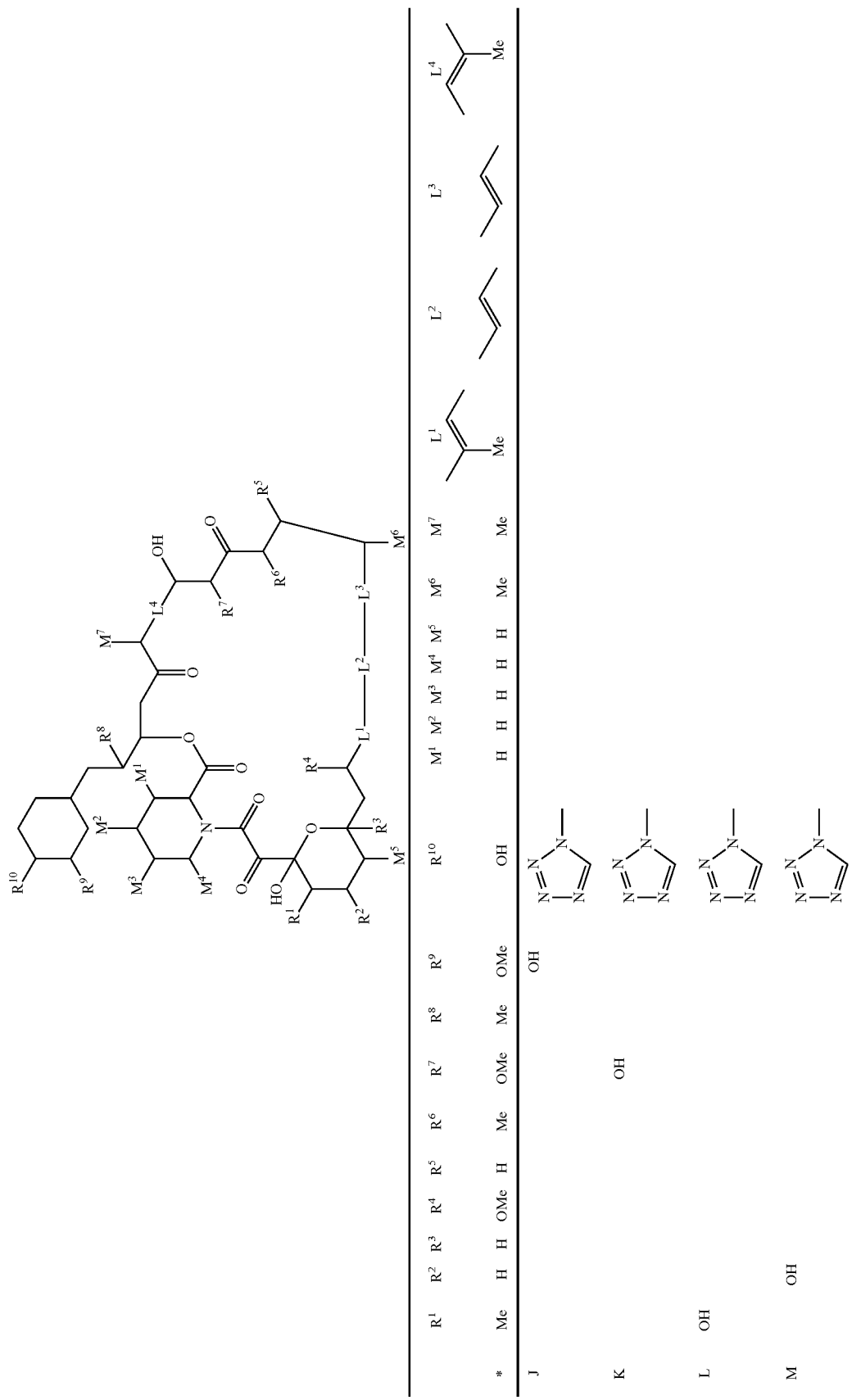

TABLE 1-continued

Table of preferred compounds.

| * | R¹ | R² | R³ | R⁴ | R⁵ | R⁶ | R⁷ | R⁸ | R⁹ | R¹⁰ | M¹ | M² | M³ | M⁴ | M⁵ | M⁶ | M⁷ | L¹ | L² | L³ | L⁴ |
|---|----|----|----|----|----|----|----|----|----|-----|----|----|----|----|----|----|----|----|----|----|----|
|   | Me | H  | H  | OMe | H | Me | OMe | Me | OMe | OH | H | H | H | H | H | H | Me | isobutenyl-Me | CH=CH | CH=CH | isobutenyl-Me |
| N |    |    |    |    | OH |   |    |    |    | N-methyl-triazolyl |   |   |   |   |   |   |   |   |   |   |   |
| O |    |    |    |    |    | OH |   |    |    | N-methyl-triazolyl |   |   |   |   |   |   |   |   |   |   |   |
| P |    |    |    |    |    |   |    |    | OH | -C(Me)(CH₂OH)₂ C(O)OMe |   |   |   |   |   |   |   |   |   |   |   |
| Q |    |    |    | OH |    |   |    |    |    | -C(Me)(CH₂OH)₂ C(O)OMe |   |   |   |   |   |   |   |   |   |   |   |

TABLE 1-continued

Table of preferred compounds.

| * | R¹ | R² | R³ | R⁴ | R⁵ | R⁶ | R⁷ | R⁸ | R⁹ | R¹⁰ | M¹ | M² | M³ | M⁴ | M⁵ | M⁶ | M⁷ | L¹ | L² | L³ | L⁴ |
|---|----|----|----|----|----|----|----|----|----|-----|----|----|----|----|----|----|----|----|----|----|----|
| R | Me | H | H | OMe | H | Me | OMe | Me | OMe | OH | H | H | H | H | H | H | Me | Me₂C=CHMe | CH=CH(Me) | CH=CH(Me) | Me₂C=CHMe |
| S |    | OH |    |    |    |    |    |    |    |    |    |    |    |    |    |    |    |    |    |    |    |
| T |    |    | OH |    |    |    | OH |    |    |    |    |    |    |    |    |    |    |    |    |    |    |
| U |    |    |    |    | OH |    |    |    |    |    |    |    |    |    |    |    |    |    |    |    |    |

TABLE 1-continued

Table of preferred compounds.

| * | R¹ | R² | R³ | R⁴ | R⁵ | R⁶ | R⁷ | R⁸ | R⁹ | R¹⁰ | L¹ | L² | L³ | L⁴ | M¹ | M² | M³ | M⁴ | M⁵ | M⁶ | M⁷ |
|---|----|----|----|----|----|----|----|----|----|-----|----|----|----|----|----|----|----|----|----|----|----|
| V | Me | H | H | OMe | H | Me | OMe | Me | OMe | OH | $\mathrm{Me_2C{=}CH{-}}$ | $-CH{=}CH-$ | $-CH{=}CH-$ | $\mathrm{Me_2C{=}CH{-}}$ | H | H | H | H | H | H | Me |
| W |  | OH |  |  |  |  |  |  |  | —OP(O)Me₂ |  |  |  |  |  |  |  |  |  |  |  |
| X |  |  | OH |  |  |  |  |  |  | —OP(O)Me₂ |  |  |  |  |  |  |  |  |  |  |  |
| Y | OH |  |  |  |  |  |  |  |  | —OP(O)Me₂ |  |  |  |  |  |  |  |  |  |  |  |
| Z |  |  |  |  |  | OH |  |  |  | —OP(O)Me₂ |  |  |  |  |  |  |  |  |  |  |  |
| AA |  |  |  |  |  |  | OH |  |  | —OP(O)Me₂ |  |  |  |  |  |  |  |  |  |  |  |
| AB |  |  |  |  | OH |  |  |  |  | —OP(O)Me₂ |  |  |  |  |  |  |  |  |  |  |  |
| AC |  |  | OH |  |  | OH |  |  | OH | —OP(O)Me₂ |  |  |  |  |  |  |  |  |  |  |  |
| AD |  |  |  |  | OH | OH |  |  | OH | HOCH₂CH₂OCH₃ |  |  |  |  |  |  |  |  |  |  |  |
| AE |  |  |  |  |  | OH |  |  |  | HOCH₂CH₂OCH₃ |  |  |  |  |  |  |  |  |  |  |  |
| AF |  |  |  |  |  |  |  |  |  | HOCH₂CH₂OCH₃ |  |  |  |  |  |  |  |  |  |  |  |
| AG | OH |  |  |  |  |  |  |  |  |  |  |  |  |  |  |  |  |  |  |  |  |

TABLE 1-continued

Table of preferred compounds.

| * | R¹ | R² | R³ | R⁴ | R⁵ | R⁶ | R⁷ | R⁸ | R⁹ | R¹⁰ | M¹ | M² | M³ | M⁴ | M⁵ | M⁶ | M⁷ | L¹ | L² | L³ | L⁴ |
|---|----|----|----|----|----|----|----|----|----|-----|----|----|----|----|----|----|----|----|----|----|----|
|   | Me | H | H | OMe | H | Me | OMe | Me | OMe | OH | H | H | H | H | H | Me | Me | (isopropenyl, Me) | (CH=CH) | (CH=CH) | (isopropenyl, Me) |
| AH | OH |   |   |   |   |   |   |   |   | MeO–CH₂CH₂–OH |   |   |   |   |   |   |   | epoxide (Me) | epoxide | epoxide |   |
| AI |    |   |   |   |   |   |   | OH |   | MeO–CH₂CH₂–OH |   |   |   |   |   |   |   | epoxide (Me) | epoxide | epoxide |   |
| AJ |    |   |   |   |   |   | OH |   |   | MeO–CH₂CH₂–OH |   |   |   |   |   |   |   |   |   |   |   |
| AK |    |   |   | OH |   |   | OH |   |   | MeO–CH₂CH₂–OH |   |   |   |   |   |   |   |   |   |   |   |
| AL |    |   |   |    |   |   |    |   |   | H–(CH₂CH₂O)₂– |   |   |   |   |   |   |   |   |   |   |   |
| AM |    |   |   | OH |   |   |    |   |   | H–(CH₂CH₂O)₂– |   |   |   |   |   |   |   |   |   |   |   |
| AN |    |   |   |    |   |   | OH |   | OH | H–(CH₂CH₂O)₂– |   |   |   |   |   |   |   |   |   |   |   |
| AO | OH |   |   |    |   |   |    |   |   | H–(CH₂CH₂O)₂– |   |   |   |   |   |   |   |   |   |   |   |

TABLE 1-continued

Table of preferred compounds.

[Structure: Macrocyclic compound with substituents R¹–R¹⁰, M¹–M⁷, and L¹–L⁴ linker positions]

| * | R¹ | R² | R³ | R⁴ | R⁵ | R⁶ | R⁷ | R⁸ | R⁹ | R¹⁰ | M¹ | M² | M³ | M⁴ | M⁵ | M⁶ | M⁷ | L¹ | L² | L³ | L⁴ |
|---|---|---|---|---|---|---|---|---|---|---|---|---|---|---|---|---|---|---|---|---|---|
| AP | Me | H | H | OMe | H | Me | OMe | Me | OMe | OH | H | H | H | H | H | H | Me | CMe=CHMe | CH=CHMe | CH=CHMe | CMe=CHMe |
| AQ | | OH | | | | | | | | H—(CH₂CH₂O)₂— | | | | | | | | | | | epoxide(Me,Me) |
| AR | | | | | OH | | | | | H—(CH₂CH₂O)₂— | | | | | | | | epoxide(Me) | epoxide | epoxide | epoxide(Me,Me) |
| AS | | | | | | | | | | | | | | | | | | | epoxide | | |
| AT | | OH | | | | | | | | | | | | | | | | CMe=CHMe | | | epoxide(Me,Me) |
| AU | | OH | | | | | | | | | | | | | | | | | epoxide | | |

TABLE 1-continued
Table of preferred compounds.
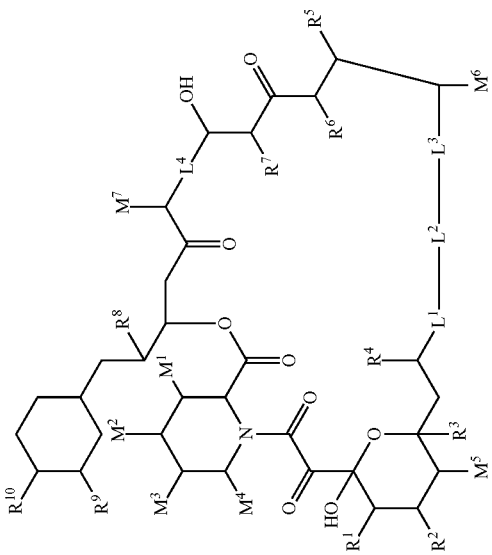
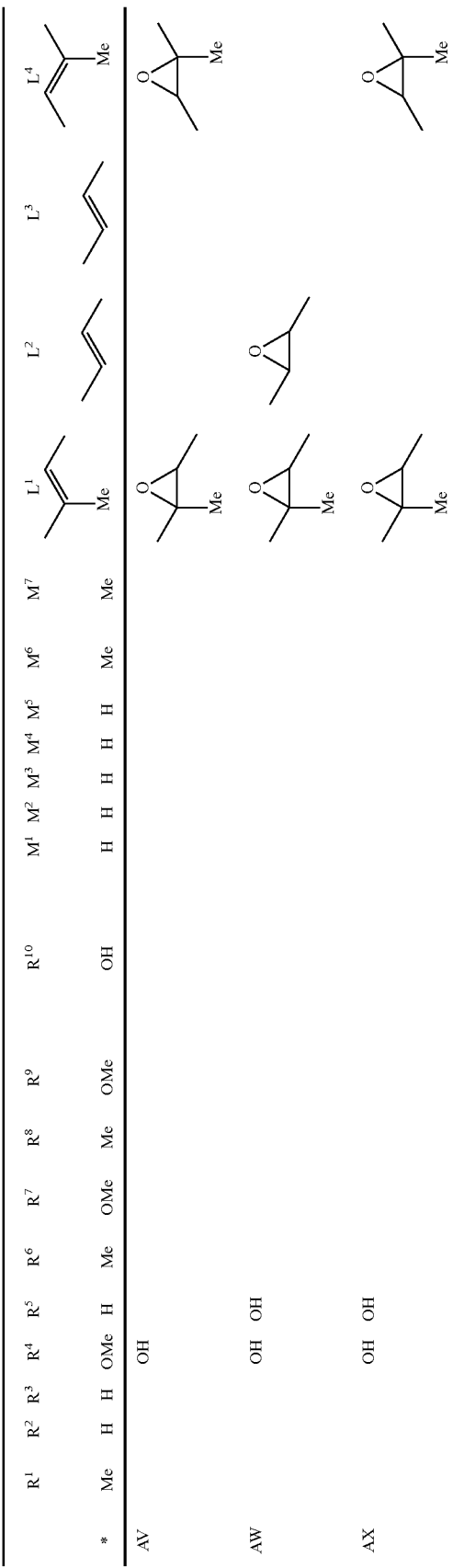
| * | R¹ | R² | R³ | R⁴ | R⁵ | R⁶ | R⁷ | R⁸ | R⁹ | R¹⁰ | M¹ | M² | M³ | M⁴ | M⁵ | M⁶ | M⁷ | L¹ | L² | L³ | L⁴ |
|---|----|----|----|----|----|----|----|----|----|-----|----|----|----|----|----|----|----|----|----|----|----|
|   | Me |    |    |    |    | Me | OMe | Me | OMe |   | H | H | H | H | H | Me | Me |    |    |    |    |
| AV |   | H | H | OMe | H |   |   |   |   | OH |   |   |   |   |   |   |   |   |   |   |   |
| AW |   |   |   | OH | OH |   |   |   |   |   |   |   |   |   |   |   |   |   |   |   |   |
| AX |   |   |   | OH | OH |   |   |   |   |   |   |   |   |   |   |   |   |   |   |   |   |

TABLE 1-continued

Table of preferred compounds.

| * | $R^1$ | $R^2$ | $R^3$ | $R^4$ | $R^5$ | $R^6$ | $R^7$ | $R^8$ | $R^9$ | $R^{10}$ | $M^1$ | $M^2$ | $M^3$ | $M^4$ | $M^5$ | $M^6$ | $M^7$ | $L^1$ | $L^2$ | $L^3$ | $L^4$ |
|---|---|---|---|---|---|---|---|---|---|---|---|---|---|---|---|---|---|---|---|---|---|
| AY | Me | H | H | OMe | H | Me | OMe | Me | OMe | OH | H | H | H | H | H | H | Me | | | | |
| AZ | | | | | | | | | | | | | | | | | | | | | |
| BA | | | | | | | | | | triazole | | | | | | | | | diol | | |
| BB | OH | | | | | | | | | | | | | | | | | | | | |
| BC | OH | | | | | | | | | | | | | | | | | | | | |
| BD | OH | | | | | | | | | | | | | | | | | | | | |
| BE | OH | | | | | | | | | | | | | | | | | | | | |
| BF | $CH_2OH$ | | | | | | | | | | | | | | | | | | | | |

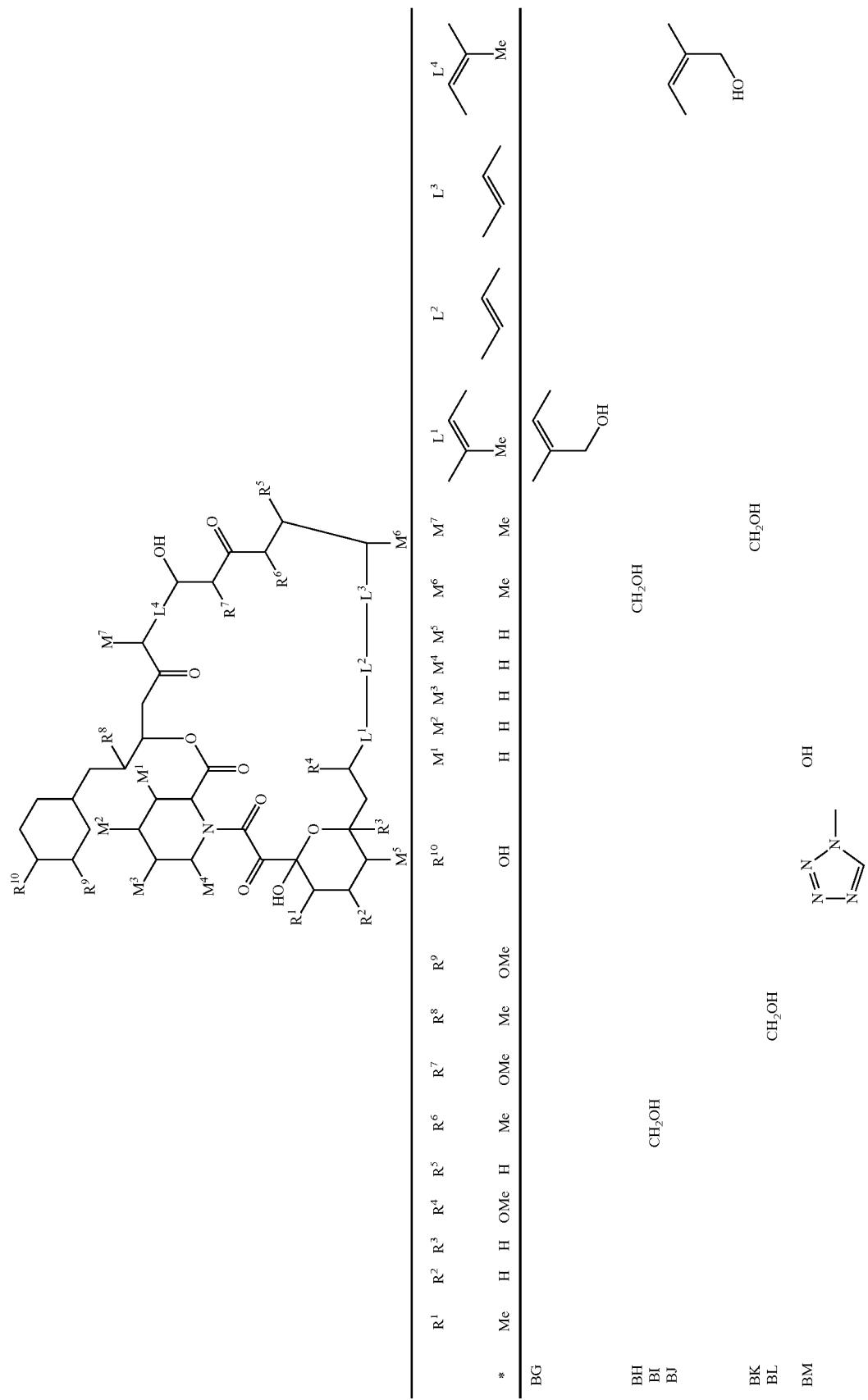
TABLE 1-continued
Table of preferred compounds.
| * | R¹ | R² | R³ | R⁴ | R⁵ | R⁶ | R⁷ | R⁸ | R⁹ | R¹⁰ | M¹ | M² | M³ | M⁴ | M⁵ | M⁶ | M⁷ | L¹ | L² | L³ | L⁴ |
|---|----|----|----|----|----|----|----|----|----|-----|----|----|----|----|----|----|----|----|----|----|----|
| BG | Me | H | H | OMe | H | Me | OMe | Me | OMe | OH | H | H | H | H | H | Me | Me | | | | |
| BH | | | | | | CH₂OH | | | | | | | | | | | | | | | |
| BI | | | | | | | | | | | | | | | | | | | | | |
| BJ | | | | | | | | CH₂OH | | | | | | | | | | | | | |
| BK | | | | | | | | | | | | | | | | | | | | | |
| BL | | | | | | | | | | | | | | | | | CH₂OH | | | | |
| BM | | | | | | | | | | | | | | | | | | | | | |

TABLE 1-continued
Table of preferred compounds.
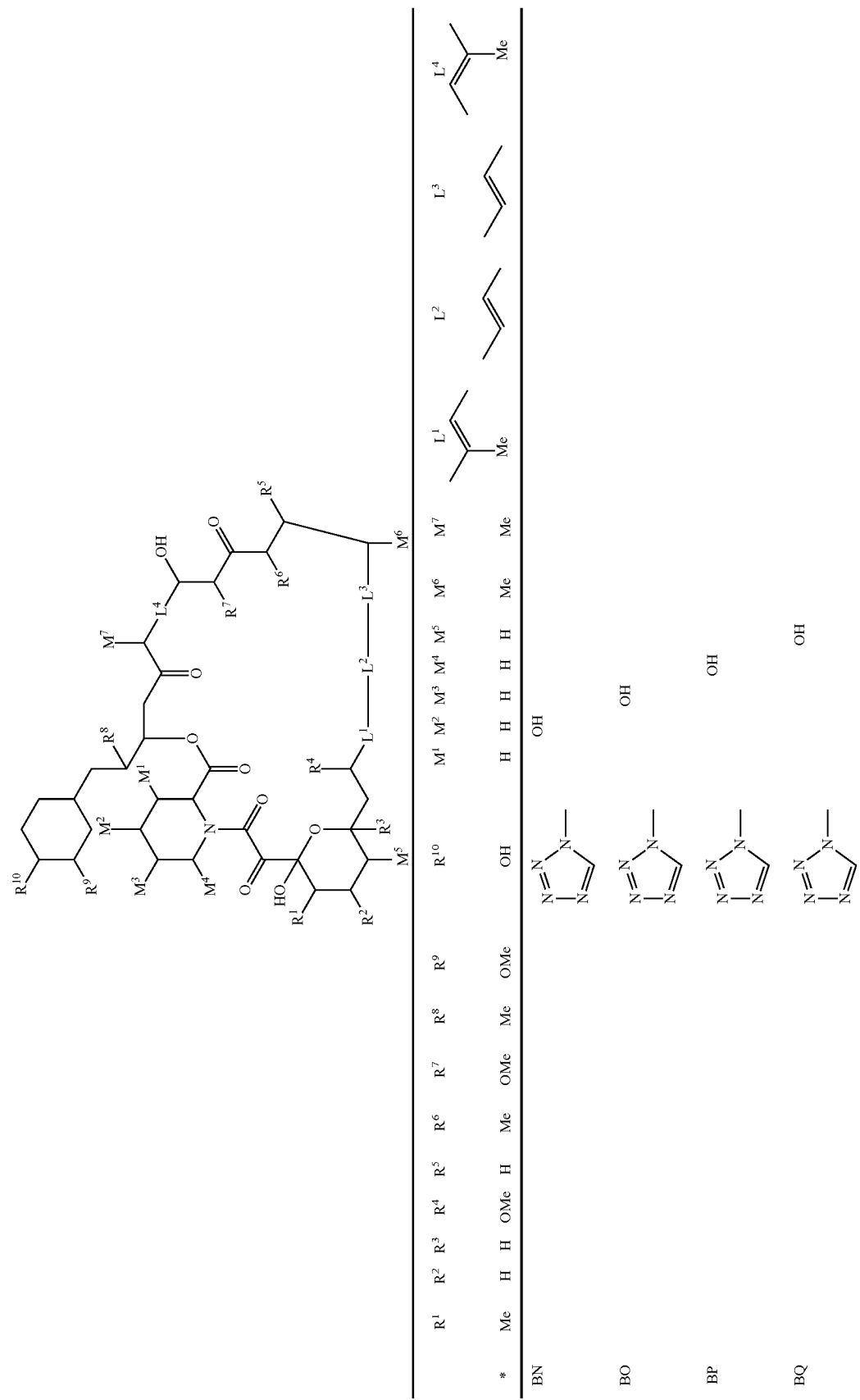
| * | $R^1$ | $R^2$ | $R^3$ | $R^4$ | $R^5$ | $R^6$ | $R^7$ | $R^8$ | $R^9$ | $R^{10}$ | $M^1$ | $M^2$ | $M^3$ | $M^4$ | $M^5$ | $M^6$ | $M^7$ | $L^1$ | $L^2$ | $L^3$ | $L^4$ |
|---|---|---|---|---|---|---|---|---|---|---|---|---|---|---|---|---|---|---|---|---|---|
| BN | Me | H | H | OMe | H | Me | OMe | Me | OMe | OH | H | H | H | H | H | H | Me | L1 | L2 | L3 | L4 |
| BO | | | | | | | | | | | OH | | | | | | | | | | |
| BP | | | | | | | | | | | | OH | | | | | | | | | |
| BQ | | | | | | | | | | | | | OH | | | | | | | | |

TABLE 1-continued

Table of preferred compounds.

| * | $R^1$ | $R^2$ | $R^3$ | $R^4$ | $R^5$ | $R^6$ | $R^7$ | $R^8$ | $R^9$ | $R^{10}$ | $M^1$ | $M^2$ | $M^3$ | $M^4$ | $M^5$ | $M^6$ | $M^7$ | $L^1$ | $L^2$ | $L^3$ | $L^4$ |
|---|---|---|---|---|---|---|---|---|---|---|---|---|---|---|---|---|---|---|---|---|---|
| BR | Me | H | H | OMe | H | Me | OMe | Me | OMe | OH | H | H | H | H | H | Me | Me | | | | |
| BS | CH₂OH | | | | | | | | | | | | | | | | | | | | |
| BT | | | | | | | | | | | | | | | | | CH₂OH | | | | |
| BU | | | | | | CH₂OH | | | | | | | | | | | | | | | |

TABLE 1-continued

Table of preferred compounds.

| * | R¹ | R² | R³ | R⁴ | R⁵ | R⁶ | R⁷ | R⁸ | R⁹ | R¹⁰ | M¹ | M² | M³ | M⁴ | M⁵ | M⁶ | M⁷ | L¹ | L² | L³ | L⁴ |
|---|---|---|---|---|---|---|---|---|---|---|---|---|---|---|---|---|---|---|---|---|---|
| BV | Me | H | H | OMe | H | Me | OMe | Me | OMe | ![1-methyltriazole] | H | H | H | H | H | Me | ![isoprenyl] | ![vinyl] | ![vinyl] | ![isoprenyl-Me] |
| BW | | | | | | | | CH₂OH | | ![1-methyltriazole] | | | | | | | | | | | |
| BX | | | | | | | | | | ![1-methyltriazole with CH₂OH] | | | | | | | | | | | |
| BY | | | | | | | | | | ![complex hydroxyl ester group] | | | | | | | | | | | ![CH₂OH isoprenyl] |

TABLE 1-continued

Table of preferred compounds.

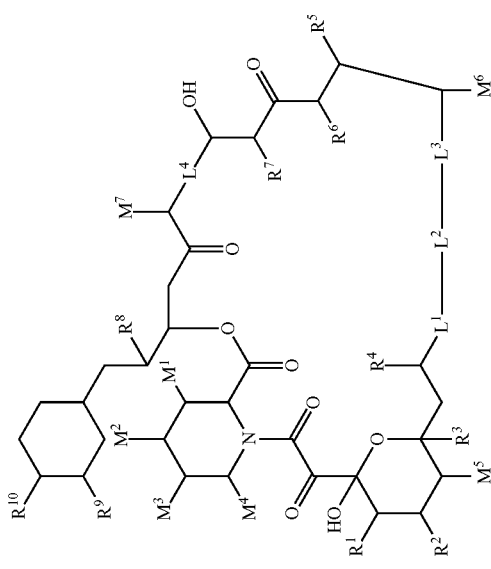

| * | R¹ | R² | R³ | R⁴ | R⁵ | R⁶ | R⁷ | R⁸ | R⁹ | R¹⁰ | M¹ | M² | M³ | M⁴ | M⁵ | M⁶ | M⁷ | L¹ | L² | L³ | L⁴ |
|---|---|---|---|---|---|---|---|---|---|---|---|---|---|---|---|---|---|---|---|---|---|
| BZ | Me | H | H | OMe | H | Me | OMe | Me | OMe | -OMe with CH₂OH) | OH | H | H | H | H | Me | Me | ⟨CMe₂=CH⟩ | ⟨CH=CH⟩ | ⟨CH=CH⟩ | ⟨CMe=CH⟩ |
| CA | Me | H | H | OMe | H | Me | OMe | Me | OMe | (same ester) | H | OH | H | H | H | Me | Me | ⟨CMe₂=CH⟩ | ⟨CH=CH⟩ | ⟨CH=CH⟩ | ⟨CMe=CH⟩ |
| CB | Me | H | H | OMe | H | Me | OMe | Me | OMe | (same ester) | H | H | OH | H | H | Me | Me | ⟨CMe₂=CH⟩ | ⟨CH=CH⟩ | ⟨CH=CH⟩ | ⟨CMe=CH⟩ |
| CC | Me | H | H | OMe | H | Me | OMe | Me | OMe | (same ester) | H | H | H | OH | H | Me | Me | ⟨CMe₂=CH⟩ | ⟨CH=CH⟩ | ⟨CH=CH⟩ | ⟨CMe=CH⟩ |

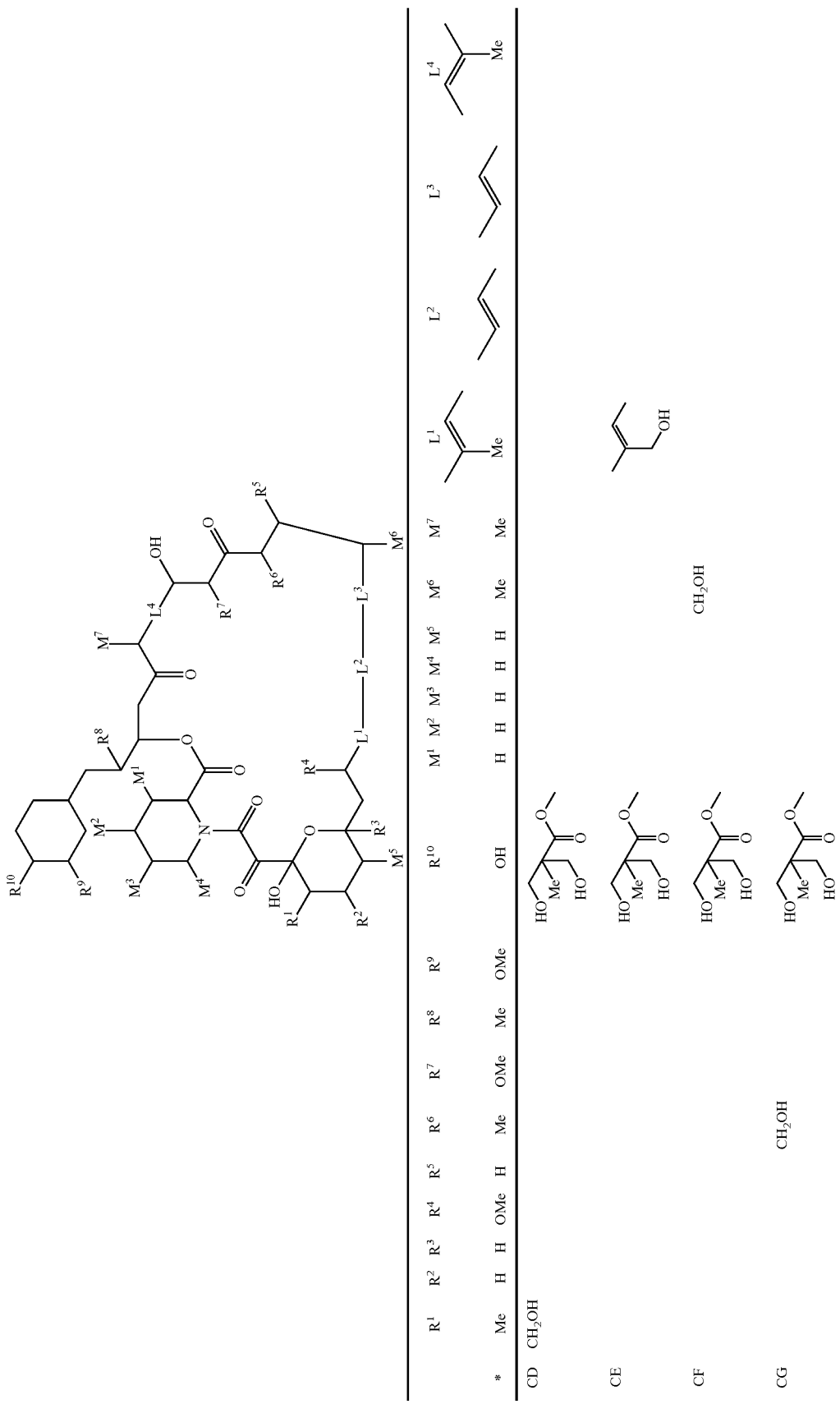

TABLE 1-continued

Table of preferred compounds.

| * | R¹ | R² | R³ | R⁴ | R⁵ | R⁶ | R⁷ | R⁸ | R⁹ | R¹⁰ | M¹ | M² | M³ | M⁴ | M⁵ | M⁶ | M⁷ | L¹ | L² | L³ | L⁴ |
|---|---|---|---|---|---|---|---|---|---|---|---|---|---|---|---|---|---|---|---|---|---|
| CH | Me | H | H | OMe | H | Me | OMe | Me | OMe | OH | H | H | H | H | H | H | Me | $\underset{Me}{\overset{Me}{\diagdown}}\!\!=\!\!$ | $-\!\!=\!\!-$ | $-\!\!=\!\!-$ | $\underset{Me}{\overset{Me}{\diagdown}}\!\!=\!\!$ |
| CI | | | | | | | | CH₂OH | | | | | | | | | | | | | $\underset{HO}{\overset{Me}{\diagdown}}\!\!=\!\!$ |
| CJ | | | | | | | CH₂OH | | | | | | | | | | | | | | |
| CK | | | | | | | | | | HOCH₂–C(Me)(CH₂OH)–C(O)OMe | | | | | | | | | | | |
| CL | | | | | | | | | | HOCH₂–C(Me)(CH₂OH)–C(O)OMe | | | | | | | | | | | |
| CM | | | | | | | | | | HOCH₂–C(Me)(CH₂OH)–C(O)OMe | | | | | | | | | | | |
| CN | | | | | | | | | | —OP(O)Me₂ OH | | | | | | | | | | | |
| CO | | | | | | | | | | —OP(O)Me₂ OH | | | | | | | | | | | |

TABLE 1-continued

Table of preferred compounds.

| * | R¹ | R² | R³ | R⁴ | R⁵ | R⁶ | R⁷ | R⁸ | R⁹ | R¹⁰ | M¹ | M² | M³ | M⁴ | M⁵ | M⁶ | M⁷ | L¹ | L² | L³ | L⁴ |
|---|---|---|---|---|---|---|---|---|---|---|---|---|---|---|---|---|---|---|---|---|---|
| CP | Me | H | H | OMe | H | Me | OMe | Me | OMe | OH | H | H | H | H | H | H | Me | | | | |
| CQ | CH₂OH | | | | | | | | | —OP(O)Me₂ | | | | | | | | 2-methyl-2-butenyl-CH₂OH | | | 2-methyl-2-butenyl-CH₂OH |
| CR | | | | | | CH₂OH | | | | —OP(O)Me₂ | | | | | | | | | | | |
| CS | | | | | | | | CH₂OH | | —OP(O)Me₂ | | | | | | | | | | | |
| CT | | | | | | | | | | —OP(O)Me₂ | | | | | | CH₂OH | | | | | |
| CU | | | | | | | | | | —OP(O)Me₂ | | | | | | | CH₂OH | | | | |
| CV | | | | | | | | | | —OP(O)Me₂ | | | | | | | | | | | |
| CW | | | | | | | | | | —O–CH₂CH₂–OH with OH | | | | | | | | | | | |
| CX | | | | | | | | | | —O–CH₂CH₂–OH with OH | | | | | | | | | | | |

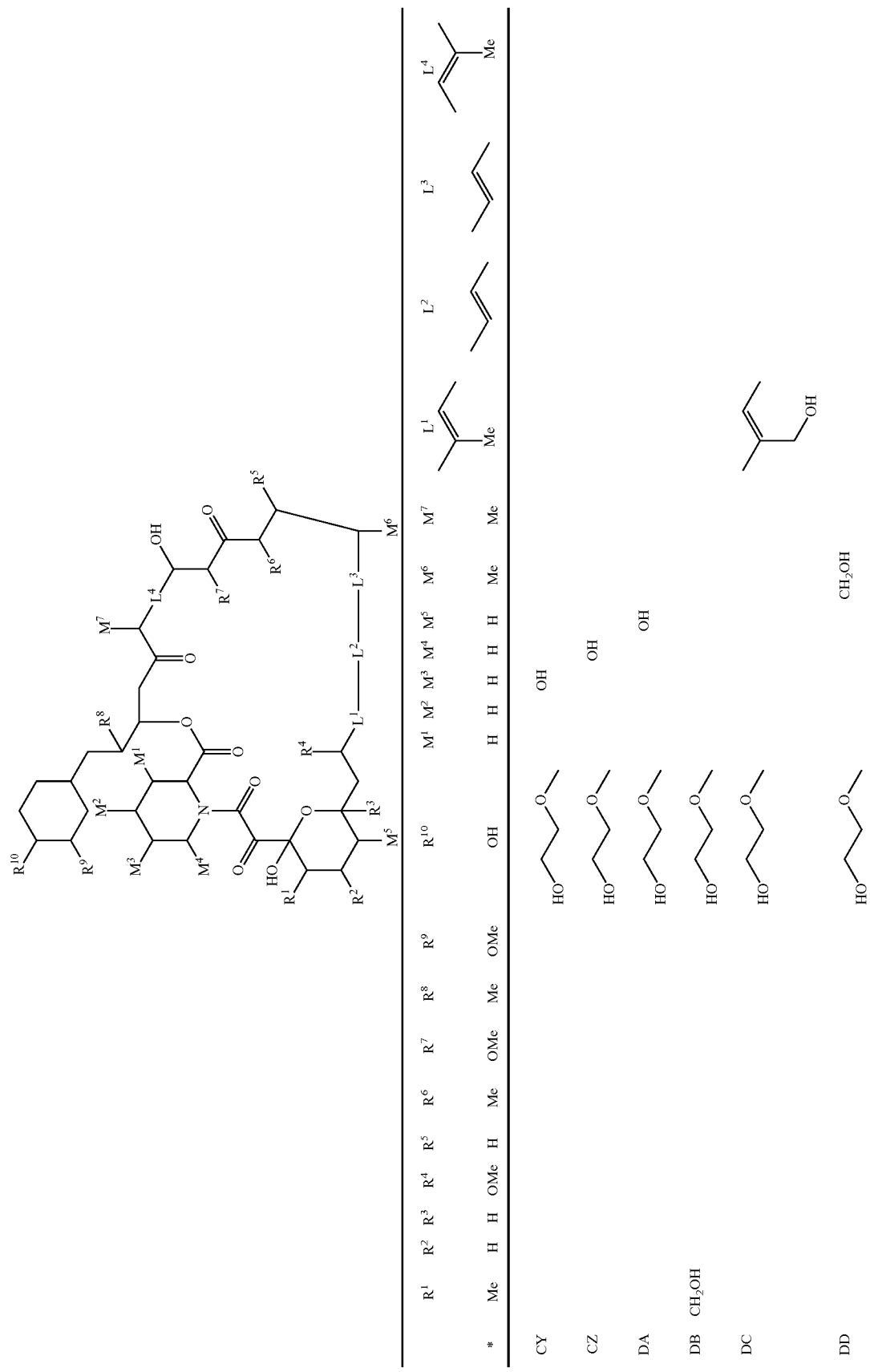

TABLE 1-continued

Table of preferred compounds.

| * | R$^1$ | R$^2$ | R$^3$ | R$^4$ | R$^5$ | R$^6$ | R$^7$ | R$^8$ | R$^9$ | R$^{10}$ | M$^1$ | M$^2$ | M$^3$ | M$^4$ | M$^5$ | M$^6$ | M$^7$ | L$^1$ | L$^2$ | L$^3$ | L$^4$ |
|---|---|---|---|---|---|---|---|---|---|---|---|---|---|---|---|---|---|---|---|---|---|
|   | Me | H | H | OMe | H | Me | OMe | Me | OMe | OH | H | H | H | H | H | H | Me | =C(Me)CH= | CH=CH | CH=CH | =C(Me)CH$_2$OH |
| DE |  |  |  |  |  | CH$_2$OH |  |  |  | —OCH$_2$CH$_2$OH |  |  |  |  |  |  |  |  |  |  |  |
| DF |  |  |  |  |  |  |  |  |  | —OCH$_2$CH$_2$OH |  |  |  |  |  |  |  |  |  |  |  |
| DG |  |  |  |  |  |  |  |  |  | —OCH$_2$CH$_2$OH |  |  |  |  |  |  | CH$_2$OH |  |  |  |  |
| DH |  |  |  |  |  |  |  | CH$_2$OH |  | —OCH$_2$CH$_2$OMe |  |  |  |  |  |  |  |  |  |  |  |
| DI |  |  |  |  |  |  |  |  |  | —OCH$_2$CH$_2$OCH$_2$CH(OH)Me |  |  |  |  |  |  |  |  |  |  |  |
| DJ |  |  |  |  |  |  |  |  |  | —OCH$_2$CH$_2$OCH$_2$CH(OH)Me |  |  |  |  |  |  |  |  |  |  |  |

TABLE 1-continued

Table of preferred compounds.

| * | R¹ | R² | R³ | R⁴ | R⁵ | R⁶ | R⁷ | R⁸ | R⁹ | R¹⁰ | M¹ | M² | M³ | M⁴ | M⁵ | M⁶ | M⁷ | L¹ | L² | L³ | L⁴ |
|---|---|---|---|---|---|---|---|---|---|---|---|---|---|---|---|---|---|---|---|---|---|
| DK | Me | H | H | OMe | H | Me | OMe | Me | OMe | OH | H | H | H | H | H | Me | Me | =C(Me)₂ | CH=CHMe | CH=CHMe | =C(Me)₂ |
| DL | | | | | | | | | | Me-O-CH₂CH₂-O-CH₂CH₂-O- | | | OH | | | | | | | | |
| DM | | | | | | | | | | Me-O-CH₂CH₂-O-CH₂CH₂-O- | | | | | OH | | | | | | |
| DN | CH₂OH | | | | | | | | | Me-O-CH₂CH₂-O-CH₂CH₂-O- | | | | | | | | | | | |
| DO | | | | | | | | | | Me-O-CH₂CH₂-O-CH₂CH₂-O- | | | | | | | | | | | |
| DP | | | | | | | | | | Me-O-CH₂CH₂-O-CH₂CH₂-O- | | | | | | CH₂OH | | | | | |
| DQ | | | | | | CH₂OH | | | | Me-O-CH₂CH₂-O-CH₂CH₂-O- | | | | | | | | CH=C(Me)CH₂OH | | | |

TABLE 1-continued
Table of preferred compounds.
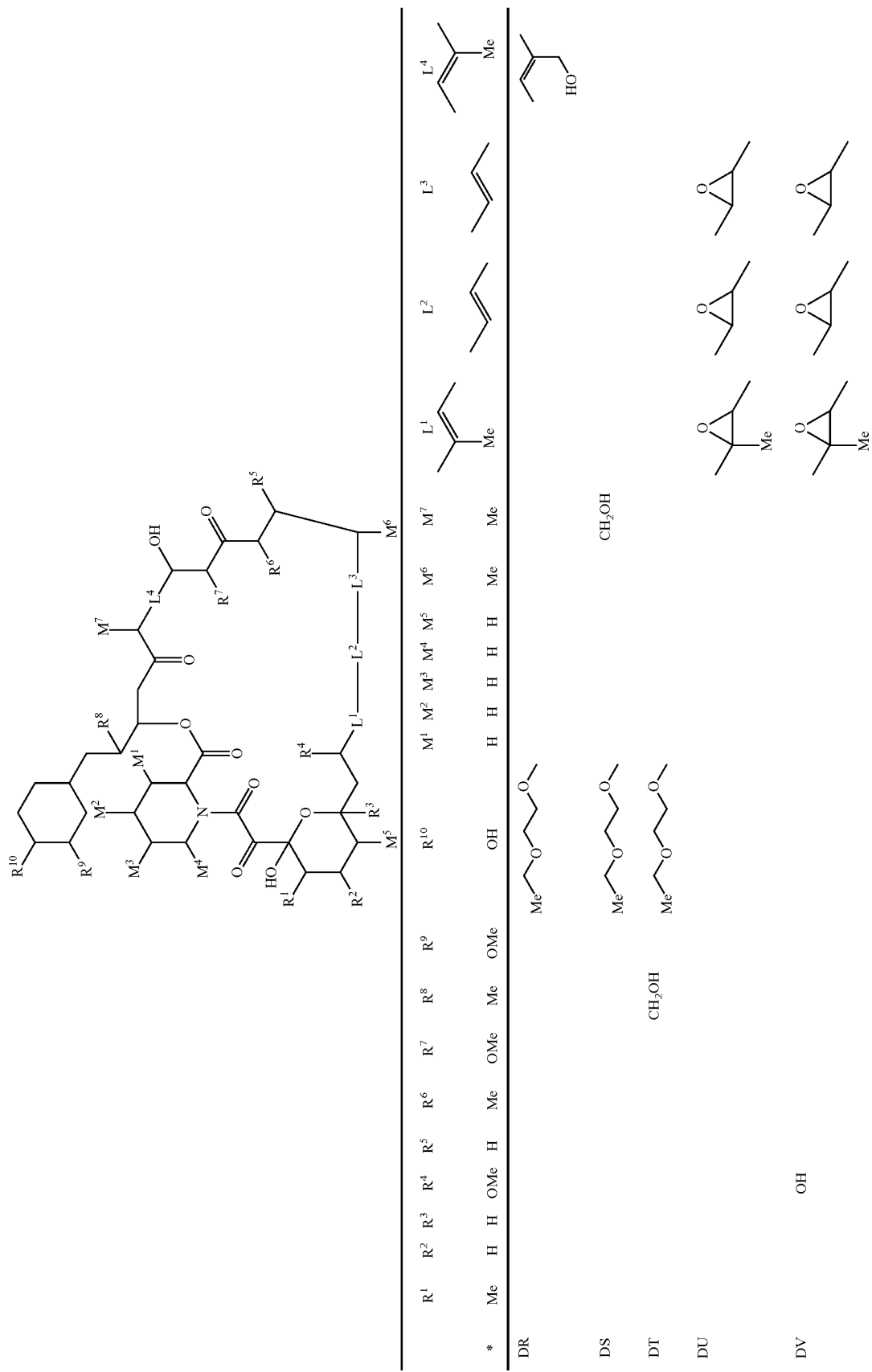
| * | R¹ | R² | R³ | R⁴ | R⁵ | R⁶ | R⁷ | R⁸ | R⁹ | R¹⁰ | M¹ | M² | M³ | M⁴ | M⁵ | M⁶ | M⁷ | L¹ | L² | L³ | L⁴ |
|---|----|----|----|----|----|----|----|----|----|-----|----|----|----|----|----|----|----|----|----|----|----|
| DR | Me | H | H | OMe | H | Me | OMe | Me | OMe | OH | H | H | H | H | H | Me | Me | | | | |
| DS |   |   |   |   |   |   |   |   |   |    |   |   |   |   |   |   |   |   |   |   |   |
|    |   |   |   |   |   |   |   |   |   |    |   |   |   |   |   |   | CH₂OH |   |   |   |   |
|    | MeO-CH₂CH₂-O-CH₂CH₂- |
| DT |   |   |   |   |   |   |   | CH₂OH |   |   |   |   |   |   |   |   |   |   |   |   |   |
|    | MeO-CH₂CH₂-O-CH₂CH₂- |
| DU |   |   |   |   |   |   |   |   |   |    |   |   |   |   |   |   |   |   |   |   |   |
|    | MeO-CH₂CH₂-O-CH₂CH₂- |
| DV |   |   |   | OH |   |   |   |   |   |    |   |   |   |   |   |   |   | epoxide-Me | epoxide | epoxide | 2-methylallyl-OH |
|    |   |   |   |   |   |   |   |   |   |    |   |   |   |   |   |   |   | epoxide-Me | epoxide | epoxide |   |

TABLE 1-continued
Table of preferred compounds.
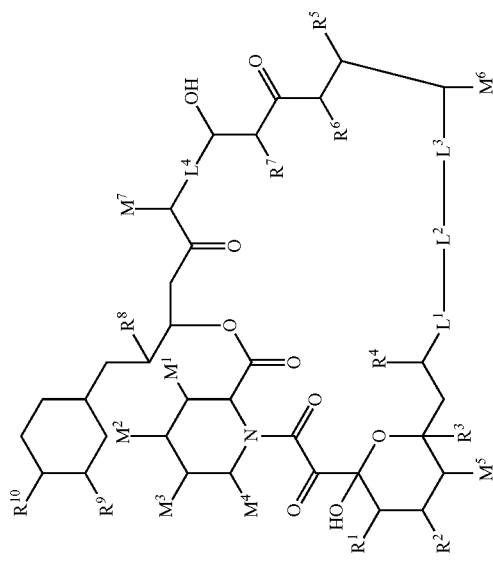
| * | R¹ | R² | R³ | R⁴ | R⁵ | R⁶ | R⁷ | R⁸ | R⁹ | R¹⁰ | M¹ | M² | M³ | M⁴ | M⁵ | M⁶ | M⁷ | L¹ | L² | L³ | L⁴ |
|---|---|---|---|---|---|---|---|---|---|---|---|---|---|---|---|---|---|---|---|---|---|
| DW | Me | H | H | OMe | H | Me | OMe | Me | OMe | OH | H | H | H | H | H | Me | Me | | | | |
| DX | | | | | | | OH | | OH | | | | | | | | | | | | |
| DY | | | | OH | | | OH | | | | | | | | | | | | | | |
| DZ | | | | | | | | | | | | | | | | | | | | | |

TABLE 1-continued
Table of preferred compounds.
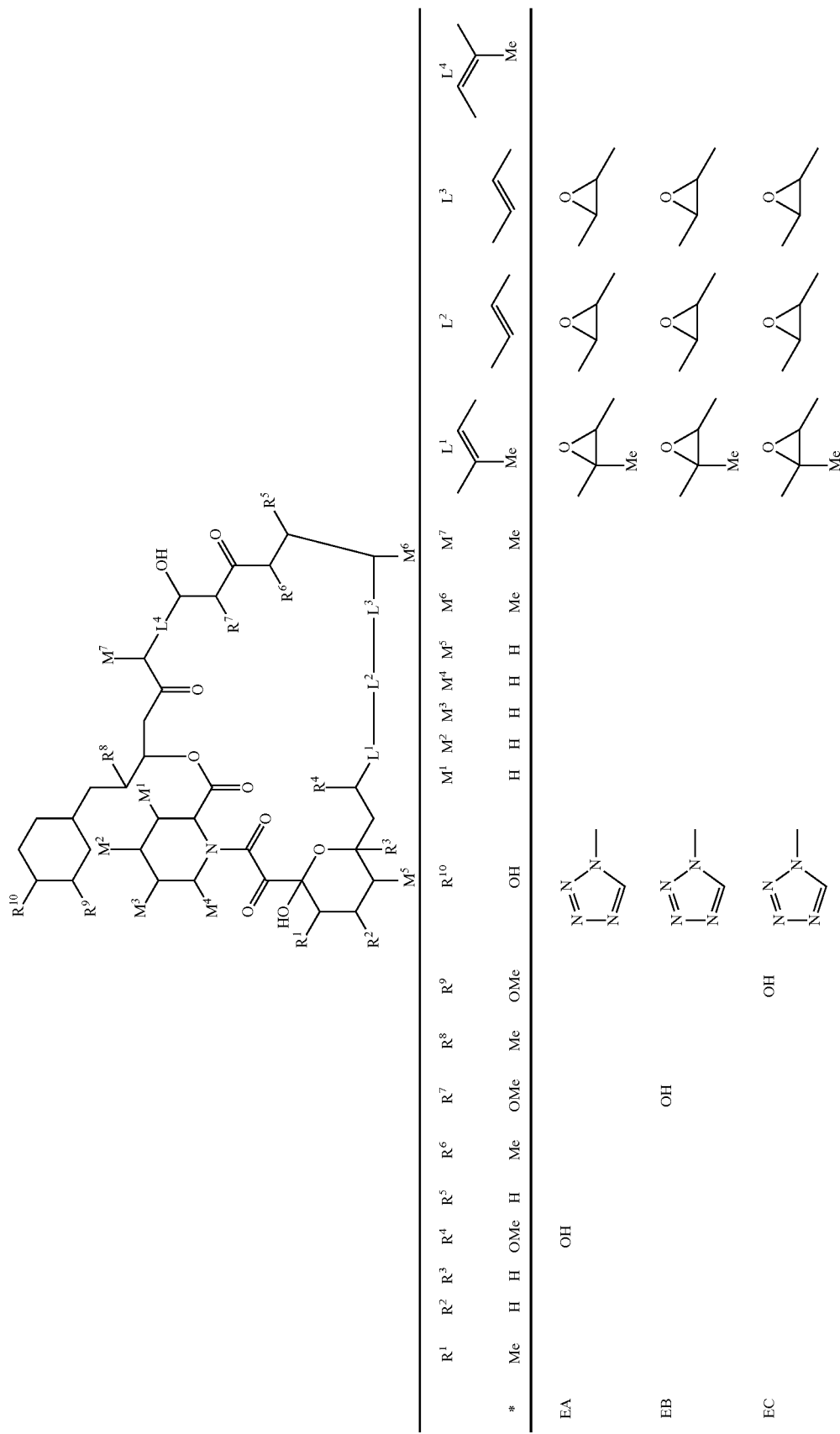
| * | $R^1$ | $R^2$ | $R^3$ | $R^4$ | $R^5$ | $R^6$ | $R^7$ | $R^8$ | $R^9$ | $R^{10}$ | $M^1$ | $M^2$ | $M^3$ | $M^4$ | $M^5$ | $M^6$ | $M^7$ | $L^1$ | $L^2$ | $L^3$ | $L^4$ |
|---|---|---|---|---|---|---|---|---|---|---|---|---|---|---|---|---|---|---|---|---|---|
| EA | Me | H | H | OMe | OH | Me | OMe | Me | OMe | OH | H | H | H | H | H | H | Me | | | | |
| EB | | | | | | | OH | | | | | | | | | | | | | | |
| EC | | | | | | | | | OH | | | | | | | | | | | | |

TABLE 1-continued
Table of preferred compounds.
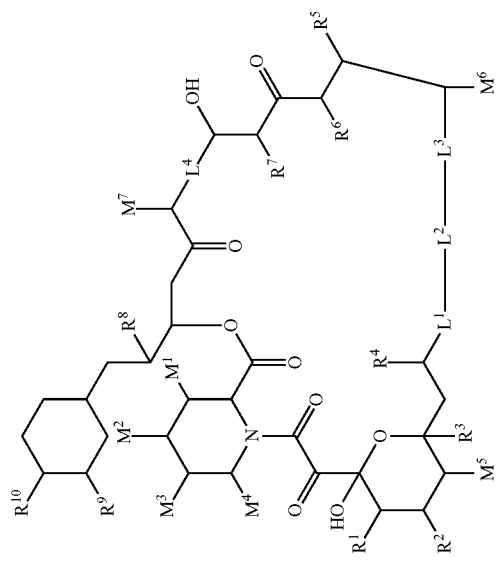
| * | R¹ | R² | R³ | R⁴ | R⁵ | R⁶ | R⁷ | R⁸ | R⁹ | R¹⁰ | M¹ | M² | M³ | M⁴ | M⁵ | M⁶ | M⁷ | L¹ | L² | L³ | L⁴ |
|---|----|----|----|----|----|----|----|----|----|-----|----|----|----|----|----|----|----|----|----|----|----|
| ED | Me | H | H | OMe | H | Me | OMe | Me | OMe | OH | H | H | H | H | H | Me | Me |  |  |  |  |
| EE | | | | OH | | | OH | | | 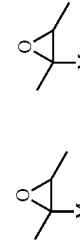 | | | | | | | | 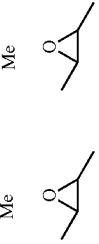 | | |  |
| EF | | | | | | | | | |  | | | | | | | |  |  |  | |
| EG | | | | OH | | | | | | | | | | | | | | | | | |

TABLE 1-continued

Table of preferred compounds.

| * | R¹ | R² | R³ | R⁴ | R⁵ | R⁶ | R⁷ | R⁸ | R⁹ | R¹⁰ | M¹ | M² | M³ | M⁴ | M⁵ | M⁶ | M⁷ | L¹ | L² | L³ | L⁴ |
|---|----|----|----|----|----|----|----|----|----|-----|----|----|----|----|----|----|----|----|----|----|----|
|   | Me | H | H | OMe | H | Me | OMe | Me | OMe | OH | H | H | H | H | H | H | Me | prenyl (=CMe₂) | but-2-enyl | but-2-enyl | prenyl (=CMe₂) |
| EH |   |   |   |   |   |   | OH |   |   | -CH(Me)(CH₂OH)₂-CO₂Me | | | | | | | | epoxide-Me,Me | but-2-enyl | but-2-enyl | prenyl |
| EI |   |   |   |   |   |   |   |   | OH | -CH(Me)(CH₂OH)₂-CO₂Me | | | | | | | | epoxide-Me,Me | epoxide | but-2-enyl | prenyl |
| EJ |   |   |   | OH |   |   | OH |   |   | -CH(Me)(CH₂OH)₂-CO₂Me | | | | | | | | epoxide-Me,Me | epoxide | epoxide | prenyl |
| EK |   |   |   |   |   |   |   |   |   | -CH(Me)(CH₂OH)₂-CO₂Me | | | | | | | | epoxide-Me,Me | epoxide | epoxide | epoxide-Me |

TABLE 1-continued

Table of preferred compounds.

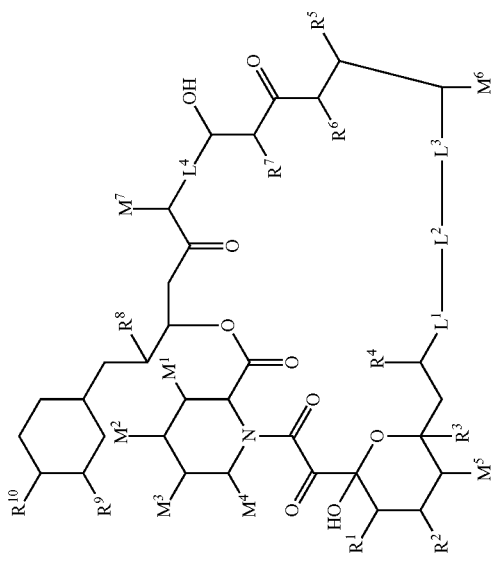

| * | R¹ | R² | R³ | R⁴ | R⁵ | R⁶ | R⁷ | R⁸ | R⁹ | R¹⁰ | M¹ | M² | M³ | M⁴ | M⁵ | M⁶ | M⁷ | L¹ | L² | L³ | L⁴ |
|---|----|----|----|----|----|----|----|----|----|-----|----|----|----|----|----|----|----|----|----|----|----|
| EL | Me | H | H | OMe | H | Me | OMe | Me | OMe | OH | —OP(O)Me₂ | H | H | H | H | H | Me | prenyl | CH=CH | CH=CH | prenyl |
| EM | Me | H | H | OH  | H | Me | OMe | Me | OMe |    | —OP(O)Me₂ | H | H | H | H | H | Me | epoxide-Me | epoxide | epoxide | prenyl |
| EN | Me | H | H | OMe | H | Me | OH  | Me | OMe |    | —OP(O)Me₂ | H | H | H | H | H | Me | epoxide-Me | epoxide | epoxide | prenyl |
| EO | Me | H | H | OMe | H | Me | OMe | Me | OH  |    | —OP(O)Me₂ | H | H | H | H | H | Me | epoxide-Me | epoxide | epoxide | prenyl |

TABLE 1-continued

Table of preferred compounds.

| * | R¹ | R² | R³ | R⁴ | R⁵ | R⁶ | R⁷ | R⁸ | R⁹ | R¹⁰ | M¹ | M² | M³ | M⁴ | M⁵ | M⁶ | M⁷ | L¹ | L² | L³ | L⁴ |
|---|---|---|---|---|---|---|---|---|---|---|---|---|---|---|---|---|---|---|---|---|---|
| | Me | H | H | OMe | H | Me | OMe | Me | OMe | OH | H | H | H | H | H | H | Me | | | | |
| EP | | | | | OH | | OH | | | | | | | | | | | | | | |
| EQ | | | | | | | | | | —OP(O)Me₂ | | | | | | | | | | | |
| ER | | | | | | | | | | —OP(O)Me₂ | | | | | | | | | | | |
| ES | | | | | OH | | | | | | | | | | | | | | | | |

TABLE 1-continued

Table of preferred compounds.

| * | R¹ | R² | R³ | R⁴ | R⁵ | R⁶ | R⁷ | R⁸ | R⁹ | R¹⁰ | M¹ | M² | M³ | M⁴ | M⁵ | M⁶ | M⁷ | L¹ | L² | L³ | L⁴ |
|---|----|----|----|----|----|----|----|----|----|-----|----|----|----|----|----|----|----|----|----|----|----|
|   | Me | H  | H  | OMe | H | Me | OMe | Me | OMe | OH | H | H | H | H | H | Me | Me | ⎬Me (isobutenyl) | ⎬ (propenyl) | ⎬ (propenyl) | ⎬Me (isobutenyl) |
| ET |   |   |   |   |   |   | OH |   |   | MeO(CH₂)₂O(CH₂)₂— |   |   |   |   |   |   |   | epoxide-Me | epoxide | epoxide |   |
| EU |   |   |   |   |   |   |   |   | OH | MeO(CH₂)₂O(CH₂)₂— |   |   |   |   |   |   |   | epoxide-Me | epoxide | epoxide |   |
| EV |   |   |   | OH |   |   | OH |   |   | MeO(CH₂)₂O(CH₂)₂— |   |   |   |   |   |   |   | epoxide-Me | epoxide | epoxide |   |
| EW |   |   |   |   |   |   |   |   |   | MeO(CH₂)₂O(CH₂)₂— |   |   |   |   |   |   |   | epoxide-Me |   |   | epoxide-Me |

TABLE 1-continued
Table of preferred compounds.
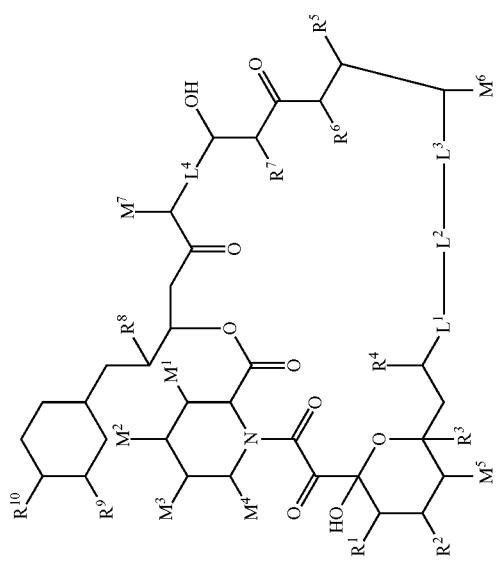
| * | R¹ | R² | R³ | R⁴ | R⁵ | R⁶ | R⁷ | R⁸ | R⁹ | R¹⁰ | M¹ | M² | M³ | M⁴ | M⁵ | M⁶ | M⁷ | L¹ | L² | L³ | L⁴ |
|---|----|----|----|----|----|----|----|----|----|-----|----|----|----|----|----|----|----|----|----|----|----|
| EX | Me | H | H | OMe | H | Me | OMe | Me | OMe | OH | H | H | H | H | H | H | Me | | | | |
| EY | | | | | OH | | OH | | | OMe-CH2CH2-OH | | | | | | | | epoxide-Me | epoxide | epoxide | |
| EZ | | | | | | | | | OH | OMe-CH2CH2-OH | | | | | | | | epoxide-Me | epoxide | epoxide | |

TABLE 1-continued
Table of preferred compounds.
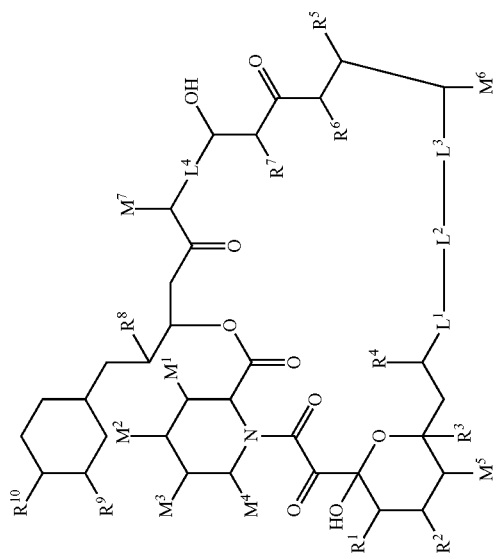
| | R¹ | R² | R³ | R⁴ | R⁵ | R⁶ | R⁷ | R⁸ | R⁹ | R¹⁰ | M¹ | M² | M³ | M⁴ | M⁵ | M⁶ | M⁷ | L¹ | L² | L³ | L⁴ |
|---|---|---|---|---|---|---|---|---|---|---|---|---|---|---|---|---|---|---|---|---|---|
| * | Me | H | H | OMe | H | Me | OMe | Me | OMe | OH | H | H | H | H | H | Me | Me | $\underset{\text{Me}}{\diagup}\!\!=\!\!\diagdown_{\text{Me}}$ | –CH=CH– | –CH=CH– | $\underset{\text{Me}}{\diagup}\!\!=\!\!\diagdown_{\text{Me}}$ |
| FA | | | | OH | | | OH | | | –OCH₂CH₂OMe | | | | | | | | epoxide (Me,Me) | epoxide | epoxide | epoxide (Me,Me) |
| FB | | | | | | | | | | –OCH₂CH₂OMe | | | | | | | | epoxide (Me,Me) | | | |

TABLE 1-continued
Table of preferred compounds.
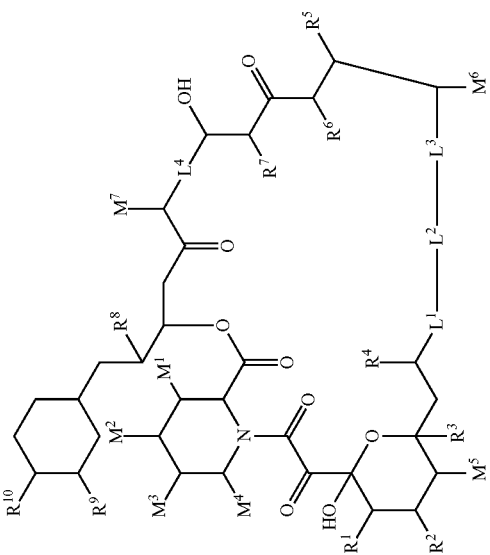
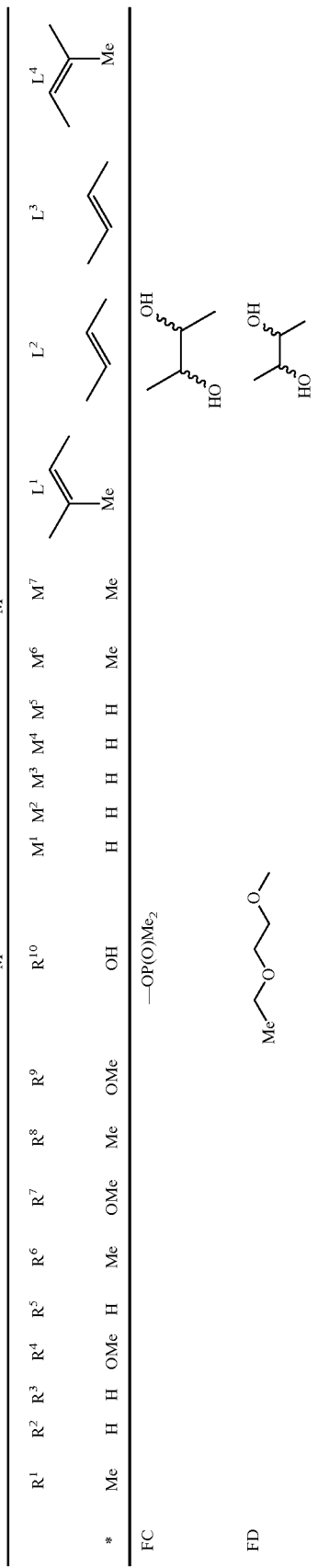
| | R¹ | R² | R³ | R⁴ | R⁵ | R⁶ | R⁷ | R⁸ | R⁹ | R¹⁰ | M¹ | M² | M³ | M⁴ | M⁵ | M⁶ | M⁷ | L¹ | L² | L³ | L⁴ |
|---|---|---|---|---|---|---|---|---|---|---|---|---|---|---|---|---|---|---|---|---|---|
| * | Me | H | H | OMe | H | Me | OMe | Me | OMe | OH | H | H | H | H | H | Me | Me | | | | |
| FC | | | | | | | | | | —OP(O)Me₂ | | | | | | | | | | | |
| FD | | | | | | | | | | MeOCH₂CH₂O— | | | | | | | | | | | |
* Rapamycin. All —OH substitutions represent a mixture of both the R and the S isomer.

In some embodiments, the compound of the present invention has the following structure:

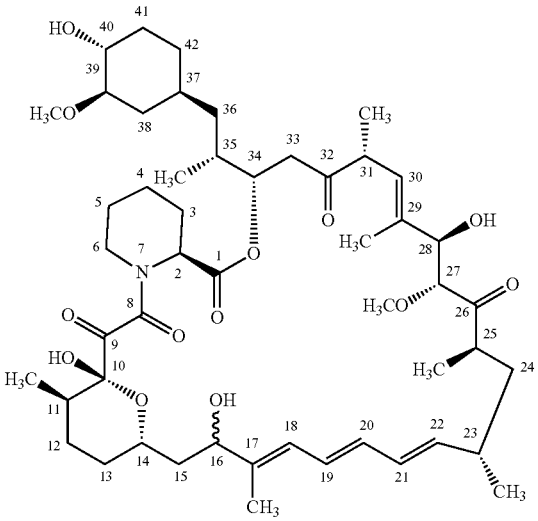

This invention covers compounds in which the stereochemistry of the 16-position is racemic (R,S) as well as the individual R and S stereoisomers at the 16-position and all other isomers of the compound.

The invention covers compounds with different polymorphic forms. This includes 16-O-demethyl macrocyclic lactone having different polymorphic forms. For example, different polymorphs form of 16-O-demethyl macrocyclic lactone are obtained from using dichloromethylene and from using a mixture of methanol and water There have been different numbering schemes proposed for macrocyclic lactones. To avoid confusion, when specific macrocyclic lactones are named herein, the names are given with reference to macrocyclic lactone using the numbering scheme of the above chemical formula. This invention also covers all the macrocyclic lactones which have different name due to a different numbering scheme if the same functional group exists in the same location within the chemical structure. For example, 39-O-demethyl macrocyclic lactone is the same compound as 41-O-demethyl macrocyclic lactone and 16-O-demethyl macrocyclic lactone is the same compound as 7-O-demethyl macrocyclic lactone.

The compounds of the present invention can be prepared by a variety of methods. In some embodiments, the compounds of the present invention are synthesized biologically by genetically modifying the strains of organisms to produce the compounds of the present invention or by other means.

In another embodiment the compounds of the present invention are prepared using chemical synthesis. Chemical synthesis of the compounds of the present invention can utilize the 17-18, 19-20, 21-22 triene structure in macrocyclic lactones, which facilitates the acid catalyzed nucleophilic substitution of the C16 methoxy group and allows the introduction of a number of different substitutions and allows the selective manipulation of macrocyclic lactone effector domain. The C16 methoxy group in macrocyclic lactones is manipulated towards acidic reagents to produce the compounds of the present invention. For example, replacement of C16 methoxy groups with different nucleophiles such as alcohols, thiols and electron rich aromatic groups can be accomplished. This method of synthesis can be performed without protection and deprotection steps.

The method of synthesis of using acidic reagents with compounds having triene functional groups can be applied to other compounds having triene functional groups to synthesize corresponding compound analogues providing a method of synthesis without protection and deprotection steps In some embodiments, the present invention provides a method of making a compound of the present invention, the method comprising contacting a macrocyclic lactone with an acid to replace an alkoxy group with a nucleophile, thereby making a compound of the present invention. In some other embodiments, the macrocyclic lactone is rapamycin. In other embodiments, the nucleophile is a member selected from the group consisting of —OH, —SH and electron rich aromatic groups. One of skill in the art will appreciate that other methods are useful for preparing the compounds of the present invention.

Figure 14:
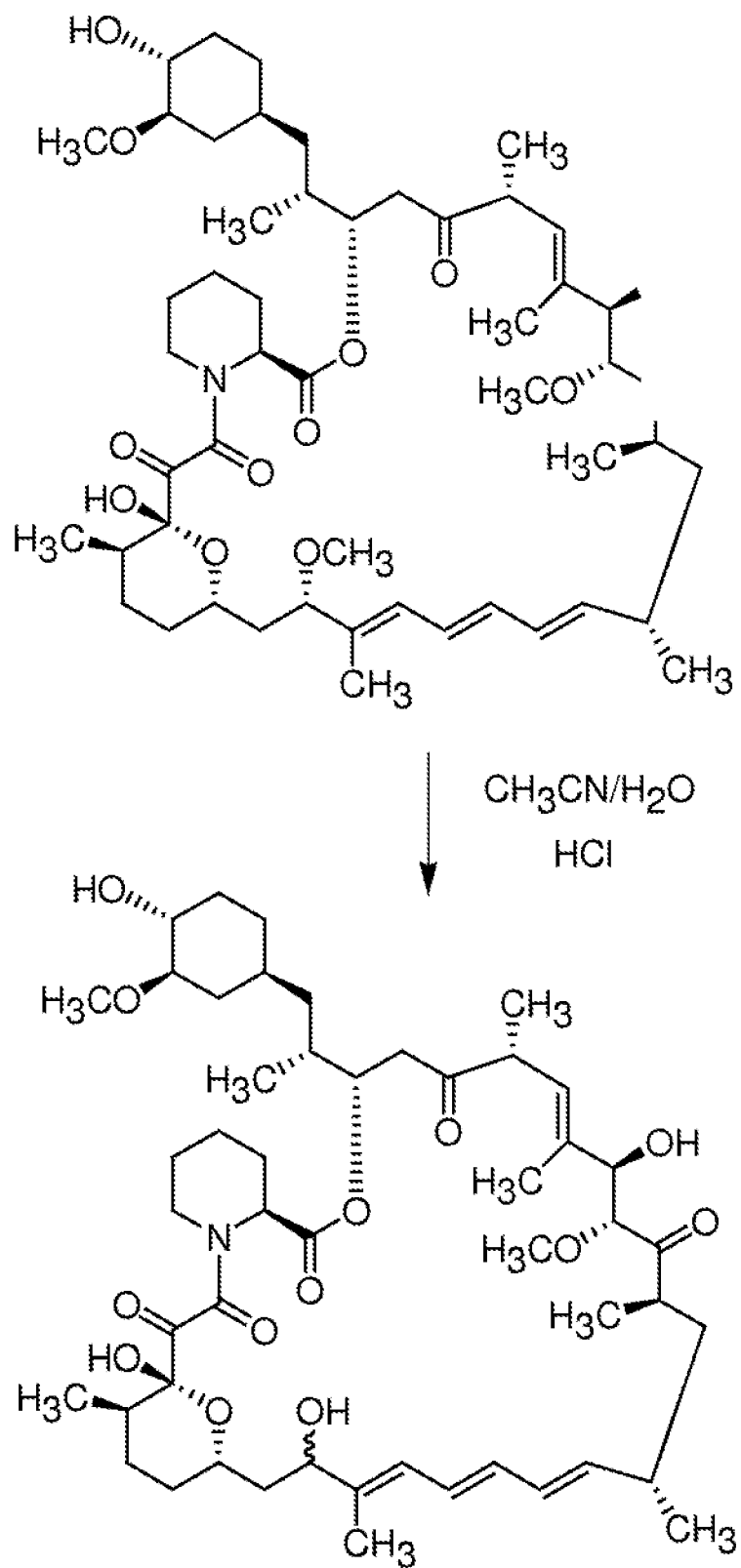
FIG. 14 shows the synthesis of 16-O-demethyl macrocyclic lactone of the present invention.
Figure 16:
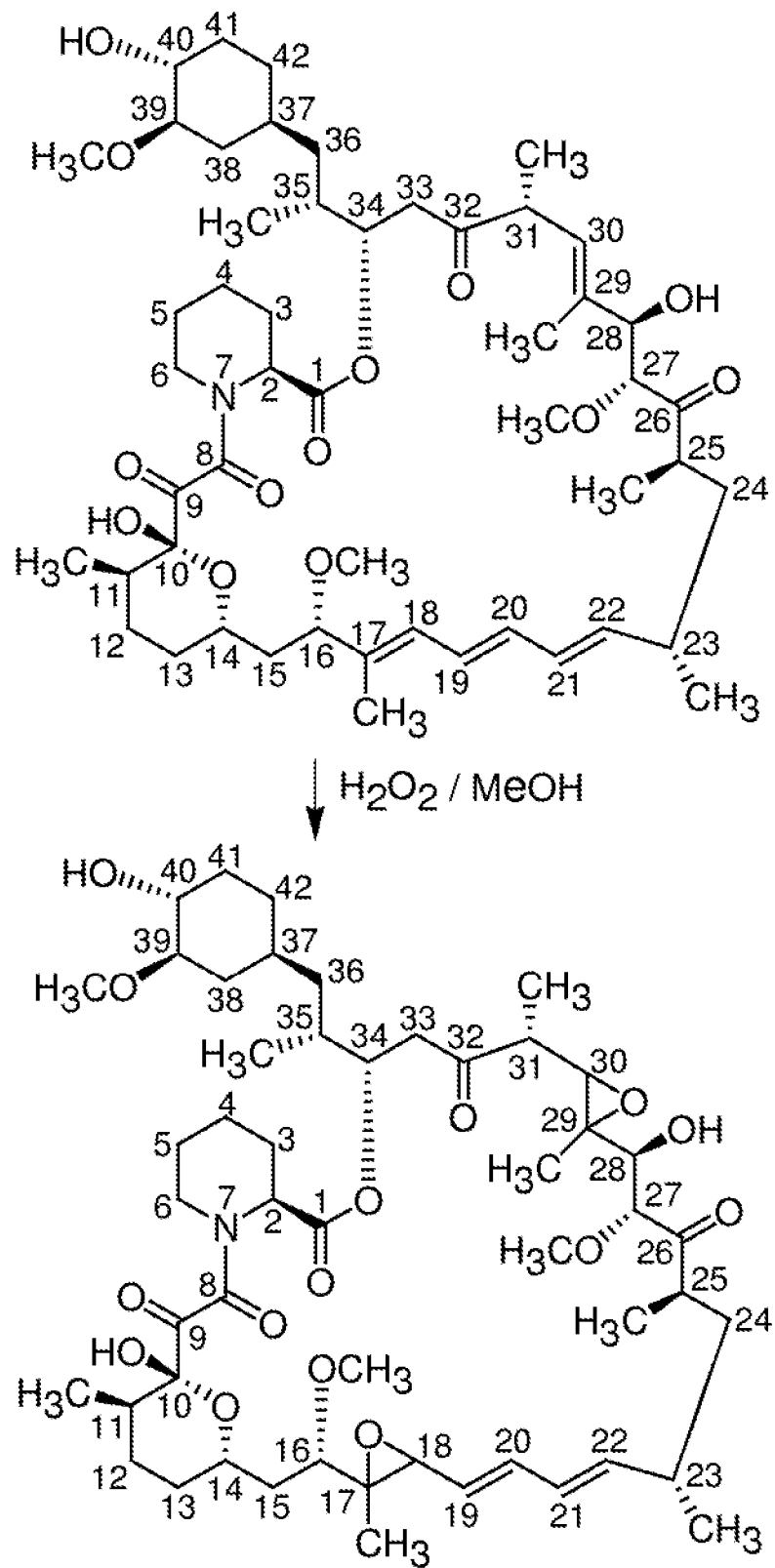
FIG. 16 shows the synthesis of 17,18-29,30-bis epoxide macrocyclic lactone.
Figure 17B:
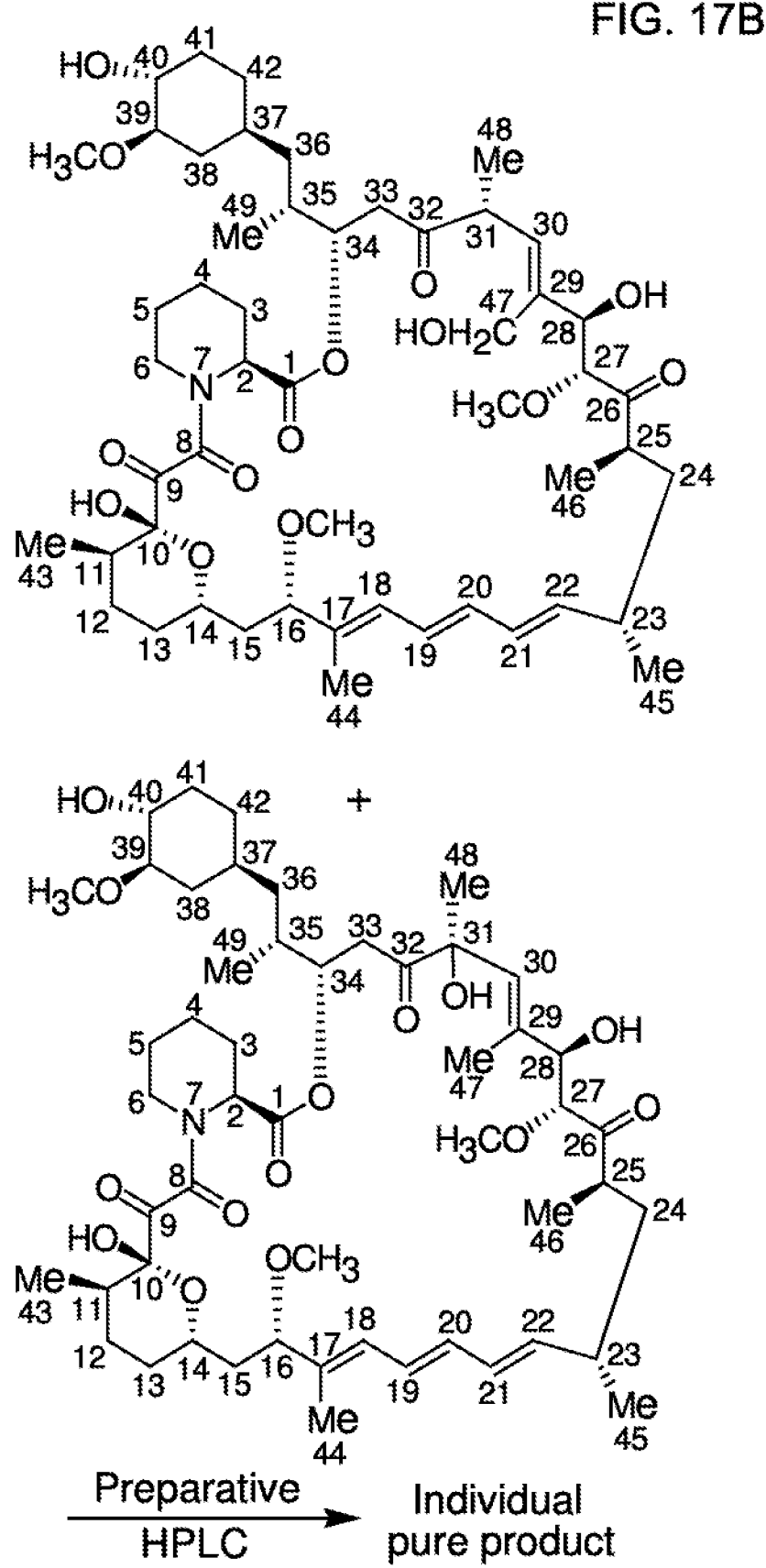
Figure 18A:
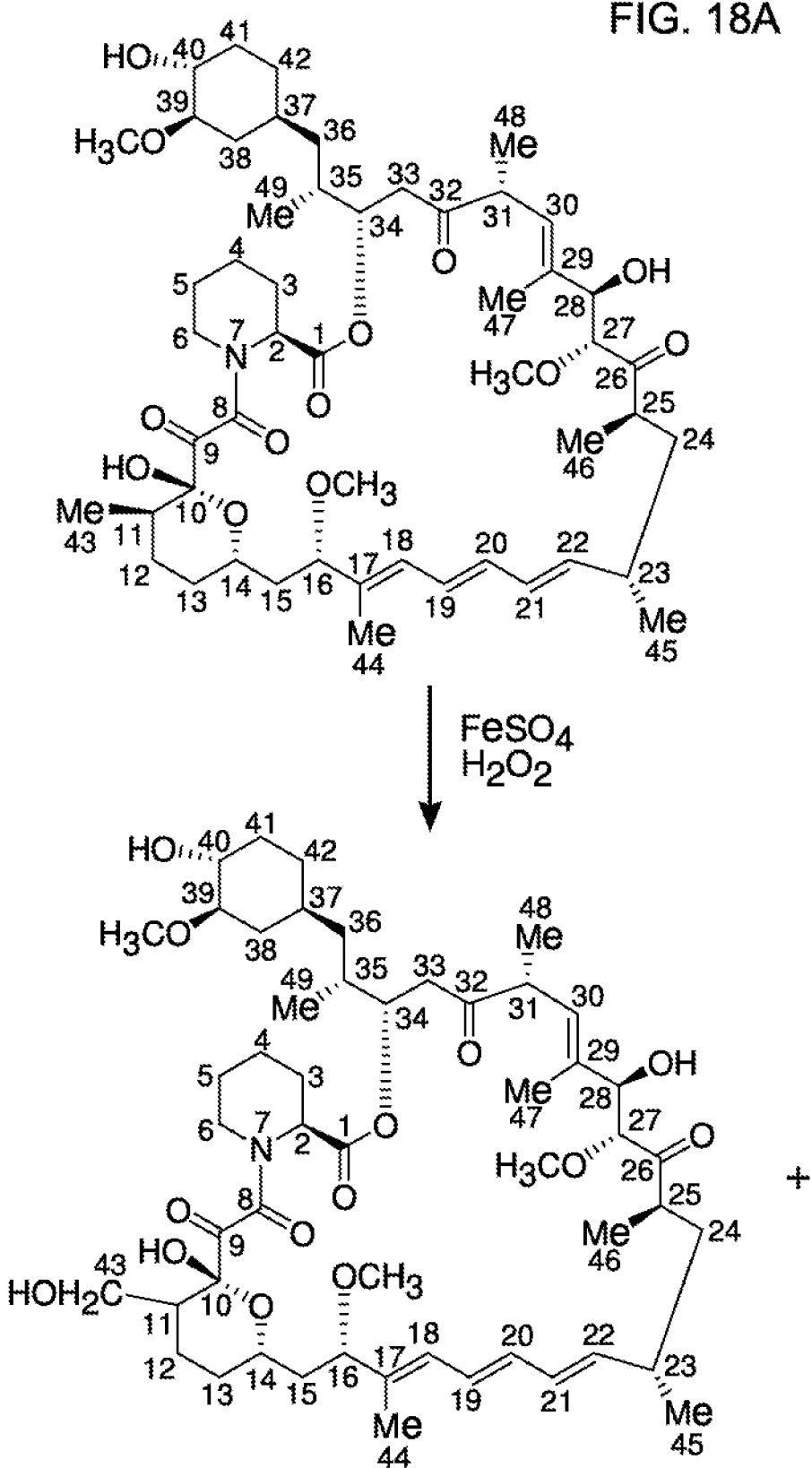
FIGS. 18A-18B show the synthesis of 43-hydroxyl and 47-hydroxyl macrocyclic lactones.
Figure 18B:
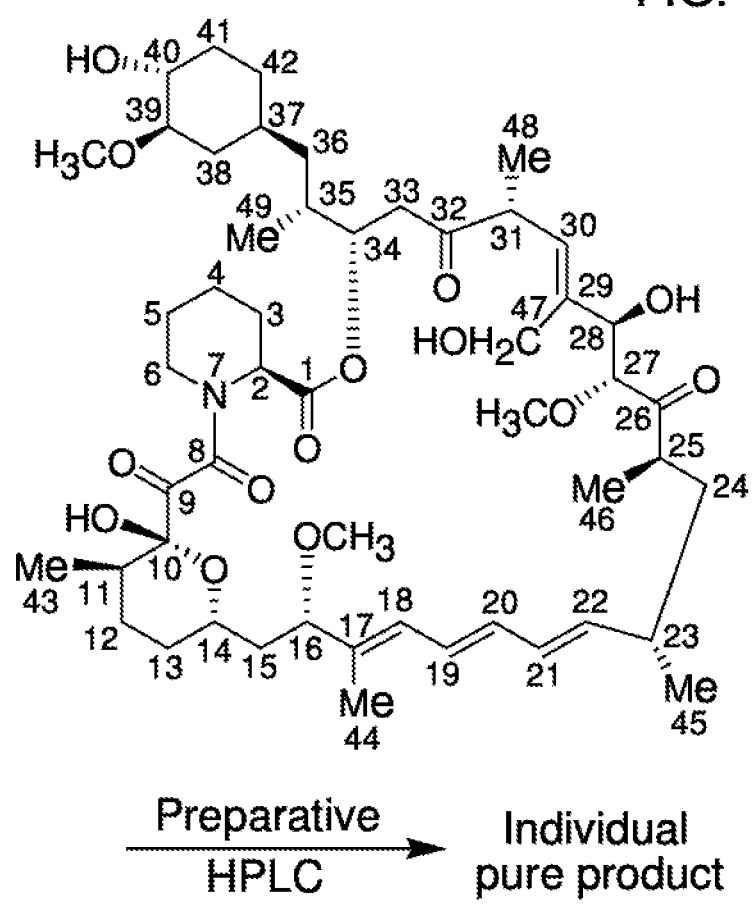

Synthesis of demethyl macrocyclic lactone is provided in FIG. 14 using 16-O-demethyl macrocyclic lactone as an example. Synthesis of hydroxy macrocyclic lactone is provided in FIGS. 15A-15B using 19, 20 bis-hydroxy macrocyclic lactone as an example. Synthesis of epoxide macrocyclic lactone is provided in FIG. 16 using 17,18-29,30-bis epoxide macrocyclic lactone as an example.

In another embodiment, the present invention provides a method of making a compound of the present invention, the method comprising contacting a macrocyclic lactone with a suitable agent such as a peracid or peroxide, to modify an alkene group to an epoxide, thereby making a compound of the present invention. Peracids useful in the methods of the present invention include, but are not limited to, peroxycarboxylic acids of the formula R—C(O)—OOH, where the R group can be groups such as H, alkyl, alkene or aryl. In some embodiments, the peracid can be peroxy-acetic acid or meta-chloro-peroxybenzoic acid (MCPBA). Peroxides useful in the methods of the present invention include, but are not limited to, hydrogen peroxide. One of skill in the art will appreciate that other epoxidation reagents are useful in the present invention.

The compounds of the present invention are optionally deuterated.

In some embodiments, the present invention provides compounds of the present invention which have a similar potency to the corresponding parent macrocyclic lactone. In another embodiment, the present invention provides compounds of the present invention which are less potent than the corresponding parent macrocyclic lactone in order to improve the safety profile of the compounds.

III. Delivery of the Compounds of the Present Invention

The compounds of the present invention can be administered in any appropriate manner. In some embodiments, the compounds are administered orally, intramuscularly, intraperitoneally, subcutaneously, pulmonarily, mucosally, transdermally, intravascularly, intraocularly or intravitreally through the eye, and others. In other embodiments, the compounds are administered site specifically through temporary or permanent drug delivery means such as an implant or a combination of systemic and site specific means. Examples include, but are not limited to catheter, stent, vascular wrap, pump, shunt or other temporary or permanent drug delivery means.

A. Device

In some embodiments, the present invention provides a device for intracorporeal use, the device comprising a vascular prosthesis; and at least one source of a compound of the present invention.

In other embodiments, the present invention provides a device configured to release the compound to a body lumen or organ within an intracorporeal body to inhibit cell proliferation or cell migration. In a further embodiment, the device is configured to release the compound to a body lumen or organ within an intracorporeal body to inhibit smooth muscle cell proliferation or neo-vascularization.

In another embodiment of the present invention the drug delivery means is a device such as an implant including graft implants, vascular implants, non-vascular implants, implantable luminal prostheses, wound closure implants, drug delivery implants, sutures, biologic delivery implants, urinary tract implants, inter-uterine implants, organ implants, ophthalmic implants, bone implants including bone plates, bone screws, dental implants, spinal disks, or the like.

When the device is configured for treatment of ophthalmic conditions or diseases, the implant of the present invention can be implanted intraocularly or intravitreally by an intervention procedure. Such implants can be non-biodegradable, biodegradable, removable or permanent. In other embodiments, implants can be placed in the duct, such as the tear duct. In still other embodiments, implants can be placed adjacent to the ocular body, or intraocularly, adjacent to the vitreal body or intravitreally. One of skill in the art will appreciate that other locations are useful in the present invention.

The implant typically allows for one or more of the following: support, contain, hold together, affix, plug, close, maintain, deliver drug, deliver biologics—to a body lumen, organ, vessel, conduit, muscle, tissue mass or bone for the prevention or treatment of disease conditions, such as for example hyper-proliferative diseases, restenosis, cardiovascular disease, inflammation, wound healing, cancer, aneurysm, diabetic disease, abdominal aortic aneurysm, hypercalcemia, or others.

The implant of the present invention can be formed of metal, metal alloy, polymer, ceramic, semi-metal, nanocomposites or combination thereof. For example, an implant can be made from metal such as tantalum, iron, magnesium, molybdenum or others; from a degradable or non degradable metal alloy such as 316L stainless steel, carbon steel, magnesium alloy, NI—Ti, Co—Cr such as L605, MP35 or other; from a polymer that is degradable or non-degradable such as poly lactic acid, poly glycolic acid, poly esters, polyamide, copolymers or others or blends of polymers; combination of metals and metals or metal alloys such as implant made from combination of layers of stainless steel and tantalum or others; nanocomposites such as nano carbon fibers or nano carbon tubules or others.

In another embodiment, the present invention provides a device wherein the implant is a vascular prosthesis. In some embodiments, the vascular prosthesis comprises an expandable structure. In other embodiments, the vascular prosthesis comprises a stent, graft, or a scaffold formed at least in part from an open lattice. In still other embodiments, the vascular prosthesis is a stent.

In another embodiment, the compounds of the present invention can be applied adjacent to the surface of the implant. For example the compounds of the present invention can be incorporated within the implant, contained within a coating, or carried on the implant.

In some embodiments, the present invention provides a device comprising a vascular prosthesis wherein the vascular prosthesis has a luminal and a tissue facing surface, and wherein the compound is associated with at least one of the luminal or tissue facing surfaces.

In a further embodiment, the compounds of the present invention are applied on all implant surfaces. In another embodiment, the compounds of the present invention are applied only to the abluminal or luminal surface. In yet another embodiment, the compounds of the present invention are applied only to high stress or low stress areas.

In another embodiment, the compounds of the present invention are contained within an erodible or non-erodible filament or filaments that are adjacent to the implant.

Figure 3:
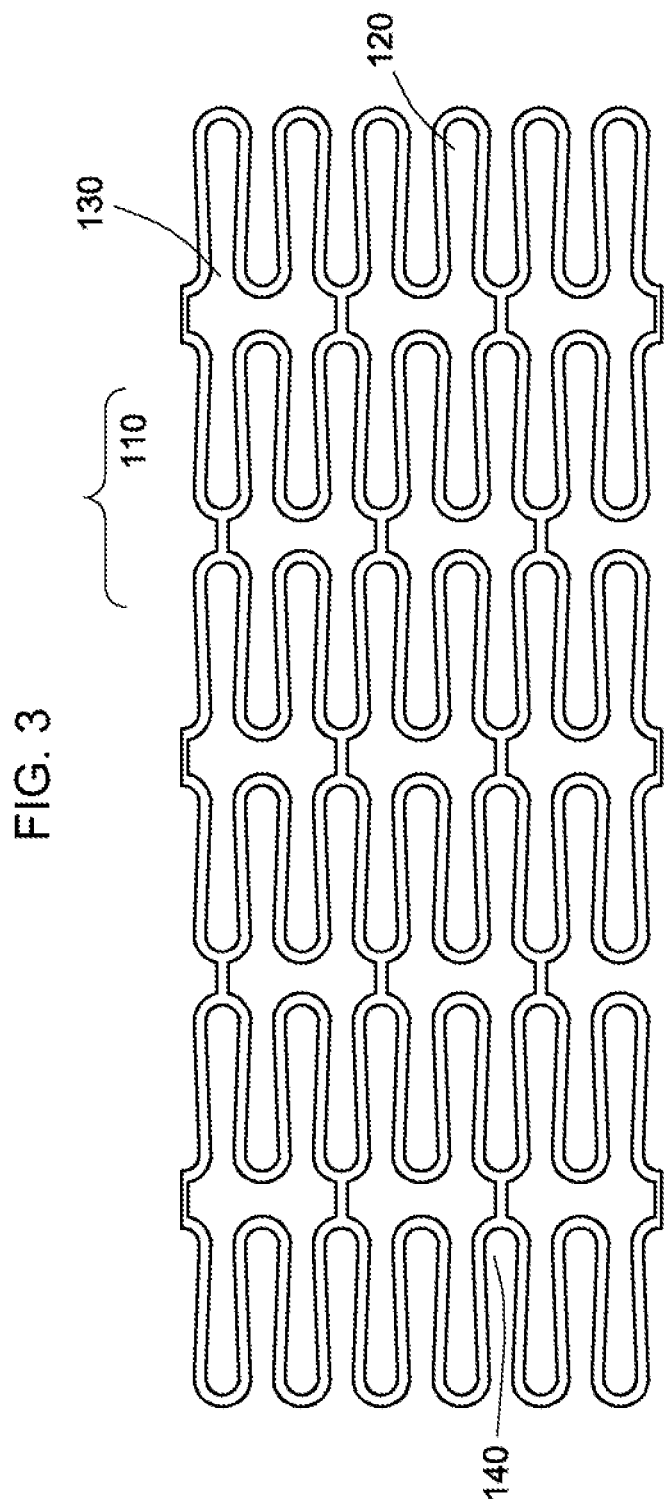
FIG. 3 shows an example of stent configuration having an expandable structure.

An example of a stent configuration for carrying a compound of the present invention is illustrated in FIG. 3 in a contracted state. The stent body is formed of multiple rings 110. The rings are formed of crowns 120 and struts 130 in a generally expandable undulating configurations such as, zigzag, sawtooth, sinusoidal wave or other. The body is joined by links or connectors 140. It is understood that the connectors may be of any length or shape, or may not be needed if the crowns are directly attached to each other. The stent has a typical contracted state diameter of between 0.25-4 mm, or more preferably between 0.7 to 1.5 mm, and a length of between 5 and 100 mm. In its expanded state, the stent diameter is typically at least twice and up to 10 times or more than that of the stent in its contracted state. Thus, a stent with a contracted diameter of between 0.7 to 1.5 mm may expand radially to 2 to 10 mm or more.

Drug eluting stents with potent macrocyclic lactone compounds such as rapamycin (Cypher™) have resulted in late lumen loss in the range of approximately 0.01 mm to 0.2 mm at approximately 4 months to 12 months angiographic follow up. The late lumen loss with bare metal stents have ranged from approximately 0.70 mm to 1.2 mm for the same time period. Lower late lumen loss typically decreased the percent stenosis. However, significantly lower late lumen loss with drug eluting stents as compared to bare metal stents in some cases results in inadequate tissue coverage of the stent surface which potentially may increase incidence of late stent thrombosis.

In a preferred embodiment, the late lumen loss for stent carrying compounds of the present invention after approximately 4 to 12 months after implantation is greater than the late lumen loss for stent carrying the corresponding parent macrocyclic lactone by 0.05 mm to 0.6 mm, preferably by 0.1 mm to 0.4 mm, more preferably by 0.15 to 0.3 mm. For example, late lumen loss after implantation ranges from 0.01 mm to 0.6 mm, preferably from 0.1 mm to 0.5 mm and most preferably from 0.2 mm to 0.4 mm. In another embodiment, the present invention provides late lumen loss for stent carrying compounds of the present invention similar to a stent carrying the corresponding parent macrocyclic lactone. In another preferred embodiment, the present invention provides late lumen loss for stent carrying compounds of the present invention being higher than for a stent carrying the corresponding parent macrocyclic lactone. Higher late lumen can provide increased tissue coverage of the stent which can improve safety of the stent.

In another preferred embodiment, the percent stenosis approximately 4 to 12 months after implantation for a stent carrying compounds of the present invention is greater by 1 to 30 percentage than the percent stenosis for a stent carrying the corresponding parent macrocyclic lactone, preferably from 3 to 20 percentage, more preferably from 5 to 15 percentage. In yet another preferred embodiment, the present invention provides percent stenosis for a stent carrying compounds of the present invention similar to a stent carrying the corresponding parent macrocyclic lactone. In another preferred embodiment, the present invention provides percent stenosis for a stent carrying compounds of the present invention higher than a stent carrying the corresponding parent macrocyclic lactone. In another preferred embodiment, the percent stenosis for a stent carrying compounds of the present invention is higher than a stent carrying the corresponding parent macrocyclic lactone but lower than the bare metal stent. Higher stenosis can provide increased tissue coverage of the stent which can improve safety of the stent.

In some embodiments, the present invention provides a device wherein the amount of compounds of the present invention on the implant is less than about 1 g/cm². In other embodiments, the amount of compounds on the implant can range from about 1 nanogram/cm² to about 1000 microgram/cm², preferably from about 1 microgram/cm² to about 500 microgram/cm², more preferably from about 10 microgram/cm² to about 400 microgram/cm². In still other embodiments, the amount of compound on the implant is less than about 1 mg. In yet other embodiments, the amount of compound on the implant is from about 1 µg to about 50 mg, preferably from about 100 µg to about 10 mg, more preferably from about 200 µg to about 500 µg.

In a further embodiment, the present invention provides a device wherein the concentration of the compound of the present invention in the tissue adjacent to the implant is from about 0.001 ng/gm tissue to about 1000 µg/gm tissue, preferably from about 1 ng/gm tissue to about 500 µg/gm tissue, more preferably from about 100 ng/gm tissue to about 100 µg/gm tissue.

In another embodiment, the compounds of the present invention can be released from the implant over a period ranging from less than 5 minutes to 2 years, preferably from 3 days to 6 months, more preferably from 1 week to 3 months. In other embodiments, the compounds of the present invention can be released from the implant over a period greater than 1 day, preferably greater than 2 weeks, more preferably greater than 1 month. In another embodiment, the compounds of the present invention can require greater than 2 years to be fully released from the stent. In some embodiments, the amount of compound released over the given time period is at least 25%. In other embodiments, the amount of compound released is at least 50%. In still other embodiments, the amount of compound released is at least 75%. In yet other embodiments, the amount of compound released can be at least 80, 85, 90, 91, 92, 93, 94, 95, 96, 97, 98 or 99%.

In a further embodiment, the present invention provides a device wherein at least 75% of the compound is released from the device in a period from about 1 day to about 2 years. In another embodiment, at least 90% of the compound is released from the device in a period from about 3 day to about 6 months. In still another embodiment, at least 90% of the compound is released from the device in a period from about 1 week to about 3 months.

When the compounds of the present invention are administered via injection or eye drop through an intraocular or intravitreal body, the concentration of compound alone or within the polymer matrix, solvent or carrier can vary from 1 ug/ml to 5 mg/ml, and preferably from 5 ug/ml to 30 ug/ml. Following administration, the concentration of the compound of the present invention in the tissue adjacent to the site of administration can be from about 0.1 nM to 500 µM, preferably from about 1 nM to 100 µM, more preferably from about 10 nM to 10 µM. One of skill in the art will appreciate that other concentrations of the compounds of the present invention are useful.

The compounds of the present invention can be released from the implant via any means known in the art. In some embodiments, the implant releases the compound through active or passive means. In other embodiments, the implant releases the compound through osmotic pressure or diffusion. One of skill in the art will appreciate that other means of releasing the compound from the implant are useful in the present invention.

In some embodiments, the present invention provides a device that further includes a therapeutic agent, such as those described below. In some other embodiments, the therapeutic agent is released prior to, concurrent with, or subsequent to the release of the compound. In other embodiments, the compound is released from a first source and the therapeutic agent is released from a second source. In still other embodiments, the compound and the therapeutic agent are released from a single source.

B. Administration

The compounds of the present invention can be administered systemically on a daily, intermittent or one-time dose basis. The daily systemic dose can range from 0.1 mg to 20 mg preferably 0.5 mg to 10 mg, most preferably from 1 mg to 5 mg per day. One of skill in the art will appreciate that other doses are also useful in the present invention.

The compounds of the present invention can be released from the implant at rates ranging from about 1 nanogram/cm²/day to about 1000 microgram/cm²/day, preferably from about 1 microgram/cm²/day to about 200 microgram/cm²/day, more preferably from about 5 microgram/cm²/day to about 100 microgram/cm²/day.

When the device of the present invention is configured for treatment of ophthalmic conditions or diseases, the compounds of the present invention can be administered through the eye as an eye drop or an injection on a daily, intermittent or one time dose basis. The dose can range from 0.1 µg to 30 mg, preferably from 10 µg to 10 mg, most preferably from 100 µg to 1 mg per day. One of skill in the art will appreciate that other doses are also useful in the present invention.

C. Pharmaceutical Formulations

In some embodiments, the present invention provides a pharmaceutical composition comprising a pharmaceutically acceptable excipient and a compound of the formula:

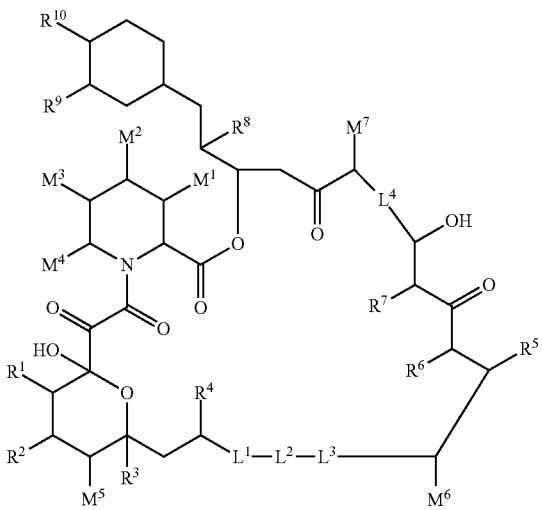

wherein $R^1$, $R^2$, $R^3$, $R^4$, $R^5$, $R^6$, $R^7$, $R^8$, $R^9$, $R^{10}$, $M^1$, $M^2$, $M^3$, $M^4$, $M^5$, $M^6$, $M^7$, $L^1$, $L^2$, $L^3$ and $L^4$ are as described above; and salts, hydrates, isomers, metabolites, N-oxides and prodrugs thereof.

In some other embodiments, the present invention provides a pharmaceutical composition including a pharmaceutically acceptable excipient and a compound of the formula:

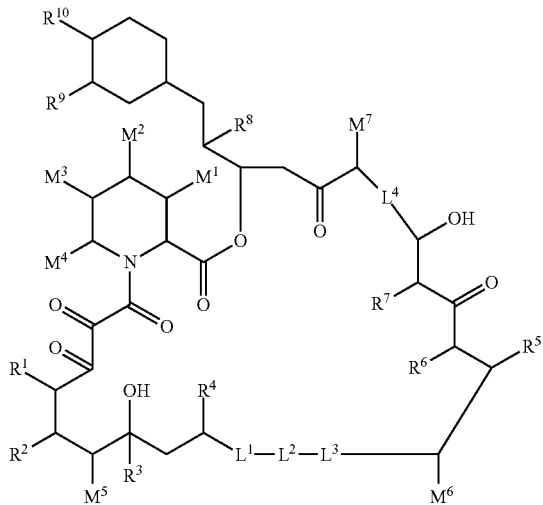

wherein $R^1$, $R^2$, $R^3$, $R^4$, $R^5$, $R^6$, $R^7$, $R^8$, $R^9$, $R^{10}$, $M^1$, $M^2$, $M^3$, $M^4$, $M^5$, $M^6$, $M^7$, $L^1$, $L^2$, $L^3$ and $L^4$ are as described above; and salts, hydrates, isomers, metabolites, N-oxides and prodrugs thereof.

In still other embodiments, the present invention provides a pharmaceutical composition including a pharmaceutically acceptable excipient and a compound of the formula:

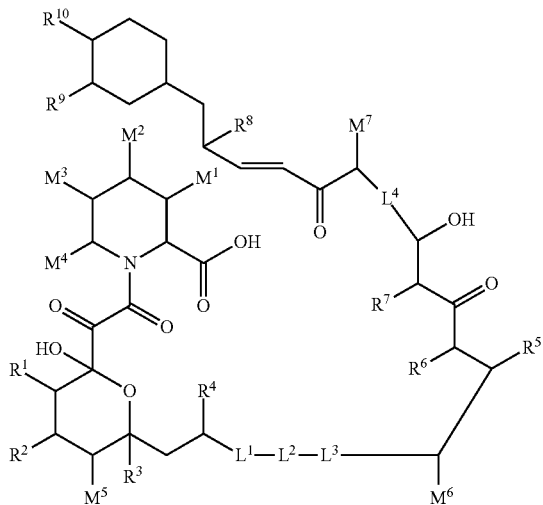

wherein $R^1$, $R^2$, $R^3$, $R^4$, $R^5$, $R^6$, $R^7$, $R^8$, $R^9$, $R^{10}$, $M^1$, $M^2$, $M^3$, $M^4$, $M^5$, $M^6$, $M^7$, $L^1$, $L^2$, $L^3$ and $L^4$ are as described above; and salts, hydrates, isomers, metabolites, N-oxides and prodrugs thereof.

In another embodiment, the pharmaceutical composition includes a compound of FIGS. 2A-2F(V). In other embodiments, $R^1$, $R^6$ and $R^8$ are each methyl, $R^2$, $R^3$ and $R^5$ are each H, $R^4$ and $R^{10}$ are each OH, $R^7$ and $R^9$ are each OMe, $M^1$, $M^2$, $M^3$, $M^4$ and $M^5$ are each H, $M^6$ and $M^7$ are each methyl, $L^1$ and $L^4$ are each

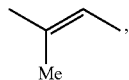

and $L^2$ and $L^3$ are each

In some embodiments, the present invention provides a pharmaceutical composition wherein the pharmaceutically acceptable excipient is a member selected from the group consisting of a polymer, a solvent, an antioxidant, a binder, a filler, a disintegrant, a lubricant, a coating, a sweetener, a flavor, a stabilizer, a colorant, a metal, a ceramic and a semi-metal. In other embodiments, the pharmaceutically acceptable excipient is a polymer.

The active ingredients of the present invention may be mixed with pharmaceutically acceptable carriers, diluents, adjuvants, excipients, or vehicles, such as preserving agents, fillers, polymers, disintegrating agents, glidants, wetting agents, emulsifying agents, suspending agents, sweetening agents, flavoring agents, perfuming agents, lubricating agents, acidifying agents, and dispensing agents, depending on the nature of the mode of administration and dosage forms. Such ingredients, including pharmaceutically acceptable carriers and excipients that may be used to formulate oral dosage forms, are described in the Handbook of Pharmaceutical Excipients, American Pharmaceutical Association (1986), incorporated herein by reference in its entirety. Examples of pharmaceutically acceptable carriers include water, ethanol, polyols, vegetable oils, fats, waxes polymers, including gel forming and non-gel forming polymers, and suitable mixtures thereof. Examples of excipients include starch, pregelatinized starch, Avicel, lactose, milk sugar, sodium citrate, calcium carbonate, dicalcium phosphate, and lake blend. Examples of disintegrating agents include starch, alginic acids, and certain complex silicates. Examples of lubricants include magnesium stearate, sodium lauryl sulphate, talc, as well as high molecular weight polyethylene glycols. One of skill in the art will appreciate that other different excipients can be used in formulations according to the present invention and the list provided herein is not exhaustive.

Suitable nondegradable or slow degrading polymer coatings include, but are not limited to, polyacrylamide, poly-N-vinylpyrrolidone, polydimethyl acrylamide, polymers and copolymers of 2-acrylamido-2-methyl-propanesulfonic acid, acrylic acid and methacrylic acid, polyurethane, polyethylenes imine, ethylene vinyl alcohol copolymer, silicone, C-flex, nylons, polyamide, polyimide, polytetrafluoroethylene (PTFE), parylene, parylast, poly (methyl methacrylate), poly(n-butyl methacrylate), poly (butyl methacrylate) copolymer or blended with poly(ethylene vinyl acetate), poly (methyl methacrylate), poly (2-hydroxy ethyl methacrylate), poly(ethylene glycol methacrylates), poly(vinyl chloride), poly(dimethyl siloxane), poly(ethylene vinyl acetate), polycarbonate, polyacrylamide gels, and the like, including other synthetic or natural polymeric substances; mixtures, copolymers, or combinations thereof.

Suitable biodegradable polymer coatings include, but are not limited to, poly(lactic acid), polylactates, poly(glycolic acid), polyglycolates and copolymers, poly dioxanone, poly (ethyl glutamate), poly(hydroxybutyrate), polyhydroxyvalerate and copolymers, polycaprolactone, polyanhydride, poly(ortho esters); poly(ether esters), poly ethylene glycols, poly(ethylene oxide), poly (trimethyl carbonate), polyethylenecarbonate, copolymers of poly(ethylenecarbonate) and poly(trimethyl carbonate), poly(propylene carbonate), poly (iminocarbonates), starch based polymers, cellulose acetate butyrate, polyester amides, polyester amines, polycyanoacrylates, polyphosphazenes, Poly N-vinyl-2-pyrrolidone, poly maleic anhydride, hyaluronic acid (hyaluronate), chondroitin sulfate, dermatan sulfate, carboxymethylcellulose, heparin sulfate, keratan sulfate, carboxymethylhydroxypropylcellulose, carboxymethylhydroxethylcellulose, cellulose sulfate, cellulose phosphate, carboxymethylguar, carboxymethylhydroxypropylguar, carboxymethylhydroxyethylguar, xanthan gum, carrageenan, anionic polysaccharides, anionic proteins and polypeptides, quaternary ammonium compounds including stearyl ammonium chloride and benzyl ammonium chloride, copolymers and other aliphatic polyesters, or suitable copolymers thereof including copolymers of poly(L-lactic acid) and poly(e-caprolactone); mixtures, copolymers, ionic polymers, or combinations thereof.

Suitable natural coatings include: fibrin, albumin, collagen, gelatin, glycosoaminoglycans, oligosaccharides and poly saccharides, chondroitin, chondroitin sulphates, hypoxyapatite, phospholipids, phosphorylcholine, glycolipids, fatty acids, proteins, cellulose, and mixtures, copolymers, or combinations thereof.

Suitable non polymeric coatings include metallic coatings such as tungsten, magnesium, cobalt, zinc, iron, bismuth, tantalum, gold, platinum, stainless steel such as 316L, 304, titanium alloys; ceramics coatings such as silicon oxide; semi-metals such as carbon, nanoporous coatings; or combination thereof.

In some embodiments, the pharmaceutically acceptable excipient is a polymer is selected from the group consisting of polyurethane, polyethylene imine, ethylene vinyl alcohol copolymer, silicone, C-flex, nylons, polyamide, polyimide, polytetrafluoroethylene (PTFE), parylene, parylast, poly (methacrylate), poly(vinyl chloride), poly(dimethyl siloxane), poly(ethylene vinyl acetate), polycarbonate, polyacrylamide gels, poly (methyl methacrylate), poly(n-butyl methacrylate), poly (butyl methacrylate) copolymer or blended with poly(ethylene vinyl acetate), poly(methyl methacrylate), poly (2-hydroxy ethyl methacrylate), poly (ethylene glycol methacrylates), poly(ethylene carbonate), Poly L lactide-glycolide copolymer, poly L lactide-trimethylene carbonate copolymer and Poly L-lactide. In a further embodiment, the polymer is poly(n-butylmethacrylate).

In a further embodiment, the present invention provides a composition wherein the compound is present in an amount of at least 10% (w/w) in a mixture of the compound and the polymer. In another embodiment, the compound is present in an amount of at least 20, 25, 30, 40, 50, 55, 60, 70, 75, 80 and 90% (w/w). In other embodiments, the compound is present in an amount of at least 25% (w/w). In some other embodiments, the compound is present in an amount of at least 50% (w/w). In still other embodiments, the compound is present in an amount of at least 75% (w/w). One of skill in the art will appreciate that other compositions are useful in the present invention.

In another embodiment, the compounds of the present invention can be applied onto a stent without a coating. In another embodiment, compounds of the present invention can be applied onto a stent in combination with a polymer coating such as a compounds of the present invention-polymer matrix. The compounds of the present invention can be fully or partially crystallized or in an amorphous form. The polymer can be non degradable, partially degradable or fully degradable. The coating can also be a non-polymeric such as metallic coating. In another embodiment, the compounds of the present invention can be applied on a stent alone or contained in a coating with a polymer or non polymer topcoat. In another embodiment, the stent includes an underlayer coating disposed between the stent surface and the compounds of the present invention or compounds of the present invention—polymer matrix. Suitable underlayer coatings can be polymeric such as paralyne C, parylene N, ethylene vinyl alcohol (EVOH), polycaprolactone, ethylvinyl hydroxylated acetate (EVA), or others or combination thereof or non polymeric such as metallic or ceramic or others.

The coatings can be applied by any of the different methods which include but are not limited to spraying, ultrasonic deposition, dipping, inkjet dispension, plasma deposition, ion implantation, sputtering, evaporation, vapor deposition, pyrolysis, electroplating, glow discharge coating, or others or combination thereof.

The coating thickness can range from 1 nanometer to 100 micrometers, preferably from 100 nanometers to 50 micrometers, more preferably from 1 micrometer to 20 micrometers.

The compounds of the present invention can be combined with antioxidants or stabilizers to prevent degradation due to oxidation or other means. Antioxidants include but are not limited to butylated hydroxytoluene (BHT), ferrous sulfate, ethylenediamine-tetra-acetic acid (EDTA), or others. Stabilizers include, but are not limited to, amglene, hydroquinone, quinine, sodium metabisulfite or others. Antioxidants and stabilizers can be combined with the compounds directly or blended with the compound formulation such as compound-polymer matrix to reduce conformation change or degradation during manufacturing processes and increase shelf life or storage life of the compounds or compound containing implant. The amount of antioxidants such as BHT in the compounds can range from 0.01% to 10%, preferable from 0.05% to 5% and most preferable from 0.1% to 1%. The amount of stabilizers such as amylene in the compounds can range from 0.001% to 0.1%, preferably from 0.005% to 0.05%, most preferably from 0.01% to 0.02%. One of skill in the art will appreciate that other antioxidants and stabilizers are useful in the present invention.

The compounds of the present invention can be administered in combination with a therapeutic agent such as anti-platelet, anti-thrombotic, anti-inflammatory, anti-angiogenic, anti-proliferative, immunosuppressant, anti-cancer or other agents or combinations thereof. One of skill in the art will appreciate that other therapeutic agents are useful in the present invention.

The therapeutic agents can be incorporated on the stent together with the compounds of the present invention and/or separately from compounds of the present invention. At least a portion of the therapeutic agent can be released from the stent prior to, concurrently or post release of the compounds of the present invention from the stent. The therapeutic agent can also be given separately through systemically or site specific administration prior to, during or post delivery of compounds of the present invention.

For example, compounds of the present invention are given with anti platelets or anti-thrombotics such as heparin, clopidogrel, coumadin, aspirin, ticlid or others. In another example, compounds of the present invention are given with anti-inflammatory agents such as aspirin, diclofenac, indomethacin, sulindac, ketoprofen, flurbiprofen, ibuprofen, naproxen, piroxicam, tenoxicam, tolmetin, ketorolac, oxaprosin, mefenamic acid, fenoprofen, nambumetone (relafen), acetaminophen, and mixtures thereof, COX-2 inhibitors, such as nimesulide, NS-398, flosulid, L-745337, celecoxib, rofecoxib, SC-57666, DuP-697, parecoxib sodium, JTE-522, valdecoxib, SC-58125, etoricoxib, RS-57067, L-748780, L-761066, APHS, etodolac, meloxicam, S-2474, tacrolimus, and mixtures thereof; glucocorticoids, such as hydrocortisone, cortisone, prednisone, prednisolone, methylprednisolone, meprednisone, triamcinolone, paramethasone, fluprednisolone, betamethasone, dexamethasone, fludrocortisone, desoxycorticosterone, or others or analogues of the above or combinations thereof.

In some embodiments, the compounds of the present invention are combined with at least one therapeutic agent for treatment of an ophthalmic condition or disorder. Any suitable therapeutic agent known to one of skill in the art can be combined with the compounds of the present invention for use in the treatment of ophthalmic conditions or diseases. Therapeutic agents that can be combined with the compounds of the present invention include, but are not limited to, lucentis, avastin, macugan, volociximab, olopatadine, mydriatcs, dexamethasone, pilocarpine, tropicamide, quinolone, galentamine, fluocinolone acetonide, triamcinolone acetonide, atropine, atropine sulfate, atropine hydrochloride, atropine methylbromide, atropine methylnitrate, atropine hyperduric, atropine N-oxide, phenylephrine, phenylephrine hydrochloride, hydroxyamphetamine, hydroxyamphetamine hydrobromide, hydroxyamphetamine hydrochloride, hydroxyamphetamine iodide, cyclopentolate, cyclopentolate hydrochloride, homatropine, homatropine hydrobromide, homatropine hydrochloride, homatropine methylbromide, scopolamine, scopolamine hydrobromide, scopolamine hydrochloride, scopolamine methylbromide, scopolamine methylnitrate, scopolamine N-oxide, tropicamide, tropicamide hydrobromide, tropicamide hydrochloride, pilocarpine, isopilocarpine, physostigmine, and quaternary ammonium compounds including stearyl ammonium chloride and benzyl ammonium chloride, including mixtures, ionic salt s, and combinations thereof.

Formulations of the compounds of the present invention for ophthalmic uses can include any polymer described above. The polymers useful in such formulations can be of any size. In some embodiments, the polymers can have a molecular weight of between about 50 kilo Daltons (kD) and 8,000 kD. One of skill in the art will appreciate that polymers of other sizes are useful in the present invention.

In some embodiments, the compounds of the present invention can be administrated alone or as part of compound-polymer formulation, compound-solvent formulation or compound-carrier formulation. All formulations of the present invention may include active and inactive ingredients. Active ingredients include, but are not limited to, anti-inflammatory agents, immunomodulating agent and anti-infective agents, antioxidants, antibody, antibiotics, anti-angiogenics, anti-vascular endotherlial growth factor agent, antihistamines and lubricant. Inactive ingredients include, but are not limited to, carrier, solvent, inorganic materials, pH-adjustor, radio-opaque, radioactive, fluorescent, NMR contrast or other "reporter or indicator" materials. Examples of solvent in the compound-solvent formulation include, but are not limited to, water, saline, alcohol, and dimethyl sulfoxide. Examples of carrier in the compound-carrier formulation are glycerin, paraffin, beeswax, ethylene glycol, propylene glycol, polyethylene glycol, and macrogels. Examples of inorganic materials include, but are not limited to, boric acid, calcium chloride, magnesium chloride, potassium chloride, sodium chloride, zinc chloride, sodium borate, povidone, and dibasic sodium phosphate. Examples of pH-adjustor include, but are not limited to, sodium hydroxide, hydrogen chloride, buffer, and other inorganic and organic acid/base. Examples of preservative include, but are not limited to, benzalkonium chloride, and a polyquaternium. Examples of lubricant include, but are not limited to, carboxymethylcellulose sodium, polyethylene glycol, propylene glycol and ethylene glycol. One of skill in the art will appreciate that other active and inactive ingredients, as well as solvents and carriers are useful in the present invention.

In some embodiments, the present invention provides a composition where less than about 5% of the compound is metabolized to rapamycin. In some other embodiments, less than about 1% of the compound is metabolized to rapamycin. In still other embodiments, less than about 0.1% of the compound is metabolized to rapamycin.

In other embodiments, the present invention provides a composition in a dosage form, having a daily systemic dose of the compound of from about 0.1 mg to about 20 mg. In some other embodiments, the daily systemic dose of the compound is from about 0.5 mg to about 10 mg. In another embodiment, the daily systemic dose of the compound is from about 1 mg to about 5 mg.

IV. Treatment

The compounds of the present invention can be used to treat conditions responsive to the class of compounds commonly known as macrocyclic trienes or macrocyclic lactones.

The compounds of the present invention can be used to treat diseases in mammals alone or in combination with other agents, including conditions such as:
 a) Treatment and prevention of acute or chronic organ or tissue transplant rejection, e.g. for the treatment of recipients of heart, lung, combined heart-lung, liver, kidney, pancreatic, skin or corneal transplants. They can also be used for the prevention of graft-versus-host disease, such as following bone marrow transplantation.
 b) Treatment and prevention of transplant vasculopathies, e.g. atherosclerosis.
 c) Treatment and prevention of cell proliferation and migration leading to vessel intimal thickening, blood vessel obstruction, obstructive vascular atherosclerosis, restenosis.
 d) Treatment and prevention of autoimmune disease and of inflammatory conditions, such as inflammatory conditions with an etiology including an autoimmune component such as arthritis (for example rheumatoid arthritis, arthritis chronica progrediente and arthritis deformans) and rheumatic diseases.
 e) Treatment and prevention of asthma.
 f) Treatment of multi-drug resistance conditions such as multidrug resistant cancer or multidrug resistant AIDS.
 g) Treatment of proliferative disorders, e.g. tumors, cancer, hyperproliferative skin disorder and the like.
 h) Treatment of infections such as fungal, bacterial and viral.

i) Treatment or prevention of cellular proliferation in vascular shunts.
j) Treatment or prevention of ophthalmic conditions and diseases.
k) Prevention of neo-vascularization.

Figure 8:
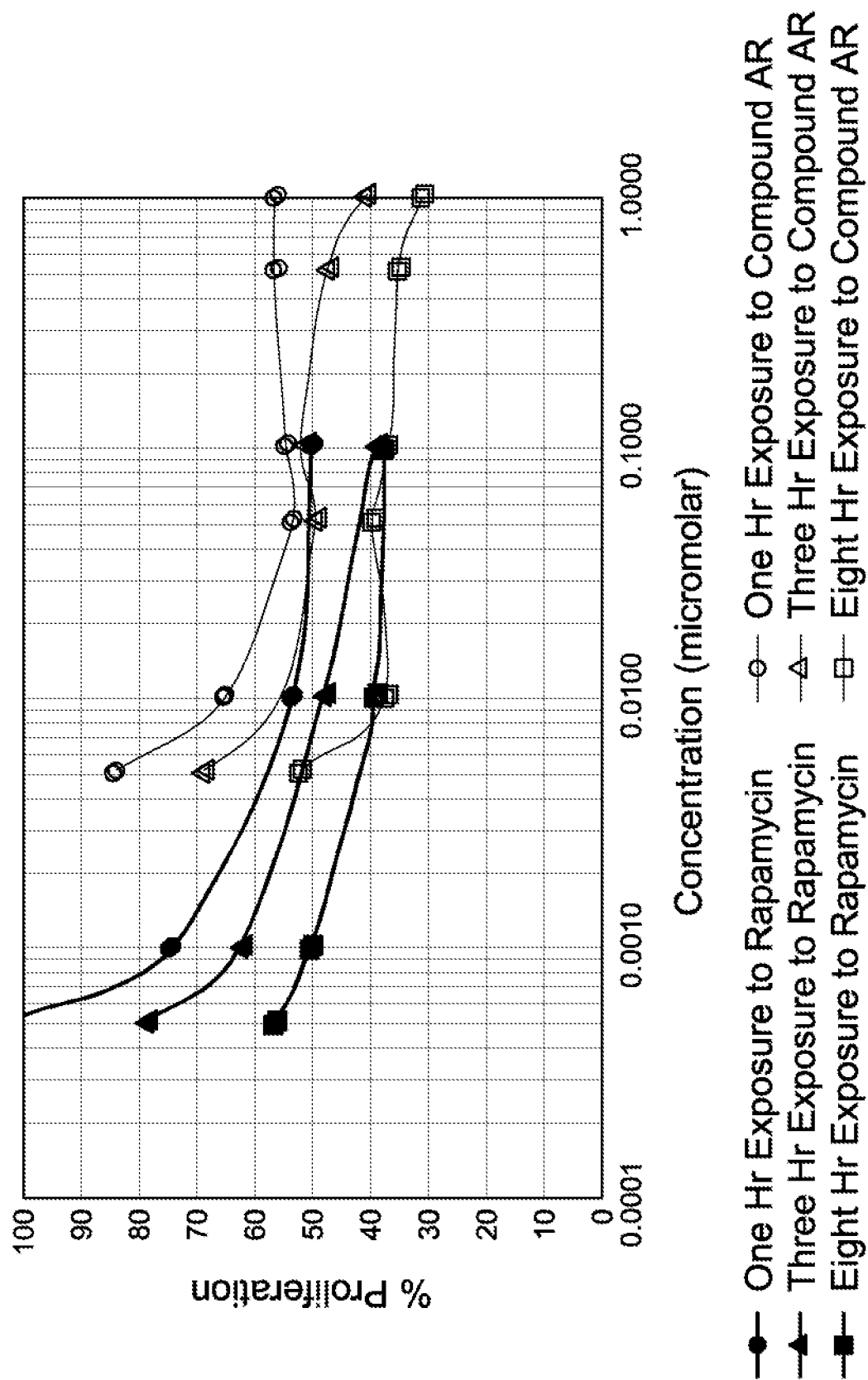
FIG. 8 shows percentage proliferation of human smooth muscle cells after exposure to varying concentrations of rapamycin and Compound AR.

The potency of Compound AR and rapamycin (Sirolimus) for inhibiting human cell proliferation is demonstrated in an in vitro model. The test is described in Example 2 and the results are shown in FIG. 8. Compound AR inhibited growth of smooth muscle cells over a range of concentrations as demonstrated in FIG. 8.

In some embodiments, the present invention provides a method of inhibiting cell proliferation or migration by administering to a subject in need thereof, a therapeutically effective amount of a compound of the present invention.

In other embodiments, the present invention provides a method wherein the compound of the present invention is administered systemically, locally or via a combination thereof.

In some other embodiments, the administration of the compound of the present invention is via oral administration, administration as a suppository, topical contact, parenteral, intravascular, intravenous, intraperitoneal, intramuscular, intralesional, intranasal, pulmonary, mucosal, transdermal, ophthalmic, subcutaneous administration or intrathecal administration.

In still other embodiments, the administration of the compound of the present invention is via delivery through a temporary device or an implant. In another embodiment, the temporary device is selected from the group consisting of a catheter and a porous balloon. In still another embodiment, the implant is a vascular prosthesis. In yet other embodiments, the vascular prosthesis comprises an expandable structure. In another embodiment, the vascular prosthesis comprises a stent, graft, or a scaffold formed at least in part from an open lattice.

In one embodiment, the inhibition concentration ($IC_{50}$) of compounds of the present invention is approximately equal to the $IC_{50}$ of its corresponding parent macrocyclic lactone (prior to the modifications in FIG. 1). In another embodiment, the $IC_{50}$ is higher than the $IC_{50}$ of its corresponding parent macrocyclic lactone. In yet another embodiment, the $IC_{50}$ is lower than the $IC_{50}$ of its corresponding parent macrocyclic lactone. For example, the $IC_{50}$ is two to thousand times lower than the $IC_{50}$ of its corresponding parent macrocyclic lactone.

In a preferred embodiment, the $IC_{50}$ of a compound of the present invention is 1.5 to 1,000 times higher than its corresponding parent macrocyclic lactone, preferably 2 to 100 times higher than the corresponding parent macrocyclic lactone and more preferably 5 to 50 times higher than the corresponding parent macrocyclic lactone. In another embodiment the $IC_{50}$ of a compound of the present invention is from about 0.1 nM to about 1 µM, preferably from about 1 nM to about 0.5 µM, more preferably from about 5 nM to about 100 nM.

Other means of measuring the effectiveness of the compounds of the present invention include measuring effective concentration ($EC_{50}$). In one embodiment, the $EC_{50}$ is approximately equal to the $EC_{50}$ of the corresponding parent macrocyclic lactone. In another embodiment, the $EC_{50}$ is higher than the $EC_{50}$ of the corresponding parent macrocyclic lactone. In yet another embodiment, the $EC_{50}$ is lower than the $EC_{50}$ of the corresponding parent macrocyclic lactone.

In some embodiments, the present invention provides a method wherein the effective dose of the compound is from about 0.1 mg to about 20 mg. In some other embodiments, the effective dose of the compound is from about 0.5 mg to about 10 mg. In still other embodiments, the effective dose of the compound is from about 1 mg to about 5 mg.

The compounds, compositions and devices of the present invention are useful for cytokine inhibition. Pro-inflammatory cytokine IL-6 is synthesized in response to diverse inflammatory stimuli and acts as a key regulatory protein in the inflammatory cascade. IL-6 plays a pivotal role in stimulating the acute-phase response after injury, including the release of fibrinogen and C-reactive protein.

IL-6 may also be directly involved in restenosis, as it has been shown to stimulate leukocyte recruitment into the vessel wall, and vascular smooth muscle cell proliferation, factors that are essential to the pathogenesis of hyperproliferative diseases such as restenosis.

Matrix metalloproteinases (MMP-9) play a key role in cellular migration and proliferation including conditions such as neointimal growth and vascular remodeling after stent implantation. Release of MMPs cause increases in proteoglycan rich, extracellular matrix which increases smooth muscle cell migration after vascular injury.

Plasma active MMP-9 levels may be a useful independent predictor of bare metal stent ISR. (Elevated Plasma Active Matrix Metalloproteinase-9 Level Is Associated With Coronary Artery In-Stent Restenosis, Arterioscler Thromb Vasc Biol. 2006; 26:e121-e125.)

Monocyte chemoattractant protein 1 (MCP-1) is a potent monocyte chemoattractant secreted by many cells in vitro, including vascular smooth muscle and endothelial cells. Eliminating MCP-1 gene or blockade of MCP-1 signals has been shown to decrease atherogenesis in hypercholesterolemic mice. MCP-1 has been shown to play a role in pathogenesis of neointimal hyperplasia in monkeys. (Importance of Monocyte Chemoattractant Protein-1 Pathway in Neointimal Hyperplasia After Periarterial Injury in Mice and Monkeys, Circ Res. 2002; 90:1167-1172.) MCP-1 is also strongly expressed in a small subset of cells in macrophage-rich regions of human and rabbit atherosclerotic lesions (Expression of Monocyte Chemoattractant Protein 1 in Macrophage-Rich Areas of Human and Rabbit Atherosclerotic Lesions, PNAS, Vol 88, 5252-5256). Inhibition of MCP-1 can have therapeutic impact on treatment and prevention of inflammatory, proliferative and other disease conditions discussed above.

Interleukin-10 (IL-10) is an anti-inflammatory cytokine with a powerful inhibitory effect on monocytes. IL-10 has been shown to reduce postinjury intimal hyperplasia (Interleukin-10 Inhibits Intimal Hyperplasia After Angioplasty or Stent Implantation in Hypercholesterolemic RabbitsCirculation. 2000; 101:908-916). Endogenous production of IL-10 by human monocytes in response to LDL stimulation inhibits IL-12 production, indicating a cross-regulatory action of IL-10 that may counterbalance the proinflammatory response.

A. Ophthalmic Conditions and Diseases

In some embodiments, the compounds, pharmaceutical compositions and devices of the present invention are useful for the treatment of ophthalmic conditions and diseases. The compounds, pharmaceutical compositions and devices of the present invention are useful in the treatment of any ophthalmic condition or disease. Ophthalmic conditions and diseases that can be treated by the compounds and devices of the present invention include, but are not limited to, disorders of the eyelid, disorders of the lacrimal system and orbit, tear duct blockage, disorders of conjunctiva, disorders of the sclera, cornea, iris and ciliary body, disorders of the lens, disorders of the choroid and retina, Age-related Macular Degeneration (AMD), Diabetic Macular Edema (DME), glaucoma, disorders of the vitreous body and globe, disorders of the optic nerve and visual pathways, disorders of the ocular muscles, binocular movement, accommodation and refraction, visual disturbances and blindness, etc. Additional ophthalmic conditions and diseases that can be treated with the compounds and devices of the present invention include inhibition of cell proliferation, prevention of inflammation, prevention of neovascularization, protection of neurovascular system, and prevention of immune response after transplantation. One of skill in the art will appreciate that other ophthalmic conditions and diseases can be treated using the compounds and devices of the present invention.

Current treatment methods include surgery and medications. Surgical treatment methods include retinal implant, high speed laser eye surgery, endothelial keratoplasty, cataract surgery, glaucoma surgery, refractive surgery, corneal surgery, vitreo-retinal surgery, eye muscle surgery, oculoplastic surgery, uses of stem cells to create corneas or part of corneas that can be transplanted into the eyes.

Ophthalmic conditions and diseases can be treated using compounds, pharmaceutical compositions and devices of the present invention, as described above. The compounds and pharmaceutical compositions of the present invention can be administered via any method known to one of skill in the art. In some embodiments, the compounds of the present invention are administered via implant, injection or eye drop. In some other embodiments, the administration is through an intraocular or intravitreal body of the eye. In other embodiments, the administration is via the implant. In other embodiments, the compounds are administered via an implant where the compound is released via a metallic, ceramic or polymer coating.

When administration is via the implant, the compound can be released by any means known in the art. In some embodiments, release of the compound from the implant can be via osmotic pressure of diffusion. One of skill in the art will appreciate that other means of releasing the compound from the implant are useful in the present invention.

In some embodiments, the compounds of the present invention are combined with at least one other therapeutic agent for treatment of an ophthalmic condition or disorder. Any suitable therapeutic agent known to one of skill in the art can be combined with the compounds of the present invention for use in the treatment of ophthalmic conditions or diseases. In some embodiments, the therapeutic agents include, but are not limited to, anti-inflammatory agents, immunomodulating agent and anti-infective agents, antioxidants, antibody, antibiotics, anti-angiogenics, anti-vascular endotherlial growth factor agent, antihistamines and lubricant. Therapeutic agents that can be combined with the compounds of the present invention include, but are not limited to, lucentis, avastin, macugan, volociximab, olopatadine, mydriatcs, dexamethasone, pilocarpine, tropicamide, quinolone, galentamine, fluocinolone acetonide, triamcinolone acetonide, atropine, atropine sulfate, atropine hydrochloride, atropine methylbromide, atropine metliylnitrate, atropine hyperduric, atropine N-oxide, phenylephrine, phenylephrine hydrochloride, hydroxyamphetamine, hydroxyamphetamine hydrobromide, hydroxyamphetamine hydrochloride, hydroxyamphetamine iodide, cyclopentolate, cyclopentolate hydrochloride, homatropine, homatropine hydrobromide, homatropine hydrochloride, homatropine methylbromide, scopolamine, scopolamine hydrobromide, scopolamine hydrochloride, scopolamine methylbromide, scopolamine methylnitrate, scopolamine N-oxide, tropicamide, tropicamide hydrobromide, tropicamide hydrochloride, pilocarpine, isopilocarpine, physostigmine, and quaternary ammonium compounds including stearyl ammonium chloride and benzyl ammonium chloride, including mixtures, ionic salts, and combinations thereof.

It can be appreciated that all embodiments disclosed in the present invention can be utilized alone or in combination with other embodiments or examples in this invention.

V. Examples

Example 1: Preparation of 16-O-demethyl macrocyclic lactone (Compound AR)

Macrocyclic lactone rapamycin (1000 mg, 10.75 mmol) in 500 ml acetonitrile was treated with 500 ml 0.1N hydrochloric acid. The resulting solution was stirred at room temperature for about 28 hours. Then the reaction mixture was extracted with dichloromethane in a separatory funnel. The organic layers were washed with water and brine, then washed with 0.1M sodium phosphate buffer (pH=7.4) twice or until pH=7, then washed three times with distilled (DI) water. Finally the organic layer was dried over $Na_2SO_4$ and placed in a refrigerator overnight. Concentration in vacuum provided an off-white powder of Compound AR (approx. 820 mg).

Compound AR was purified by preparative HPLC on an Ascentis C18 (21.2×250 mm, 10 μm) column from SUPECO using Methanol:water (80:20) as mobile phase from 0-12 min then changed to 100% Methanol from 12.01-20 min at a flow rate of 15 ml/min. The loading concentration was 350 mg/ml and the injection volume was 100 ul. The compound was monitored by UV absorbance at 254 nm. Under these conditions, Compound AR eluted between 9.0-11.5 min whereas the starting materials and by products eluted between 17.0-20.0 min.

Figure 4:
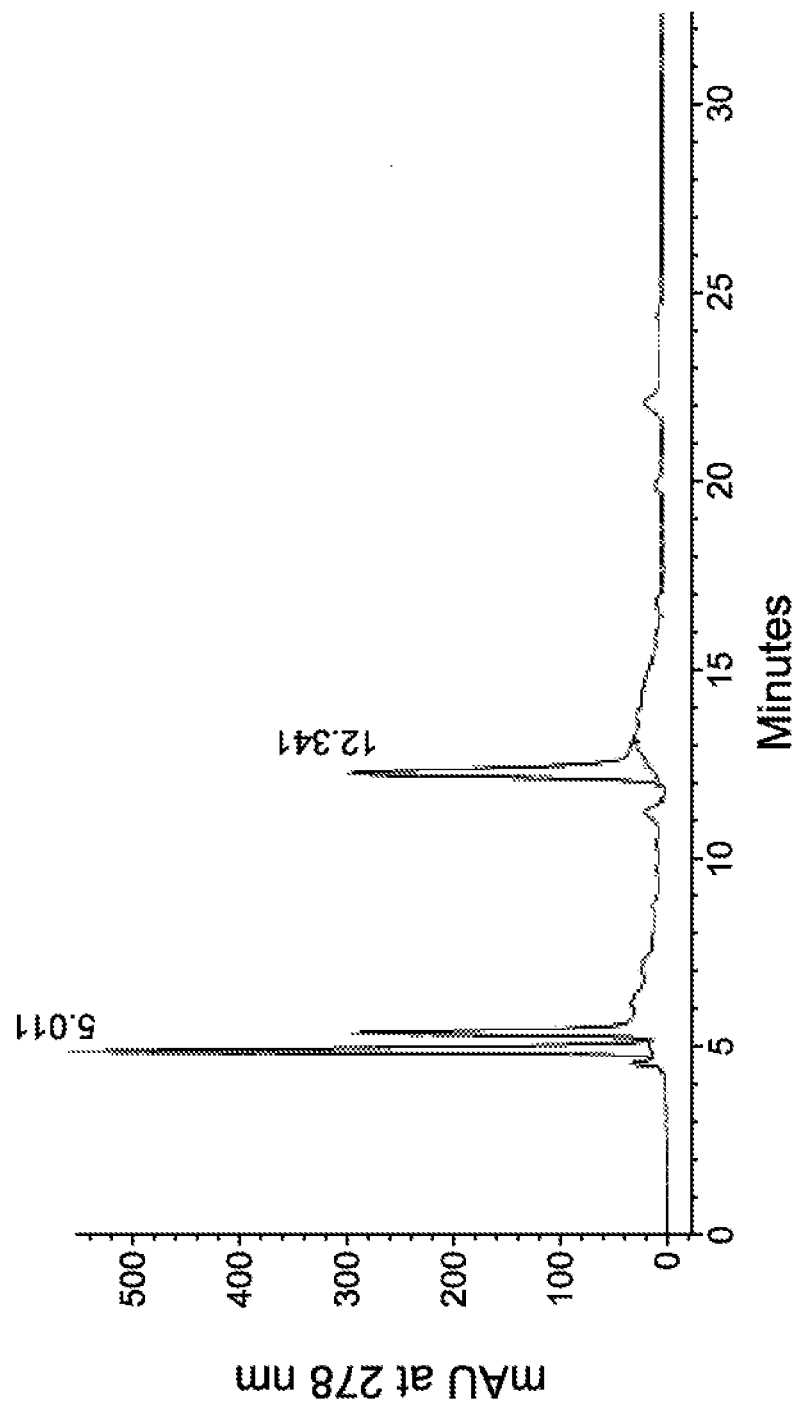
FIG. 4 shows a preparative HPLC chromatogram of Compound AR.

The preparative HPLC can also be conducted using a gradient of acetonitrile:water (starting from 70:30) as mobile phase and monitored by UV absorbance at 278 nm. The preparative HPLC chromatogram using this method of separation is shown in FIG. 4.

The fractions containing Compound AR were collected and pooled together, then solvent was evaporated by using a rotovac and freeze drier to give an off-white powder of Compound AR.

Figure 5:
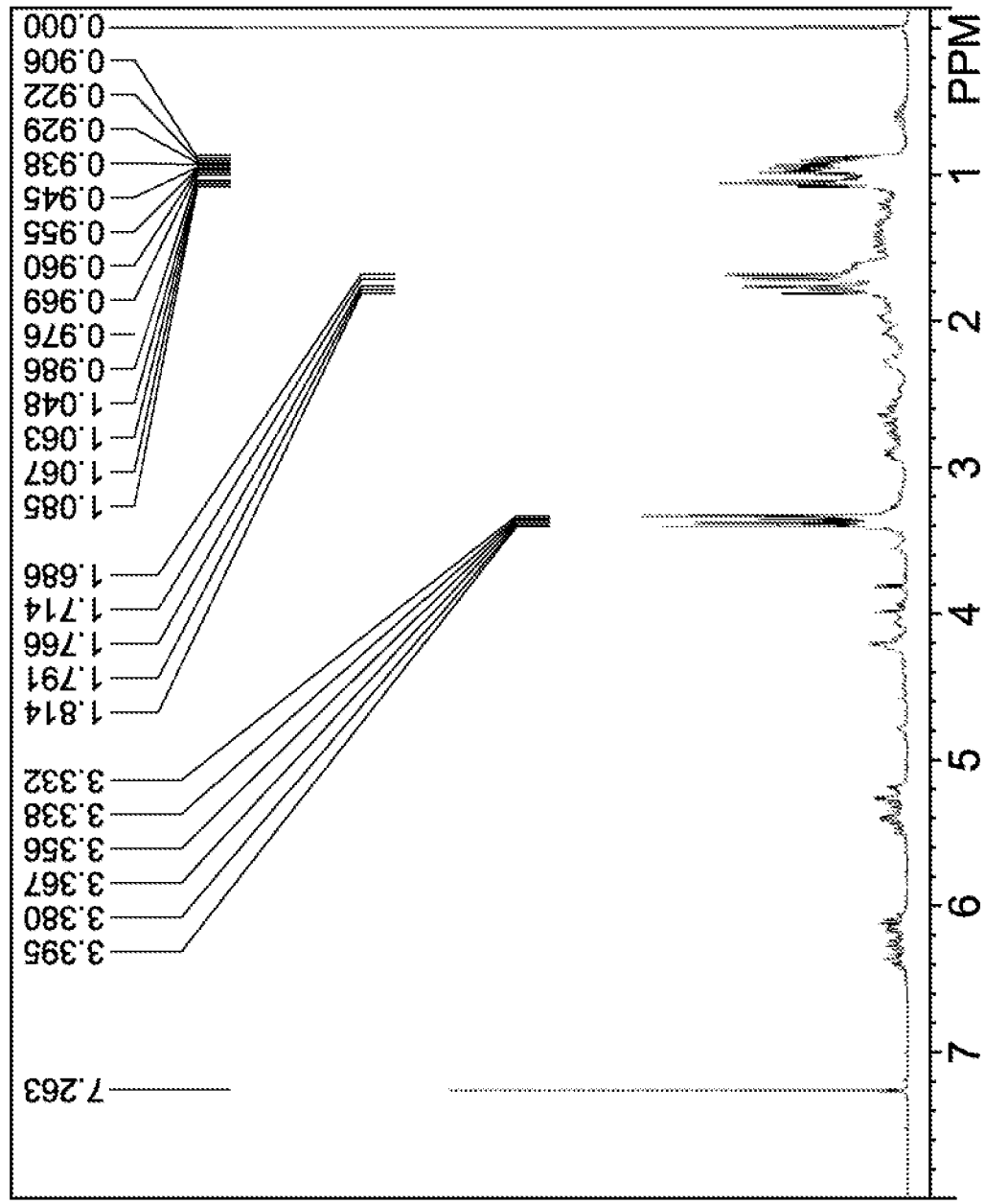
FIG. 5 shows a Proton-NMR spectra of Compound AR.

$^1$H NMR ($CDCl_3$, 400 MHz, mixture of trans: cis amide rotamers, chemical shifts in parentheses refer to the major rotamer) is presented in FIG. 5. δ, ppm 0.532 (q, J=12 Hz, 1H), 0.890 (d, J=6.8 Hz, 3H), 0.921 (d, J=6.8 Hz, 3H), 0.931 (d, J=6.4 Hz, 3H), 0.971 (d, J=6.8 Hz, 3H), 0.991 (d, J=6.6 Hz, 3H), 1.005 (d, J=6.4 Hz, 3H), 1.686 (s, 3H), 1.772 (s, 3H), 1.773 (s, 3H), 1.823 (s, 3H), 3.330 (s, 3H), 3.380 (s, 3H), 3.859 (d, J=5.2 Hz, 1H), 4.001 (d, J=3.6 Hz, 1H), 4.03-4.07 (m, 1H), 4.22 (br, 1H), 5.21-5.28 (m, 3H), 5.336 (d, J=11.6 Hz, 1H), 5.384 (dd, J=14.8, 9.6 Hz, 1H), 6.117 (dd, J=14.4, 10.8 Hz, 1H), 6.243 (dd, J=14.4, 10.4 Hz, 1H), 6.376 (dd, J=14.8, 11.2 Hz, 1H).

Compared with the proton NMR of the parent compound, the disappearance of the peak at 3.14 ppm demonstrates the demethylation at the C16 position only and completion of reaction. (See *Journal of Antibiotics* 1991, 44(6), 688 for assignment of the NMR spectra for rapamycin.)

The chemical structure of Compound AR was further verified by mass spectrometric experiments. The fragmentation patterns indicated the presence of the m/z 900 whereas Rapamycin provides m/z 914 under the same conditions. The results of liquid chromatography and mass spectroscopy experiments are provided in FIGS. 6A and 6B which show the identification of Compound AR with m/z 900.

Figure 7A:
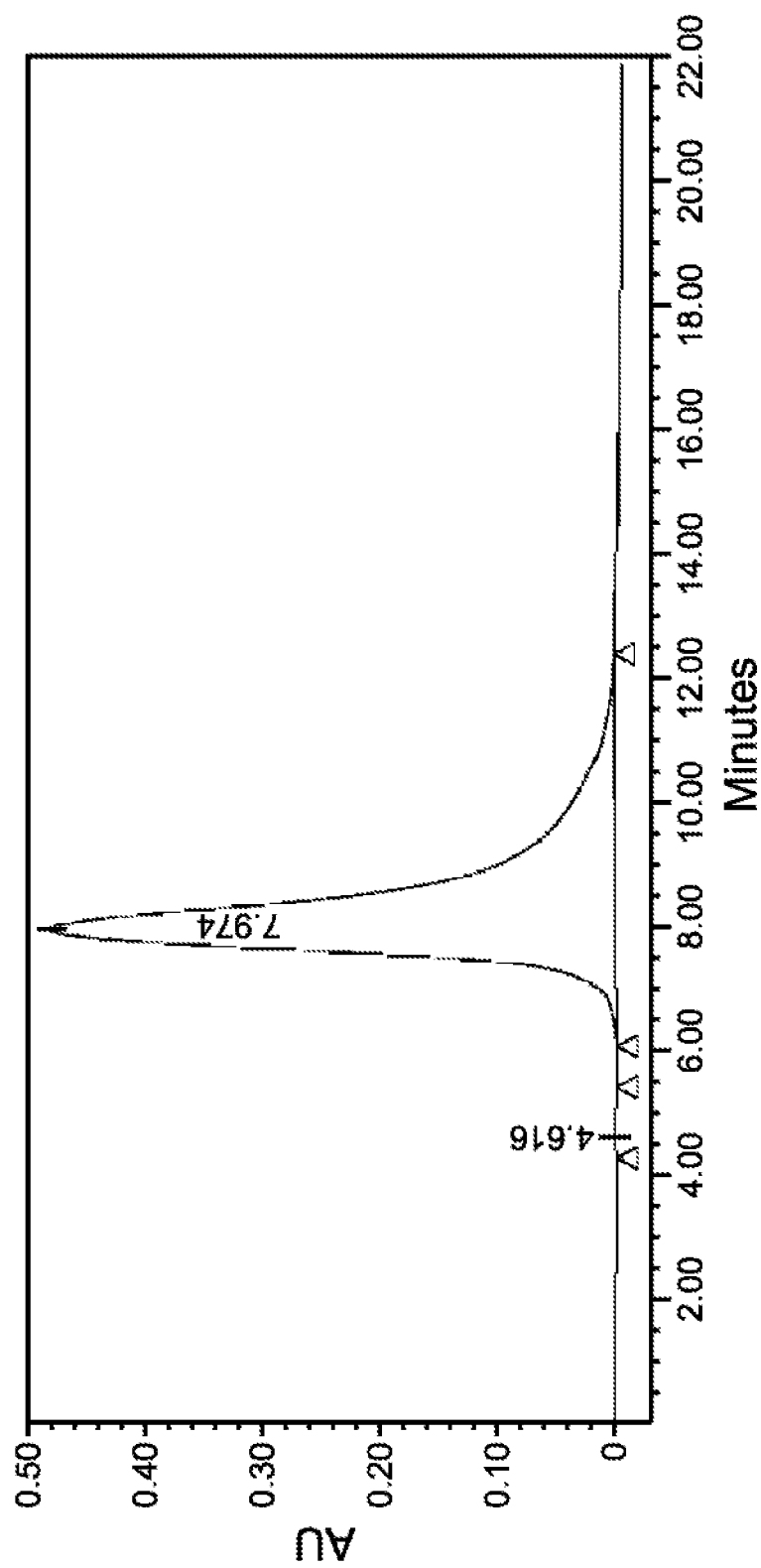
FIG. 7A shows an analytical HPLC chromatogram of Compound AR.
Figure 7B:
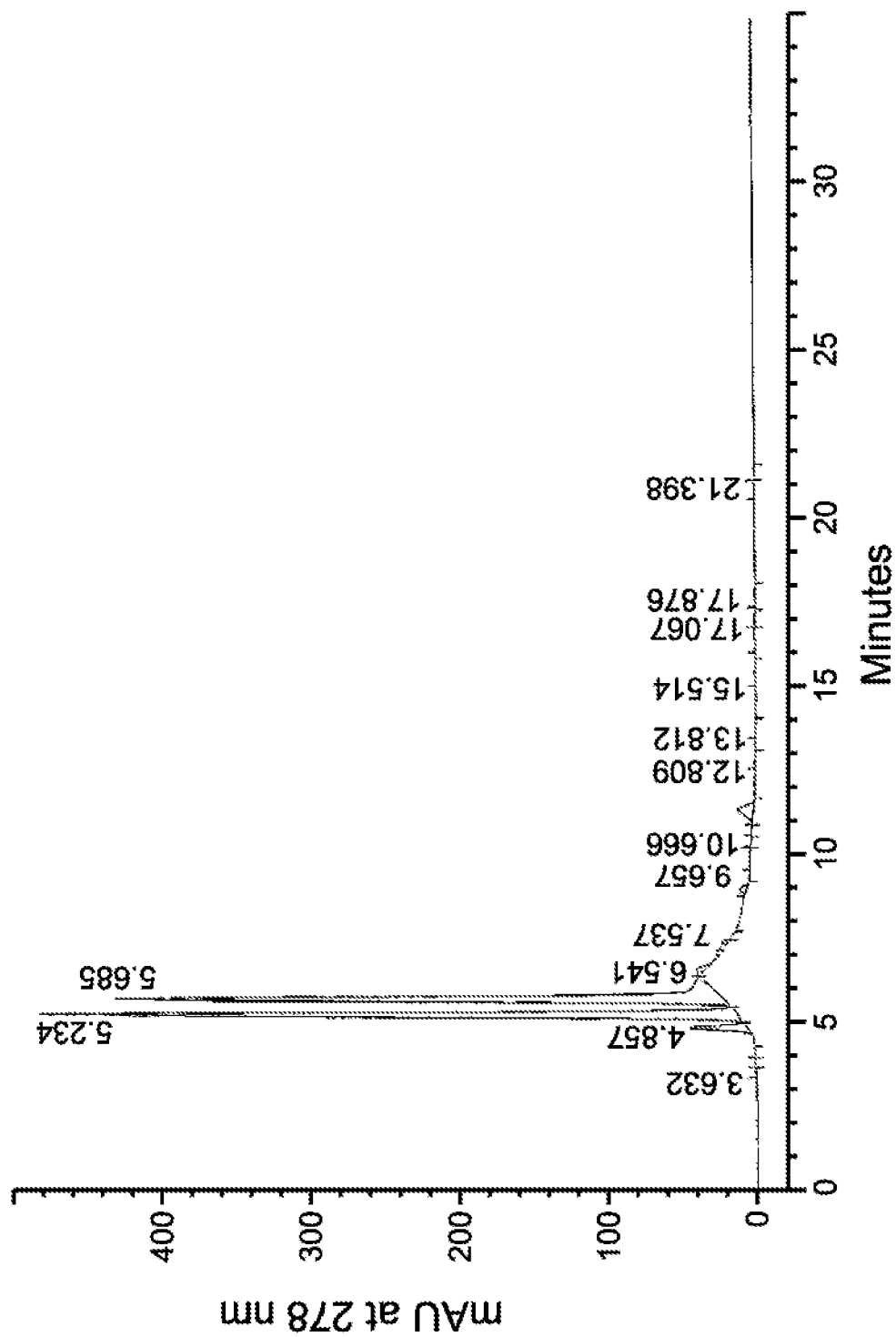
FIG. 7B shows an analytical HPLC chromatogram of Compound AR with isomers.

The total content of Compound AR was determined by a reverse phase HPLC using a Supelco C18 (4.6×150 mm, 5 μm) column from Sigma Aldrich using methanol:water (90:10) as mobile phase and a flow rate of 1 ml/min. Compound AR was monitored by UV absorbance at 254 nm. Compound AR had a retention time of 7.97 min. FIG. 7A shows the analytical HPLC chromatogram of Compound AR with total content of >98%. The purity of Compound AR was determined by a reverse phase HPLC using a YMC ODS-AL C18 (4.6×250 mm, 5 μm) column from Waters Corporation using an acetonitrile:water gradient mobile phase and a flow rate of 1.0 ml/min. FIG. 7B shows major isomers of Compound AR with a purity >98% as monitored by UV absorbance at 278 nm.

As a means to minimize oxidation of the Compound AR, 0.1% w/w of Butylated Hydroxytoluene (BHT) was added after preparative HPLC.

Example 2: Biological Activity of Compound AR

Potency of the Compound AR was demonstrated by in vitro human smooth muscle cell culture testing. The amounts of incorporated thymidine for samples of Compound AR of varying concentrations (0.005, 0.01, 0.05, 0.1, 0.5, and 1 μM) and of rapamycin of varying concentrations (0.0005, 0.001, 0.01, and 0.1 μM) were measured after exposure for different times of 1, 3 and 8 hours. The $IC_{50}$ for Compound AR and rapamycin were approximately 0.05 and 0.01 μM, respectively, after smooth muscle cells were exposed to Compound AR and rapamycin for the shorter periods of 1 and 3 hours (as shown in Table 1 and FIG. 8). The $IC_{50}$ of Compound AR and rapamycin was approximately 0.005 and 0.001 μM, respectively, after smooth muscle cells were exposure to Compound AR and rapamycin for 8 hours. The $IC_{50}$ of Compound AR was approximately five times higher than that of rapamycin.

TABLE I

Data of percentage proliferation of human smooth muscle cells after exposure to varying concentrations of rapamycin and Compound AR Compound AR

| Concentration (micromolar) | 0.005 | 0.01 | 0.05 | 0.1 | 0.5 |
|---|---|---|---|---|---|
| % Proliferation After One Hr Exposure to Compound AR | 84 | 66 | 54 | 55 | 57 |
| % Proliferation After Three Hr Exposure to Compound AR | 69 | 56 | 50 | 52 | 48 |
| % Proliferation After Eight Hr Exposure to Compound AR | 52 | 38 | 40 | 36 | 35 |

Rapamycin

| Concentration (micromolar) | 0.0005 | 0.001 | 0.01 | 0.1 |
|---|---|---|---|---|
| % Proliferation After One Hr Exposure to Rapamycin | 105 | 75 | 54 | 50 |
| % Proliferation After Three Hr Exposure to Rapamycin | 79 | 63 | 48 | 39 |
| % Proliferation After Eight Hr Exposure to Rapamycin | 57 | 51 | 40 | 38 |

Example 3: Preparation of Stents Containing Compound AR 15 mg poly(n-butyl methacrylate) (PBMA) was dissolved into 3 mL dichloromethane at room temperature. 10 mg of Compound AR was placed in a vial and dissolved in 2 mL dichloromethane with or without 0.1% (w/w) BHT. The solutions were combined and further diluted with 10 mL dichloromethane.

A microprocessor-controlled ultrasonic sprayer was used to apply 450 ug of the drug containing PBMA solution to the entire surface of a18 mm metal stent (available from Elixir Medical Corp, Sunnyvale, Calif.). After coating, the stent was placed in a vacuum chamber. The stent was then mounted on the balloon of a 3.0×20 mm PTCA delivery catheter. The catheter was then inserted in a coil and packaged in a Tyvek® pouch. The pouch was sterilized by ethylene oxide. The Tyvek® pouch was further packaged in a foil pouch with oxygen scavengers and nitrogen purge and vacuum sealed.

Example 4: In Vivo Testing of Stents Eluting Compound AR

The efficacy of a Compound AR eluting stent system (as prepared above) from Example 3 was evaluated by comparing 28±2 day angiographic outcomes in porcine coronary arteries to the rapamycin eluting stent system, Cypher™ Coronary Stent (Cordis Corporation) in the non-diseased porcine coronary artery model.

The nonatherosclerotic swine model was chosen as this model has been used extensively for stent and angioplasty studies resulting in a large volume of data on the vascular response properties and its correlation to human vascular response (Schwartz et al, Circulation. 2002; 106:1867-1873). The animals were housed and cared for in accordance the Guide for the Care and Use of Laboratory Animals as established by the National Research Council.

All animals were pretreated with aspirin (325 mg) and clopidogel (75 mg) per oral dose beginning at least 3 days prior to the intervention and continuing for the duration of the study. After induction of anesthesia, the left or right femoral artery was accessed using standard techniques and an arterial sheath was introduced and advanced into the artery.

Vessel angiography was performed under fluoroscopic guidance, a 7 Fr. guide catheter was inserted through the sheath and advanced to the appropriate location where intracoronary nitroglycerin was administered. A segment of coronary artery ranging from 2.25 to 4.0 mm mean lumen diameter was chosen and a 0.014" guidewire inserted. Quantitative Coronary Angiography (QCA) was performed to document the reference vessel diameter.

The appropriately sized stent was advanced to the deployment site. The balloon was inflated at a steady rate to a pressure sufficient to achieve a balloon to artery ratio of 1.30:1.0. Pressure was maintained for approximately 10 seconds. Angiography was performed to document post-procedural vessel patency and diameter.

Follow-up angiography was performed at the designated endpoint for each of the animals. Each angiogram was qualitatively evaluated for evidence of stent migration, lumen narrowing, stent apposition, presence of dissection or aneurysms, and flow characteristics. Upon completion of follow-up angiography, the animals were euthanized.

The hearts were harvested from each animal and the coronary arteries were perfused with 10% buffered formalin at 100 to 120 mm Hg. The hearts were immersed in 10% buffered formalin. Any myocardial lesions or unusual observations were reported.

Angiographic parameters measured or calculated included:

Marginal vessel (proximal and distal) mean lumen diameter (post-stent and final only)

Mean lumen diameter of the target region (all angiograms)

Minimal lumen diameter (MLD) of the target region (post-stent and final only)

Diameter stenosis [1−(MLD/RVD)]×100% where RVD is a calculation of the reference diameter at the position of the obstruction (measure obtained by a software-based iterative linear regression technique to generate an intrapolation of a projected vessel without the lesion) (final angiogram only)

Balloon to artery ratio [balloon/pre-stent mean luminal diameter]

Stent to artery ratio [post-stent/pre-stent mean luminal diameter]

Late loss ratio [MLD final-MLD post-stent]

Figure 9:
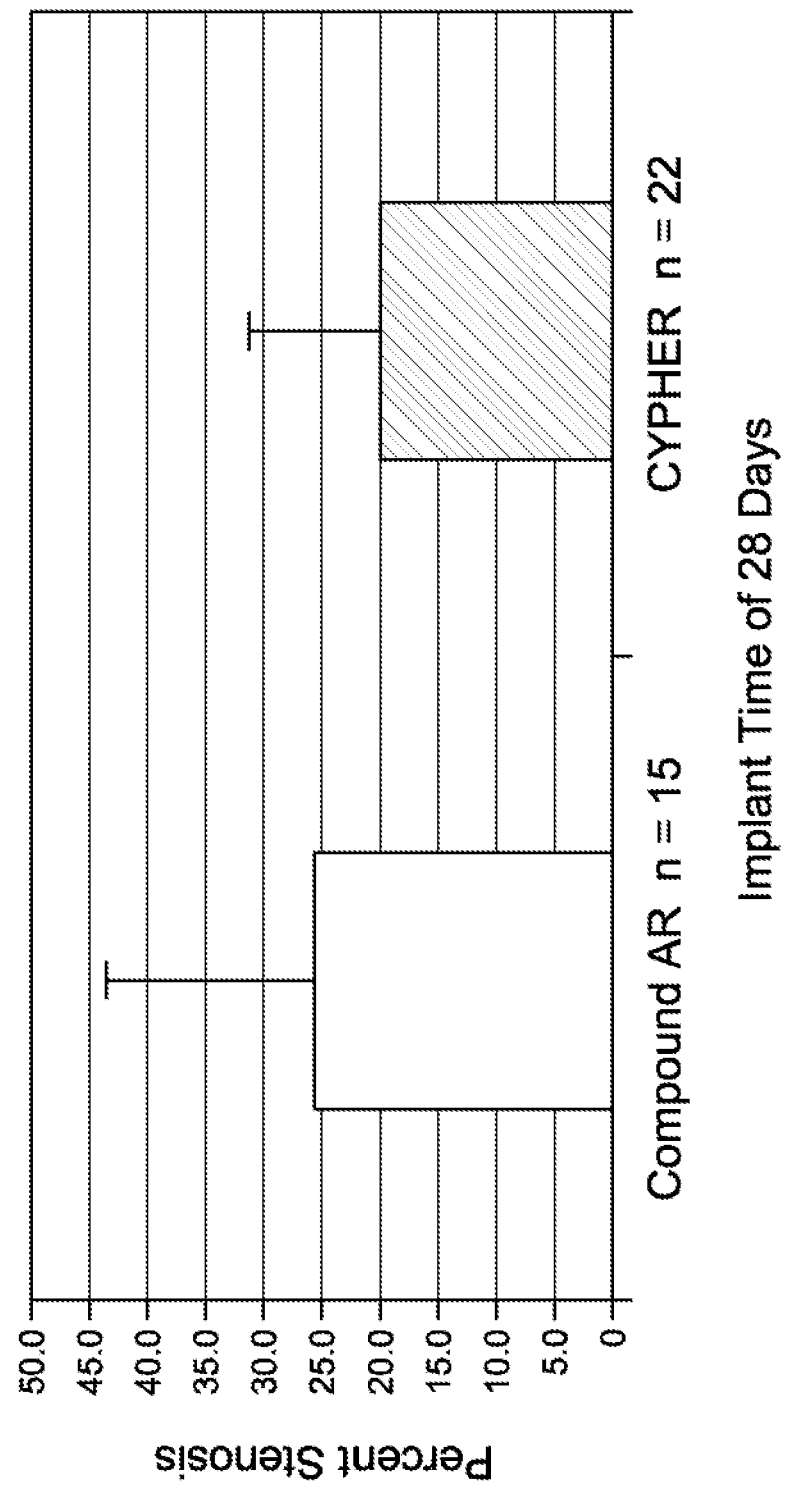
FIG. 9 shows quantitative coronary angiography (QCA) stenosis of the Compound AR eluting stent as compared to rapamycin eluting Cypher stent after 28 day implantation in a porcine coronary artery model.

All animal survived to the designated end point. There were no documented incidents of stent migration, stent malapposition, persistent dissection or evidence of aneurysm. Three outlying data points (total occlusion or near total occlusion) for the Cypher Stent were excluded. The average percent stenosis for the Compound AR stent (approx. 10 microgram/mm length drug dose) was 25.7±17.8 (n=15) as compared to Cypher Stent pooled data from this and previous studies with similar protocols which provided an average percent stenosis of 20.21±11.45 (n=22) for Cypher stents. (FIG. 9).

The Compound AR eluting stents in this example when implanted in the porcine model for 28 days resulted in higher percentage stenosis as compared to the Cypher Stent.

Example 5: In Vivo Pharmacokinetics of Stents Eluting Compound AR

Pharmacokinetic evaluation of the Compound AR stent system from Example 3 was performed at 6 hours, 3 days, 7 days, and 28 days in the porcine coronary artery model. The interventional procedures used were similar to the in vivo angiographic study described in Example 4 up to stent implantation.

The appropriately sized stent was advanced to the deployment site. The balloon was inflated at a steady rate to a pressure sufficient to achieve a balloon to artery ratio of 1:1. Pressure was maintained for approximately 10 seconds. Angiography was performed to document post-procedural vessel patency and diameter. A total of 9 stents (3 per time point) were implanted.

At the appropriate time point the animals were euthanized and the hearts excised. The stented segment including approximately 10 mm of vessel proximal and 10 mm distal to the stented section was excised. The proximal and distal sections were separated and stored in separate vials. The tissue surrounding the stent was carefully removed from stent and each place in separate vials. All were then frozen to −70° C. prior to being analyzed using liquid chromatography mass spectroscopy (LCMS).

Figure 10:
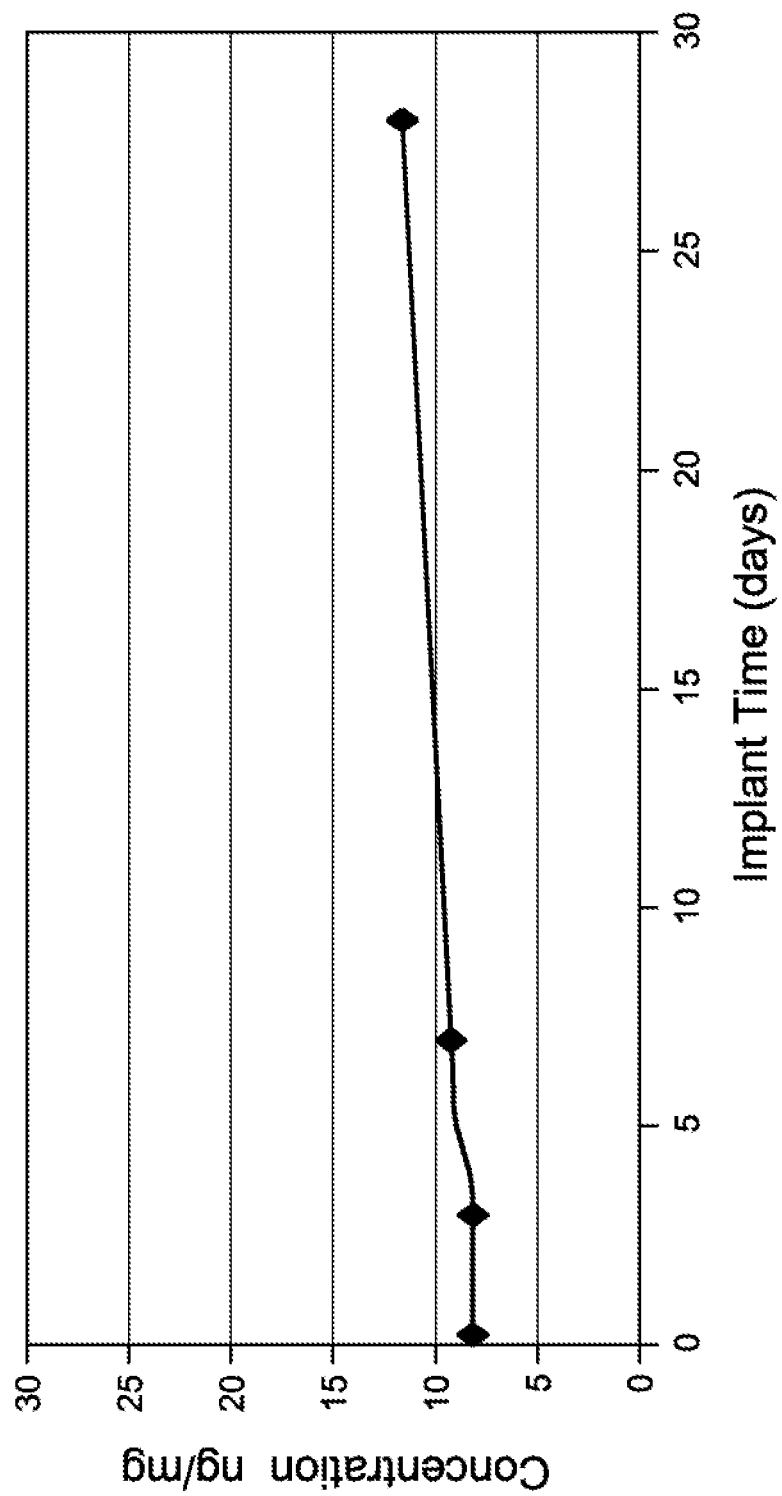
FIG. 10 shows tissue concentration of Compound AR at different time points in a porcine coronary artery model.
Figure 11:
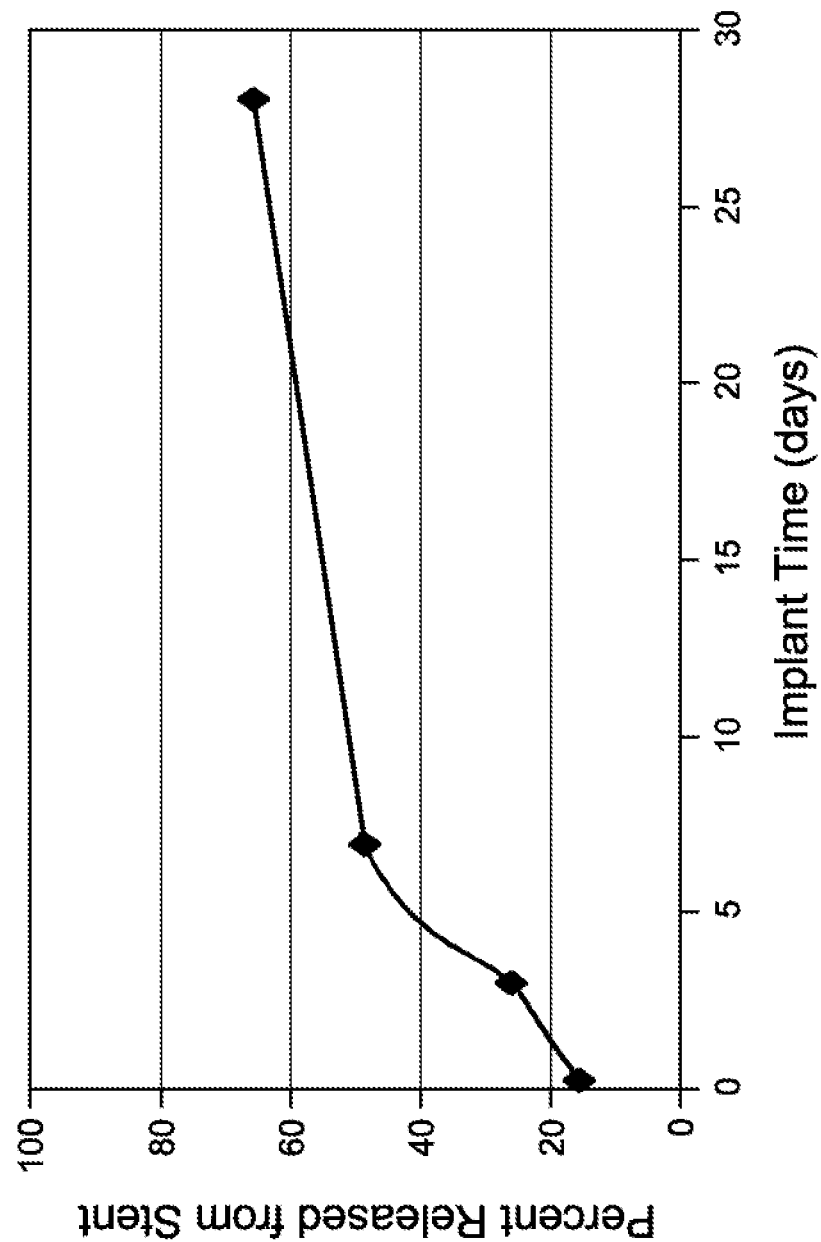
FIG. 11 shows percentage of Compound AR released from the stent in a porcine coronary artery model.

All animal survived to the designated end point. The average tissue concentrations for the Compound AR and stent release rates are presented in FIGS. 10 and 11. The Compound AR eluting stent, in this example demonstrates release of Compound AR from the stent with greater than 40% of the drug released at 7 days.

Example 6: Preparation of 17, 18-29, 30-bis-epoxide macrocyclic lactone (AS)

Add 0.8 mL 5% NaOH-MeOH and 2 ml 30% $H_2O_2$ to a solution of 1 gram Rapamycin in 40 ml methanol. The reaction mixture was stirred at room temperature for 24 hours. If TLC indicated some rapamycin was still unreacted, additional mixture of 0.8 mL 5% NaOH-MeOH and 2 ml 30% $H_2O_2$ was added to the reaction solution. Stirring continued at room temperature until TLC indicated the reaction has completed. The solution was extracted with dichloromethane and brine 3 times. The organic layers were combined and washed with brine and water, dried over anhydrous $MgSO_4$, filtered MgSO4 and the solution was evaporated to leave a raw product. This raw product was further purified using TLC plate and giving 0.40 g (40% yields) light yellow powder. $^1$H NMR (CDCl$_3$) (~4:1 mixture of conformers, only signals of major conformer listed) Major changes compared with rapamycin δ (ppm) 1.75 (s, 1H), 1.98 (s, 1H), 6.71 (ddd, 5H, J1=16 Hz, J2=8 Hz, J3=2.8 Hz). $^{13}$C DEPT 135 NMR (CDCl$_3$) (~4:1 mixture of conformers, only signals of major conformer listed) δ (ppm) 152, 140, 133, 128, 127, 126, 84, 83, 76, 74, 67, 59, 56, 44, 43, 41, 40, 36, 35, 34, 33, 31, 29, 28, 22, 21, 20, 17, 16, 15, 13. Mass Spectra m/z=962 with Rapamycin m/z=930.

Example 7: Biological Activity of 17, 18-29, 30-bis-epoxide macrocyclic lactone (AS)

Figure 13:
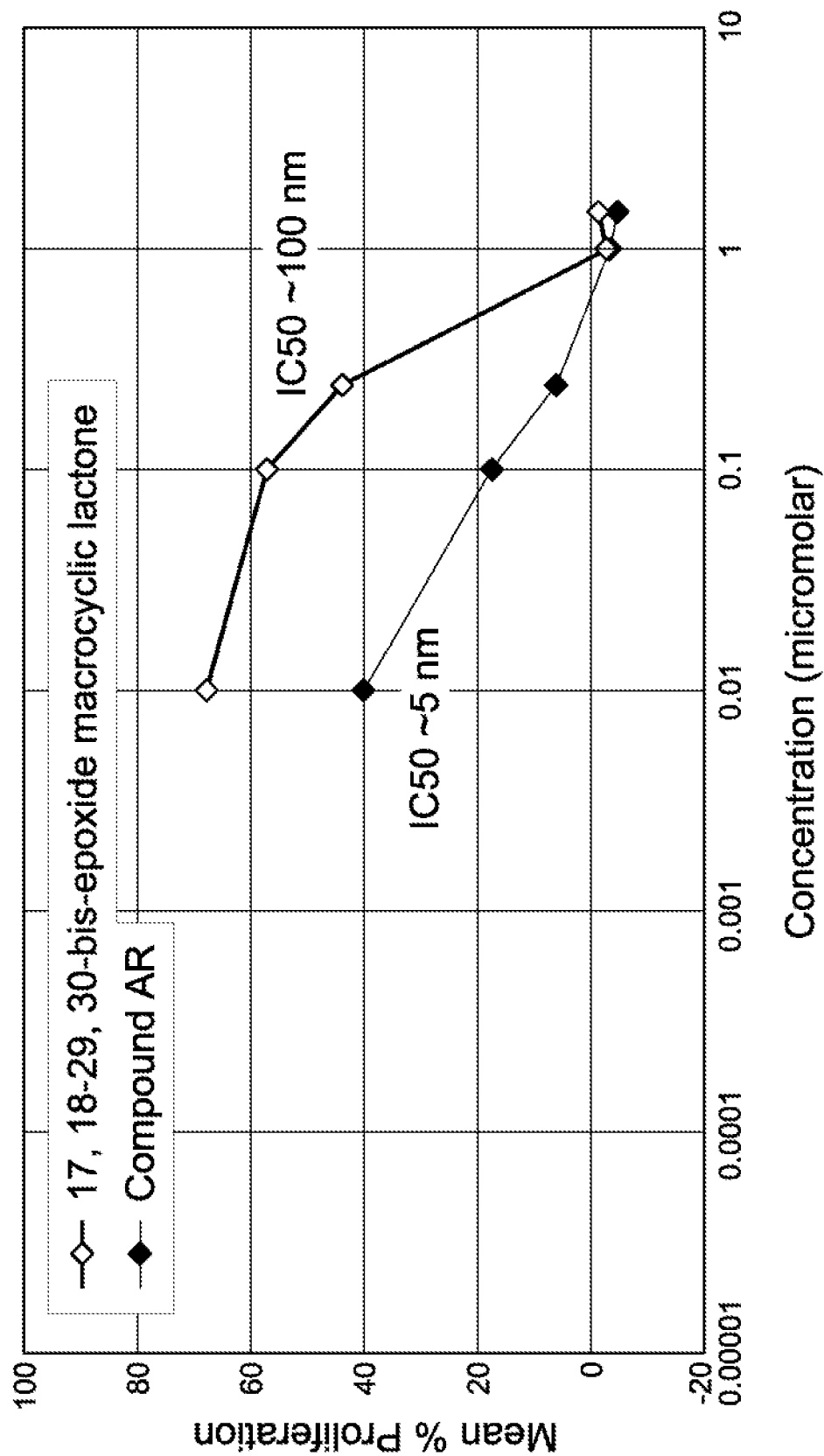
FIG. 13 shows percentage proliferation of human smooth muscle cells after exposure to varying concentrations of 17,18-29,30-bis-epoxide macrocyclic lactone and Compound AR.

Potency of the 17, 18-29, 30-bis-epoxide macrocyclic lactone was demonstrated by in vitro human smooth muscle cell culture testing. The amounts of incorporated thymidine for samples of 17, 18-29, 30-bis-epoxide macrocyclic lactone of varying concentrations (0.005, 0.01, 0.05, 0.1, 0.5, and 1 µM) and of Compound AR of varying concentrations (0.0005, 0.001, 0.01, and 0.1 µM) were measured after exposure for 8 hours. The $IC_{50}$ of 17, 18-29, 30-bis-epoxide macrocyclic lactone and Compound AR was approximately 0.1 and 0.005 µM, respectively, after smooth muscle cells were exposed to 17, 18-29, 30-bis-epoxide macrocyclic lactone and Compound AR for 8 hours (FIG. 13). The $IC_{50}$ of 17, 18-29, 30-bis-epoxide macrocyclic lactone was approximately 20 times higher than that of Compound AR.

Example 8: Preparation of 17, 18-19, 20-21, 22-tris-epoxide macrocyclic lactone (AY)

m-chloro-peroxybenzoic acid 0.93 g (3.22 mmol) was added to a solution of 0.50 g (0.5371 mmol) rapamycin in 10 ml CHCl$_3$ at room temperature. The mixture was stirred at room temperature for 24 hours. If TLC indicated some rapamycin was still unreacted, additional m-chloroperoxybenzoic acid 0.50 g and 5 mL CHCl$_3$ was added. Stirring was continued at room temperature until no Rapamycin was indicated by TLC. After completion of the reaction, the solution was diluted with dichloromethane, treated with aqueous sodium sulfite until the washings give a negative test with starch-iodide paper. This ensures all excess peracid has been destroyed and the aqueous layer was extracted with several portions of CH$_2$Cl$_2$. Then organic layer was washed with two 20 ml portion of 5% sodium bicarbonate to remove benzoic acid. The combined organic extracts were washed with water, dried with anhydrous MgSO$_4$, filtered and evaporated to leave a crude white solid 0.46 g. The raw product was further purified using TLC plate. MS m/z 978 with Rapamycin m/z 930.

Example 9: Cytokine Inhibition by Macrocyclic Lactone

In cell culture studies, macrophages were activated to secrete cytokines such as 11-6, MMP-9, MCP-1 and IL-10 by treating the cells to E Coli lippopolysaccharide (LPS). Inhibition of these cytokines upon treatment of the activated macrophages with Compound AR and rapamycin with 10 nM concentration was tested using ELISA assay. The inhibition of pro-inflammatory and cell proliferation and migration inducing cytokines upon exposure to the macrocyclic lactone is presented in FIG. 12A. The inhibition of anti-inflammatory cytokine IL-10 upon exposure to macrocyclic lactone Compound AR and Sirolimus are presented in FIG. 12B.

MMP-9 levels in the 1st, 3rd and 7th day after stent implantation were positively correlated to the late loss index 6 months after stent implantation (Elevated matrix metalloproteinase expression after stent implantation is associated with restenosis. Int J Cardiol. 2006; 112(1):85-90).

Compound AR and Sirolimus did not show any significant inhibition of release of IL-6. Compound AR significantly reduced the production of both the cytokines MMP-9 and MCP-1 as compared to Sirolimus which increased the production of MMP-9 and did not impact the production of MCP-1.

Compound AR and Sirolimus did not show any difference in inhibition of release of IL-6. On the other hand, Compound AR reduced the production of cytokine MMP-9 while Sirolimus increased the production of MMP-9. Compound AR reduced the production of cytokine MCP-1 as compared to Sirolimus which did not impact the production of MCP-1. Compound AR and Sirolimus both inhibit the production of anti-inflammatory cytokine IL-10.

Compounds claimed in the present invention, such as Compound AR can provide better therapeutic response with higher levels of anti-inflammatory effect (such as greater inhibition of pro-inflammatory cytokine MCP-1) and higher levels of anti-cell proliferative and anti-cell migratory effect (such as greater inhibition of pro-proliferative and migration cytokine MMP-9).

Example 10: Testing of Compound AR Eluting Stents in Human Clinical Trial

Clinical testing of the Compound AR coated stent was conducted on 15 human subjects. Safety of the Compound AR coated stent was evaluated clinically through the evaluation of major adverse cardiac events defined as: death, myocardial infarction (both Q-wave and non-Q-wave), and target lesion revascularization. Efficacy was evaluated through angiographic and intravascular ultrasound (IVUS) results at 4 months. The primary endpoint of the study was angiographic in-stent late lumen loss. Secondary endpoints were Major Adverse Cardiac Events (MACE) and additional angiographic and IVUS evaluation. The clinical study was approved by local Ethics Committee and all patients signed an Ethics approved informed consent before entry into the clinical study.

All patients were pretreated with aspirin and ticlopidine (500 mg) per oral beginning at least 1 day prior or on the day of the index procedure. Aspirin (>100 mg/day and Clopidogrel (75 mg/day) were continued through for at least six months. In accordance with hospital standard percutaneous practice, the left or right femoral artery was accessed using standard techniques and an arterial sheath was introduced and advanced into the artery.

Index procedure vessel angiography was performed under fluoroscopic guidance, a 6 or 7 Fr. guide catheter was inserted through the sheath and advanced to the appropriate location; intracoronary nitroglycerin was administered. A segment of coronary artery ranging from 3.0 mm to 3.5 mm mean lumen diameter was chosen and a 0.014" guidewire inserted. Quantitative Coronary Angiography (QCA) was performed to document the reference vessel diameter. Predilatation of the lesion was performed prior to stent implantation using standard technique.

Following predilatation, the appropriately sized stent (3.0×18 mm or 3.5×18 mm was advanced to the deployment site. The balloon was inflated at a steady rate to a pressure to fully deploy the stent. Pressure was maintained for approximately 30 seconds. Post dilatation of the stent could be performed as needed to assure good stent apposition to the vessel wall. Angiographic and intravascular ultrasound imaging (IVUS) was performed and recorded.

Follow-up angiography and IVUS was performed at the designated endpoint of 4 months for each patient. Each angiogram was qualitatively evaluated for evidence of lumen narrowing, stent apposition, and flow characteristics.

Angiographic and IVUS parameters measured or calculated included:
Marginal vessel (proximal and distal) mean lumen diameter (post-stent and final)
Mean lumen diameter of the target region (all angiograms)
Minimal lumen diameter (MLD) of the target region (post-stent and final only)
Diameter stenosis [1−(MLD/RVD)]×100%] where RVD is a calculation of the reference diameter at the position of the obstruction (measure obtained by a software-based iterative linear regression technique to generate an intrapolation of a projected vessel without the lesion) (final angiogram only).
In-stent Late Lumen Loss [MLD final-MLD post-stent]
In-stent percent neointimal volume as assessed by IVUS
All patients underwent 4 month clinical and angiographic follow-up. No patients experience any major adverse cardiac events during the follow-up period. Angiographic results demonstrated that the primary endpoint of angiographic in-stent late lumen loss was 0.16±0.32 mm. IVUS analysis was conducted on 13 of 15 patients and the results demonstrated in-stent percent neointimal volume of 3.7±2.7%.

As a comparison, Cypher stent tested in a pilot study and demonstrated similar clinical safety with no clinical events and angiographic results at 4 months of in-stent late lumen loss for the slow release group (the current commercially available formulation) of 0.09±0.3 mm and in-stent percent neointimal volume by IVUS to be 0.3±0.6% (Sousa, J E, Circulation 2001; 103; 192-195).

Example 11: Preparation of 31-hydroxyl, 44-hydroxyl (Compound BG) and 47-hydroxyl (Compound BJ) macrocyclic lactone Macrocyclic lactone rapamycin (1 g, 1.1 mmol) in 100 ml absolute ethanol was added to selenium dioxide (122 mg, 1.10 mmol) absolute ethanol (50 ml) solution. The mixture was stirred at room temperature until TLC analysis showed the disappearance of rapamycin (about 15 h). The reaction mixture was concentrated and the residue was partitioned between ether and water and extracted with ether 3×80 ml. The organic layers was dried over anhydrous sodium sulfate, filtered and concentrated. The final individual pure product 31-hydroxyl, 44-hydroxyl, 47-hydroxyl macrocyclic lactone were obtained by prepared HPLC.

The characterized spectra changes compared with macrocyclic lactone rapamycin are shown as follows:

| | Sample name | | |
|---|---|---|---|
| | 31-hydroxyl macrocyclic lactone | 44-hydroxyl macrocyclic lactone (compound BG) | 47-hydroxyl macrocyclic lactone (compound BJ) |
| Mass M/Z [M + H] | 929 | 929 | 929 |
| $^1$HNMK (1:1 THF-$d_8$/$D_2O$) | Loss of 0.87, 3.21, 3.27 ppm peak; Gain 1.38 ppm peak | Loss of 1.58 ppm single peak; Gain 4.07 ppm peak | Loss of 1.72 ppm single peak; Gain 4.07 ppm peak |

Example 12: Preparation of 43-hydroxyl(Compound BF), 47-hydroxyl(Compound BJ) macrocyclic lactone A solution of 1 gram macrocyclic lactone rapamycin (1.1 mmol) was dissolved in 100 ml acetonitrile. 0.3 gram Ferrous Sulfate heptahydrate (1.1 mmol) was added to the solution with stirring and nitrogen purging for 20-30 minutes. The mixture was then cooled to −16° C. to −18° C. with ice-bath. A solution of 1 ml 30% $H_2O_2$ in 10 ml acetonitrile was then slowly added to above mixture over 30 min with stirring and nitrogen purging. After complete addition of hydrogen peroxide, continued stirring and nitrogen purging until TLC analysis showed the disappearance of rapamycin. The solution was extracted with dichloromethane and brine 3 times. The organic layer was combined and washed with brine and water, dried over anhydrous $MgSO_4$, filtered $MgSO_4$ and the solution was evaporated to leave a raw product. The pure product 43-hydroxyl, 47-hydroxyl macrocyclic lactone were obtained by prepared HPLC.

The characterized spectra changes compared with macrocyclic lactone rapamycin are shown as follows:

| | Sample name | |
|---|---|---|
| | 43-hydroxyl macrocyclic lactone (compound BF) | 47-hydroxyl macrocyclic lactone (compound BJ) |
| Mass M/Z [M + H] | 929 | 929 |
| $^1$HNMR, (1:1 THF-$d_8$/$D_2O$) | Loss of 0.74 ppm peak; Gain 3.49, 3.24 ppm peaks | Loss of 1.72 ppm single peak; Gain 4.07 ppm peak |

Although the foregoing invention has been described in some detail by way of illustration and example for purposes of clarity of understanding, one of skill in the art will appreciate that certain changes and modifications may be practiced within the scope of the appended claims. In addition, each reference provided herein is incorporated by reference in its entirety to the same extent as if each reference was individually incorporated by reference.

What is claimed is:

1. A method for the treatment or prevention of acute or chronic transplant rejection in a patient, comprising implanting to the patient in need thereof, an implant having a surface coated with a therapeutically effective amount of a compound of the formula:

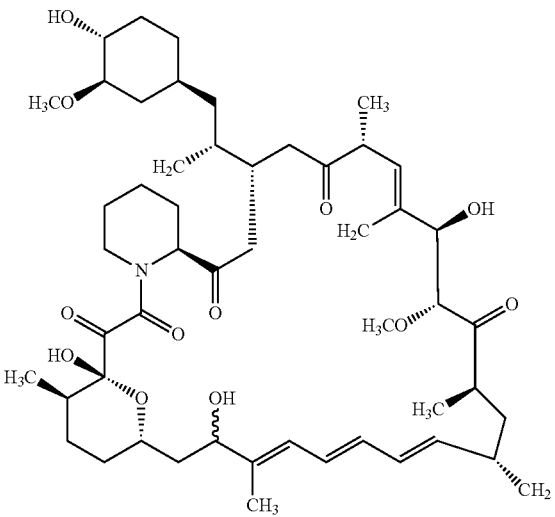

or a salt, isomer, or N-oxide thereof, thereby treating or preventing the transplant rejection.

2. The method of claim 1, wherein the compound is released from the implant via osmotic pressure or diffusion.

3. The method of claim 1, wherein the implant is a biodegradable implant.

4. The method of claim 1, wherein the effective amount of the compound is from 0.1 mg to 20 mg.

5. The method of claim 4, wherein the effective amount of the compound is from 0.5 mg to 10 mg.

6. The method of claim 4, wherein the effective amount of the compound is from 1 mg to 5 mg.

* * * * *